United States Patent
McQuiston et al.

(10) Patent No.: US 12,178,592 B2
(45) Date of Patent: *Dec. 31, 2024

(54) METHODS FOR AIDING IN DIAGNOSING AND EVALUATING A MILD TRAUMATIC BRAIN INJURY IN A HUMAN SUBJECT USING CARDIAC TROPONIN I

(71) Applicant: Abbott Laboratories, Abbott Park, IL (US)

(72) Inventors: Beth McQuiston, Abbott Park, IL (US); Frederick Korley, Ann Arbor, MI (US); Agim Beshiri, Abbott Park, IL (US); Jaime Marino, Abbott Park, IL (US); Saul Datwyler, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 359 days.

This patent is subject to a terminal disclaimer.

(21) Appl. No.: 17/411,511

(22) Filed: Aug. 25, 2021

(65) Prior Publication Data

US 2022/0047205 A1    Feb. 17, 2022

Related U.S. Application Data

(63) Continuation of application No. 15/993,589, filed on May 30, 2018, now Pat. No. 11,129,564.

(60) Provisional application No. 62/528,214, filed on Jul. 3, 2017, provisional application No. 62/512,710, filed on May 30, 2017, provisional application No. 62/512,688, filed on May 30, 2017.

(51) Int. Cl.
| | |
|---|---|
| *A61B 5/00* | (2006.01) |
| *C12Q 1/6883* | (2018.01) |
| *G01N 33/543* | (2006.01) |
| *G01N 33/564* | (2006.01) |
| *G01N 33/577* | (2006.01) |
| *G01N 33/68* | (2006.01) |
| *G01N 33/533* | (2006.01) |

(52) U.S. Cl.
CPC ..... *A61B 5/4064* (2013.01); *G01N 33/54346* (2013.01); *G01N 33/54366* (2013.01); *G01N 33/577* (2013.01); *G01N 33/6896* (2013.01); *C12Q 1/6883* (2013.01); *G01N 33/533* (2013.01); *G01N 33/564* (2013.01); *G01N 33/6893* (2013.01); *G01N 2800/28* (2013.01); *G01N 2800/52* (2013.01); *G01N 2800/56* (2013.01); *G01N 2800/60* (2013.01)

(58) Field of Classification Search
CPC ........... A61B 5/4064; G01N 33/54346; G01N 33/577; G01N 2800/52; G01N 33/54366; G01N 33/6896; G01N 33/533; G01N 33/564; G01N 33/6893; G01N 2800/28; G01N 2800/56; G01N 2800/60; C12Q 1/6883

See application file for complete search history.

(56) References Cited

U.S. PATENT DOCUMENTS

| | | | |
|---|---|---|---|
| 7,456,027 B2 | 11/2008 | Wang et al. | |
| 8,492,107 B2 | 7/2013 | Wang et al. | |
| 9,265,441 B2 | 2/2016 | Pereira et al. | |
| 2003/0199000 A1 | 10/2003 | Valkirs et al. | |
| 2007/0042425 A1 | 2/2007 | Hochstrasser et al. | |
| 2010/0261286 A1 | 10/2010 | Kim et al. | |
| 2011/0143375 A1 | 6/2011 | Wang et al. | |
| 2012/0181184 A1 | 7/2012 | Whitesides et al. | |
| 2012/0202231 A1 | 8/2012 | Wang et al. | |
| 2013/0029859 A1 | 1/2013 | Svetlov et al. | |
| 2014/0303041 A1 | 10/2014 | Hayes et al. | |
| 2014/0342381 A1 | 11/2014 | Hayes et al. | |
| 2014/0370531 A1 | 12/2014 | Blyth et al. | |
| 2015/0141528 A1 | 5/2015 | Larner | |
| 2015/0224499 A1 | 8/2015 | Wang et al. | |
| 2015/0268252 A1 | 9/2015 | Svetlov et al. | |
| 2016/0178643 A1 | 6/2016 | Everett et al. | |
| 2017/0089926 A1 | 3/2017 | Travis et al. | |
| 2017/0144156 A1 | 5/2017 | Tang et al. | |

(Continued)

FOREIGN PATENT DOCUMENTS

| | | |
|---|---|---|
| CN | 105085629 A | 11/2015 |
| CN | 112881700 A | 6/2021 |

(Continued)

OTHER PUBLICATIONS

Papa Linda et al: "Evaluating glial and neuronal blood biomarkers GFAP and UCH-L1 as gradients of brain injury in concussive, subconcussive and non-concussive trauma: a prospective cohort study", BMJ Paediatrics Open, vol. 3, No. 1, Aug. 1, 2019 (Aug. 1, 2019), p. e000473, XP055951121, DOI: 10.1136/bmjpo-2019-000473 Retrieved from the Internet: URL:https://bmjpaedsopen.bmj.com/content/b mjpo/3/1/e000473.ful1.pdf>.

Rhine Tara et al: "2443 : Investigating markers of early traumatic brain injury (iMet): An interim analysis", Journal of Clinical and Translational Science, vol. 1, No. S1, Sep. 1, 2017 (Sep. 1, 2017), pp. 78-78, XP055951100, DOI: 10.1017/cts.2017.276.

International Searching Authority, International Search Report and Written Opinion for PCT Application No. PCT/US2022/029798, mailed Aug. 31, 2022.

(Continued)

*Primary Examiner* — Olga N Chernyshev
(74) *Attorney, Agent, or Firm* — Lisa Mueller; Casimir Jones SC

(57) ABSTRACT

Disclosed herein are methods that aid in the diagnosis and evaluation of a human subject that has sustained or may have sustained an injury to the head, such as mild or moderate, severe, or moderate to severe traumatic brain injury (TBI), using cTnI. Also disclosed are methods for determining whether to perform a head computerized tomography on a subject by detecting levels of cTnI. Finally, also disclosed are methods of outcome in subjects suffering from a mild TBI.

19 Claims, 29 Drawing Sheets

Specification includes a Sequence Listing.

(56) References Cited

U.S. PATENT DOCUMENTS

| | | |
|---|---|---|
| 2017/0176460 A1 | 6/2017 | Larner |
| 2018/0031577 A1 | 2/2018 | Wang et al. |
| 2018/0064342 A1 | 3/2018 | Wedan |
| 2018/0106800 A1 | 4/2018 | Datwyler et al. |
| 2018/0106818 A1 | 4/2018 | Jewell et al. |
| 2018/0120305 A1 | 5/2018 | Harel |
| 2018/0313837 A1 | 11/2018 | McQuiston et al. |
| 2019/0064187 A1 | 2/2019 | Svetlov et al. |
| 2019/0091687 A1 | 3/2019 | Alhasnani |
| 2019/0219598 A1 | 7/2019 | McQuiston et al. |
| 2019/0302127 A1 | 10/2019 | Lukaszewska |
| 2020/0116739 A1 | 4/2020 | Everett et al. |

FOREIGN PATENT DOCUMENTS

| | | |
|---|---|---|
| EP | 105085629 A1 | 3/2005 |
| EP | 1838442 B1 | 9/2013 |
| EP | 3916387 A1 | 12/2021 |
| JP | 2012500388 A | 1/2012 |
| JP | 2017125853 A | 7/2017 |
| WO | WO 2005/029088 | 3/2005 |
| WO | WO 2005/106038 | 10/2005 |
| WO | WO 2005/113798 | 12/2005 |
| WO | 2007009125 A2 | 1/2007 |
| WO | WO 2009/100131 | 8/2009 |
| WO | 2010019553 A2 | 2/2010 |
| WO | 2010102279 A1 | 9/2010 |
| WO | 2010148391 A2 | 12/2010 |
| WO | WO 2010/148391 | 12/2010 |
| WO | WO 2011/011334 A2 | 1/2011 |
| WO | WO 2011/032155 | 3/2011 |
| WO | WO 2011/160096 A2 | 12/2011 |
| WO | WO 2012/051519 | 4/2012 |
| WO | 2013090285 A1 | 6/2013 |
| WO | 2014124174 A2 | 8/2014 |
| WO | WO 2014/194329 | 12/2014 |
| WO | WO 2015/009907 | 1/2015 |
| WO | WO 2015/066211 | 5/2015 |
| WO | WO 2015/157300 | 10/2015 |
| WO | WO 2016/055148 A2 | 4/2016 |
| WO | WO 2016/166419 A1 | 10/2016 |
| WO | WO 2016/196522 A1 | 12/2016 |
| WO | WO 2018/067468 A1 | 4/2018 |
| WO | WO 2018/067474 | 4/2018 |
| WO | WO 2018/081649 A1 | 5/2018 |
| WO | WO 2018/136825 A1 | 7/2018 |
| WO | WO 2018/175942 | 9/2018 |
| WO | WO 2018/191531 | 10/2018 |
| WO | 2018217792 A1 | 11/2018 |
| WO | WO 2018/200823 | 11/2018 |
| WO | WO 2018/214169 | 11/2018 |
| WO | WO 2018/222783 | 12/2018 |
| WO | WO 2018/222784 | 12/2018 |
| WO | WO 2019/112860 | 6/2019 |
| WO | WO 2019/113525 | 6/2019 |
| WO | WO 2019/133717 | 7/2019 |
| WO | 2019199869 A1 | 10/2019 |
| WO | 2021026261 A1 | 2/2021 |

OTHER PUBLICATIONS

Metzger Ryan R. et al: "Temporal response profiles of serum ubiquitin C-terminal hydrolase-L1 and the 145-kDa alpha II-spectrin breakdown product after severe traumatic brain injury in children", Journal of Neurosurgery. Pediatrics, vol. 22, No. 4, Oct. 1, 2018 (Oct. 1, 2018), pp. 369-374, XP055951102, us, ISSN: 1933-0707, DOI: 10.3171/2018.4.PEDS17593.

Rhine Tara et al.: "Investigating Markers of Early Traumatic Brain Injury (iMet)", Pediatrics, Aug. 1, 2019 (Aug. 1, 2019), pp. 1-4, XP055951099, Retrieved from the Internet: URL:https://publications.aap.org/pediatrics/article/144/2_MeetingAbstract/429/3499/Investigating-Markers-of-Early-Traumatic-Brain.

Lynne Babcock et al: "Are UCH-L1 and GFAP promising biomarkers for children with mild traumatic brain injury?", Brain Injury, vol. 30, No. 10, Aug. 23, 2016 (Aug. 23, 2016), pp. 1231-1238, XP055951118, GB, ISSN: 0269-9052, DOI: 10.1080/02699052. 2016.1178396 Retrieved from the Internet: URL:https://www.ncbi.nlm.nih.gov/pmc/articles/PMC5818714/pdf/nihms831590.pdf>.

International Searching Authority, International Search Report and Written Opinion for International Application No. PCT/US2022/033337, mailed Nov. 14, 2022.

Salim, A., et al., "Significance of Troponin Elevation After Severe Traumatic Brain Injury," The Journal of Trauma Injury, Infection, and Critical Care, Jan. 1, 2008.

Lippi, G., et al., "The concentration of highly-sensitive troponin I is increased with patients with brain injury after mild head trauma," Letter to the Editor, vol. 168, Issue 2, p. 1617-1618, Sep. 30, 2013, International Journal of Cardiology.

International Searching Authority, International Search Report and Written Opinion for International Application No. PCT/US2022/077128, mailed Jan. 3, 2023.

Lawrence M. Lewis et al., Utility of Serum Biomarkers in the Diagnosis and Stratification of Mild Traumatic Brain Injury, Academic Emergency Medicine, Jun. 1, 2017, vol. 24, No. 6, pp. 710-720.

International Searching Authority, International Search Report and Written Opinion for International Application No. PCT/US2022/075638, mailed Dec. 16, 2022.

Andrew K. Ottens et al, "Neuroproteomics: A Biochemical Means to Discriminate the Extent and Modality of Brain Injury", Journal of Neurotrauma, Mary Ann Liebert, Inc., publishers., Oct. 1, 2010, 27(10), 1837-1852.

European Patent Office, Partial Search Report for EP Application No. 20806307.3 mailed Jun. 26, 2023.

Bazarian Jeffrey J. et al: "Persistent, Long-term Cerebral White Matter Changes after Sports-Related Repetitive Head Impacts", PLOS One, vol. 9, No. 4, Apr. 16, 2014 (Apr. 16, 2014), pp. 1-12, XP93054623.

Koerte Inga K. et al: "A Review of Neuroimaging Findings in Repetitive Brain Trauma: Neuroimaging Findings in Repetitive Brain Trauma", Brain Pathology. vol. 25, No. 3, Apr. 23, 2015 (Apr. 23, 2015), pp. 318-349, XP055792317.

Sengupta Mohor B et al: "Increased expression of ApoAI after neuronal injury may be beneficial for healing", Molecular and Cellular Biochemistry, Springer US, New York, vol. 424, No. 1, Oct. 13, 2016 (Oct. 13, 2016), pp. 45-55, XP036127824.

E. Mark Haacke, "Common Data Elements in Radiologic Imaging of Traumatic Brain Injury," Journal of Magnetic Resonance Imaging 32, Apr. 28, 2010, pp. 516-543.

Jennifer Middleton, "UCH-L1 and GFAP Testing (i-STAT TBI Plasma) for the Detection of Intracranial Injury Following Mild Traumatic Brain Injury," Am Fam Physician, Mar. 1, 2022;105(3):313-314.

Wheeler, S., et al. "Effectiveness of Interventions to Improve Occupational Performance for People with Psychosocial, Behavioral, and Emotional Impairments After Brain Injury: A Systematic Review," The American Journal of Occupational Therapy, 70(3):1-9 (May/Jun. 2016).

Ustinova, K.I., et al. entitled "Physical therapy for correcting postural and coordination deficits in patients with mild-to-moderate traumatic brain injury," Physiotherapy Theory and Practice, 31(1):1-7 (2015).

International Searching Authority, International Search Report and Written Opinion for International Application No. PCT/US2022/080578, mailed Mar. 24, 2023.

Korley, F. K., et al., "Comparison of GFAP and UCH-L1 Measurements from Two Prototype Assays: The Abbott i-STAT and Architect Assays," Neurotrauma Reports, vol. 2, No. 1, Apr. 7, 2021, pp. 193-199.

International Searching Authority, International Search Report and Written Opinion for International Application No. PCT/US2022/082449, mailed Mar. 24, 2023.

International Searching Authority, International Search Report and Written Opinion for International Application No. PCT/US2023/061894, mailed May 11, 2023.

(56) References Cited

OTHER PUBLICATIONS

Natarajan Satheesh et al: "A novel time-resolved fluorescent lateral flow immunoassay for quantitative detection of the trauma brain injury biomarker-glial fibrillary acidic protein", Sensors & Diagnostics, vol. 1, No. 1, Jan. 20, 2022 (Jan. 20, 2022), pp. 193-197.
Evgeni Eltzov et al: "Lateral Flow Immunoassays—from Paper Strip to Smartphone Technology", Electroanalysis, VHC Publishers, Inc, US, vol. 27, No. 9, Aug. 24, 2015 (Aug. 24, 2015), pp. 2116-2130.
De Puig Helena et al: "Challenges of the Nano-Bio Interface in Lateral Flow and Dipstick Immunoassays", Trends in Biotechnology, vol. 35, No. 12, Dec. 2017 (Dec. 2017), pp. 1169-1180.
International Searching Authority, International Search Report and Written Opinion for International Application No. PCT/US2022/081763, mailed May 19, 2023.
Hauser Janosch, et al., "An Antonomous Microfluidic Device for Generating Volume-Defined Dried Plasma Spots," Analytical Chemistry, vol. 91, No. 11, May 7, 2019, pp. 7125-7130.
Agoston, Denes V. et al., "Biofluid Biomarkers of Traumatic Brain Injury" Brain Injury, 31(9):1195-1203 (Jul. 29, 2017).
Banyan BTI Brain Trauma Indicator, Publicly available Feb. 2018.
Bazarian et al., "Serum GFAP and UCH-L1 for prediction of absence of intracranial injuries on head CT (Alert-TBI): a multicentre observational study" The Lancelot, Neurology, vol. 17, Issue 9, p. 782-789, Sep. 1, 2018.
Benninger et al., "Glial fibrillary acidic protein as a marker of astrocytic activation in the cerebrospinal fluid of patients with amyotrophic lateral sclerosis." Journal of Clinical Neuroscience, 26:75-78 (Nov. 2015).
Berger, et al., "Serum Concentrations of Ubiquitin C-Terminal Hydrolase-L1 and all-Spectrin Breakdown Product 145 kDa Correlate with Outcome after Pediatric TBI." Journal of Neurotrauma, Jan. 1, 2012; 29:162-167.
Blyth, Brian J. et al., "Elevated Serum Ubiquitin Carboxy-Terminal Hydrolase L1 is Associated with Abnormal Blood-Brain Barrier Function after Traumatic Brain Injury", Journal of Neurotrauma., 28(12): 2453-2462 (Dec. 1, 2011).
Bogoslovsky T. et al., "Fluid Biomarkers of Traumatic Brain Injury and Intended Context of Use." Diagnostics (Basel). Oct. 18, 2016; 6(4). pii: E37.
Brophy, M. et al., "Biokinetic analysis of ubiquitin C-terminal hydrolase-L1 (UCH-L1) in severe traumatic brain injury patient biofluids." J Neurotrauma. Jun. 2011; 28(6):861-70.
Cai et al., "The role of cardiac troponin I in prognostication of patients with isolated severe traumatic brain injury." J. Trauma Acute Care Surg., 80(3):477-483 (Mar. 2016).
Dash et al.; "Biomarkers for Diagnosis, Prognosis, and Evaluation of Treatment Efficacy for Traumatic Brain Injury." Neurotherapeutics, Jan. 2010, 7(1): 100-114.
Diaz-Arrastia, et al., "Acute biomarkers of traumatic brain injury: relationship between plasma levels of ubiquitin C-terminal hydrolase-L1 and glial fibrillary acidic protein.", Journal of Neurotrauma, 31:19-25 (Jan. 1, 2014).
Hamdi, et al., "Predictive Value of Cardiac Troponin I in Traumatic Brain Injury.", Egypt J. Neurol. Psychiat. Neurosurg, 49(4):365-373 (Oct. 2012) (cross cite in all applications).
International Preliminary Report on Patentability issued Apr. 9, 2019 for International Application No. PCT/US2017/054787, 7 pages.
International Preliminary Report on Patentability issued Apr. 9, 2019 for International Application No. PCT/US2017/054775, 7 pages.
International Preliminary Report on Patentability mailed Dec. 5, 2019 for International Application No. PCT/US2018/034694, 14 pages.
International Preliminary Report on Patentability mailed Dec. 12, 2019 for International Application No. PCT/US2018/035232, 8 pages.
International Preliminary Report on Patentability mailed Dec. 12, 2019 for International Application No. PCT/US2018/035231, 8 pages.
International Preliminary Report on Patentability mailed Jan. 16, 2020 for International Application No. PCT/US2018/040612, 7 pages.
International Preliminary Report on Patentability mailed Nov. 7, 2019 for International Application No. PCT/US2018/029585, 14 pages.
International Preliminary Report on Patentability mailed Oct. 3, 2019 for International Application No. PCT/US2018/024112, 11 pages.
International Preliminary Report on Patentability mailed Oct. 3, 2019 for International Application No. PCT/US2018/027353, 13 pages.
International Search Report & Written Opinion mailed Apr. 2, 2019 for International Application No. PCT/US2018/062888, 18 pages.
International Search Report & Written Opinion mailed Aug. 2, 2018 for International Application No. PCT/US2018/027353, 21 pages.
International Search Report & Written Opinion mailed Aug. 2, 2018 for International Application No. PCT/US2018/029585, 23 pages.
International Search Report & Written Opinion mailed Dec. 1, 2017 for International Application No. PCT/US2017/054775, 14 pages.
International Search Report & Written Opinion mailed Dec. 1, 2017 for International Application No. PCT/US2018/035232, 15 pages.
International Search Report & Written Opinion mailed Dec. 7, 2017 for International Application No. PCT/US2017/054787, 15 pages.
International Search Report & Written Opinion mailed Jun. 4, 2019 for International Application No. PCT/US2018/064587, 26 pages.
International Search Report & Written Opinion mailed May 31, 2019 for International Application No. PCT/US2018/067683, 21 pages.
International Search Report & Written Opinion mailed Sep. 10, 2018 for International Application No. PCT/US2018/024112, 19 pages.
International Search Report & Written Opinion mailed Sep. 10, 2018 for International Application No. PCT/US2018/034694, 15 pages.
International Search Report & Written Opinion mailed Sep. 17, 2018 for International Application No. PCT/US2018/040612, 15 pages.
International Search Report & Written Opinion mailed Sep. 3, 2018 for PCT/US2018/035231, 14 pages.
Kiiski, H. et al., "Increased plasma UCH-L1 after aneurysmal subarachnoid hemorrhage is associated with unfavorable neurological outcome." J Neurol Sci. Feb. 15, 2016; 361:144-9.
Kiviniemi et al., "Serum levels of GFAP and EGFR in primary and recurrent high-grade gliomas: correlation to tumor volume molecular markers, and progression-free survival." Journal of Neuro-Oncology, 124(2):237-245 (Jun. 2015).
Kobeissy, Firas H. et al., "Novel Differential Neuroproteomics Analysis of Traumatic Brain Injury in Rats" Molecular & Cellular Proteomics, 5(10):1887-1898 (Oct. 1, 2006).
Kochanek et al., "Multi-Center Pre-clinical Consortia to Enhance Translation of Therapies and Biomarkers for Traumatic Brain Injury: Operation Brain Trauma Therapy and Beyond." Frontiers in Neurology Aug. 2018, vol. 9, 13 pages.
Korley et al., "Performance Evaluation of a Multiplex Assay for Simultaneous Detection of Four Clinically Relevant Traumatic Brain Injury Biomarkers." Journal of Neurotrauma, 2015, 35:1-6.
Kou et al., "Combining Biochemical and Imaging Markers to Improve Diagnosis and Characterization of Mild Traumatic Brain Injury in the Acute Setting: Results from a Pilot Study." PLOS One Nov. 2013, 8(11): e80296, 14 pages.
Lecky, "Should plasma GFAP guide the management of patients with traumatic brain injury and a negative CT scan?" Lancet Neurol 2019, 2 pages.
Lee et al., "A Role of Serum-Based Neuronal and Glial Markers as Potential Predictors for Distinguishing Severity and Related Outcomes in Traumatic Brain Injury", J. Korean Neurosurgical Society, 58(2):93-100 (Aug. 2015).

(56) References Cited

OTHER PUBLICATIONS

Lippi et al., "The concentration of highly-sensitive troponin I is increased in patients with brain injury after mild head trauma." *International Journal of Cardiology*, 168(2):1617-1618 (Sep. 2013).

Liu et al., "Ubiquitin C-terminal hydrolase-L1 as a biomarker for ischemic and traumatic brain injury in rats", *Eur. J. Neurosci.*, 31(4):722-732 (Feb. 2010).

Luger et al., "Glial Fibrillary Acidic Protein Serum Levels Distinguish between Intracerebral Hemorrhage and Cerebral Ischemia in the Early Phase of Stroke", *Clinical Chemistry*, 63(1):377-385 (Nov. 23, 2016).

McMahon et al., "Measurement of the glial fibrillary acidic protein and its breakdown products GFAP-BDP biomarker for the detection of traumatic brain injury compared to computed tomography and magnetic resonance imaging." J Neurotrauma. Apr. 15, 2015; 32(8):527-33.

Metting et al., "Glial fibrillary acidic protein in serum after traumatic brain injury and multiple trauma", *Journal of Trauma, Williams & Wilkins, US*, 57(5):1006-1012 (Oct. 31, 2004).

Missler et al., "Measurement of Glial Fibrillary Acidic Protein in Human Blood: Analytical Method and Preliminary Clinical Results." Clinical Chemistry, 45(1):138-141 (1999).

Mondello et al., "Clinical utility of serum levels of ubiquitin cterminal hydrolase as a biomarker for severe traumatic brain injury" Neurosurgery. Mar. 2012; 70(3): 666-675.

Mondello et al., "Neuronal and glial markers are differently associated with computed tomography findings and outcome in patients with severe traumatic brain injury: a case control study." Care 2011, 15:R156, 10 pages.

Mondello et al., "Serum Concentrations of Ubiquitin C-Terminal Hydrolase-L1 and Glial Fibrillary Acidic Protein after Pediatric Traumatic Brain Injury." *Scientific Reports*, 6(28203):1-6 (Jun. 2016).

Nylen et al., "Increased serum-GFAP in patients with severe traumatic brain injury is related to outcome" J. of Neurological Sciences, 240: 85-91 (2006).

Okonkwo et al., "GFAP-BDP as an acute diagnostic marker in traumatic brain injury: results from the prospective transforming research and clinical knowledge in traumatic brain injury study." J Neurotrauma. Sep. 1, 2013; 30(17):1490-7.

Papa et al., "Elevated levels of serum glial fibrillary acidic protein breakdown products in mild and moderate traumatic brain injury are associated with intracranial lesions and neurosurgical intervention." Ann Emerg Med. Jun. 2012;59(6):471-83.

Papa et al., "Serum levels of Ubiquitin C-terminal Hydrolase (UCH-L1) distinguish mild traumatic brain injury (TBI) from trauma controls and are elevated in mild and moderate TBI patients with intracranial lesions and neurosurgical intervention", *J. Trauma Acute Care Surg.*, 72(5):1335-1344 (May 2012).

Papa et al., "Time Course and Diagnostic Accuracy of Glial and Neuronal Blood Biomarkers GFAP and UCH-L1 in a Large Cohort of Trauma Patients With and Without Mild Traumatic Brain Injury." *JAMA*, 73(5) 551-560 (Mar. 28, 2016).

Papa et al., "Ubiquitin C-terminal hydrolase is a novel biomarker in humans for severe traumatic brain injury*", *Crit. Care Med.*, 38(1):138-144 (Jan. 2010).

Pelinka et al., "Glial fibrillary acidic protein in serum after traumatic brain injury and multiple trauma." J Trauma. Nov. 2004; 57(5):1006-12.

Posti et al., "Glial Fibrillary Acidic Protein and Ubiquitin C-Terminal Hydrolase-L1 Are Not Specific Biomarkers for Mild CT-Negative Traumatic Brain Injury" Journal of Neurotrauma, 34(7):1427-1438 (Apr. 1, 2017).

Prieto et al., "Proteomic analysis of traumatic brain injury: the search for biomarkers." Expert Rev Proteomics. Apr. 2008; 5(2):283-91.

Puvenna et al., "Significance of ubiquitin carboxy-terminal hydrolase L1 elevations in athletes after sub-concussive head hits.", *PLOS One*, 9(5):e96296 (May 2014).

Rhine et al., "Are UCH-L1 and GFAP promising biomarkers for children with mild traumatic brain injury?" Brain Injury 2016, Early Online: 1-8.

Salim et al., "Significance of Troponin Elevation After Severe Traumatic Brain Injury." The Journal of Trauma Injury, Infection, and Critical Care 2008, 64 (1): 46-52.

Shahjouei et al., "The diagnostic values of UCH-L1 in traumatic brain injury: A meta analysis" Brain Injury (2017).

Song et al., "Development of Digital Elisas for Ultrasensitive Measurement of Serum Glial Fibrillary Acid Protein and Ubiquitin C-Terminal Hydrolase With Clinical Utilities in Human Traumatic Brain Injury." Alzheimer's & Dementia, 13(7):P3-240 (Jul. 2017).

Stephen et al., "The Role of Cardiac Troponin I in Prognostication of Patients with Isolated Severe Traumatic Brain Injury." J Trauma Acute Care Surg. Mar. 2016; 80(3):477-483.

Strathmann et al., "Blood-based biomarkers for traumatic brain injury: evaluation of research approaches, available methods and potential utility from the clinician and clinical laboratory perspectives." Clin Biochem. Jul. 2014; 47(10-11):876-88.

Streeter et al., "Diagnostic Protein Biomarkers for Severe, Moderate, and Mild Traumatic Brain Injury", *Sensing Technologies for Global Health, Military Medicine, Disaster Response, and Environmental Monitoring; and Biometric Technology for Human Identification VIII*, 8029(1):1-16 (May 13, 2011).

Takala et al., "Glial Fibrillary Acidic Protein and Ubiquitin C-Terminal Hydrolase-L1 as Outcome Predictors in Traumatic Brain Injury." World Neurosurg. Mar. 2016; 87:8-20.

Thelin et al., "Serial Sampling of Serum Protein Biomarkers for Monitoring Human Traumatic Brain injury Dynamics: A Systematic Review." Frontiers in Neurology Jul. 2017, vol. 8, Article 300, 23 pages.

Thermofisher ELISA (2006; retrieved from http://tools.thermofisher.com/contents/sfs/brochures/1602127-Assay Development-Handbook.pdf.

Vos et al., "Glial and neuronal proteins in serum predict outcome after severe traumatic brain injury." Neurology. Apr. 27, 2004; 62(8):1303-10.

Wang et al., "An update on diagnostic and prognostic biomarkers for traumatic brain injury." Expert Review of Molecular Diagnostics, 18(2):165-180 (Jan. 2018).

Wang et al., "Proteomic identification of biomarkers of traumatic brain injury" Expert Review of Proteomics, 2(4):603-614 (Aug. 2005).

Welch et al., "Ability of Serum Glial Fibrillary Acidic Protein, Ubiquitin C-Terminal Hydrolase-L1, and S100B To Differentiate Normal and Abnormal Head Computed Tomography Findings in Patients with Suspected Mild or Moderate Traumatic Brain Injury." *Journal of Neurotrauma*, 33:203-214 (Jan. 15, 2016).

Yamauchi et al., "Ubiquitin-mediated stress response in the spinal cord after transient ischemia." Stroke. Jun. 2008; 39(6):1883-9.

Yue et al., "Association between plasma GFAP concentrations and MRI abnormalities in patients with CT-negative traumatic brain injury in the Track-TBI cohort: a prospective multicentre study." Lancet Neurol 2019, 9 pages.

Zhang et al., "Biomarkers of Traumatic Brain Injury and Their Relationship to Pathology", Laskowitz D, Grant G, editors. Translational Research in Traumatic Brain Injury, Chapter 12, Taylor and Francis Group, 2016, 12 pages.

Zoltewicz et al., "Characterization of Antibodies that Detect Human GFAP after Traumatic Brain Injury." Biomarker Insights 2012; 7:71-79.

Hart et al., "Anger Self-Management in Chronic Traumatic Brain Injury: Protocol for a Psycho-educational Treatment With a Structurally Equivalent Control and an Evaluation of Treatment Enactment," Contemp. Clin. Trials., 40:180-192 (2015).

Gomez-de-Regil, et al., "Psychological Intervention in Traumatic Brain Injury Patients," Behavioural Neurology, pp. 1-8 (2019).

Zhang Z, et al. Human traumatic brain injury induces autoantibody response against glial fibrillary acidic protein and its breakdown products. PLoS One. Mar. 25, 2014;9(3):e92698. doi: 10.1371/journal.pone.0092698. Erratum in: PLoS One. 2014;9(6):e101712.

Kim, et al. Large-scale femtoliter droplet array for digital counting of single biomolecules, Lab Chip, 2012,12, 4986-4991.

(56) References Cited

OTHER PUBLICATIONS

Haacke EM, et al. Imaging iron stores in the brain using magnetic resonance imaging. Magn Reson Imaging. Jan. 2005;23(1):1-25.
Ward MD, Weber A, et al., Predictive Performance of Traumatic Brain Injury Biomarkers in High-Risk Elderly Patients. J Appl Lab Med. May 1, 2020;5(3):608.
Johns Hopkins Medicine, Rehabilitation After Traumatic Brain Injury, Available at: https://www.hopkinsmedicine.org/health/treatment-tests-and-therapies/rehabilitation-after-traumatic-brain-injury Published online: Nov. 19, 2019.
Ustinova KI, et al., Physical therapy for correcting postural and coordination deficits in patients with mild-to-moderate traumatic brain injury. Physiother Theory Pract. Jan. 2015;31(1):1-7. doi: 10.3109/09593985.2014.945674. Epub Aug. 1, 2014.
Wheeler, S., et al., Effectiveness of Interventions to Improve Occupational Performance for People With Psychosocial, Behavioral, and Emotional Impairments After Brain Injury: A Systematic Review, Am J Occup Ther. May-Jun 2016;70(3):7003180060p1-9. doi: 10.5014/ajot.115.020677.
Neselius Sanna et al: "CSF-Biomarkers in Olympic Boxing: Diagnosis and Effects of Repetitive Head Trauma", PLOS One, vol. 7, No. 4, Apr. 4, 2012 (Apr. 4, 2012), p. e33606, XP093111333.
Biberthaler Peter et al: "Evaluation of Acute Glial Fibrillary Acidic Protein and Ubiquitin C-Terminal Hydrolase- L1 Plasma Levels in Traumatic Brain Injury Patients with and without Intracranial Lesions", Neurotrauma Reports, vol. 2, No. 1, Dec. 1, 2021 (Dec. 1, 2021), pp. 617-625, XP093043101.
Czeiter Endre et al: "Brain Injury Biomarkers May Improve the Predictive Power of the Impact Outcome Calculator", Journal of Neurotrauma., vol. 29, No. 9, Jun. 10, 2012 (Jun. 10, 2012), pp. 1770-1778, XP093111467.
International Searching Authority, International Search Report and Written Opinion for International Application No. PCT/2023/074185 mailed Jan. 5, 2024.
European Patent Office, Communication Pursuant to Article 94(3) EPC for European Application No. 18731687.2 mailed Feb. 2, 2024.
European Patent Office, Communication Pursuant to Article 94(3) EPC for European Application No. 18830037 mailed Dec. 12, 2023.
European Patent Office, Extended European Search Report for European Application No. 20806307.3 mailed Dec. 15, 2023.
Giuseppe Lippi, et al., The concentration of highly-sensitive troponin I is increased in patients with brain injury after mild head trauma, International Journal of Cardiology, Jan. 1, 2013, vol. 168, No. 2, pp. 1617-1618.
Stephen S. Cai, et al., The Role of Cardiac Troponin I in Prognostication of Patients with Isolated Severe Traumatic Brain Injury, J Trauma Acute Care Surg., Jan. 1, 2016, vol. 80, No. 3, pp. 477-483.
Japan Patent Office, First Office Action for Japanese Patent Application No. 2019-565417, Mailing Date: Nov. 2, 2021.
Japan Patent Office, First Office Action for Japanese Patent Application No. 2019-565410 Mailing Date: Nov. 2, 2021.
Japan Patent Office, Office Action for Japanese Patent Application No. 2019-556261, Mailing Date: Oct. 26, 2021.
European Patent Office, Office Action for European Application No. 18731687 mailed Jun. 14, 2021.
Yuh Esther L. et al: "Magnetic resonance imaging improves 3-month outcome prediction in mild traumatic brain Injury : MRI in MTBI", Annals of Neurology, vol. 73, No. 2, Dec. 7, 2012 (Dec. 7, 2012), pp. 224-235, XP055811737, Boston, US, ISSN: 0364-5134, DOI: 10.1002/ana.23783.
Japan Patent Office, First Office Action for Japanese Patent Application No. 2019-555751. Mailing Date: Mar. 8, 2022.
China National Intellectual Property Administration, First Office Action for Chinese Patent Application No. 201780061647.7 mailed Dec. 14, 2021.
Canadian Intellectual Property Office, Office Action for Canadian Application No. 3,036,717, mailed Jul. 9, 2021.
IP Australia, Examination report No. 1 for standard patent application for Australian Application No. 2017339858, mailed Feb. 5, 2021.
IP Australia, Examination report No. 2 for standard patent application for Australian Application No. 2017339858, mailed Jun. 3, 2021.
Japan Patent Office, First Office Action for Japanese Patent Application No. 2019-517951. Mailing Date: Aug. 3, 2021.
Japan Patent Office, First Office Action for Japanese Patent Application No. 2019-552078. Mailing Date: Mar. 8, 2022.
Petzold A,, et, "An ELISA for glial fibrillary acidic protein", J Immunol Methods, (Apr. 2004), vol. 287, No. 1-2, pp. 169-177, DOI: 10.1016/j.jim.2004.01.015, Apr. 2004 (accepted Jan. 27, 2004).
International Searching Authority, International Search Report and Written Opinion for International Application No. PCT/US2024/022929 mailed Jul. 16, 2024.
International Searching Authority, International Search Report and Written Opinion for International Application No. PCT/US2024/026505 mailed Aug. 13, 2024.
Staples Emily et al.: "Optimising the quantification of cytokines present at low concentrations in small human mucosa' tissue samples using Luminex assays", Journal of Immunological Methods, Elsevier Science Publishers B.V., Amsterdam, Nl, vol. 394, No. 1, May 1, 2013 (2013-05-01), pp. 1-9.
Anon: "Benzonase endonuclease", Jan. 1, 2020 (Jan. 1, 2020), xP093172436, Retrieved from the Internet: URL:https://www.weichilab.com/upload/files /202004220201123129.pdf.
Burns BS, et al. "Increasing Use of Rapid Magnetic Resonance Imaging for Children with Blunt Head Injury." J Pediatr. Sep. 2024; 272:114099. doi: 10.1016/j.jpeds.2024.114099. Epub May 14, 2024.
Ottens A et al., 'Neuroproteomics: A Biochemical Means To Discriminate the Extent and Modality of Brain Injury', Journal of Neurotrauma. (2010), vol. 27, No. 10, pp. 1837-1852.
International Searching Authority, International Search Report and Written Opinion for International Application No. PCT/US2024/026502 mailed Aug. 9, 2024.

SEQUENCE LISTING

```
<160> NUMBER OF SEQ ID NOS: 4

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45
```

```
Leu Lys Thr Leu Leu Leu Gln Ile Ala Lys Gln Glu Leu Glu Arg Glu
     50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
                 85                  90                  95

Cys Arg Gln Leu His Ala Arg Val Asp Lys Val Asp Gly Glu Arg Tyr
                100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
            195                 200                 205

Glu Ser
    210

<210> SEQ ID NO 2
<211> LENGTH: 6
<212> TYPE: PRT
<213> ORGANISM: Artificial sequence
<220> FEATURE:
<223> OTHER INFORMATION: Synthetic

<400> SEQUENCE: 2

His His His His His His
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic

<400> SEQUENCE: 3

Asp Asp Asp Asp Lys
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic

<400> SEQUENCE: 4

Ala Asp Asp Asp Asp Lys
1               5
```

METHODS FOR AIDING IN DIAGNOSING AND EVALUATING A MILD TRAUMATIC BRAIN INJURY IN A HUMAN SUBJECT USING CARDIAC TROPONIN I

RELATED APPLICATION INFORMATION

This application is a continuation of U.S. application Ser. No. 15/993,589 filed on May 30, 2018, which claims priority to U.S. Application No. 62/512,688 filed on May 30, 2017, U.S. Application No. 62/512,710 filed on May 30, 2017, and U.S. Application No. 62/528,214 filed on Jul. 3, 2017, the contents of each of which are herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,787 Byte ASCII (Text) file named "36102-303_ST25.TXT," created on Aug. 25, 2021.

TECHNICAL FIELD

The present disclosure relates to methods for aiding in diagnosing and evaluating a human subject that has sustained or may have sustained an (or has an has an actual or suspected) injury to the head, such as mild traumatic brain injury (TBI), by detecting levels of cardiac troponin I (cTnI) in samples (or biological samples) taken from the human subject at time points of injury after the subject has sustained or may have sustained (or has an has an actual or suspected) the injury to the head. The present disclosure also provides methods of determining whether to perform a head computerized tomography on a subject based on detecting various levels of cTnI. The present disclosure also provides methods of predicting outcome in subjects suffering from a TBI.

BACKGROUND

More than 5 million mild traumatic brain injuries (TBIs) occur each year in the United States alone. Currently, there is no simple, objective, accurate measurement available to help in patient assessment. In fact, much of TBI evaluation and diagnosis is based on subjective data. Unfortunately, objective measurements such as head CT and Glasgow Coma Score (GCS) are not very comprehensive or sensitive in evaluating mild TBI. Moreover, head CT is unrevealing for the vast majority of the time for mild TBI, is expensive, and exposes the patient to unnecessary radiation. Additionally, a negative head CT does not mean the patient has been cleared from having a concussion; rather it just means certain interventions, such as surgery, are not warranted. Clinicians and patients need objective, reliable information to accurately evaluate this condition to promote appropriate triage and recovery. To date, limited data have been available for the use of cardiac troponin I in the acute care setting or hyperacute care setting (very early acute time points after injury) to aid in patient evaluation and management.

Mild TBI or concussion is much harder to objectively detect and presents an everyday challenge in emergency care units globally. Concussion usually causes no gross pathology, such as hemorrhage, and no abnormalities on conventional computed tomography scans of the brain, but rather rapid-onset neuronal dysfunction that resolves in a spontaneous manner over a few days to a few weeks. Approximately 15% of mild TBI patients suffer persisting cognitive dysfunction. There is an unmet need for mild TBI victims on scene, in emergency rooms and clinics, in the sports area and in military activity (e.g., combat).

Current algorithms for assessment of the severity of brain injury include Glasgow Coma Scale score and other measures. These measures may at times be adequate for relating acute severity but are insufficiently sensitive for subtle pathology which can result in persistent deficit. GCS and other measures also do not enable differentiation among types of injury and may not be adequate. Thus patients grouped into a single GCS level entering a clinical trial may have vastly heterogeneous severity and type of injury. Because outcomes also vary accordingly, inappropriate classification undermines the integrity of a clinical trial. Improved classification of injury will enable more precise delineation of disease severity and type for TBI patients in clinical trials.

Additionally, current brain injury trials rely on outcome measures such as Glasgow Outcome Scale Extended, which capture global phenomena but fail to assess for subtle differences in outcome. Thus 30 consecutive trials for brain injury therapeutics have failed. Sensitive outcome measures are needed to determine how well patients have recovered from brain injury in order to test therapeutics and prophylactics.

Traumatic brain injury (TBI) patients are at least three times more likely to die from cardiovascular causes than the general population. Cardiac injury from TBI is also associated with neurogenic pulmonary edema. The phenomenon of cardiac injury in neurologic conditions has been described in patients with spontaneous subarachnoid hemorrhage and is believed to result from a fulminant surge in catecholamine levels. However, the mechanisms underlining excess cardiovascular mortality in TBI have been poorly studied and therefore are not well understood. Consequently, it is unclear whether: the onset of cardiac injury occurs in the acute or chronic phase of TBI; there are particular sub-types of TBI that are preferentially affected by cardiac injury; and what the biological triggers of cardiac injury in TBI are. A number of retrospective studies have investigated myocardial injury in the acute phase of TBI. Using conventional cardiac troponin assays, these studies have reported cardiac injury (as determined by elevated troponin levels) within 24 hours of injury in 30% of severe TBI patient. Cardiac injury in TBI is associated with injury severity and age. TBI patients with cardiac injury have a higher risk of in-patient mortality than those without cardiac injury. However, these findings are subject to spectrum bias since they are derived from retrospective studies and troponin measurements were performed at the discretion of clinicians (they are rarely done in the routine care of TBI patients). Furthermore, the association between cardiac injury and neurologic outcome in TBI has not been studied. Additionally, the role of cardiac injury in mild and moderate TBI has not been studied.

SUMMARY

In some embodiments, the present disclosure relates to a method for aiding in the diagnosis and evaluation of mild traumatic brain injury in a human subject. The method can comprise the steps of:
  a) performing an assay on a sample obtained from the subject within about 24 hours after an actual or suspected injury to the head to measure or detect a level of cardiac troponin I (cTnI); and b) determining whether the subject has sustained a mild or a moderate, severe, or moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI.

In some embodiments of the above method, the subject is diagnosed or determined to have sustained a mild traumatic brain injury. In other embodiments of the above method, the subject is diagnosed or determined to have sustained a moderate traumatic brain injury. In yet other embodiments of the above method, the subject is diagnosed or determined to have sustained a severe traumatic brain injury. In yet other embodiments, the subject is diagnosed or determined to have sustained a moderate to severe traumatic brain injury.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments in the above method, the subject is suspected as having moderate, severe, or moderate to severe traumatic brain injury based on the Glasgow Coma Scale score.

In some embodiments in the above method, the reference level is correlated with (corresponds to) subjects having a moderate, severe, or a moderate to severe traumatic brain injury. In some embodiments in the above method, the reference level is correlated with (corresponds to) a moderate traumatic brain injury. In other embodiments of the above method, the reference level is correlated with (corresponds to) a severe traumatic brain injury.

In some embodiments, the subject may be suspected as having mild TBI based on the Glasgow Coma Scale score. In other aspects, the subject may be suspected of having a moderate TBI based on the Glasgow Coma Scale score. In other aspects, the subject may be suspected of having a severe TBI based on the Glasgow Coma Scale Score. In other aspects, the subject may be suspect as having a moderate to severe TBI based on the Glasgow Coma scale score. In other aspects, the reference level of GFAP or the reference level correlates with or correspond to a Glasgow Coma Scale score of 13-15 (a mild TBI). In other aspects, the reference level correlates or correspond to a Glasgow Coma Scale score of 3-8 (a severe TBI). In other aspects, the reference level correlates or correspond to a Glasgow Coma Scale score of 9-13 (a moderate TBI). In other aspects, the reference level correlates with or correspond to a Glasgow Coma Scale score of 3-12 (a moderate to severe TBI).

In some embodiments in the above method, the reference level for cTnI is about 1.94 pg/mL, about 2.54 pg/mL, about 21.23 pg/mL, or about 43.79 pg/mL. In some embodiments in the above method, the reference level for cTnI is about 1.94 pg/mL. In some embodiments in the above method, the reference level for cTnI is about 2.54 pg/mL. In some embodiments in the above method, the reference level for cTnI is about 21.23 pg/mL. In some embodiments in the above method, the reference level for cTnI is about 43.79 pg/mL.

In some embodiments in the above method, the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 1 pg/mL to about 50 pg/mL. In some embodiments in the above method, the reference level is determined by an assay having a sensitivity of between at least about 85% to 100% and a specificity of between at least about 30% to 100%. In some embodiments in the above method, the reference level is determined by an assay having a sensitivity of at least about 87.5% and a specificity of at least about 31%. In some embodiments in the above method, the reference level is between at least about 1 pg/mL to about 50 pg/mL.

In some embodiments in the above method, the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of actual or suspected injury to the head. Specifically, in some embodiments of the above method, the sample is taken within about 30 minutes of actual or suspected injury to the head. In other embodiments of the above method, the sample is taken within about 1 hour of actual or suspected injury to the head. In other embodiments of the above method, the sample is taken within about 2 hours of actual or suspected injury to the head. In other embodiments of the above method, the sample is taken within about 3 hours of actual or suspected injury to the head. In other embodiments of the above method, the sample is taken within about 4 hours of actual or suspected injury to the head. In other embodiments of the above method, the sample is taken within about 5 hours of actual or suspected injury to the head. In other embodiments of the above method, the sample is taken within about 6 hours of actual or suspected injury to the head. In other embodiments of the above method, the sample is taken within about 7 hours of actual or suspected injury to the head. In other embodiments of the above method, the sample is taken within about 8 hours of actual or suspected injury to the head. In other embodiments of the above method, the sample is taken within about 9 hours of actual or suspected injury to the head. In other embodiments of the above method, the sample is taken within about 10 hours of actual or suspected injury to the head. In other embodiments of the above method, the sample is taken within about 11 hours of actual or suspected injury to the head. In other embodiments of the above method, the sample is taken within about 12 hours of actual or suspected injury to the head. In other embodiments of the above method, the sample is taken within about 13 hours of actual or suspected injury to the head. In other embodiments of the above method, the sample is taken within about 14 hours of actual or suspected injury to the head. In other embodiments of the above method, the sample is taken within about 15 hours of actual or suspected injury to the head. In other embodiments of the above method, the sample is taken within about 16 hours of actual or suspected injury to the head. In other embodiments of the above method, the sample is taken within about 17 hours of actual or suspected injury to the head. In other embodiments of the above method, the sample is taken within about 18 hours of actual or suspected injury to the head. In other embodiments of the above method, the sample is taken within about 19 hours of actual or suspected injury to the head. In other embodiments of the above method, the sample is taken within about 20 hours of actual or suspected injury to the head. In other embodiments of the above method, the sample is taken within about 21 hours of actual or suspected injury to the head. In other embodiments of the above method, the sample is taken within about 22 hours of actual or suspected injury to the head. In other embodiments of the above method, the sample is taken within about 23 hours of actual or suspected injury to the head. In other embodiments of the above method, the sample is taken within about 24 hours of actual or suspected injury to the head.

In some embodiments, the above method further comprises treating the subject assessed as having a moderate, severe or moderate to severe traumatic brain injury with a traumatic brain injury treatment. In some embodiments, the above method further comprises monitoring the subject assessed as having a moderate, severe, or moderate to severe traumatic brain injury before treatment with a traumatic brain injury treatment. In some embodiments, the above method further comprises monitoring the subject assessed as having a moderate, severe, or moderate to severe traumatic brain injury after treatment with a traumatic brain injury treatment.

In some embodiments, the above method further comprises monitoring the subject assessed as having mild traumatic brain injury. In some embodiments, the above method further comprises treating the subject assessed as having a mild traumatic brain injury with a traumatic brain injury treatment. In some embodiments, the above method comprises monitoring the subject assessed as having a mild traumatic brain injury before treating with a traumatic brain injury treatment. In other embodiments, the above method comprises monitoring the subject assessed as having a mild traumatic brain injury after treatment with a traumatic brain injury treatment.

In another embodiment, the present disclosure relates to aiding in the determination of whether to perform a head computerized tomography (CT) scan on a human subject that has sustained or may have sustained an (or has an actual or suspected) injury to the head. The method can comprise the steps of:
 a) performing an assay on a sample obtained from the subject within about 24 hours after an actual or suspected injury to the head to measure or detect a level of cTnI in the sample; and
 b) performing a CT scan on the subject when the level of cTnI in the sample is higher than a reference level of cTnI and not performing a CT scan on the subject when the level of cTnI in the sample is lower than a reference level of cTnI.

In some embodiments of the above method, a CT scan is performed on the subject. In other embodiments of the above method, a CT scan is not performed on the subject.

In some embodiments in the above method, the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of an actual or suspected injury to the head. Specifically, in some embodiments of the above method, the sample is taken within about 30 minutes of an actual or suspected injury to the head. In other embodiments of the above method, the sample is taken within about 1 hour of an actual or suspected injury to the head. In other embodiments of the above method, the sample is taken within about 2 hours of an actual or suspected injury to the head. In other embodiments of the above method, the sample is taken within about 3 hours of actual or suspected injury to the head. In other embodiments of the above method, the sample is taken within about 4 hours of actual or suspected injury to the head. In other embodiments of the above method, the sample is taken within about 5 hours of actual or suspected injury to the head. In other embodiments of the above method, the sample is taken within about 6 hours of actual or suspected injury to the head. In other embodiments of the above method, the sample is taken within about 7 hours of actual or suspected injury to the head. In other embodiments of the above method, the sample is taken within about 8 hours of actual or suspected injury to the head. In other embodiments of the above method, the sample is taken within about 9 hours of actual or suspected injury to the head. In other embodiments of the above method, the sample is taken within about 10 hours of actual or suspected injury to the head. In other embodiments of the above method, the sample is taken within about 11 hours of actual or suspected injury to the head. In other embodiments of the above method, the sample is taken within about 12 hours of actual or suspected injury to the head. In other embodiments of the above method, the sample is taken within about 13 hours of actual or suspected injury to the head. In other embodiments of the above method, the sample is taken within about 14 hours of actual or suspected injury to the head. In other embodiments of the above method, the sample is taken within about 15 hours of actual or suspected injury to the head. In other embodiments of the above method, the sample is taken within about 16 hours of actual or suspected injury to the head. In other embodiments of the above method, the sample is taken within about 17 hours of actual or suspected injury to the head. In other embodiments of the above method, the sample is taken within about 18 hours of actual or suspected injury to the head. In other embodiments of the above method, the sample is taken within about 19 hours of actual or suspected injury to the head. In other embodiments of the above method, the sample is taken within about 20 hours of actual or suspected injury to the head. In other embodiments of the above method, the sample is taken within about 21 hours of actual or suspected injury to the head. In other embodiments of the above method, the sample is taken within about 22 hours of actual or suspected injury to the head. In other embodiments of the above method, the sample is taken within about 23 hours of actual or suspected injury to the head. In other embodiments of the above method, the sample is taken within about 24 hours of actual or suspected injury to the head.

In some embodiments of the above-described method, the subject has received a CT scan before or after the assay is performed, and wherein the subject is suspected as having a TBI based on the CT scan result. In some embodiments, the subject may be suspected of having a traumatic brain injury based on a CT scan that already was performed. For example, depending upon a subject's medical condition (such as, if the patient is unconscious), a CT scan may be conducted shortly after the subject arrives at an emergency room, trauma center, or other site in order to assess and/or evaluate whether the subject has a TBI. Such a CT scan may be performed prior to the assay being performed to confirm and determine whether the subject has a mild or a moderate, severe, or a moderate to severe TBI. After the assay is performed, one or more subsequent CT scans can be performed based on the results of the assay as part of the physician's (or other medical personnel's) management of the TBI (such as, for example, to determine whether surgical and/or pharmacological intervention may be required). In other embodiments, the subject may not have received a CT scan before the assay is performed.

In some embodiments in the above method, the subject is suspected of having a traumatic brain injury based on the CT scan. In some embodiments, the subject is diagnosed as having a traumatic brain injury based on the CT scan. In other embodiments, the subject is diagnosed as not having a traumatic brain injury based on the CT scan.

In some embodiments in the above method, the reference level is correlated with (corresponds to) a positive head computed tomography.

In some embodiments in the above method, the reference level is correlated with (corresponds to) control subjects that have not sustained a head injury.

In some embodiments in the above method, the reference level for cTnI is about 1.65 pg/mL, about 2.16 pg/mL, about 14.75 pg/mL, or about 30.43 pg/mL. In some embodiments in the above method, the reference level for cTnI is about 1.65 pg/mL. In some embodiments in the above method, the reference level for cTnI is about 2.16 pg/mL. In some embodiments in the above method, the reference level for cTnI is about 14.75 pg/mL. In some embodiments in the above method, the reference level for cTnI is about 30.43 pg/mL.

In some embodiments in the above method, the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 1.0 pg/mL to about 50 pg/mL. In some embodiments in the above method, the reference level is determined by an assay having a sensitivity of between at least about 65% to 100% and a specificity of between at least about 30% to 100%. In some embodiments in the above method, the reference level is determined by an assay having a sensitivity of at least about 85% and a specificity of at least about 33%. In some embodiments in the above method, the reference level is between at least about 1.0 pg/mL to about 50 pg/mL.

In another embodiment, the present disclosure relates to a method for aiding in the diagnosis and evaluation of mild traumatic brain injury in a human subject. The method can comprise the steps of:

a) performing an assay on samples from the human subject to measure or detect a level of cTnI in a first sample and a second sample, wherein the first sample is taken from the human subject at a first time point within about 24 hours after head injury and the second sample is taken from the human subject about 3 hours to about 6 hours after the first sample, wherein the samples are biological samples;

b) determining whether the amount of cTnI has increased or decreased from the first sample to the second sample; and c) confirming the occurrence of a moderate, severe or moderate to severe traumatic brain injury if the level of cTnI detected has increased from the first sample to the second sample and confirming the absence of mild traumatic brain injury if the level of cTnI detected has remained unchanged or has decreased from the first sample to the second sample.

In some embodiments of the above method, the subject is confirmed to have a mild traumatic brain injury. In other embodiments of the above method, the subject is confirmed to have a moderate traumatic brain injury. In yet other embodiments of the above method, the subject is confirmed to have to have a severe traumatic brain injury. In yet other embodiments, the subject is confirmed to have to have a moderate to severe traumatic brain injury.

In some embodiments in the above method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of an actual or suspected injury to the head. Specifically, in some embodiments of the above method, the sample is taken within about 30 minutes of actual or suspected injury to the head. In other embodiments of the above method, the sample is taken within about 1 hour of actual or suspected injury to the head. In other embodiments of the above method, the sample is taken within about 2 hours of actual or suspected injury to the head. In other embodiments of the above method, the sample is taken within about 3 hours of actual or suspected injury to the head. In other embodiments of the above method, the sample is taken within about 4 hours of actual or suspected injury to the head. In other embodiments of the above method, the sample is taken within about 5 hours of actual or suspected injury to the head. In other embodiments of the above method, the sample is taken within about 6 hours of actual or suspected injury to the head. In other embodiments of the above method, the sample is taken within about 7 hours of actual or suspected injury to the head. In other embodiments of the above method, the sample is taken within about 8 hours of actual or suspected injury to the head. In other embodiments of the above method, the sample is taken within about 9 hours of actual or suspected injury to the head. In other embodiments of the above method, the sample is taken within about 10 hours of actual or suspected injury to the head. In other embodiments of the above method, the sample is taken within about 11 hours of actual or suspected injury to the head. In other embodiments of the above method, the sample is taken within about 12 hours of actual or suspected injury to the head. In other embodiments of the above method, the sample is taken within about 13 hours of actual or suspected injury to the head. In other embodiments of the above method, the sample is taken within about 14 hours of actual or suspected injury to the head. In other embodiments of the above method, the sample is taken within about 15 hours of actual or suspected injury to the head. In other embodiments of the above method, the sample is taken within about 16 hours of actual or suspected injury to the head. In other embodiments of the above method, the sample is taken within about 17 hours of actual or suspected injury to the head. In other embodiments of the above method, the sample is taken within about 18 hours of actual or suspected injury to the head. In other embodiments of the above method, the sample is taken within about 19 hours of actual or suspected injury to the head. In other embodiments of the above method, the sample is taken within about 20 hours of actual or suspected injury to the head. In other embodiments of the above method, the sample is taken within about 21 hours of actual or suspected injury to the head. In other embodiments of the above method, the sample is taken within about 22 hours of actual or suspected injury to the head. In other embodiments of the above method, the sample is taken within about 23 hours of actual or suspected injury to the head. In other embodiments of the above method, the sample is taken within about 24 hours of actual or suspected injury to the head.

In some embodiments in the above method, the subject has an abnormal head CT.

In some embodiments in the above method, the amount of cTnI in the first sample is from about 1.0 to about 50 pg/mL.

In some embodiments in the above method, the amount of cTnI in the second sample is from about 1.0 to about 50 pg/mL.

In some embodiments in the above method, the method further comprises treating the subject assessed as having a moderate, severe, or moderate to severe traumatic brain injury with a traumatic brain injury treatment. In some embodiments, the above method further comprises monitoring the subject assessed as having a moderate, severe, or moderate to severe traumatic brain injury before treatment with a traumatic brain injury treatment. In some embodiments, the above method further comprises monitoring the subject assessed as having a moderate, severe, or moderate to severe traumatic brain injury after treatment with a traumatic brain injury treatment.

In some embodiments, the above method further comprises monitoring the subject assessed as having mild traumatic brain injury. In some embodiments, the above method further comprises treating the subject assessed as having a mild traumatic brain injury with a traumatic brain injury treatment. In some embodiments, the above method comprises monitoring the subject assessed as having a mild traumatic brain injury before treating with a traumatic brain injury treatment. In other embodiments, the above method comprises monitoring the subject assessed as having a mild traumatic brain injury after treatment with a traumatic brain injury treatment.

In another embodiment, the present disclosure relates to a method for aiding in the diagnosis and evaluation of mild traumatic brain injury in a human subject. The method can comprise the steps of:
a) performing an assay on samples from the human subject to measure or detect a level of cTnI in a first sample and a second sample, wherein the first sample is taken from the human subject at a first time point within about 24 hours after head injury and the second sample is taken from the human subject about 1 hours to about 4 hours after the first sample, wherein the samples are biological samples;
b) determining whether the amount of cTnI has increased or decreased from the first sample to the second sample; and
c) confirming the occurrence of a moderate, severe or moderate to severe traumatic brain injury if the level of cTnI detected has increased from the first sample to the second sample and confirming the absence of mild traumatic brain injury if the level of cTnI detected has remained unchanged or has decreased from the first sample to the second sample.

In some embodiments of the above method, the subject is confirmed to have a mild traumatic brain injury. In other embodiments of the above method, the subject is confirmed to have a moderate traumatic brain injury. In yet other embodiments of the above method, the subject is confirmed to have to have a severe traumatic brain injury. In yet other embodiments, the subject is confirmed to have to have a moderate to severe traumatic brain injury.

In some embodiments in the above method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of an actual or suspected injury to the head. Specifically, in some embodiments of the above method, the sample is taken within about 30 minutes of actual or suspected injury to the head. In other embodiments of the above method, the sample is taken within about 1 hour of actual or suspected injury to the head. In other embodiments of the above method, the sample is taken within about 2 hours of actual or suspected injury to the head. In other embodiments of the above method, the sample is taken within about 3 hours of actual or suspected injury to the head. In other embodiments of the above method, the sample is taken within about 4 hours of actual or suspected injury to the head. In other embodiments of the above method, the sample is taken within about 5 hours of actual or suspected injury to the head. In other embodiments of the above method, the sample is taken within about 6 hours of actual or suspected injury to the head. In other embodiments of the above method, the sample is taken within about 7 hours of actual or suspected injury to the head. In other embodiments of the above method, the sample is taken within about 8 hours of actual or suspected injury to the head. In other embodiments of the above method, the sample is taken within about 9 hours of actual or suspected injury to the head. In other embodiments of the above method, the sample is taken within about 10 hours of actual or suspected injury to the head. In other embodiments of the above method, the sample is taken within about 11 hours of actual or suspected injury to the head. In other embodiments of the above method, the sample is taken within about 12 hours of actual or suspected injury to the head. In other embodiments of the above method, the sample is taken within about 13 hours of actual or suspected injury to the head. In other embodiments of the above method, the sample is taken within about 14 hours of actual or suspected injury to the head. In other embodiments of the above method, the sample is taken within about 15 hours of actual or suspected injury to the head. In other embodiments of the above method, the sample is taken within about 16 hours of actual or suspected injury to the head. In other embodiments of the above method, the sample is taken within about 17 hours of actual or suspected injury to the head. In other embodiments of the above method, the sample is taken within about 18 hours of actual or suspected injury to the head. In other embodiments of the above method, the sample is taken within about 19 hours of actual or suspected injury to the head. In other embodiments of the above method, the sample is taken within about 20 hours of actual or suspected injury to the head. In other embodiments of the above method, the sample is taken within about 21 hours of actual or suspected injury to the head. In other embodiments of the above method, the sample is taken within about 22 hours of actual or suspected injury to the head. In other embodiments of the above method, the sample is taken within about 23 hours of actual or suspected injury to the head. In other embodiments of the above method, the sample is taken within about 24 hours of actual or suspected injury to the head.

In some embodiments in the above method, the subject has an abnormal head CT.

In some embodiments in the above method, the amount of cTnI in the first sample is from about 1.0 to about 50 pg/mL.

In some embodiments in the above method, the amount of cTnI in the second sample is from about 1.0 to about 50 pg/mL.

In some embodiments in the above method, the method further comprises treating the subject assessed as having a moderate, severe, or moderate to severe traumatic brain injury with a traumatic brain injury treatment. In some embodiments, the above method further comprises monitoring the subject assessed as having a moderate, severe, or moderate to severe traumatic brain injury before treatment with a traumatic brain injury treatment. In some embodiments, the above method further comprises monitoring the subject assessed as having a moderate, severe, or moderate to severe traumatic brain injury after treatment with a traumatic brain injury treatment.

In some embodiments, the above method further comprises monitoring the subject assessed as having mild traumatic brain injury. In some embodiments, the above method further comprises treating the subject assessed as having a mild traumatic brain injury with a traumatic brain injury treatment. In some embodiments, the above method comprises monitoring the subject assessed as having a mild traumatic brain injury before treating with a traumatic brain injury treatment. In other embodiments, the above method comprises monitoring the subject assessed as having a mild traumatic brain injury after treatment with a traumatic brain injury treatment.

In another embodiment, the present disclosure relates to a method of aiding in the diagnosis and evaluation of a human subject that has sustained or may have sustained an (or has an actual or suspected) injury to the head. The method can comprise the steps of:
a) performing an assay on a sample obtained from the subject within about 2 hours after an injury or suspected injury to the head to measure or detect a level of cTnI; and
b) determining whether the subject has sustained a mild or a moderate, severe, or moderate to severe traumatic brain injury (TBI), wherein the subject is determined as having (1) a moderate, severe, or a moderate to severe traumatic brain injury when the level of cTnI in the sample is higher than a reference level of cTnI or (2) a mild traumatic brain injury when the level of cTnI in the sample is lower than a reference level of cTnI.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments, the subject may be suspected as having mild TBI based on the Glasgow Coma Scale score. In other aspects, the subject may be suspected of having a moderate TBI based on the Glasgow Coma Scale score. In other aspects, the subject may be suspected of having a severe TBI based on the Glasgow Coma Scale Score. In other aspects, the subject may be suspect as having a moderate to severe TBI based on the Glasgow Coma scale score. In other aspects, the reference level of GFAP or the reference level correlates with or correspond to a Glasgow Coma Scale score of 13-15 (a mild TBI). In other aspects, the reference level correlates or correspond to a Glasgow Coma Scale score of 3-8 (a severe TBI). In other aspects, the reference level correlates or correspond to a Glasgow Coma Scale score of 9-13 (a moderate TBI). In other aspects, the reference level correlates with or correspond to a Glasgow Coma Scale score of 3-12 (a moderate to severe TBI).

In some embodiments in the above method, the reference level for cTnI is about 1.15 pg/mL. In some embodiments in the above method, the reference level for cTnI is about 1.29 pg/mL.

In some embodiments in the above method, the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 0.5 pg/mL to about 30 pg/mL. In some embodiments in the above method, the reference level is determined by an assay having a sensitivity of between at least about 85% to 100% and a specificity of between at least about 30% to 100%. In some embodiments in the above method, the reference level is determined by an assay having a sensitivity of at least about 87.5% and a specificity of at least about 31%. In some embodiments in the above method, the reference level is between at least about 0.5 pg/mL to about 30 pg/mL.

In some embodiments in the above method, the sample is taken within about 5 minutes, within about 10 minutes, within about 12 minutes, within about 15 minutes, within about 20 minutes, within about 30 minutes, within about 60 minutes, or within about 90 minutes after an actual or suspected injury to the head. In some embodiments of the above-identified method, the sample is taken within about 5 minutes after an actual or suspected injury to the head. In other embodiments, the sample is taken within about 10 minutes of suspected injury to the head. In yet other embodiments, the sample is taken within about 12 minutes of suspected injury to the head. In yet other embodiments, the sample is taken within about 15 minutes of suspected injury to the head. In yet other embodiments, the sample is taken within about 20 minutes of suspected injury to the head. In yet other embodiments, the sample is taken within about 60 minutes of suspected injury to the head. In yet sill other embodiments, the sample is taken within about 90 minutes of suspected injury to the head.

In some embodiments, the above method further comprises monitoring the subject assessed as having a moderate, severe, or moderate to severe traumatic brain injury before treatment with a traumatic brain injury treatment. In some embodiments, the above method further comprises monitoring the subject assessed as having a moderate, severe, or moderate to severe traumatic brain injury after treatment with a traumatic brain injury treatment.

In some embodiments, the above method further comprises monitoring the subject assessed as having mild traumatic brain injury. In some embodiments, the above method further comprises treating the subject assessed as having a mild traumatic brain injury with a traumatic brain injury treatment. In some embodiments, the above method comprises monitoring the subject assessed as having a mild traumatic brain injury before treating with a traumatic brain injury treatment. In other embodiments, the above method comprises monitoring the subject assessed as having a mild traumatic brain injury after treatment with a traumatic brain injury treatment.

In another embodiment, the present disclosure relates to a method of aiding in the determination of whether to perform a head computerized tomography (CT) scan on a human subject that has sustained or may have sustained an (or has an actual or suspected) injury to the head. The method can comprise the steps of:
  a) performing an assay on a sample obtained from the subject within about 2 hours after an actual or suspected injury to the head to measure or detect a level of cTnI in the sample; and
  b) performing a CT scan on the subject when the level of cTnI in the sample is higher than a reference level of cTnI and not performing a CT scan on the subject when the level of cTnI in the sample is lower than a reference level of cTnI.

In some embodiments of the above method, a CT scan is performed on the subject. In other embodiments of the above method, a CT scan is not performed on the subject.

In some embodiments of the above-described method, the subject has received a CT scan before or after the assay is performed, and wherein the subject is suspected as having a TBI based on the CT scan result. In some embodiments, the subject may be suspected of having a traumatic brain injury based on a CT scan that already was performed. For example, depending upon a subject's medical condition (such as, if the patient is unconscious), a CT scan may be conducted shortly after the subject arrives at an emergency room, trauma center, or other site in order to assess and/or evaluate whether the subject has a TBI. Such a CT scan may be performed prior to the assay being performed to confirm and determine whether or not the subject has a mild or moderate, severe or a moderate to severe TBI. After the assay is performed, one or more subsequent CT scans can be performed based on the results of the assay as part of the physician's (or other medical personnel's) management of the TBI (such as, for example, to determine whether surgical and/or pharmacological intervention may be required). In other embodiments, the subject may not have received a CT scan before the assay is performed.

In some embodiments in the above method, the subject is suspected of having a traumatic brain injury based on the CT scan. In some embodiments, the subject is diagnosed as having a traumatic brain injury based on the CT scan. In some embodiments, the subject is diagnosed as not having a traumatic brain injury based on the CT scan.

In some embodiments in the above method, the reference level is correlated with (or corresponds to) a positive head computed tomography.

In some embodiments in the above method, the reference level is correlated with (or corresponds with) control subjects that have not sustained a head injury.

In some embodiments in the above method, the reference level for cTnI is about 5.8 pg/mL. In some embodiments in the above method, the reference level for cTnI is about 4.7 pg/mL.

In some embodiments in the above method, the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL. In some embodiments in the above method, the reference level is determined by an assay having a sensitivity of between at least about 65% to 100% and a specificity of between at least about 30% to 100%. In some embodiments in the above method, the reference level is determined by an assay having a sensitivity of at least about 85% and a specificity of at least about 33%. In some embodiments in the above method, the reference level is between at least about 0.5 pg/mL to about 25 pg/mL.

In some embodiments in the above method, the sample is taken within about 5 minutes, within about 10 minutes, within about 12 minutes, within about 15 minutes, within about 20 minutes, within about 30 minutes, within about 60 minutes, or within about 90 minutes after an actual or suspected injury to the head. In some embodiments of the above-identified method, the sample is taken within about 5 minutes after an actual or suspected injury to the head. In other embodiments, the sample is taken within about 10 minutes of an actual or suspected injury to the head. In yet other embodiments, the sample is taken within about 12 minutes of an actual or suspected injury to the head. In yet other embodiments, the sample is taken within about 15 minutes of an actual or suspected injury to the head. In yet other embodiments, the sample is taken within about 20 minutes of an actual suspected injury to the head. In yet other embodiments, the sample is taken within about 60 minutes of an actual or suspected injury to the head. In yet sill other embodiments, the sample is taken within about 90 minutes of an actual or suspected injury to the head.

In yet another embodiment, the present disclosure relates to methods of treating a mild or moderate, severe, or moderate to severe TBI, the method comprising: a) performing an assay on a sample obtained from the subject within about 24 hours after an injury to the head to measure or detect a level of cTnI; b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI; and c) treating the subject assessed as having a mild, moderate, severe, or moderate to severe traumatic brain injury with a traumatic brain injury treatment.

Embodiments of the above method further involve monitoring the subject assessed as having a mild traumatic brain injury. Embodiments of the above method further involve monitoring the subject assessed as having a moderate, severe, or moderate to severe traumatic brain injury.

In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof. Optionally, such methods may also involve providing one or more cardioprotective therapies. Such cardioprotective therapies can be administered in combination with the treatments for the TBI or alone without any TBI treatment, depending on the circumstances.

In yet another embodiment, the present disclosure relates to a method of treating a mild or moderate, severe, or moderate to severe traumatic brain injury in a human subject, the method comprising: a) performing an assay on samples from the human subject to measure or detect a level of cTnI in a first sample and a second sample, wherein the first sample is taken from the human subject at a first time point and the second sample is taken from the human subject about 3 hours to about 6 hours after the first sample, wherein the samples are biological samples; b) determining whether the amount of cTnI has increased or decreased from the first sample to the second sample; c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample; and d) treating the subject assessed as having a mild, moderate, severe, or moderate to severe traumatic brain injury with a traumatic brain injury treatment.

Embodiments of the above method further involve monitoring the subject assessed as having a mild traumatic brain injury. Embodiments of the above method further involve monitoring the subject assessed as having a moderate, severe, or moderate to severe traumatic brain injury.

In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof. Optionally, such methods may also involve providing one or more cardioprotective therapies. Such cardioprotective therapies can be administered in combination with the treatments for the TBI or alone without any TBI treatment, depending on the circumstances.

In yet another embodiment, the present disclosure relates to a method of treating a mild or moderate, severe, or moderate to severe traumatic brain injury in a human subject, the method comprising: a) performing an assay on samples from the human subject to measure or detect a level of cTnI in a first sample and a second sample, wherein the first sample is taken from the human subject at a first time point and the second sample is taken from the human subject about 1 hours to about 4 hours after the first sample, wherein the samples are biological samples; b) determining whether the amount of cTnI has increased or decreased from the first sample to the second sample; c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample; and d) treating the subject assessed as having a mild, moderate, severe, or moderate to severe traumatic brain injury with a traumatic brain injury treatment.

Embodiments of the above method further involve monitoring the subject assessed as having a mild traumatic brain injury. Embodiments of the above method further involve monitoring the subject assessed as having a moderate, severe, or moderate to severe traumatic brain injury.

In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof. Optionally, such methods may also involve providing one or more cardioprotective therapies. Such cardioprotective therapies can be administered in combination with the treatments for the TBI or alone without any TBI treatment, depending on the circumstances.

In still yet another embodiment, the present disclosure relates to a method for aiding in predicting or predicting the outcome of human subjects having mild traumatic brain injury, the method comprising: a) performing an assay on samples from the human subject to measure or detect a level of cTnI in a first sample and a second sample, wherein the first sample is taken from the human subject at a first time point within 24 hours after a injury to the head and the second sample is taken from the human subject about 0 to about 4 hours after the first sample, wherein the samples are biological samples; b) determining whether the amount of cTnI has increased or decreased from the first sample to the second sample; and c) predicting an unfavorable outcome in the human subject if the level of cTnI detected has increased from the first sample to the second sample by at least about 20% and predicting a favorable outcome in the human subject if the level of cTnI detected has remained unchanged, decreased, or increased less than about 20% from the first sample to the second sample.

In some embodiments of the above described method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after an injury to the head. In another embodiment, the first sample is taken from the subject within about 30 minutes after an injury to the head. In another embodiment, the first sample is taken from the subject within about 1 hour after an injury to the head. In some embodiments of the above method, the first sample is taken from the subject within about 2 hours after an injury to the head. In some embodiments of the above method, the first sample is taken from the subject within about 3 hours after an injury to the head. In some embodiments of the above method, the first sample is taken from the subject within about 4 hours after an injury to the head. In some embodiments of the above method, the first sample is taken from the subject within about 5 hours after an injury to the head. In some embodiments of the above method, the first sample is taken from the subject within about 6 hours after an injury to the head. In some embodiments of the above method, the first sample is taken from the subject within about 7 hours after an injury to the head. In some embodiments of the above method, the first sample is taken from the subject within about 8 hours after an injury to the head. In some embodiments of the above method, the first sample is taken from the subject within about 9 hours after an injury to the head. In some embodiments of the above method, the first sample is taken from the subject within about 10 hours after an injury to the head. In some embodiments of the above method, the first sample is taken from the subject within about 11 hours after an injury to the head. In some embodiments of the above method, the first sample is taken from the subject within about 12 hours after an injury to the head. In some embodiments of the above method, the first sample is taken from the subject within about 13 hours after an injury to the head. In some embodiments of the above method, the first sample is taken from the subject within about 14 hours after an injury to the head. In some embodiments of the above method, the first sample is taken from the subject within about 15 hours after an injury to the head. In some embodiments of the above method, the first sample is taken from the subject within about 16 hours after an injury to the head. In some embodiments of the above method, the first sample is taken from the subject within about 17 hours after an injury to the head. In some embodiments of the above method, the first sample is taken from the subject within about 18 hours after an injury to the head. In some embodiments of the above method, the first sample is taken from the subject within about 19 hours after an injury to the head. In some embodiments of the above method, the first sample is taken from the subject within about 20 hours after an injury to the head. In some embodiments of the above method, the first sample is taken from the subject within about 21 hours after an injury to the head. In some embodiments of the above method, the first sample is taken from the subject within about 22 hours after an injury to the head. In some embodiments of the above method, the first sample is taken from the subject within about 23 hours after an injury to the head. In some embodiments of the above method, the first sample is taken from the subject within about 24 hours after an injury to the head.

In some embodiments of the above method, the method predicts a favorable outcome of the subject at about 1 month after an injury to the head. In some embodiments of the above method, the method predicts an unfavorable outcome of the subject at about 1 month after an injury to the head. In some embodiments of the above method, the method predicts a favorable outcome of the subject at about 3 months after an injury to the head. In some embodiments of the above method, the method predicts an unfavorable outcome of the subject at about 3 months after an injury to the head. In some embodiments of the above method, the method predicts a favorable outcome of the subject at about 6 months after an injury to the head. In some embodiments of the above method, the method predicts an unfavorable outcome of the subject at about 6 months after an injury to the head.

In some embodiments of the above method, the subject has a normal head CT scan.

In some embodiments of the above method, the subject has an abnormal head CT scan.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether or not the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments of the above method, the subject has an Extended Glasgow Outcome (GOSE) score of 5 or less. In some embodiments of the above method, the GOSE score is obtained before or after the assay is performed.

In some embodiments of the above method, the subject (having a mild TBI or a moderate, severe, or moderate to severe TBI) that is assessed as having an unfavorable outcome is treated with a traumatic brain injury treatment. In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof.

In some embodiments of the above method, the subject having been assessed as having an unfavorable outcome may also be monitored. Said subject may be monitored regardless of whether the subject is receiving a traumatic brain injury treatment or other treatment (such as one or more cardioprotective therapies).

The present disclosure is directed to a method for aiding in predicting or predicting the outcome of human subjects having mild traumatic brain injury, the method comprising: a) performing an assay on a sample obtained from the subject within about 28 hours after an injury to the head to measure or detect a level of cTnI, wherein the sample is a biological sample; and b) predicting an unfavorable outcome in the human subject if the level of cTnI in the sample is higher than a reference level of cTnI and predicting a favorable outcome in the human subject if the level of cTnI in the sample is lower than a reference level of cTnI.

In some embodiments of the above described method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of after an injury to the head. In another embodiment, the first sample is taken from the subject within about 30 minutes after an injury to the head. In another embodiment, the first sample is taken from the subject within about 1 hour after an injury to the head. In some embodiments of the above method, the first sample is taken from the subject within about 2 hours after an injury to the head. In some embodiments of the above method, the first sample is taken from the subject within about 3 hours after an injury to the head. In some embodiments of the above method, the first sample is taken from the subject within about 4 hours after an injury to the head. In some embodiments of the above method, the first sample is taken from the subject within about 5 hours after an injury to the head. In some embodiments of the above method, the first sample is taken from the subject within about 6 hours after an injury to the head. In some embodiments of the above method, the first sample is taken from the subject within about 7 hours after an injury to the head. In some embodiments of the above method, the first sample is taken from the subject within about 8 hours after an injury to the head. In some embodiments of the above method, the first sample is taken from the subject within about 9 hours after an injury to the head. In some embodiments of the above method, the first sample is taken from the subject within about 10 hours after an injury to the head. In some embodiments of the above method, the first sample is taken from the subject within about 11 hours after an injury to the head. In some embodiments of the above method, the first sample is taken from the subject within about 12 hours after an injury to the head. In some embodiments of the above method, the first sample is taken from the subject within about 13 hours after an injury to the head. In some embodiments of the above method, the first sample is taken from the subject within about 14 hours after an injury to the head. In some embodiments of the above method, the first sample is taken from the subject within about 15 hours after an injury to the head. In some embodiments of the above method, the first sample is taken from the subject within about 16 hours after an injury to the head. In some embodiments of the above method, the first sample is taken from the subject within about 17 hours after an injury to the head. In some embodiments of the above method, the first sample is taken from the subject within about 18 hours after an injury to the head. In some embodiments of the above method, the first sample is taken from the subject within about 19 hours after an injury to the head. In some embodiments of the above method, the first sample is taken from the subject within about 20 hours after an injury to the head. In some embodiments of the above method, the first sample is taken from the subject within about 21 hours after an injury to the head. In some embodiments of the above method, the first sample is taken from the subject within about 22 hours after an injury to the head. In some embodiments of the above method, the first sample is taken from the subject within about 23 hours after an injury to the head. In some embodiments of the above method, the first sample is taken from the subject within about 24 hours after an injury to the head.

In some embodiments of the above method, the method predicts a favorable outcome of the subject at about 1 month after an injury to the head. In some embodiments of the above method, the method predicts an unfavorable outcome of the subject at about 1 month after an injury to the head. In some embodiments of the above method, the method predicts a favorable outcome of the subject at about 3 months after an injury to the head. In some embodiments of the above method, the method predicts an unfavorable outcome of the subject at about 3 months after an injury to the head. In some embodiments of the above method, the method predicts a favorable outcome of the subject at about 6 months after an injury to the head. In some embodiments of the above method, the method predicts an unfavorable outcome of the subject at about 6 months after an injury to the head.

In some embodiments of the above method, the subject has a normal head CT scan.

In some embodiments of the above method, the subject has an abnormal head CT scan.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments of the above method, the subject has an Extended Glasgow Outcome (GOSE) score of 5 or less. In some embodiments of the above method, the GOSE score is obtained before or after the assay is performed.

In some embodiments of the above method, the reference level is reference level is determined by an assay having a sensitivity of between at least about 80% to 100% and a specificity of between at least about 45% to 100%. In some embodiments of the above method, the reference level is reference level is determined by an assay having a sensitivity of at least about 83.3% and a specificity of at least about 54.9%. In some embodiments of the above method, the reference level is reference level is determined by an assay having a sensitivity of at least about 100% and a specificity of at least about 49.2%. In some embodiments of the above method, the reference level is reference level between at least about 1 pg/mL to about 50 pg/mL.

In other embodiments of the above method, the reference level for cTnI is about 5.6 pg/mL. In other embodiments of the above method, the reference level for cTnI is about 5.7 pg/mL.

In some embodiments of the above method, the subject (having a mild TBI or a moderate, severe, or moderate to severe TBI) that is assessed as having an unfavorable outcome is treated with a traumatic brain injury treatment. In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof.

In some embodiments of the above method, the subject having been assessed as having an unfavorable outcome may also be monitored. Said subject may be monitored regardless of whether the subject is receiving a traumatic brain injury treatment or other treatment (such as one or more cardioprotective therapies).

In yet another embodiment, the present disclosure is directed to a method for aiding in predicting or predicting the outcome of human subjects having mild traumatic brain injury, the method comprising: a) performing an assay on samples from the human subject to measure or detect a level of cTnI in a first sample and a second sample, wherein the first sample is taken from the human subject at a first time point within about 24 hours after head injury and the second sample is taken from the human subject about 4 hours after the first sample, wherein the samples are biological samples; b) determining whether the amount of cTnI has increased or decreased from the first sample to the second sample; and c) predicting an unfavorable outcome in the human subject if the level of cTnI in the sample has increased from the first sample to the second sample and predicting a favorable outcome in the human subject if the level of cTnI in the sample has remained unchanged or has decreased from the first sample to the second sample.

In some embodiments of the above described method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of after an injury to the head. In another embodiment, the first sample is taken from the subject within about 30 minutes after an injury to the head. In another embodiment, the first sample is taken from the subject within about 1 hour after an injury to the head. In some embodiments of the above method, the first sample is taken from the subject within about 2 hours after an injury to the head. In some embodiments of the above method, the first sample is taken from the subject within about 3 hours after an injury to the head. In some embodiments of the above method, the first sample is taken from the subject within about 4 hours after an injury to the head. In some embodiments of the above method, the first sample is taken from the subject within about 5 hours after an injury to the head. In some embodiments of the above method, the first sample is taken from the subject within about 6 hours after an injury to the head. In some embodiments of the above method, the first sample is taken from the subject within about 7 hours after an injury to the head. In some embodiments of the above method, the first sample is taken from the subject within about 8 hours after an injury to the head. In some embodiments of the above method, the first sample is taken from the subject within about 9 hours after an injury to the head. In some embodiments of the above method, the first sample is taken from the subject within about 10 hours after an injury to the head. In some embodiments of the above method, the first sample is taken from the subject within about 11 hours after an injury to the head. In some embodiments of the above method, the first sample is taken from the subject within about 12 hours after an injury to the head. In some embodiments of the above method, the first sample is taken from the subject within about 13 hours after an injury to the head. In some embodiments of the above method, the first sample is taken from the subject within about 14 hours after an injury to the head. In some embodiments of the above method, the first sample is taken from the subject within about 15 hours after an injury to the head. In some embodiments of the above method, the first sample is taken from the subject within about 16 hours after an injury to the head. In some embodiments of the above method, the first sample is taken from the subject within about 17 hours after an injury to the head. In some embodiments of the above method, the first sample is taken from the subject within about 18 hours after an injury to the head. In some embodiments of the above method, the first sample is taken from the subject within about 19 hours after an injury to the head. In some embodiments of the above method, the first sample is taken from the subject within about 20 hours after an injury to the head. In some embodiments of the above method, the first sample is taken from the subject within about 21 hours after an injury to the head. In some embodiments of the above method, the first sample is taken from the subject within about 22 hours after an injury to the head. In some embodiments of the above method, the first sample is taken from the subject within about 23 hours after an injury to the head. In some embodiments of the above method, the first sample is taken from the subject within about 24 hours after an injury to the head.

In some embodiments of the above method, the method predicts a favorable outcome of the subject at about 1 month after an injury to the head. In some embodiments of the above method, the method predicts an unfavorable outcome of the subject at about 1 month after an injury to the head. In some embodiments of the above method, the method predicts a favorable outcome of the subject at about 3 months after an injury to the head. In some embodiments of the above method, the method predicts an unfavorable outcome of the subject at about 3 months after an injury to the head. In some embodiments of the above method, the method predicts a favorable outcome of the subject at about 6 months after an injury to the head. In some embodiments of the above method, the method predicts an unfavorable outcome of the subject at about 6 months after an injury to the head.

In some embodiments of the above method, the subject has a normal head CT scan.

In some embodiments of the above method, the subject has an abnormal head CT scan.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments of the above method, the subject has an Extended Glasgow Outcome (GOSE) score of 5 or less. In some embodiments of the above method, the GOSE score is obtained before or after the assay is performed.

In some embodiments of the above method, the amount of cTnI in the first sample is from about 1.0 to about 50 pg/mL.

In some embodiments of the above method, the amount of cTnI in the second sample is from about 1.0 to about 50 pg/mL.

In some embodiments of the above method, the level of cTnI decreases or increase by at least an absolute amount from the first sample to the second sample. More specifically, the absolute amount is determined by an assay having a sensitivity of between at least about 80% to 100% and a specificity of between at least about 45% to 100%. In some embodiments of the above method, the absolute amount is determined by an assay having a sensitivity of at least about 82.4% and a specificity of at least about 69.5%. In some embodiments of the above method, the absolute amount is between at least about 1 pg/mL to about 50 pg/mL.

In some embodiments of the above method, the absolute amount is about 5.6 pg/mL.

In some embodiments of the above method, the subject (having a mild TBI or a moderate, severe, or moderate to severe TBI) that is assessed as having an unfavorable outcome is treated with a traumatic brain injury treatment. In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof.

In some embodiments of the above method, the subject having been assessed as having an unfavorable outcome may also be monitored. Said subject may be monitored regardless of whether the subject is receiving a traumatic brain injury treatment or other treatment (such as one or more cardioprotective therapies).

The present disclosure is directed to a method for aiding in the diagnosis and evaluation of mild traumatic brain injury in a human subject, the method comprising: a) performing an assay on samples from the human subject to measure or detect a level of cTnI in a first sample and a second sample, wherein the first sample is taken from the human subject at a first time point and the second sample is taken from the human subject about 1 hours to about 4 hours after the first sample, wherein the samples are biological samples; b) determining whether the amount of cTnI has increased or decreased from the first sample to the second sample; and c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample.

The present disclosure is directed to a method for aiding in predicting or predicting the outcome of human subjects having mild traumatic brain injury, the method comprising: a) performing an assay on samples from the human subject to measure or detect a level of cTnI in a first sample and a second sample, wherein the first sample is taken from the human subject at a first time point within 24 hours after an injury to the head and the second sample is taken from the human subject about 0 to about 4 hours after the first sample, wherein the samples are biological samples; b) determining the age of the subject; and c) predicting an unfavorable outcome in the human subject if the level of cTnI in the first sample and/or second sample are higher than a reference level of cTnI and the age of the subject is above a reference age and predicting a favorable outcome in the human subject if the level of cTnI in the first sample and second sample are lower than a reference levels of cTnI and/or the age of the subject is below the reference age.

In some embodiments of the above described method, the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of after an injury to the head. In another embodiment, the first sample is taken from the subject within about 30 minutes after an injury to the head. In another embodiment, the first sample is taken from the subject within about 1 hour after an injury to the head. In some embodiments of the above method, the first sample is taken from the subject within about 2 hours after an injury to the head. In some embodiments of the above method, the first sample is taken from the subject within about 3 hours after an injury to the head. In some embodiments of the above method, the first sample is taken from the subject within about 4 hours after an injury to the head. In some embodiments of the above method, the first sample is taken from the subject within about 5 hours after an injury to the head. In some embodiments of the above method, the first sample is taken from the subject within about 6 hours after an injury to the head. In some embodiments of the above method, the first sample is taken from the subject within about 7 hours after an injury to the head. In some embodiments of the above method, the first sample is taken from the subject within about 8 hours after an injury to the head. In some embodiments of the above method, the first sample is taken from the subject within about 9 hours after an injury to the head. In some embodiments of the above method, the first sample is taken from the subject within about 10 hours after an injury to the head. In some embodiments of the above method, the first sample is taken from the subject within about 11 hours after an injury to the head. In some embodiments of the above method, the first sample is taken from the subject within about 12 hours after an injury to the head. In some embodiments of the above method, the first sample is taken from the subject within about 13 hours after an injury to the head. In some embodiments of the above method, the first sample is taken from the subject within about 14 hours after an injury to the head. In some embodiments of the above method, the first sample is taken from the subject within about 15 hours after an injury to the head. In some embodiments of the above method, the first sample is taken from the subject within about 16 hours after an injury to the head. In some embodiments of the above method, the first sample is taken from the subject within about 17 hours after an injury to the head. In some embodiments of the above method, the first sample is taken from the subject within about 18 hours after an injury to the head. In some embodiments of the above method, the first sample is taken from the subject within about 19 hours after an injury to the head. In some embodiments of the above method, the first sample is taken from the subject within about 20 hours after an injury to the head. In some embodiments of the above method, the first sample is taken from the subject within about 21 hours after an injury to the head. In some embodiments of the above method, the first sample is taken from the subject within about 22 hours after an injury to the head. In some embodiments of the above method, the first sample is taken from the subject within about 23 hours after an injury to the head. In some embodiments of the above method, the first sample is taken from the subject within about 24 hours after an injury to the head.

In some embodiments of the above method, the age of the subject is 18 to 30 years. In other embodiments of the above method, the age of the subject is 31 to 50 years. In yet other embodiments of the above method, the age of the subject is 51 to 70 years. In yet other embodiments of the above method, the age of the subject is 70 to 100 years. In yet other embodiments of the above method, the age is 18 years or less. In yet other embodiments of the above method, the age is 19-50 years. In still further embodiments, the age is 51-70 years. In yet other embodiments of the above method, the age is greater than 70 years. In yet other embodiments of the above method, the age of the subject is 20 to 30 years. In yet other embodiments of the above method, the age of the subject is 31 to 40 years. In yet other embodiments of the above method, the age of the subject is 41 to 50 years. In yet other embodiments of the above method, the age of the subject is 51 to 60 years. In yet other embodiments of the above method, the age of the subject is 61 to 70 years. In yet other embodiments of the above method, the age of the subject is 71 to 80 years. In yet other embodiments of the above method, the age of the subject is 81 to 90 years. In yet other embodiments of the above method, the age of the subject is 91 to 100 years.

In some embodiments of the above method, the method predicts a favorable outcome of the subject at about 1 month after an injury to the head. In some embodiments of the above method, the method predicts an unfavorable outcome of the subject at about 1 month after an injury to the head. In some embodiments of the above method, the method predicts a favorable outcome of the subject at about 3 months after an injury to the head. In some embodiments of the above method, the method predicts an unfavorable outcome of the subject at about 3 months after an injury to the head. In some embodiments of the above method, the method predicts a favorable outcome of the subject at about 6 months after an injury to the head. In some embodiments of the above method, the method predicts an unfavorable outcome of the subject at about 6 months after an injury to the head.

In some embodiments of the above method, the subject has a normal head CT scan.

In some embodiments of the above method, the subject has an abnormal head CT scan.

In some embodiments in the above method, the subject has received a Glasgow Coma Scale score before or after the assay is performed. In some embodiments, the subject may be suspected of having a traumatic brain injury based on a Glasgow Coma Scale score that was previously performed. For example, depending upon a subject's medical condition, a Glasgow Coma Scale score may be assessed shortly after the subject arrives at an emergency room, trauma center, or other site in order to assess and/or evaluate whether the subject has a TBI. Such a Glasgow Coma Scale score may be provided prior to the assay being performed to confirm and determine whether or not the subject has a mild or moderate, severe, or moderate to severe TBI. After the assay is performed, one or more subsequent Glasgow Coma Scale scores can be performed based on the results of the assay as part of the physician's (or other medical personnel's) management of the TBI (such as, for example, to determine whether surgical and/or pharmacological intervention may be required). In other embodiments, the subject may not have received a Glasgow Coma Scale score before the assay is performed.

In some embodiments of the above method, the subject has an Extended Glasgow Outcome (GOSE) score of 5 or less. In some embodiments of the above method, the GOSE score is obtained before or after the assay is performed.

In some embodiments of the above method, the subject (having a mild TBI or a moderate, severe, or moderate to severe TBI) that is assessed as having an unfavorable outcome is treated with a traumatic brain injury treatment. In some embodiments of the above method, the traumatic brain injury treatment for a subject suffering from a mild TBI can involve having the subject rest for a certain period of time, abstain from physical activities for a certain period of time, administration of one or more therapeutics (e.g., drugs to provide relief for a headache or migraine, etc.) or combinations thereof. In other embodiments of the above method, the traumatic brain injury treatment for a subject suffering from a moderate, severe, or moderate to severe TBI, the treatment involves the administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt or providing of one or more therapies (such as rehabilitation, physical therapy, occupational therapy, cognitive behavioral therapy, anger management, etc.) or any combinations thereof.

In some embodiments of the above method, the subject having been assessed as having an unfavorable outcome may also be monitored. Said subject may be monitored regardless of whether the subject is receiving a traumatic brain injury treatment or other treatment (such as one or more cardioprotective therapies).

In some embodiments, in any of the above methods, the methods further comprise providing a cardioprotective therapy to the subject. Such cardioprotective treatment can be any cardioprotective treatment known in the art, optionally including but not limited to one or more of a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof. Such one or more cardioprotective therapies can be given alone or in combination with one or more traumatic brain injury treatments.

In some embodiments in any of the above methods, the level of cTnI is measured by an immunoassay or clinical chemistry assay. In other embodiments, the level of cTnI in the above methods is measured by:
  A. contacting the sample, either simultaneously or sequentially, in any order with:
    (1) a cTnI-capture antibody, which binds to an epitope on cTnI or cTnI fragment to form a cTnI-capture antibody-cTnI antigen complex, and
    (2) a cTnI-detection antibody which includes a detectable label and binds to an epitope on cTnI that is not bound by the cTnI-capture antibody, to form a cTnI antigen-cTnI-detection antibody complex,
  such that a cTnI-capture antibody-cTnI antigen-cTnI-detection antibody complex is formed, and
  B. measuring the amount or concentration of cTnI in the sample based on the signal generated by the detectable label in the cTnI-capture antibody-cTnI antigen-cTnI-detection antibody complex.

In some embodiments of any of the above methods, the sample is selected from the group consisting of a whole blood sample, a serum sample, a cerebrospinal fluid sample, and a plasma sample. In some embodiments in the above methods, the sample is obtained after the subject sustained an injury to the head caused by physical shaking, blunt impact by an external mechanical or other force that results in a closed or open head trauma, one or more falls, explosions or blasts or other types of blunt force trauma. In yet other embodiments in the above methods, the sample is obtained after the subject has ingested or been exposed to a chemical, toxin or combination of a chemical and toxin. In some embodiments in the above methods, the chemical or toxin is fire, mold, asbestos, a pesticide, an insecticide, an organic solvent, a paint, a glue, a gas, an organic metal, a drug of abuse or one or more combinations thereof. In some embodiments in the above methods, the sample is obtained from a subject that suffers from an autoimmune disease, a metabolic disorder, a brain tumor, hypoxia, a virus, meningitis, hydrocephalus or combinations thereof.

In some embodiments of any of the above methods, the methods can be carried out on any subject without regard to factors selected from the group consisting of the subject's clinical condition, the subject's laboratory values, the subject's classification as suffering from mild, moderate, severe, or a moderate to severe traumatic brain injury, the subject's exhibition of low or high levels of cTnI, and the timing of any event wherein said subject may have sustained an injury to the head.

In some embodiments, in any of the above methods, the sample is a whole blood sample.

In some embodiments, in any of the above methods, the sample is a plasma sample.

In some embodiments, in any of the above methods, the sample is a serum sample.

In some embodiments, in any of the above methods, the assay is an immunoassay.

In some embodiments, in any of the above methods, the assay is a clinical chemistry assay.

In some embodiments, in any of the above methods, the assay is a single molecule detection assay.

In some embodiments, in any of the above methods, the sample is a whole blood sample and the assay is an immunoassay. In other embodiments, the sample is a plasma sample and the assay is an immunoassay. In yet other embodiments, the sample is a serum sample and the assay is an immunoassay. In other embodiments, in the above methods, the sample is a whole blood sample and the assay is a clinical chemistry assay. In other embodiments, the sample is a plasma sample and the assay is a clinical chemistry assay. In yet other embodiments, the sample is a serum sample and the assay is a clinical chemistry. In other embodiments, in the above methods, the sample is a whole blood sample and the assay is a single molecule detection assay. In other embodiments, the sample is a plasma sample and the assay is a single molecule detection assay. In yet other embodiments, the sample is a serum sample and the assay is a single molecule detection assay.

DETAILED DESCRIPTION

Figure 1:
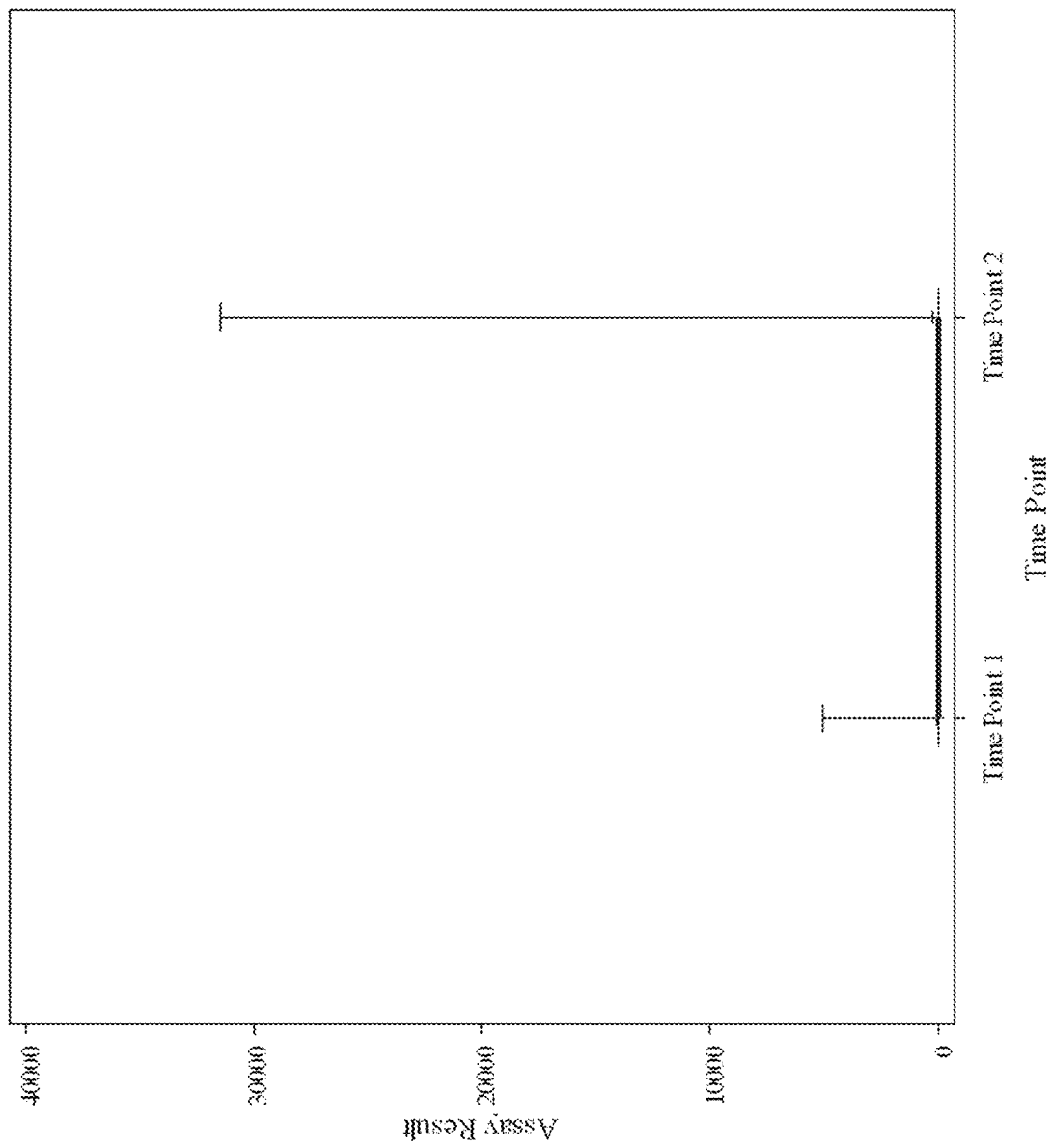
FIG. 1 shows a box plot of hsTnI assay results by time point.

The present disclosure relates to several discoveries involving the use of cardiac troponin I (cTnI) as a biomarker in connection with traumatic brain injury (TBI). Cardiac troponin I is well known in the art as a highly specific biomarker for myocardial injury. In fact, several commercial assays are available for measuring cTnI in blood or plasma for this purpose. However, it is also known in the art that cardiac dysfunction is frequently observed in subjects that have suffered a severe TBI. However, the significance of such cardiac dysfunction in these subjects traditionally has been poorly understood.

In contrast, the present disclosure provides new and improved methods of using levels and/or changes in the levels of cTnI (e.g., by performing an assay to determine the level of cTnI in one or more biological samples and then comparing those level(s) to one or more reference level(s)) as an aid in the evaluation, diagnoses and/or stratification of whether a subject that has suffered an injury or is believed to have suffered an injury to the head has suffered mild TBI, a moderate TBI, a severe TBI, a moderate to severe TBI or no TBI whatsoever. The methods described herein can be performed quickly—in as little as 2 hours and up to about 24 hours after an injury or suspected injury to the head. The use of cTnI to differentiate between mild, moderate, severe, moderate to severe or no TBI in this manner is previously unknown. Not only do such methods allow a physician to quickly determine and classify (or reclassify) or triage a patient as having a TBI or no TBI, for those patients identified or determined to have suffered a TBI, the methods described herein allow the physician to determine the type of TBI (mild versus moderate, severe, or moderate to severe). The ability to quickly determine whether classify a TBI as mild, moderate, severe or moderate to severe allows the physician to development an appropriate course of treatment (e.g., treatment plan) for the subject. Such a treatment plan can include whether to (1) order one or more additional tests to obtain further clinical information about the TBI (e.g., such as a MRI, etc.); (2) begin (continue) monitoring the subject; (3) begin treating the subject with a traumatic brain injury treatment (and if treatment is begun, what type of treatment to begin (e.g, one or more therapeutic treatments, protecting the airway, one or more surgical treatments, ordering rest, etc.); (4) begin any cardioprotective treatment to protect the heart of the subject (such as, optionally, by the administration of one or more beta-blockers, diuretics, angiotensin-converting inhibitors, calcium channel blockers, lipid lowering therapies, statins, nitrates, antiplatelet therapy, anticlotting agents, anticoagulation agents or combinations thereof, or other cardioprotective agents known in the art); or (5) perform any combinations of (1)-(4).

Additionally, the present disclosure provides methods of using levels or changes in the levels of cTnI as an aid in determining whether a head computerized tomography (CT) should be performed on a subject that has suffered or is believed to have suffered a TBI. The methods described herein can be performed quickly—in as little as 2 hours and up to about 24 hours after an injury or suspected injury to the head. The use of cTnI as an aid in assisting a physician to determine whether or to perform a head CT in subjects that have suffered or believed to have suffered a TBI is previously not known.

Moreover, the present disclosure also provides methods of using levels or changes in the levels of cTnI to determine the outcome of subjects suffering from a mild TBI. Specifically, the methods described herein can be used to determine whether a subject diagnosed with a mild TBI is more likely than not to have (1) a favorable outcome (optionally, the favorable outcome can be that the subject fully recovers and does not continue to experience one or more symptoms of a mild TBI); or (2) an unfavorable outcome (optionally, the unfavorable outcome can be that the subject does not fully recover and does continue to experience one or more symptoms of a mild TBI).

Alternatively and optionally, a favorable outcome can mean that the subject is more likely than not to suffer no more than one post-concussion syndrome symptom as a result of the mild TBI such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g., personality changes, irritability, depression, apathy, etc.); or (d) sleep difficulties (e.g., insomnia, etc.). Alternatively and optionally, subject who have an unfavorable outcome are more likely to suffer from more than one post-concussion syndrome symptom such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g, personality changes, irritability, depression, apathy, etc.); (d) sleep difficulties (e.g., insomnia, etc.); or (e) any combinations of (a)-(d)). Alternatively and optionally, an unfavorable outcome can also mean that a subject exhibits one or more symptoms of mild TBI. Alternatively and optionally, an unfavorable outcome can also mean that the subject's conditions worsens from mild TBI to moderate, moderate to severe or severe. Additionally, subjects having a favorable outcome are likely to have a GOSE score of 5 or greater whereas subjects having an unfavorable outcome are likely to have a GOSE score of less than 5.

Subjects unlikely to make a full recovery from the mild TBI will likely need one or more of additional therapeutic treatment, physical therapy and/or occupational therapy for at least 1 day, 2 days, 3 days, 4 days, 5 days 6 days, 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months 12 months, 13 months, 14 months, 15 months, 16 months, 17 months, 18 months, 19 months, 20 months, 21 months, 22 months, 23 months, 24 months, 3 years, 4 years, 5 years, 6 years, 7 years, 8 years, 9 years, 10 years, 11 years, 12 years, 13 years, 14 years, 15 years, 20 years, 25 years, 30 years, 35 years, 40 years, 45 years or 50 years after diagnosis of the mild TBI. The use of cTnI in predicting outcome in mild TBI subjects is previously not known.

Additionally, the present disclosure provides methods of treating a traumatic brain injury. Specifically, the methods involve using levels and/or changes in the levels of cTnI as described herein (e.g., by performing an assay to determine the level of cTnI in one or more biological samples and then comparing those level(s) to one or more reference level(s)) to evaluate, diagnose and/or stratify whether a subject that has suffered an injury to the head or is believed to have suffered an injury to the head has suffered mild TBI, a moderate TBI, severe TBI, moderate to severe TBI or no TBI. Once a subject has been identified, determined, classified or stratified as having a mild TBI or a moderate, severe or moderate to severe TBI, then depending on the type of TBI (mild versus moderate, severe or moderate to severe), the subject can be treated with an appropriate traumatic brain injury treatment. For example, for a mild TBI, the traumatic brain injury treatment may involve one or more of having the subject rest for a certain period of time, abstain from physical activities for a certain period of time, administration of one or more therapeutics (e.g., drugs to provide relief for a headache or migraine, etc.) or combinations thereof. For a moderate, severe, or moderate to severe TBI, the traumatic brain injury treatment may involve administration of one or more therapeutics (e.g., drugs such as diuretics, anti-seizure drugs), performing one or more surgical procedures (e.g., such as removal of a hematoma, repairing a skull fracture, decompressive craniectomy, etc.), receipt of one or more therapies (such as rehabilitation, physical therapy, occupational therapy, cognitive behavioral therapy, anger management, etc.) or combinations thereof. Optionally, such methods may also involve providing one or more cardioprotective therapies. Such cardioprotective therapies can be administered in combination with the treatments for the TBI or alone without any TBI treatment, depending on the circumstances.

In addition to performing the above described methods, one skilled in the art (e.g., physician) would understand and know how to perform additional testing in order to detect or assess other comorbidities (e.g., other diseases, disorders, or conditions other than TBI). Furthermore, in order to confirm that the changes in amounts or levels cTnI in the methods described herein are attributable to a head injury or a suspected injury to the head of a subject and not the result of an acute cardiac syndrome (such as a myocardial infarction, heart failure, etc.), a physician or other healthcare provider could conduct or perform one or more additional tests or procedures to confirm the absence of an acute cardiac syndrome. Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity matured antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, *J. Mol. Biol.*, 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-cardiac troponin I antibody or a cardiac troponin I antibody).

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., *Nature*, 305(5934): 537-540 (1983)), by chemical conjugation of two different monoclonal antibodies (see, Staerz et al., *Nature*, 314(6012): 628-631 (1985)), or by knob-into-hole or similar approaches, which introduce mutations in the Fc region (see Holliger et al., *Proc. Natl. Acad. Sci. USA*, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

As used herein, the terms "cardiac troponin I", "cTnI" or "troponin I" as used interchangeably herein, refers to one of two unique forms of cardiac troponin (the other unique form being cardiac troponin T (also referred to as "cTnT")), released into the blood from cardiac muscle for which several species may exist in the blood. Not only does the term "cardiac troponin I" or "cTnI" include the full-length version of this form but it also includes: (1) various complexes of cTnI (namely, with each other and/or with cardiac troponin C (cTnC)); (2) fragments of cTnI which result from proteolytic degradation; (3) phosphorylated and oxidized forms of cTnI (See, for example, U.S. Pat. No. 6,991,907, the contents of which are herein incorporated by reference); and (4) any isoforms of cTnI.

In some embodiments, the methods of the present disclosure allow for the detection and/or determination of concentration of one or more of the various forms of cTnI in a sample as a separate entity, e.g., complexed cTnI, free cTnI (e.g., such as fully length, fragments, isoforms, etc.), mud-died cTnI (e.g., oxidized or phosphorylated), and, optionally, provides a concentration for the cTnI in the biological sample.

More specifically, in some embodiments, the disclosure described herein employs highly sensitivity assays that allow for the detection and quantification of cTnI at levels 10- to 100-fold lower than levels measured by traditional troponin assays (e.g., immunoassays) known in the art. More specifically, assays are defined as high sensitivity (e.g., high sensitivity assays for troponin) if such assays meet at least the following two conditions: 1) a coefficient of variance less than 10% at the 99th percentile value of the reference healthy population and 2) concentrations above the assay's limit of detection are measurable in greater than 50% of healthy individuals (See, Apple F S, et al., *Clin Chem.*, 58:54-61 (2012), the contents of which are hereby incorporated by reference). Examples of assays known in the art that allow for the high-sensitive detection of troponin include those available from Quanterix (Simoa Human Troponin-I immunoassay) for research use only as well as those described in U.S. Pat. No. 9,182,405, the contents of which are hereby incorporated by reference.

"Cardiac Troponin I status" or "cTnI status" as used interchangeably herein can mean either the level or amount of cardiac troponin I at a point in time (such as with a single measure of troponin I), the level or amount of cardiac troponin I associated with monitoring (such as with a repeat test on a subject to identify an increase or decrease in cardiac troponin I amount), the level or amount of cardiac troponin I associated with treatment for traumatic brain injury (whether a primary brain injury and/or a secondary brain injury) or combinations thereof.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.*, 196: 901-917 (1987); and Chothia et al., *Nature*, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.*, 9: 133-139 (1995), and MacCallum, *J. Mol. Biol.*, 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"Correlated to" as used herein refers to compared to.

"CT scan" as used herein refers to a computerized tomography (CT) scan. A CT scan combines a series of X-ray images taken from different angles and uses computer processing to create cross-sectional images, or slices, of the bones, blood vessels and soft tissues inside your body. The CT scan may use X-ray CT, positron emission tomography (PET), single-photon emission computed tomography (SPECT), computed axial tomography (CAT scan), or computer aided tomography. The CT scan may be a conventional CT scan or a spiral/helical CT scan. In a conventional CT scan, the scan is taken slice by slice and after each slice the scan stops and moves down to the next slice, e.g., from the top of the abdomen down to the pelvis. The conventional CT scan requires patients to hold their breath to avoid movement artefact. The spiral/helical CT scan is a continuous scan which is taken in a spiral fashion and is a much quicker process where the scanned images are contiguous.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Determined by an assay" is used herein to refer to the determination of a reference level by any appropriate assay. The determination of a reference level may, in some embodiments, be achieved by an assay of the same type as the assay that is to be applied to the sample from the subject (for example, by an immunoassay, clinical chemistry assay, a single molecule detection assay, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS)). The determination of a reference level may, in some embodiments, be achieved by an assay of the same type and under the same assay conditions as the assay that is to be applied to the sample from the subject. As noted herein, this disclosure provides exemplary reference levels (e.g., calculated by comparing reference levels at different time points). It is well within the ordinary skill of one in the art to adapt the disclosure herein for other assays to obtain assay-specific reference levels for those other assays based on the description provided by this disclosure. For example, a set of training samples comprising samples obtained from human subjects known to have sustained an injury to the head (and more particularly, samples obtained from human subjects known to have sustained a (i) mild TBI; and/or (ii) moderate, severe, or moderate to severe TBI and samples obtained from human subjects known not to have sustained an injury to the head may be used to obtain assay-specific reference levels. It will be understood that a reference level "determined by an assay" and having a recited level of "sensitivity" and/or "specificity" is used herein to refer to a reference level which has been determined to provide a method of the recited sensitivity and/or specificity when said reference level is adopted in the methods of the disclosure. It is well within the ordinary skill of one in the art to determine the sensitivity and specificity associated with a given reference level in the methods of the disclosure, for example by repeated statistical analysis of assay data using a plurality of different possible reference levels.

Practically, when discriminating between a subject as having a traumatic brain injury or not having a traumatic brain injury or a subject as having a a mild versus a moderate, severe, or moderate to severe traumatic brain injury, the skilled person will balance the effect of raising a cutoff on sensitivity and specificity. Raising or lowering a cutoff will have a well-defined and predictable impact on sensitivity and specificity, and other standard statistical measures. It is well known that raising a cutoff will improve specificity but is likely to worsen sensitivity (proportion of those with disease who test positive). In contrast, lowering a cutoff will improve sensitivity but will worsen specificity (proportion of those without disease who test negative). The ramifications for detecting traumatic brain injury or determining a mild versus moderate, severe, or moderate to severe traumatic brain injury will be readily apparent to those skilled in the art. In discriminating whether a subject has or does not have a traumatic brain injury or a mild versus a moderate, severe, or moderate to severe traumatic brain injury, the higher the cutoff, specificity improves as more true negatives (i.e., subjects not having a traumatic brain injury, not having a mild traumatic brain injury, not have a moderate traumatic brain injury, not having a severe traumatic brain injury or not having a moderate to severe traumatic brain injury) are distinguished from those having a traumatic brain injury, a mild traumatic brain injury, a moderate traumatic brain injury, a severe traumatic brain injury or a moderate to severe traumatic brain injury. But at the same time, raising the cutoff decreases the number of cases identified as positive overall, as well as the number of true positives, so the sensitivity must decrease. Conversely, the lower the cutoff, sensitivity improves as more true positives (i.e., subjects having a traumatic brain injury, having a mild traumatic brain injury, having a moderate traumatic brain injury, having a severe traumatic brain injury or having a moderate to severe traumatic brain injury) are distinguished from those who do not have a traumatic brain injury, a mild traumatic brain injure, a moderate traumatic brain injury, a severe traumatic brain injury or a moderate to severe traumatic brain injury. But at the same time, lowering the cutoff increases the number of cases identified as positive overall, as well as the number of false positives, so the specificity must decrease.

Generally, a high sensitivity value helps one of skill rule out disease or condition (such as a traumatic brain injury, mild traumatic brain injury, moderate traumatic brain injury, severe traumatic brain injury or moderate to severe traumatic brain injury), and a high specificity value helps one of skill rule in disease or condition. Whether one of skill desires to rule out or rule in disease depends on what the consequences are for the patient for each type of error. Accordingly, one cannot know or predict the precise balancing employed to derive a test cutoff without full disclosure of the underlying information on how the value was selected. The balancing of sensitivity against specificity and other factors will differ on a case-by-case basis. This is why it is sometimes preferable to provide alternate cutoff (e.g., reference) values so a physician or practitioner can choose.

"Drugs of abuse" is used herein to refer to one or more additive substances (such as a drug) taken for non-medical reasons (such as for, example, recreational and/or mind-altering effects). Excessive overindulgence, use or dependence of such drugs of abuse is often referred to as "substance abuse". Examples of drugs of abuse include alcohol, barbiturates, benzodiazepines, *cannabis*, cocaine, hallucinogens (such as ketamine, mescaline (peyote), PCP, psilocybin, DMT and/or LSD), methaqualone, opioids, amphetamines (including methamphetamines), anabolic steroids, inhalants (namely, substances which contain volatile substances that contain psychoactive properties such as, for example, nitrites, spray paints, cleaning fluids, markers, glues, etc.) and combinations thereof.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (e.g., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes e.g., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C—(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of cardiac troponin I. Non-limiting examples of a DVD-Ig binding protein include a DVD-Ig binding protein that binds one or more epitopes of cardiac troponin I, a DVD-Ig binding protein that binds an epitope of a human cardiac troponin I and an epitope of cardiac troponin I of another species (for example, mouse), and a DVD-Ig binding protein that binds an epitope of a human cardiac troponin I and an epitope of another target molecule.

"Dynamic range" as used herein refers to range over which an assay readout is proportional to the amount of target molecule or analyte in the sample being analyzed.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the VL, VH, CL and CH1 domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"$F(ab')_2$ fragment" as used herein refers to antibodies generated by pepsin digestion of whole IgG antibodies to remove most of the Fc region while leaving intact some of the hinge region. $F(ab')_2$ fragments have two antigen-binding F(ab) portions linked together by disulfide bonds, and therefore are divalent with a molecular weight of about 110 kDa. Divalent antibody fragments ($F(ab')_2$ fragments) are smaller than whole IgG molecules and enable a better penetration into tissue thus facilitating better antigen recognition in immunohistochemistry. The use of $F(ab')_2$ fragments also avoids unspecific binding to Fc receptor on live cells or to Protein A/G. $F(ab')_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, —H2, and —H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Glasgow Coma Scale" or "GCS" as used herein refers to a 15 point scale for estimating and categorizing the outcomes of brain injury on the basis of overall social capability or dependence on others. The test measures the motor response, verbal response and eye opening response with these values: I. Motor Response (6—Obeys commands fully; 5—Localizes to noxious stimuli; 4—Withdraws from noxious stimuli; 3—Abnormal flexion, i.e., decorticate posturing; 2—Extensor response, i.e., decerebrate posturing; and 1—No response); II. Verbal Response (5—Alert and Oriented; 4—Confused, yet coherent, speech; 3—Inappropriate words and jumbled phrases consisting of words; 2—Incomprehensible sounds; and 1—No sounds); and III. Eye Opening (4—Spontaneous eye opening; 3—Eyes open to speech; 2—Eyes open to pain; and 1—No eye opening). The final score is determined by adding the values of I+II+III. The final score can be categorized into four possible levels for survival, with a lower number indicating a more severe injury and a poorer prognosis: Mild (13-15); Moderate Disability (9-12) (Loss of consciousness greater than 30 minutes; Physical or cognitive impairments which may or may resolve; and Benefit from Rehabilitation); Severe Disability (3-8) (Coma: unconscious state. No meaningful response, no voluntary activities); and Vegetative State (Less Than 3) (Sleep wake cycles; Arousal, but no interaction with environment; No localized response to pain). Moderate brain injury is defined as a brain injury resulting in a loss of consciousness from 20 minutes to 6 hours and a Glasgow Coma Scale of 9 to 12. Severe brain injury is defined as a brain injury resulting in a loss of consciousness of greater than 6 hours and a Glasgow Coma Scale of 3 to 8.

"Glasgow Outcome Scale" as used herein refers to a global scale for functional outcome that rates patient status into one of five categories: Dead, Vegetative State, Severe Disability, Moderate Disability or Good Recovery.

"Extended Glasgow Outcome Scale" or "GOSE" as used interchangeably herein provides more detailed categorization into eight categories by subdividing the categories of severe disability, moderate disability and good recovery into a lower and upper category as shown in Table 1.

TABLE 1

| 1 Death | D | |
|---|---|---|
| 2 Vegetative state | VX | Condition of unawareness with only reflex responses but with periods of spontaneous eye opening |
| 3 Lower severe disability | SD− | Patient who is dependent for daily support for mental or physical disability, usually a combination of both. If the patient can be left alone for more than 8 hours at home it is upper level of SD, if not then it is low level of SD. |
| 4 Upper severe disability | SD+ | |
| 5 Lower moderate disability | MD− | Patients have some disability such as aphasia, hemiparesis or epilepsy and/or deficits of memory or personality but are able to look after themselves. They are independent at home but dependent outside. If they are able to return to work even with special arrangement it is upper level of MD, if not then it is low level of MD. |
| 6 Upper moderate disability | MD+ | |
| 7 Lower good recovery | GR− | Resumption of normal life with the capacity to work even if pre-injury status has not been achieved. Some patients have minor neurological or psychological deficits. If these deficits are not disabling then it is upper level of GR, if disabling then it is lower level of GR. |
| 8 Upper good recovery | GR+ | |

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 8000, at least 85%, at least 90%, at least 9500, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Hyperacute" as used herein refers to extremely acute or within a course of about 2 hours of the injury or suspected injury to the head. Hyperacute is within an early stage, e.g., a hyperacute biomarker is an early biomarker, such as cTnI, that can be used to assess injury or suspected injury within the early stage of about 2 hours of injury or suspected injury.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Injury to the head" or "head injury" as used interchangeably herein, refers to any trauma to the scalp, skull, or brain. Such injuries may include only a minor bump on the skull or may be a serious brain injury. Such injuries include primary injuries to the brain and/or secondary injuries to the brain. Primary brain injuries occur during the initial insult and result from displacement of the physical structures of the brain. More specifically, a primary brain injury is the physical damage to parenchyma (tissue, vessels) that occurs during the traumatic event, resulting in shearing and compression of the surrounding brain tissue. Secondary brain injuries occur subsequent to the primary injury and may involve an array of cellular processes. More specifically, a secondary brain injury refers to the changes that evolve over a period of time (from hours to days) after the primary brain injury. It includes an entire cascade of cellular, chemical, tissue, or blood vessel changes in the brain that contribute to further destruction of brain tissue.

An injury to the head can be either closed or open (penetrating). A closed head injury refers to a trauma to the scalp, skull or brain where there is no penetration of the skull by a striking object. An open head injury refers a trauma to the scalp, skull or brain where there is penetration of the skull by a striking object. An injury to the head may be caused by physical shaking of a person, by blunt impact by an external mechanical or other force that results in a closed or open head trauma (e.g., vehicle accident such as with an automobile, plane, train, etc.; blow to the head such as with a baseball bat, or from a firearm), a cerebral vascular accident (e.g., stroke), one or more falls (e.g., as in sports or other activities), explosions or blasts (collectively, "blast injuries") and by other types of blunt force trauma. Alternatively, an injury to the head may be caused by the ingestion and/or exposure to a chemical, toxin or a combination of a chemical and toxin. Examples of such chemicals and/or toxins include fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. Alternatively, an injury to the head may be caused as a result of a subject suffering from an autoimmune disease, a metabolic disorder, a brain tumor, one or more viruses, meningitis, hydrocephalus, hypoxia or any combinations thereof. In some cases, it is not possible to be certain whether any such event or injury has occurred or taken place. For example, there may be no history on a patient or subject, the subject may be unable to speak, the subject may be aware of what events they were exposed to, etc. Such circumstances are described herein as the subject "may have sustained an injury to the head." In certain embodiments herein, the closed head injury does not include and specifically excludes a cerebral vascular accident, such as stroke.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oregon. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., *Bioorg. Med. Chem. Lett.* 16: 1324-1328 (2006); Adamczyk et al., *Bioorg. Med. Chem. Lett.* 4: 2313-2317 (2004); Adamczyk et al., *Biorg. Med. Chem. Lett.* 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamczyk et al., *J. Org. Chem.* 63: 5636-5639 (1998); Adamczyk et al., *Tetrahedron* 55: 10899-10914 (1999); Adamczyk et al., *Org. Lett.* 1: 779-781 (1999); Adamczyk et al., *Bioconjugate Chem.* 11: 714-724 (2000); Mattingly et al., In *Luminescence Biotechnology: Instruments and Applications; Dyke, K. V. Ed.*; CRC Press: Boca Raton, pp. 77-105 (2002); Adamczyk et al., *Org. Lett.* 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, MI). Methods for preparing acridinium 9-carboxylate aryl esters are described in McCapra et al., *Photochem. Photobiol.* 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697, 835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6× His tag, which has an amino acid sequence of HHHHHH (SEQ ID NO:2), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:3) and derivatives thereof (e.g., ADDDDK (SEQ ID NO:4), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Magnetic resonance imaging" or "MRI" as used interchangeably herein refers to a medical imaging technique used in radiology to form pictures of the anatomy and the physiological processes of the body in both health and disease. MRI is a form of medical imaging that measures the response of the atomic nuclei of body tissues to high-frequency radio waves when placed in a strong magnetic field, and that produces images of the internal organs. MRI scanners, which is based on the science of nuclear magnetic resonance (NMR), use strong magnetic fields, radio waves, and field gradients to generate images of the inside of the body.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Negative predictive value" or "NPV" as used interchangeably herein refers to the probability that a subject has a negative outcome given that they have a negative test result.

"Reference level" as used herein refers to an assay cutoff value that is used to assess diagnostic, prognostic, or therapeutic efficacy and that has been linked or is associated herein with various clinical parameters (e.g., presence of disease, stage of disease, severity of disease, progression, non-progression, or improvement of disease, etc.). An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e., regardless of whether it is positive or negative.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amounts may vary between assays, the findings as described herein should be generally applicable and capable of being extrapolated to other assays.

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long term care and/or hospice facility). Examples of point-of-care devices include those produced by Abbott Laboratories (Abbott Park, IL) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Positive predictive value" or "PPV" as used interchangeably herein refers to the probability that a subject has a positive outcome given that they have a positive test result.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a reference level or control level (e.g., "low", "medium", or "high" levels), can be used. Multiple calibrators (i.e., more than one calibrator or a varying amount of calibrator(s)) can be used in conjunction to comprise a "sensitivity panel."

A "receiver operating characteristic" curve or "ROC" curve refers to a graphical plot that illustrates the performance of a binary classifier system as its discrimination threshold is varied. For example, an ROC curve can be a plot of the true positive rate against the false positive rate for the different possible cutoff points of a diagnostic test. It is created by plotting the fraction of true positives out of the positives (TPR=true positive rate) vs. the fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "specimen," "biological sample", "sample from a subject," and "patient sample" as used herein may be used interchangeable and may be a sample of blood such as whole blood, tissue, urine, serum, plasma, amniotic fluid, cerebrospinal fluid, placental cells or tissue, endothelial cells, leukocytes, or monocytes. In some embodiments, the sample is a whole blood sample. In some embodiments, the sample is a serum sample. In yet other embodiments, the sample is a plasma sample. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

A variety of cell types, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, red blood cells, platelets, interstitial fluid, cerebral spinal fluid, etc. Cell types and tissues may also include lymph fluid, cerebrospinal fluid, a fluid collected by A tissue or cell type may be provided by removing a sample of cells from a human and a non-human animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Sensitivity" of an assay as used herein refers to the proportion of subjects for whom the outcome is positive that are correctly identified as positive (e.g., correctly identifying those subjects with a disease or medical condition for which they are being tested). For example, this might include correctly identifying subjects as having a TBI from those who do not have a TBI, correctly identifying subjects having a moderate, severe, or moderate to severe TBI from those having a mild TBI, correctly identifying subjects as having a mild TBI from those having a moderate, severe, or moderate to severe TBI, correctly identifying subjects as having a moderate, severe, or moderate to severe TBI from those having no TBI or correctly identifying subjects as having a mild TBI from those having no TBI, correctly identifying subjects as likely to benefit from imaging or a head CT scan or a MRI from those who are not likely to benefit from a head imaging or a CT scan or MRI, etc.).

"Specificity" of an assay as used herein refers to the proportion of subjects for whom the outcome is negative that are correctly identified as negative (e.g., correctly identifying those subjects who do not have a disease or medical condition for which they are being tested). For example, this might include correctly identifying subjects having an TBI from those who do not have a TBI, correctly identifying subjects not having a moderate, severe, or moderate to severe TBI from those having a mild TBI, correctly identifying subjects as not having a mild TBI from those having a moderate, severe, or moderate to severe TBI or correctly identifying subjects as not having any TBI, or correctly identifying subjects as having a mild TBI from those having no TBI, etc.).

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Statistically significant" as used herein refers to the likelihood that a relationship between two or more variables is caused by something other than random chance. Statistical hypothesis testing is used to determine whether the result of a data set is statistically significant. In statistical hypothesis testing, a statistical significant result is attained whenever the observed p-value of a test statistic is less than the significance level defined of the study. The p-value is the probability of obtaining results at least as extreme as those observed, given that the null hypothesis is true. Examples of statistical hypothesis analysis include Wilcoxon signed-rank test, t-test, Chi-Square or Fisher's exact test. "Significant" as used herein refers to a change that has not been determined to be statistically significant (e.g., it may not have been subject to statistical hypothesis testing).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. In some embodiments, the subject is a human. The subject or patient may be undergoing other forms of treatment. In some embodiments, when the subject is a human, the subject does not include any humans who have suffered a cerebrovascular accident (e.g., a stroke).

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Traumatic Brain Injury" or "TBI" as used interchangeably herein refers to a complex injury with a broad spectrum of symptoms and disabilities. TBI is most often an acute event similar to other injuries. TBI can be classified as "mild," "moderate," or "severe." The causes of TBI are diverse and include, for example, physical shaking by a person, a car accident, injuries from firearms, cerebral vascular accidents (e.g., strokes), falls, explosions or blasts and other types of blunt force trauma. Other causes of TBI include the ingestion and/or exposure to one or more chemicals or toxins (such as fires, molds, asbestos, pesticides and insecticides, organic solvents, paints, glues, gases (such as carbon monoxide, hydrogen sulfide, and cyanide), organic metals (such as methyl mercury, tetraethyl lead and organic tin), one or more drugs of abuse or combinations thereof). Alternatively, TBI can occur in subjects suffering from an autoimmune disease, a metabolic disorder, a brain tumor, hypoxia, one or more viruses, meningitis, hydrocephalus or combinations thereof. Young adults and the elderly are the age groups at highest risk for TBI. In certain embodiments herein, traumatic brain injury or TBI does not include and specifically excludes cerebral vascular accidents such as strokes.

"Mild TBI" as used herein refers to a brain injury where loss of consciousness is brief and usually a few seconds or minutes and/or confusion and disorientation is shorter than 1 hour. Mild TBI is also referred to as a concussion, minor head trauma, minor TBI, minor brain injury, and minor head injury. While MRI and CT scans are often normal, the individual with mild TBI may have cognitive problems such as headache, difficulty thinking, memory problems, attention deficits, mood swings and frustration.

Mild TBI is the most prevalent TBI and is often missed at time of initial injury. Typically, a subject has a Glasgow Coma scale number of between 13-15 (such as 13-15 or 14-15). Fifteen percent (15%) of people with mild TBI have symptoms that last 3 months or more. Mild TBI is defined as the result of the forceful motion of the head or impact causing a brief change in mental status (confusion, disorientation or loss of memory) or loss of consciousness for less than 30 minutes. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

"Moderate TBI" as used herein refers to a brain injury where loss of consciousness and/or confusion and disorientation is between 1 and 24 hours and the subject has a Glasgow Coma scale number of between 9-13 (such as 9-12 or 9-13). The individual with moderate TBI have abnormal brain imaging results. "Severe TBI" as used herein refers to a brain injury where loss of consciousness is more than 24 hours and memory loss after the injury or penetrating skull injury longer than 24 hours and the subject has a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

"Moderate to severe" TBI as used herein refers to a spectrum of brain injury that includes moderate to severe and thus encompasses moderate TBI alone, severe TBI alone and moderate to severe TBI combined. Subjects suffering from a moderate to severe TBI can have a Glasgow Coma scale number of between 3-13 (such as 3-12 or 3-13). For example, in some clinical situations, a subject may initially be diagnosed as having a moderate TBI but who, over the course of time (minutes, hours or days), progress to having a severe TBI (such, as for example, in situations when there is a brain bleed). Such subjects would be examples of patients that could be classified as "moderate to severe". Common symptoms of moderate to severe TBI include cognitive deficits including difficulties with attention, concentration, distractibility, memory, speed of processing, confusion, perseveration, impulsiveness, language processing, and/or "executive functions", not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), hearing, such as decrease or loss of hearing, ringing in the ears (tinnitus), increased sensitivity to sounds, loss or diminished sense of smell (anosmia), loss or diminished sense of taste, the convulsions associated with epilepsy that can be several types and can involve disruption in consciousness, sensory perception, or motor movements, control of bowel and bladder, sleep disorders, loss of stamina, appetite changes, regulation of body temperature, menstrual difficulties, dependent behaviors, emotional ability, lack of motivation, irritability, aggression, depression, disinhibition, or denial/lack of awareness.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-cTnI antibody that differs from the corresponding fragment of anti-cTnI antibody in amino acid sequence but is still antigenically reactive and can compete with the corresponding fragment of anti-cTnI antibody for binding with cTnI. "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Methods of Aiding in the Diagnosis and Evaluation of Whether a Human Subject has Sustained or May have Sustained an (or has an Actual or Suspected) Injury to the Head Using Cardiac Troponin I (cTnI)

The present disclosure relates, among other methods, to a method of aiding in the diagnosis and evaluation of whether a human subject has sustained or may have sustained (or has an actual or suspected) an injury to the head using cardiac troponin I (cTnI) levels or changes in cTnI levels. Specifically, the methods described herein can aid in determining the extent of traumatic brain injury in a human subject with an actual or suspected injury to the head, e.g., determining whether the subject has mild traumatic brain injury or moderate, severe, or moderate to severe traumatic brain injury. As used here, "determining whether the subject has mild traumatic brain injury or moderate, severe, or moderate to severe traumatic brain injury" refers to the fact that the aforementioned method can be used, e.g., with other information (e.g., clinical assessment data), to determine that the subject is more likely than not to have mild traumatic brain injury, moderate, severe, or moderate to severe traumatic brain injury or no traumatic brain injury. The method can include performing an assay on a sample obtained from the human subject within about 24 hours, such as within about 2 hours, after an actual or suspected injury to the head to measure or detect a level of cardiac troponin I (cTnI) in the sample and determining whether the subject has sustained a mild, a moderate, severe, moderate to severe traumatic brain injury (TBI) or no TBI. In some embodiments, the subject is determined as having (1) a moderate, severe, or moderate to severe TBI when the level of cTnI in the sample is higher than a reference level of cTnI, or (2) a mild TBI when the level of cTnI in the sample is lower than a reference level of cTnI. The sample can be a biological sample. In some aspects, the biological sample is a whole blood sample. In other aspects, the biological sample is a serum sample. In yet other aspects, the biological sample is a plasma sample.

In some embodiments, the method can include obtaining a sample within about 24 hours, such as within about 2 hours, of an actual or suspected injury to the subject and contacting the sample with an antibody for cTnI to allow formation of a complex of the antibody and cTnI. The method also includes detecting the resulting antibody-cTnI complex.

In some embodiments, the sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of a suspect injury to the head.

In some embodiments, the sample is taken from the human subject within about 2 hours of (an actual) injury or suspected injury to the head. For example, the sample can be taken from the human subject within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours of injury or suspected injury to the head. In some embodiments, the onset of the presence of cTnI appears within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours after injury to the head.

In some embodiments, the subject may have received a Glasgow Coma Scale score before or after the level of cardiac troponin is determined at one or more time points. In certain embodiments, the subject may be suspected of having a mild traumatic brain injury based on the Glasgow Coma Scale score. In certain embodiments, the subject may be suspected of having a mild traumatic brain injury based on an abnormal head CT. In some embodiments, the subject has received a CT scan before or after the assay is performed. In some embodiments, the subject has a normal head CT.

In some embodiments, the reference level of cTnI is correlated with subjects having a moderate, severe, or moderate to severe traumatic brain injury. In some embodiments, the reference level of cTnI is correlated with a Glasgow Coma Scale score of 3-12 (moderate to severe TBI). In some embodiments, the reference level of cTnI is correlated with a Glasgow Coma Scale score of 3-8 (a severe TBI). In some embodiments, the reference level of cTnI is correlated with a Glasgow Coma Scale score of 9-13 (a moderate TBI). In some embodiments, the subject is suspected as having mild traumatic brain injury based on the Glasgow Coma Scale score. In some embodiments, the reference level of cTnI is correlated with subjects having mild traumatic brain injury. In some embodiments, the reference level of cTnI is correlated with a Glasgow Coma Scale score of 13-15 (a mild TBI).

Generally, a reference level of cTnI can also be employed as a benchmark against which to assess results obtained upon assaying a test sample for cTnI. Generally, in making such a comparison, the reference level of cTnI is obtained by running a particular assay a sufficient number of times and under appropriate conditions such that a linkage or association of analyte presence, amount or concentration with a particular stage or endpoint of TBI or with particular indicia can be made. Typically, the reference level of cTnI is obtained with assays of reference subjects (or populations of subjects). The cTnI measured can include fragments thereof, degradation products thereof, and/or enzymatic cleavage products thereof.

In certain embodiments, the reference level may be correlated with control subjects that have not sustained a head injury.

In some embodiments, the reference level of cTnI is determined by an assay having a sensitivity of between at least about 65% to about 100% and a specificity of between at least about 30% to about 100%. In some embodiments, the sensitivity is between at least about 65% to about 100%, between at least about 65% to at least about 99%, between at least about 65% to at least about 95%, between at least about 65% to at least about 90%, between at least about 65% to at least about 85%, between at least about 65% to at least about 80%, between at least about 65% to at least about 75%, between at least about 65% to at least about 70%, between at least about 75% to about 100%, between at least about 75% to at least about 99%, between at least about 75% to at least about 95%, between at least about 75% to at least about 90%, between at least about 75% to at least about 85%, between at least about 75% to at least about 80%, between at least about 85% to about 100%, between at least about 85% to at least about 99%, between at least about 85% to at least about 95%, between at least about 85% to at least about 90%, between at least about 95% to about 100%, or between at least about 95% to at least about 99%. In some embodiments, the sensitivity is at least about 65.0%, at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is at least about 100% and the specificity is at least about 100%.

In some embodiments, the amount of cardiac troponin I in the sample is from about 1 pg/mL to about 50 pg/mL, about 1 pg/mL to about 45 pg/mL, about 1 pg/mL to about 40 pg/mL, about 1 pg/mL to about 35 pg/mL, about 1 pg/mL to about 30 pg/mL, about 1 pg/mL to about 25 pg/mL, about 1 pg/mL to about 20 pg/mL, about 1 pg/mL to about 15 pg/mL, about 1 pg/mL to about 10 pg/mL, about 1 pg/mL to about 9 pg/mL, about 1 pg/mL to about 8 pg/mL, about 1 pg/mL to about 7 pg/mL, about 1 pg/mL to about 6 pg/mL, about 1 pg/mL to about 5 pg/mL, about 1 pg/mL to about 4 pg/mL, about 1 pg/mL to about 3 pg/mL, about 1 pg/mL to about 2 pg/mL, about 1 pg/mL to about 1.5 pg/mL, about 1.5 pg/mL to about 50 pg/mL, about 1.5 pg/mL to about 45 pg/mL, about 1.5 pg/mL to about 40 pg/mL, about 1.5 pg/mL to about 35 pg/mL, about 1.5 pg/mL to about 30 pg/mL, about 1.5 pg/mL to about 25 pg/mL, about 1.5 pg/mL to about 20 pg/mL, about 1.5 pg/mL to about 15 pg/mL, about 1.5 pg/mL to about 10 pg/mL, about 1.5 pg/mL to about 9 pg/mL, about 1.5 pg/mL to about 8 pg/mL, about 1.5 pg/mL to about 7 pg/mL, about 1.5 pg/mL to about 6 pg/mL, about 1.5 pg/mL to about 5 pg/mL, about 1.5 pg/mL to about 4 pg/mL, about 1.5 pg/mL to about 3 pg/mL, about 1.5 pg/mL to about 2 pg/mL, about 2 pg/mL to about 50 pg/mL, about 2 pg/mL to about 45 pg/mL, about 2 pg/mL to about 40 pg/mL, about 2 pg/mL to about 35 pg/mL, about 2 pg/mL to about 30 pg/mL, about 2 pg/mL to about 25 pg/mL, about 2 pg/mL to about 20 pg/mL, about 2 pg/mL to about 15 pg/mL, about 2 pg/mL to about 10 pg/mL, about 2 pg/mL to about 9 pg/mL, about 2 pg/mL to about 8 pg/mL, about 2 pg/mL to about 7 pg/mL, about 2 pg/mL to about 6 pg/mL, about 2 pg/mL to about 5 pg/mL, about 2 pg/mL to about 4 pg/mL, about 2 pg/mL to about 3 pg/mL, about 3 pg/mL to about 50 pg/mL, about 3 pg/mL to about 45 pg/mL, about 3 pg/mL to about 40 pg/mL, about 3 pg/mL to about 35 pg/mL, about 3 pg/mL to about 30 pg/mL, about 3 pg/mL to about 25 pg/mL, about 3 pg/mL to about 20 pg/mL, about 3 pg/mL to about 15 pg/mL, about 3 pg/mL to about 10 pg/mL, about 3 pg/mL to about 9 pg/mL, about 3 pg/mL to about 8 pg/mL, about 3 pg/mL to about 7 pg/mL, about 3 pg/mL to about 6 pg/mL, about 3 pg/mL to about 5 pg/mL, about 3 pg/mL to about 4 pg/mL, about 4 pg/mL to about 50 pg/mL, about 4 pg/mL to about 45 pg/mL, about 4 pg/mL to about 40 pg/mL, about 4 pg/mL to about 35 pg/mL, about 4 pg/mL to about 30 pg/mL, about 4 pg/mL to about 25 pg/mL, about 4 pg/mL to about 20 pg/mL, about 4 pg/mL to about 15 pg/mL, about 4 pg/mL to about 10 pg/mL, about 4 pg/mL to about 9 pg/mL, about 4 pg/mL to about 8 pg/mL, about 4 pg/mL to about 7 pg/mL, about 4 pg/mL to about 6 pg/mL, about 4 pg/mL to about 5 pg/mL, about 5 pg/mL to about 50 pg/mL, about 5 pg/mL to about 45 pg/mL, about 5 pg/mL to about 40 pg/mL, about 5 pg/mL to about 35 pg/mL, about 5 pg/mL to about 30 pg/mL, about 5 pg/mL to about 25 pg/mL, about 5 pg/mL to about 20 pg/mL, about 5 pg/mL to about 15 pg/mL, about 5 pg/mL to about 10 pg/mL, about 5 pg/mL to about 9 pg/mL, about 5 pg/mL to about 8 pg/mL, about 5 pg/mL to about 7 pg/mL, about 5 pg/mL to about 6 pg/mL, about 6 pg/mL to about 50 pg/mL, about 6 pg/mL to about 45 pg/mL, about 6 pg/mL to about 40 pg/mL, about 6 pg/mL to about 35 pg/mL, about 6 pg/mL to about 30 pg/mL, about 6 pg/mL to about 25 pg/mL, about 6 pg/mL to about 20 pg/mL, about 6 pg/mL to about 15 pg/mL, about 6 pg/mL to about 10 pg/mL, about 6 pg/mL to about 9 pg/mL, about 6 pg/mL to about 8 pg/mL, about 6 pg/mL to about 7 pg/mL, about 7 pg/mL to about 50 pg/mL, about 7 pg/mL to about 45 pg/mL, about 7 pg/mL to about 40 pg/mL, about 7 pg/mL to about 35 pg/mL, about 7 pg/mL to about 30 pg/mL, about 7 pg/mL to about 25 pg/mL, about 7 pg/mL to about 20 pg/mL, about 7 pg/mL to about 15 pg/mL, about 7 pg/mL to about 10 pg/mL, about 7 pg/mL to about 9 pg/mL, about 7 pg/mL to about 8 pg/mL, about 8 pg/mL to about 50 pg/mL, about 8 pg/mL to about 45 pg/mL, about 8 pg/mL to about 40 pg/mL, about 8 pg/mL to about 35 pg/mL, about 8 pg/mL to about 30 pg/mL, about 8 pg/mL to about 25 pg/mL, about 8 pg/mL to about 20 pg/mL, about 8 pg/mL to about 15 pg/mL, about 8 pg/mL to about 10 pg/mL, about 8 pg/mL to about 9 pg/mL, about 9 pg/mL to about 50 pg/mL, about 9 pg/mL to about 45 pg/mL, about 9 pg/mL to about 40 pg/mL, about 9 pg/mL to about 35 pg/mL, about 9 pg/mL to about 30 pg/mL, about 9 pg/mL to about 25 pg/mL, about 9 pg/mL to about 20 pg/mL, about 9 pg/mL to about 15 pg/mL, about 9 pg/mL to about 10 pg/mL, about 10 pg/mL to about 50 pg/mL, about 10 pg/mL to about 45 pg/mL, about 10 pg/mL to about 40 pg/mL, about 10 pg/mL to about 35 pg/mL, about 10 pg/mL to about 30 pg/mL, about 10 pg/mL to about 25 pg/mL, about 10 pg/mL to about 20 pg/mL, about 10 pg/mL to about 15 pg/mL, about 20 pg/mL to about 50 pg/mL, about 20 pg/mL to about 45 pg/mL, about 20 pg/mL to about 40 pg/mL, about 20 pg/mL to about 35 pg/mL, about 20 pg/mL to about 30 pg/mL, or about 20 pg/mL to about 25 pg/mL. In some embodiments, the amount of cTnI can be at least about 0.5 pg/mL, at least about 1.0 pg/mL, at least about 1.5 pg/mL, at least about 2.0 pg/mL, at least about 2.5 pg/mL, at least about 3.0 pg/mL, at least about 4.0 pg/mL, at least about 5.0 pg/mL, at least about 6.0 pg/mL, at least about 7.0 pg/mL, at least about 8.0, pg/mL, at least about 9.0 pg/mL, at least about 10 pg/mL, at least about 15 pg/mL, at least about 20 pg/mL, at least about 25 pg/mL, at least about 30 pg/mL, at least about 35 pg/mL, at least about 40 pg/mL, at least about 45 pg/mL, or at least about 50 pg/mL.

In addition to performing the above described methods, one skilled in the art (e.g., physician) would understand and know how to perform additional testing in order to detect or assess other comorbidities (e.g., other diseases, disorders, or conditions other than TBI). Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In one embodiment, in order to confirm that the changes in amounts or levels cTnI in the methods described herein are attributable to a head injury or a suspected injury to the head of a subject and not the result of an acute cardiac syndrome (such as a myocardial infarction, heart failure, etc.), a physician or other healthcare provider could conduct or perform one or more additional tests or procedures to confirm the absence of an acute cardiac syndrome. Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In some embodiments, the method further includes treating the human subject assessed as having a moderate, severe, or a moderate to severe traumatic brain injury with a traumatic brain injury treatment, as described below. In some embodiments, the method further includes monitoring the human subject assessed as having mild traumatic brain injury, as described below. In some embodiments, the method further includes ordering additional tests to obtain further clinical information about the traumatic brain injury. In some embodiments, the method includes treating the human subject assessed as having a mild, moderate, severe, or a moderate to severe brain injury with a cardioprotective treatment to protect the heart as described below.

The nature of the assay employed in the methods described herein is not critical and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in a clinical chemistry format such as would be known by one of ordinary skill in the art. Such assays are described in further detail herein in Sections 11-13. It is known in the art that the values (e.g., reference levels, cutoffs, thresholds, specificities, sensitivities, concentrations of calibrators and/or controls etc.) used in an assay that employs specific sample type (e.g., such as an immunoassay that utilizes serum or a point-of-care device that employs whole blood) can be extrapolated to other assay formats using known techniques in the art, such as assay standardization. For example, one way in which assay standardization can be performed is by applying a factor to the calibrator employed in the assay to make the sample concentration read higher or lower to get a slope that aligns with the comparator method. Other methods of standardizing results obtained on one assay to another assay are well known and have been described in the literature (See, for example, David Wild, *Immunoassay Handbook*, 4$^{th}$ edition, chapter 3.5, pages 315-322, the contents of which are herein incorporated by reference).

3. Method of Aiding in the Determination of Whether to Perform a CT Scan on a Human Subject Who May have Sustained or has Sustained an (or has an Actual or Suspected) Injury to the Head Using Cardiac Troponin I (cTnI)

The present disclosure relates, among other methods, to a method of aiding in determining whether to perform a computerized tomography (CT) scan on a human subject who has sustained or may have sustained an (or has an actual or suspected) injury to the head. As used here, "determination of whether to perform a CT scan on a human subject" refers to the fact that the aforementioned method can be used, e.g., with other information (e.g., clinical assessment data), to determine that the subject is more likely than not to have a positive head CT scan. Specifically, such a method can comprise the steps of: (a) performing an assay on a sample obtained from the subject within about 24 hours, such as within about 2 hours, after an actual or suspected injury to the head to measure or detect a level of cardiac troponin I (cTnI) in the sample; and (b) performing a CT scan on the subject when the level of cTnI in the sample is higher than a reference level of cTnI and not performing a CT scan on the subject when the level of cTnI in the sample is lower than a reference level of cTnI. The sample can be a biological sample.

In some embodiments, the method can include obtaining a sample within about 24 hours, such as within about 2 hours, of an actual or suspected injury to the subject and contacting the sample with an antibody for cTnI to allow formation of a complex of the antibody and cTnI. The method also includes detecting the resulting antibody-cTnI complex.

In some embodiments, the sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of an actual or suspect injury to the head.

In some embodiments, the sample is taken from the human subject within about 2 hours of injury or suspected injury to the head. For example, the sample can be taken from the human subject within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours of injury or suspected injury to the head. In some embodiments, the onset of the presence of cTnI appears within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours after injury to the head.

In some embodiments, the subject has received a CT scan before or after the assay is performed. In some embodiments, the subject is suspected as having a traumatic brain injury based on the CT scan. In some embodiments, the reference level of cTnI is correlated with positive head CT scan.

Generally, a reference level of cTnI can be employed as a benchmark against which to assess results obtained upon assaying a test sample for cTnI. Generally, in making such a comparison, the reference level of cTnI is obtained by running a particular assay a sufficient number of times and under appropriate conditions such that a linkage or association of analyte presence, amount or concentration with a particular stage or endpoint of TBI or with particular indicia can be made. Typically, the reference level of cTnI is obtained with assays of reference subjects (or populations of subjects). The cTnI measured can include fragments thereof, degradation products thereof, and/or enzymatic cleavage products thereof.

In some embodiments, the reference level of cTnI is determined by an assay having a sensitivity of between at least about 65% to about 100% and a specificity of between at least about 30% to about 100%. In some embodiments, the sensitivity is between at least about 65% to about 100%, between at least about 65% to at least about 99%, between at least about 65% to at least about 95%, between at least about 65% to at least about 90%, between at least about 65% to at least about 85%, between at least about 65% to at least about 80%, between at least about 65% to at least about 75%, between at least about 65% to at least about 70%, between at least about 75% to about 100%, between at least about 75% to at least about 99%, between at least about 75% to at least about 95%, between at least about 75% to at least about 90%, between at least about 75% to at least about 85%, between at least about 75% to at least about 80%, between at least about 85% to about 100%, between at least about 85% to at least about 99%, between at least about 85% to at least about 95%, between at least about 90% to at least about 95%, between at least about 95% to about 100%, or between at least about 95% to at least about 99%. In some embodiments, the sensitivity is at least about 65.0%, at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is at least about 100% and the specificity is at least about 100%.

In some embodiments, the amount of cardiac troponin I in the sample is from about 1 pg/mL to about 50 pg/mL, about 1 pg/mL to about 45 pg/mL, about 1 pg/mL to about 40 pg/mL, about 1 pg/mL to about 35 pg/mL, about 1 pg/mL to about 30 pg/mL, about 1 pg/mL to about 25 pg/mL, about 1 pg/mL to about 20 pg/mL, about 1 pg/mL to about 15 pg/mL, about 1 pg/mL to about 10 pg/mL, about 1 pg/mL to about 9 pg/mL, about 1 pg/mL to about 8 pg/mL, about 1 pg/mL to about 7 pg/mL, about 1 pg/mL to about 6 pg/mL, about 1 pg/mL to about 5 pg/mL, about 1 pg/mL to about 4 pg/mL, about 1 pg/mL to about 3 pg/mL, about 1 pg/mL to about 2 pg/mL, about 1 pg/mL to about 1.5 pg/mL, about 1.5 pg/mL to about 50 pg/mL, about 1.5 pg/mL to about 45 pg/mL, about 1.5 pg/mL to about 40 pg/mL, about 1.5 pg/mL to about 35 pg/mL, about 1.5 pg/mL to about 30 pg/mL, about 1.5 pg/mL to about 25 pg/mL, about 1.5 pg/mL to about 20 pg/mL, about 1.5 pg/mL to about 15 pg/mL, about 1.5 pg/mL to about 10 pg/mL, about 1.5 pg/mL to about 9 pg/mL, about 1.5 pg/mL to about 8 pg/mL, about 1.5 pg/mL to about 7 pg/mL, about 1.5 pg/mL to about 6 pg/mL, about 1.5 pg/mL to about 5 pg/mL, about 1.5 pg/mL to about 4 pg/mL, about 1.5 pg/mL to about 3 pg/mL, about 1.5 pg/mL to about 2 pg/mL, about 2 pg/mL to about 50 pg/mL, about 2 pg/mL to about 45 pg/mL, about 2 pg/mL to about 40 pg/mL, about 2 pg/mL to about 35 pg/mL, about 2 pg/mL to about 30 pg/mL, about 2 pg/mL to about 25 pg/mL, about 2 pg/mL to about 20 pg/mL, about 2 pg/mL to about 15 pg/mL, about 2 pg/mL to about 10 pg/mL, about 2 pg/mL to about 9 pg/mL, about 2 pg/mL to about 8 pg/mL, about 2 pg/mL to about 7 pg/mL, about 2 pg/mL to about 6 pg/mL, about 2 pg/mL to about 5 pg/mL, about 2 pg/mL to about 4 pg/mL, about 2 pg/mL to about 3 pg/mL, about 3 pg/mL to about 50 pg/mL, about 3 pg/mL to about 45 pg/mL, about 3 pg/mL to about 40 pg/mL, about 3 pg/mL to about 35 pg/mL, about 3 pg/mL to about 30 pg/mL, about 3 pg/mL to about 25 pg/mL, about 3 pg/mL to about 20 pg/mL, about 3 pg/mL to about 15 pg/mL, about 3 pg/mL to about 10 pg/mL, about 3 pg/mL to about 9 pg/mL, about 3 pg/mL to about 8 pg/mL, about 3 pg/mL to about 7 pg/mL, about 3 pg/mL to about 6 pg/mL, about 3 pg/mL to about 5 pg/mL, about 3 pg/mL to about 4 pg/mL, about 4 pg/mL to about 50 pg/mL, about 4 pg/mL to about 45 pg/mL, about 4 pg/mL to about 40 pg/mL, about 4 pg/mL to about 35 pg/mL, about 4 pg/mL to about 30 pg/mL, about 4 pg/mL to about 25 pg/mL, about 4 pg/mL to about 20 pg/mL, about 4 pg/mL to about 15 pg/mL, about 4 pg/mL to about 10 pg/mL, about 4 pg/mL to about 9 pg/mL, about 4 pg/mL to about 8 pg/mL, about 4 pg/mL to about 7 pg/mL, about 4 pg/mL to about 6 pg/mL, about 4 pg/mL to about 5 pg/mL, about 5 pg/mL to about 50 pg/mL, about 5 pg/mL to about 45 pg/mL, about 5 pg/mL to about 40 pg/mL, about 5 pg/mL to about 35 pg/mL, about 5 pg/mL to about 30 pg/mL, about 5 pg/mL to about 25 pg/mL, about 5 pg/mL to about 20 pg/mL, about 5 pg/mL to about 15 pg/mL, about 5 pg/mL to about 10 pg/mL, about 5 pg/mL to about 9 pg/mL, about 5 pg/mL to about 8 pg/mL, about 5 pg/mL to about 7 pg/mL, about 5 pg/mL to about 6 pg/mL, about 6 pg/mL to about 50 pg/mL, about 6 pg/mL to about 45 pg/mL, about 6 pg/mL to about 40 pg/mL, about 6 pg/mL to about 35 pg/mL, about 6 pg/mL to about 30 pg/mL, about 6 pg/mL to about 25 pg/mL, about 6 pg/mL to about 20 pg/mL, about 6 pg/mL to about 15 pg/mL, about 6 pg/mL to about 10 pg/mL, about 6 pg/mL to about 9 pg/mL, about 6 pg/mL to about 8 pg/mL, about 6 pg/mL to about 7 pg/mL, about 7 pg/mL to about 50 pg/mL, about 7 pg/mL to about 45 pg/mL, about 7 pg/mL to about 40 pg/mL, about 7 pg/mL to about 35 pg/mL, about 7 pg/mL to about 30 pg/mL, about 7 pg/mL to about 25 pg/mL, about 7 pg/mL to about 20 pg/mL, about 7 pg/mL to about 15 pg/mL, about 7 pg/mL to about 10 pg/mL, about 7 pg/mL to about 9 pg/mL, about 7 pg/mL to about 8 pg/mL, about 8 pg/mL to about 50 pg/mL, about 8 pg/mL to about 45 pg/mL, about 8 pg/mL to about 40 pg/mL, about 8 pg/mL to about 35 pg/mL, about 8 pg/mL to about 30 pg/mL, about 8 pg/mL to about 25 pg/mL, about 8 pg/mL to about 20 pg/mL, about 8 pg/mL to about 15 pg/mL, about 8 pg/mL to about 10 pg/mL, about 8 pg/mL to about 9 pg/mL, about 9 pg/mL to about 50 pg/mL, about 9 pg/mL to about 45 pg/mL, about 9 pg/mL to about 40 pg/mL, about 9 pg/mL to about 35 pg/mL, about 9 pg/mL to about 30 pg/mL, about 9 pg/mL to about 25 pg/mL, about 9 pg/mL to about 20 pg/mL, about 9 pg/mL to about 15 pg/mL, about 9 pg/mL to about 10 pg/mL, about 10 pg/mL to about 50 pg/mL, about 10 pg/mL to about 45 pg/mL, about 10 pg/mL to about 40 pg/mL, about 10 pg/mL to about 35 pg/mL, about 10 pg/mL to about 30 pg/mL, about 10 pg/mL to about 25 pg/mL, about 10 pg/mL to about 20 pg/mL, about 10 pg/mL to about 15 pg/mL, about 20 pg/mL to about 50 pg/mL, about 20 pg/mL to about 45 pg/mL, about 20 pg/mL to about 40 pg/mL, about 20 pg/mL to about 35 pg/mL, about 20 pg/mL to about 30 pg/mL, or about 20 pg/mL to about 25 pg/mL. In some embodiments, the amount of cTnI can be at least about 0.5 pg/mL, at least about 1.0 pg/mL, at least about 1.5 pg/mL, at least about 2.0 pg/mL, at least about 2.5 pg/mL, at least about 3.0 pg/mL, at least about 4.0 pg/mL, at least about 5.0 pg/mL, at least about 6.0 pg/mL, at least about 7.0 pg/mL, at least about 8.0, pg/mL, at least about 9.0 pg/mL, at least about 10 pg/mL, at least about 15 pg/mL, at least about 20 pg/mL, at least about 25 pg/mL, at least about 30 pg/mL, at least about 35 pg/mL, at least about 40 pg/mL, at least about 45 pg/mL, or at least about 50 pg/mL.

In addition to performing the above described methods, one skilled in the art (e.g., physician) would understand and know how to perform additional testing in order to detect or assess other comorbidities (e.g., other diseases, disorders, or conditions other than TBI). Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In one embodiment, in order to confirm that the changes in amounts or levels cTnI in the methods described herein are attributable to a head injury or a suspected injury to the head of a subject and not the result of an acute cardiac syndrome (such as a myocardial infarction, heart failure, etc.), a physician or other healthcare provider could conduct or perform one or more additional tests or procedures to confirm the absence of an acute cardiac syndrome. Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In some embodiments, the method further includes treating the human subject with a traumatic brain injury treatment and/or monitoring the human subject, as described below. In some embodiments, the method further includes ordering additional tests to obtain further clinical information about the traumatic brain injury. In some embodiments, the method includes treating the human subject assessed as having a mild, moderate, severe, or a moderate to severe brain injury with a cardioprotective treatment to protect the heart as described below.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Also, the assay can be employed in clinical chemistry format such as would be known by one skilled in the art. Such assays are described in further detail herein in Sections 11-13.

4. Methods of Aiding in the Diagnosis and Evaluation of Whether a Human Subject May have or has Sustained an (or has an Actual or Suspected) Injury to the Head Based on Changes in Cardiac Troponin I (cTnI) Levels The present disclosure relates, among other methods, to a method of aiding in the diagnosis and evaluation of whether a human subject has sustained or may have sustained an (or has an actual or suspected) injury to the head. The method can aid in determining the extent of traumatic brain injury in a human subject with an actual or suspected injury to the head, e.g., determining whether the subject has mild traumatic brain injury or a moderate, severe, or moderate to severe traumatic brain injury. As used here, "determining whether the subject has mild traumatic brain injury or moderate, severe, or moderate to severe traumatic brain injury" refers to the fact that the aforementioned method can be used, e.g., with other information (e.g., clinical assessment data), to determine that the subject is more likely than not to have mild traumatic brain injury or moderate, severe, or moderate to severe traumatic brain injury. The method can include performing an assay on at least two samples obtained from the subject, the first sample taken from the subject within about 24 hours, such as within about 2 hours, after an injury or suspected injury to the head and the second sample taken from the subject from about 3 to about 6 hours after the first sample is taken; detecting in the at least two samples cardiac troponin I (cTnI); and determining whether the subject has sustained a mild or a moderate, severe, or moderate to severe traumatic brain injury (TBI). The subject is determined as having (1) a moderate, severe, or moderate to severe traumatic brain injury when the level of cTnI decreases or increases by at least an absolute amount from the first sample to the second sample or (2) a mild traumatic brain injury when there is no decrease or increase by at least an absolute amount in the level of cTnI from the first sample to the second sample. The samples can be biological samples.

In an alternative, the method can include performing an assay on at least two samples obtained from the subject, the first sample taken from the subject within about 24 hours, such as within about 2 hours, after an injury or suspected injury to the head and the second sample taken from the subject from about 3 to about 6 hours after the first sample is taken; detecting in the at least two samples cTnI; and determining whether the subject has sustained a mild or a moderate, severe, or moderate to severe traumatic brain injury (TBI), wherein the subject is determined as having (1) a moderate, severe, or a moderate to severe traumatic brain injury when the level of cTnI decreases or increases by at least a first absolute amount from the first sample to the second sample or (2) a mild traumatic brain injury when there is no decrease or increase by at least a second absolute amount in the level of cTnI from the first sample to the second sample. The samples can be biological samples.

In some embodiments, the method can include contacting the samples with an antibody for cTnI, to allow formation of a complex of the antibody and cTnI. The method also includes detecting the resulting antibody-cTnI complex to determine the levels of cTnI for each of the first sample and second sample. The onset of the presence of cTnI appears within about 0 to about 2 hours after the onset of the suspected injury. In some embodiments, the onset of the presence of cTnI appears within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours after injury to the head.

In some embodiments, the first sample is obtained at a first time point within about 24 hours of the suspected injury and the second sample is obtained at second time point, or optionally a third time point or fourth time point, after the first time point. In some embodiments, the first sample is taken within about 24 hours after the suspected injury and the second sample is taken within about 3 hours to about 6 hours after the first sample. In some embodiments, the first sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of an injury or suspected injury to the head.

In some embodiments, the first sample is obtained at a first time point within about 2 hours of the suspected injury and the second sample is obtained at second time point, or optionally a third time point or fourth time point, after the first time point. In some embodiments, the first sample is taken within about 2 hours after the suspected injury and the second sample is taken within about 3 hours to about 6 hours after the first sample. In some embodiments, the first sample is taken about 0 to about 2 hours after the injury or suspected injury to the head. For example, the first sample can be taken between about 0 to about 2 hours, about 0 hours to about 90 minutes, about 0 hours to about 60 minutes, about 0 hours to about 45 minutes, about 0 hours to about 30 minutes, about 0 hours to about 20 minutes, about 0 hours to about 15 minutes, about 0 hours to about 10 minutes, about 0 hours to about 5 minutes, about 5 minutes to about 90 minutes, about 5 minutes to about 60 minutes, about 5 minutes to about 45 minutes, about 5 minutes to about 30 minutes, about 5 minutes to about 20 minutes, about 5 minutes to about 15 minutes, about 5 minutes to about 10 minutes, about 10 minutes to about 90 minutes, about 10 minutes to about 60 minutes, about 10 minutes to about 45 minutes, about 10 minutes to about 30 minutes, about 10 minutes to about 20 minutes, about 10 minutes to about 15 minutes, about 15 minutes to about 90 minutes, about 15 minutes to about 60 minutes, about 15 minutes to about 45 minutes, about 15 minutes to about 30 minutes, about 15 minutes to about 20 minutes, about 20 minutes to about 90 minutes, about 20 minutes to about 60 minutes, about 20 minutes to about 45 minutes, or about 20 minutes to about 30 minutes after the suspected injury. For example, the first sample can be taken from the human subject within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours of injury or suspected injury to the head.

In some embodiments, the second sample is taken about 1 hour to about 10 hours after the first time point, such as about 3 hours to about 6 hours after the first time point. In some embodiments, the second sample is taken about 1 hour, about 2 hours, about 3 hours, about 4 hours, about 5 hours, about 6 hours, about 7 hours, about 8 hours, about 9 hours, or about 10 hours after the first sample.

In some embodiments, the subject may have received a Glasgow Coma Scale score before or after the level of cardiac troponin is determined at one or more time points. In certain embodiments, the subject may be suspected of having a mild traumatic brain injury based on the Glasgow Coma Scale score. In certain embodiments, the subject may be suspected of having a mild traumatic brain injury based on an abnormal head CT. In some embodiments, the subject has received a CT scan before or after the assay is performed. In some embodiments, the subject has a normal head CT.

In some embodiments, the reference level of cTnI is correlated with subjects having a moderate, severe, or moderate to severe traumatic brain injury. In some embodiments, the reference level of cTnI is correlated with a Glasgow Coma Scale score of 3-12 (moderate to severe TBI). In some embodiments, the reference level of cTnI is correlated with a Glasgow Coma Scale score of 3-8 (a severe TBI). In some embodiments, the reference level of cTnI is correlated with a Glasgow Coma Scale score of 9-13 (a moderate TBI). In some embodiments, the subject is suspected as having mild traumatic brain injury based on the Glasgow Coma Scale score. In some embodiments, the reference level of cTnI is correlated with subjects having mild traumatic brain injury. In some embodiments, the reference level of cTnI is correlated with a Glasgow Coma Scale score of 13-15 (a mild TBI).

In some embodiments, the absolute amount can be determined by an assay having a sensitivity of between at least about 65% to about 100% and a specificity of between at least about 65% to about 100%. For example, the absolute amount can be determined by an assay having a sensitivity of between at least about 80% to 100% and a specificity of between at least about 65% to 100%. In some embodiments, the sensitivity is at least about 65.0%, the sensitivity is at least about 70.0%, at least about 75.0%, at least about 80.0%, at least about 85.0%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 65.0%, at least about 70.0%, at least about 75.0%, at least about 80.0%, at least about 85.0%, at least about 90.0%, at least about 91.0%, at least about 92.0%, at least about 93. %, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 100% and the specificity is at least about 75%, the sensitivity is at least about 99% and the specificity is at least about 99%, or the sensitivity is at least about 87% and the specificity is at least about 95%.

In some embodiments, the absolute amount of cardiac troponin I in the sample is from about 1 pg/mL to about 50 pg/mL, about 1 pg/mL to about 45 pg/mL, about 1 pg/mL to about 40 pg/mL, about 1 pg/mL to about 35 pg/mL, about 1 pg/mL to about 30 pg/mL, about 1 pg/mL to about 25 pg/mL, about 1 pg/mL to about 20 pg/mL, about 1 pg/mL to about 15 pg/mL, about 1 pg/mL to about 10 pg/mL, about 1 pg/mL to about 9 pg/mL, about 1 pg/mL to about 8 pg/mL, about 1 pg/mL to about 7 pg/mL, about 1 pg/mL to about 6 pg/mL, about 1 pg/mL to about 5 pg/mL, about 1 pg/mL to about 4 pg/mL, about 1 pg/mL to about 3 pg/mL, about 1 pg/mL to about 2 pg/mL, about 1 pg/mL to about 1.5 pg/mL, about 1.5 pg/mL to about 50 pg/mL, about 1.5 pg/mL to about 45 pg/mL, about 1.5 pg/mL to about 40 pg/mL, about 1.5 pg/mL to about 35 pg/mL, about 1.5 pg/mL to about 30 pg/mL, about 1.5 pg/mL to about 25 pg/mL, about 1.5 pg/mL to about 20 pg/mL, about 1.5 pg/mL to about 15 pg/mL, about 1.5 pg/mL to about 10 pg/mL, about 1.5 pg/mL to about 9 pg/mL, about 1.5 pg/mL to about 8 pg/mL, about 1.5 pg/mL to about 7 pg/mL, about 1.5 pg/mL to about 6 pg/mL, about 1.5 pg/mL to about 5 pg/mL, about 1.5 pg/mL to about 4 pg/mL, about 1.5 pg/mL to about 3 pg/mL, about 1.5 pg/mL to about 2 pg/mL, about 2 pg/mL to about 50 pg/mL, about 2 pg/mL to about 45 pg/mL, about 2 pg/mL to about 40 pg/mL, about 2 pg/mL to about 35 pg/mL, about 2 pg/mL to about 30 pg/mL, about 2 pg/mL to about 25 pg/mL, about 2 pg/mL to about 20 pg/mL, about 2 pg/mL to about 15 pg/mL, about 2 pg/mL to about 10 pg/mL, about 2 pg/mL to about 9 pg/mL, about 2 pg/mL to about 8 pg/mL, about 2 pg/mL to about 7 pg/mL, about 2 pg/mL to about 6 pg/mL, about 2 pg/mL to about 5 pg/mL, about 2 pg/mL to about 4 pg/mL, about 2 pg/mL to about 3 pg/mL, about 3 pg/mL to about 50 pg/mL, about 3 pg/mL to about 45 pg/mL, about 3 pg/mL to about 40 pg/mL, about 3 pg/mL to about 35 pg/mL, about 3 pg/mL to about 30 pg/mL, about 3 pg/mL to about 25 pg/mL, about 3 pg/mL to about 20 pg/mL, about 3 pg/mL to about 15 pg/mL, about 3 pg/mL to about 10 pg/mL, about 3 pg/mL to about 9 pg/mL, about 3 pg/mL to about 8 pg/mL, about 3 pg/mL to about 7 pg/mL, about 3 pg/mL to about 6 pg/mL, about 3 pg/mL to about 5 pg/mL, about 3 pg/mL to about 4 pg/mL, about 4 pg/mL to about 50 pg/mL, about 4 pg/mL to about 45 pg/mL, about 4 pg/mL to about 40 pg/mL, about 4 pg/mL to about 35 pg/mL, about 4 pg/mL to about 30 pg/mL, about 4 pg/mL to about 25 pg/mL, about 4 pg/mL to about 20 pg/mL, about 4 pg/mL to about 15 pg/mL, about 4 pg/mL to about 10 pg/mL, about 4 pg/mL to about 9 pg/mL, about 4 pg/mL to about 8 pg/mL, about 4 pg/mL to about 7 pg/mL, about 4 pg/mL to about 6 pg/mL, about 4 pg/mL to about 5 pg/mL, about 5 pg/mL to about 50 pg/mL, about 5 pg/mL to about 45 pg/mL, about 5 pg/mL to about 40 pg/mL, about 5 pg/mL to about 35 pg/mL, about 5 pg/mL to about 30 pg/mL, about 5 pg/mL to about 25 pg/mL, about 5 pg/mL to about 20 pg/mL, about 5 pg/mL to about 15 pg/mL, about 5 pg/mL to about 10 pg/mL, about 5 pg/mL to about 9 pg/mL, about 5 pg/mL to about 8 pg/mL, about 5 pg/mL to about 7 pg/mL, about 5 pg/mL to about 6 pg/mL, about 6 pg/mL to about 50 pg/mL, about 6 pg/mL to about 45 pg/mL, about 6 pg/mL to about 40 pg/mL, about 6 pg/mL to about 35 pg/mL, about 6 pg/mL to about 30 pg/mL, about 6 pg/mL to about 25 pg/mL, about 6 pg/mL to about 20 pg/mL, about 6 pg/mL to about 15 pg/mL, about 6 pg/mL to about 10 pg/mL, about 6 pg/mL to about 9 pg/mL, about 6 pg/mL to about 8 pg/mL, about 6 pg/mL to about 7 pg/mL, about 7 pg/mL to about 50 pg/mL, about 7 pg/mL to about 45 pg/mL, about 7 pg/mL to about 40 pg/mL, about 7 pg/mL to about 35 pg/mL, about 7 pg/mL to about 30 pg/mL, about 7 pg/mL to about 25 pg/mL, about 7 pg/mL to about 20 pg/mL, about 7 pg/mL to about 15 pg/mL, about 7 pg/mL to about 10 pg/mL, about 7 pg/mL to about 9 pg/mL, about 7 pg/mL to about 8 pg/mL, about 8 pg/mL to about 50 pg/mL, about 8 pg/mL to about 45 pg/mL, about 8 pg/mL to about 40 pg/mL, about 8 pg/mL to about 35 pg/mL, about 8 pg/mL to about 30 pg/mL, about 8 pg/mL to about 25 pg/mL, about 8 pg/mL to about 20 pg/mL, about 8 pg/mL to about 15 pg/mL, about 8 pg/mL to about 10 pg/mL, about 8 pg/mL to about 9 pg/mL, about 9 pg/mL to about 50 pg/mL, about 9 pg/mL to about 45 pg/mL, about 9 pg/mL to about 40 pg/mL, about 9 pg/mL to about 35 pg/mL, about 9 pg/mL to about 30 pg/mL, about 9 pg/mL to about 25 pg/mL, about 9 pg/mL to about 20 pg/mL, about 9 pg/mL to about 15 pg/mL, about 9 pg/mL to about 10 pg/mL, about 10 pg/mL to about 50 pg/mL, about 10 pg/mL to about 45 pg/mL, about 10 pg/mL to about 40 pg/mL, about 10 pg/mL to about 35 pg/mL, about 10 pg/mL to about 30 pg/mL, about 10 pg/mL to about 25 pg/mL, about 10 pg/mL to about 20 pg/mL, about 10 pg/mL to about 15 pg/mL, about 20 pg/mL to about 50 pg/mL, about 20 pg/mL to about 45 pg/mL, about 20 pg/mL to about 40 pg/mL, about 20 pg/mL to about 35 pg/mL, about 20 pg/mL to about 30 pg/mL, or about 20 pg/mL to about 25 pg/mL. In some embodiments, the absolute amount can be at least about 0.5 pg/mL, at least about 1.0 pg/mL, at least about 1.5 pg/mL, at least about 2.0 pg/mL, at least about 2.5 pg/mL, at least about 3.0 pg/mL, at least about 4.0 pg/mL, at least about 5.0 pg/mL, at least about 6.0 pg/mL, at least about 7.0 pg/mL, at least about 8.0, pg/mL, at least about 9.0 pg/mL, at least about 10 pg/mL, at least about 15 pg/mL, at least about 20 pg/mL, at least about 25 pg/mL, at least about 30 pg/mL, at least about 35 pg/mL, at least about 40 pg/mL, at least about 45 pg/mL, or at least about 50 pg/mL.

In addition to performing the above described methods, one skilled in the art (e.g., physician) would understand and know how to perform additional testing in order to detect or assess other comorbidities (e.g., other diseases, disorders, or conditions other than TBI). Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In one embodiment, in order to confirm that the changes in amounts or levels cTnI in the methods described herein are attributable to a head injury or a suspected injury to the head of a subject and not the result of an acute cardiac syndrome (such as a myocardial infarction, heart failure, etc.), a physician or other healthcare provider could conduct or perform one or more additional tests or procedures to confirm the absence of an acute cardiac syndrome. Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In some embodiments, the method further includes treating the human subject assessed as having a moderate, severe, or moderate to severe traumatic brain injury with a traumatic brain injury treatment, as described below. In some embodiments, the method further includes monitoring the human subject assessed as having mild traumatic brain injury, as described below. In some embodiments, the method further includes ordering additional tests to obtain further clinical information about the traumatic brain injury. In some embodiments, the method includes treating the human subject assessed as having a mild, moderate, severe, or a moderate to severe brain injury with a cardioprotective treatment to protect the heart as described below.

The nature of the assay employed in the methods described herein is not critical, and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Also, the assay can be employed in clinical chemistry format such as would be known by one skilled in the art. Such assays are described in further detail herein in Sections 11-13.

5. Method of Aiding in the Determination of Whether to Perform a CT Scan on a Human Subject Who May have Sustained or Sustained (or has an Actual or Suspected) an Injury to the Head Based on Changes in Cardiac Troponin I (cTnI) Levels The present disclosure relates, among other methods, to a method of aiding in determining whether to perform a computerized tomography (CT) scan on a human subject who has sustained or may have sustained an (or has an actual or suspected) injury to the head. As used here, "determination of whether to perform a CT scan on a human subject" refers to the fact that the aforementioned method can be used, e.g., with other information (e.g., clinical assessment data), to determine that the subject is more likely than not to have a positive head CT scan. Specifically, such a method can comprise the steps of: performing an assay on at least two samples obtained from the subject, the first sample taken from the subject within about 24 hours, such as within about 2 hours, of the suspected injury and the second sample taken from the subject from about 3 to about 6 hours after the first sample is taken; detecting in the at least two samples cardiac troponin I (cTnI); and performing a CT scan on the subject when the level of cTnI decreases or increases by at least an absolute amount from the first sample to the second sample and not performing a CT scan on the subject when there is no decrease or increase by at least an absolute amount in the level of cTnI from the first sample to the second sample. The samples can be biological samples.

In some embodiments, the method can include contacting the samples with an antibody for cTnI, to allow formation of a complex of the antibody and cTnI. The method also includes detecting the resulting antibody-cTnI complex to determine the levels of cTnI for each of the first sample and second sample. The onset of the presence of cTnI appears within about 0 to about 24 hours, such as within about 2 hours, after the onset of the suspected injury. In some embodiments, the onset of the presence of cTnI appears within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, or about 2 hours after injury to the head.

In some embodiments, the first sample is obtained at a first time point within about 24 hours of the suspected injury and the second sample is obtained at second time point, or optionally a third time point or fourth time point, after the first time point. In some embodiments, the first sample is taken within about 24 hours after the suspected injury and the second sample is taken within about 3 hours to about 6 hours after the first sample. In some embodiments, the first sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of an actual or suspected injury to the head.

In some embodiments, a first sample is obtained at a first time point within about 2 hours of the suspected injury and a second sample is obtained at second time point, or optionally a third time point or fourth time point, after the first time point to determine whether the subject will have a positive or negative head CT scan. In some embodiments, the first sample is taken within about 2 hours after the suspected injury and the second sample is taken within about 3 hours to about 6 hours after the first sample. In some embodiments, the first time point is about 0 to about 2 hours after the injury or suspected injury to the head. For example, the first time point can be between about 0 to about 2 hours, about 0 hours to about 90 minutes, about 0 hours to about 60 minutes, about 0 hours to about 45 minutes, about 0 hours to about 30 minutes, about 0 hours to about 20 minutes, about 0 hours to about 15 minutes, about 0 hours to about 10 minutes, about 0 hours to about 5 minutes, about 5 minutes to about 90 minutes, about 5 minutes to about 60 minutes, about 5 minutes to about 45 minutes, about 5 minutes to about 30 minutes, about 5 minutes to about 20 minutes, about 5 minutes to about 15 minutes, about 5 minutes to about 10 minutes, about 10 minutes to about 90 minutes, about 10 minutes to about 60 minutes, about 10 minutes to about 45 minutes, about 10 minutes to about 30 minutes, about 10 minutes to about 20 minutes, about 10 minutes to about 15 minutes, about 15 minutes to about 90 minutes, about 15 minutes to about 60 minutes, about 15 minutes to about 45 minutes, about 15 minutes to about 30 minutes, about 15 minutes to about 20 minutes, about 20 minutes to about 90 minutes, about 20 minutes to about 60 minutes, about 20 minutes to about 45 minutes, or about 20 minutes to about 30 minutes after the suspected injury.

In some embodiments, the second time point, or optionally a third time point or fourth time point, is about 1 hour to about 10 hours after the first time point, such as about 3 hours to about 6 hours after the first time point. In some embodiments, the second time point is about 1 hour, about 2 hours, about 3 hours, about 4 hours, about 5 hours, about 6 hours, about 7 hours, about 8 hours, about 9 hours, or about 10 hours after the first time point.

In some embodiments, the absolute amount can be determined by an assay having a sensitivity of between at least about 65% to about 100% and a specificity of between at least about 65% to about 100%. For example, the absolute amount can be determined by an assay having a sensitivity of between at least about 80% to 100% and a specificity of between at least about 65% to 100%. In some embodiments, the sensitivity is at least about 65.0%, the sensitivity is at least about 70.0%, at least about 75.0%, at least about 80.0%, at least about 85.0%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 65.0%, at least about 70.0%, at least about 75.0%, at least about 80.0%, at least about 85.0%, at least about 90.0%, at least about 91.0%, at least about 92.0%, at least about 93. %, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 100% and the specificity is at least about 75%, the sensitivity is at least about 99% and the specificity is at least about 99%, or the sensitivity is at least about 87% and the specificity is at least about 95%.

In some embodiments, the absolute amount of cardiac troponin I in the sample is from about 1 pg/mL to about 50 pg/mL, about 1 pg/mL to about 45 pg/mL, about 1 pg/mL to about 40 pg/mL, about 1 pg/mL to about 35 pg/mL, about 1 pg/mL to about 30 pg/mL, about 1 pg/mL to about 25 pg/mL, about 1 pg/mL to about 20 pg/mL, about 1 pg/mL to about 15 pg/mL, about 1 pg/mL to about 10 pg/mL, about 1 pg/mL to about 9 pg/mL, about 1 pg/mL to about 8 pg/mL, about 1 pg/mL to about 7 pg/mL, about 1 pg/mL to about 6 pg/mL, about 1 pg/mL to about 5 pg/mL, about 1 pg/mL to about 4 pg/mL, about 1 pg/mL to about 3 pg/mL, about 1 pg/mL to about 2 pg/mL, about 1 pg/mL to about 1.5 pg/mL, about 1.5 pg/mL to about 50 pg/mL, about 1.5 pg/mL to about 45 pg/mL, about 1.5 pg/mL to about 40 pg/mL, about 1.5 pg/mL to about 35 pg/mL, about 1.5 pg/mL to about 30 pg/mL, about 1.5 pg/mL to about 25 pg/mL, about 1.5 pg/mL to about 20 pg/mL, about 1.5 pg/mL to about 15 pg/mL, about 1.5 pg/mL to about 10 pg/mL, about 1.5 pg/mL to about 9 pg/mL, about 1.5 pg/mL to about 8 pg/mL, about 1.5 pg/mL to about 7 pg/mL, about 1.5 pg/mL to about 6 pg/mL, about 1.5 pg/mL to about 5 pg/mL, about 1.5 pg/mL to about 4 pg/mL, about 1.5 pg/mL to about 3 pg/mL, about 1.5 pg/mL to about 2 pg/mL, about 2 pg/mL to about 50 pg/mL, about 2 pg/mL to about 45 pg/mL, about 2 pg/mL to about 40 pg/mL, about 2 pg/mL to about 35 pg/mL, about 2 pg/mL to about 30 pg/mL, about 2 pg/mL to about 25 pg/mL, about 2 pg/mL to about 20 pg/mL, about 2 pg/mL to about 15 pg/mL, about 2 pg/mL to about 10 pg/mL, about 2 pg/mL to about 9 pg/mL, about 2 pg/mL to about 8 pg/mL, about 2 pg/mL to about 7 pg/mL, about 2 pg/mL to about 6 pg/mL, about 2 pg/mL to about 5 pg/mL, about 2 pg/mL to about 4 pg/mL, about 2 pg/mL to about 3 pg/mL, about 3 pg/mL to about 50 pg/mL, about 3 pg/mL to about 45 pg/mL, about 3 pg/mL to about 40 pg/mL, about 3 pg/mL to about 35 pg/mL, about 3 pg/mL to about 30 pg/mL, about 3 pg/mL to about 25 pg/mL, about 3 pg/mL to about 20 pg/mL, about 3 pg/mL to about 15 pg/mL, about 3 pg/mL to about 10 pg/mL, about 3 pg/mL to about 9 pg/mL, about 3 pg/mL to about 8 pg/mL, about 3 pg/mL to about 7 pg/mL, about 3 pg/mL to about 6 pg/mL, about 3 pg/mL to about 5 pg/mL, about 3 pg/mL to about 4 pg/mL, about 4 pg/mL to about 50 pg/mL, about 4 pg/mL to about 45 pg/mL, about 4 pg/mL to about 40 pg/mL, about 4 pg/mL to about 35 pg/mL, about 4 pg/mL to about 30 pg/mL, about 4 pg/mL to about 25 pg/mL, about 4 pg/mL to about 20 pg/mL, about 4 pg/mL to about 15 pg/mL, about 4 pg/mL to about 10 pg/mL, about 4 pg/mL to about 9 pg/mL, about 4 pg/mL to about 8 pg/mL, about 4 pg/mL to about 7 pg/mL, about 4 pg/mL to about 6 pg/mL, about 4 pg/mL to about 5 pg/mL, about 5 pg/mL to about 50 pg/mL, about 5 pg/mL to about 45 pg/mL, about 5 pg/mL to about 40 pg/mL, about 5 pg/mL to about 35 pg/mL, about 5 pg/mL to about 30 pg/mL, about 5 pg/mL to about 25 pg/mL, about 5 pg/mL to about 20 pg/mL, about 5 pg/mL to about 15 pg/mL, about 5 pg/mL to about 10 pg/mL, about 5 pg/mL to about 9 pg/mL, about 5 pg/mL to about 8 pg/mL, about 5 pg/mL to about 7 pg/mL, about 5 pg/mL to about 6 pg/mL, about 6 pg/mL to about 50 pg/mL, about 6 pg/mL to about 45 pg/mL, about 6 pg/mL to about 40 pg/mL, about 6 pg/mL to about 35 pg/mL, about 6 pg/mL to about 30 pg/mL, about 6 pg/mL to about 25 pg/mL, about 6 pg/mL to about 20 pg/mL, about 6 pg/mL to about 15 pg/mL, about 6 pg/mL to about 10 pg/mL, about 6 pg/mL to about 9 pg/mL, about 6 pg/mL to about 8 pg/mL, about 6 pg/mL to about 7 pg/mL, about 7 pg/mL to about 50 pg/mL, about 7 pg/mL to about 45 pg/mL, about 7 pg/mL to about 40 pg/mL, about 7 pg/mL to about 35 pg/mL, about 7 pg/mL to about 30 pg/mL, about 7 pg/mL to about 25 pg/mL, about 7 pg/mL to about 20 pg/mL, about 7 pg/mL to about 15 pg/mL, about 7 pg/mL to about 10 pg/mL, about 7 pg/mL to about 9 pg/mL, about 7 pg/mL to about 8 pg/mL, about 8 pg/mL to about 50 pg/mL, about 8 pg/mL to about 45 pg/mL, about 8 pg/mL to about 40 pg/mL, about 8 pg/mL to about 35 pg/mL, about 8 pg/mL to about 30 pg/mL, about 8 pg/mL to about 25 pg/mL, about 8 pg/mL to about 20 pg/mL, about 8 pg/mL to about 15 pg/mL, about 8 pg/mL to about 10 pg/mL, about 8 pg/mL to about 9 pg/mL, about 9 pg/mL to about 50 pg/mL, about 9 pg/mL to about 45 pg/mL, about 9 pg/mL to about 40 pg/mL, about 9 pg/mL to about 35 pg/mL, about 9 pg/mL to about 30 pg/mL, about 9 pg/mL to about 25 pg/mL, about 9 pg/mL to about 20 pg/mL, about 9 pg/mL to about 15 pg/mL, about 9 pg/mL to about 10 pg/mL, about 10 pg/mL to about 50 pg/mL, about 10 pg/mL to about 45 pg/mL, about 10 pg/mL to about 40 pg/mL, about 10 pg/mL to about 35 pg/mL, about 10 pg/mL to about 30 pg/mL, about 10 pg/mL to about 25 pg/mL, about 10 pg/mL to about 20 pg/mL, about 10 pg/mL to about 15 pg/mL, about 20 pg/mL to about 50 pg/mL, about 20 pg/mL to about 45 pg/mL, about 20 pg/mL to about 40 pg/mL, about 20 pg/mL to about 35 pg/mL, about 20 pg/mL to about 30 pg/mL, or about 20 pg/mL to about 25 pg/mL. In some embodiments, the absolute amount can be at least about 0.5 pg/mL, at least about 1.0 pg/mL, at least about 1.5 pg/mL, at least about 2.0 pg/mL, at least about 2.5 pg/mL, at least about 3.0 pg/mL, at least about 4.0 pg/mL, at least about 5.0 pg/mL, at least about 6.0 pg/mL, at least about 7.0 pg/mL, at least about 8.0, pg/mL, at least about 9.0 pg/mL, at least about 10 pg/mL, at least about 15 pg/mL, at least about 20 pg/mL, at least about 25 pg/mL, at least about 30 pg/mL, at least about 35 pg/mL, at least about 40 pg/mL, at least about 45 pg/mL, or at least about 50 pg/mL.

In addition to performing the above described methods, one skilled in the art (e.g., physician) would understand and know how to perform additional testing in order to detect or assess other comorbidities (e.g., other diseases, disorders, or conditions other than TBI). Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In one embodiment, in order to confirm that the changes in amounts or levels cTnI in the methods described herein are attributable to a head injury or a suspected injury to the head of a subject and not the result of an acute cardiac syndrome (such as a myocardial infarction, heart failure, etc.), a physician or other healthcare provider could conduct or perform one or more additional tests or procedures to confirm the absence of an acute cardiac syndrome. Such additional tests or procedures include one or more of an electrocardiogram, a complete blood cell (CBC) count, a comprehensive metabolic panel, a lipid profile (e.g., to determine HDL, LDL, triglycerides, etc.), an angiogram, one or more tests to detect or determine the levels of one or more of c reactive protein (CRP), brain natriuretic peptide, plasma ceramides, etc.

In some embodiments, the method further includes treating the human subject who was determined to have a CT scan with a traumatic brain injury treatment, as described below. In some embodiments, the method further includes monitoring, as described below, the human subject who was determined to have a CT scan. In some embodiments, the method further includes ordering additional tests to obtain further clinical information about the traumatic brain injury. In some embodiments, the method includes treating the human subject assessed as having a mild, moderate, severe, or a moderate to severe brain injury with a cardioprotective treatment to protect the heart as described below.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Also, the assay can be employed in clinical chemistry format such as would be known by one skilled in the art. Such assays are described in further detail herein in Sections 11-13.

6. Methods of Aiding in Predicting or Predicting the Outcome of a Human Subject Having Mild Traumatic Brain Injury Using Cardiac Troponin I (cTnI)

The present disclosure relates, among other methods, to a method of aiding in predicting (or predicting) the outcome of a human subject having mild traumatic brain injury (TBI), e.g., determining whether the subject will have an unfavorable outcome or a favorable outcome. As used herein, the phrase "determining whether the subject has a favorable outcome" refers to the fact that the aforementioned method can be used, e.g., with other information (e.g., clinical assessment data), to determine that the subject is more likely than not to have a positive outcome from the mild TBI. Additionally, as used herein, the phrase "determining whether the subject has an unfavorable outcome" refers to the fact that the aforementioned method can be used, e.g., with other information (e.g., clinical assessment data), to determine that the subject is more likely than not to have an unfavorable or negative outcome from the mild TBI. As mentioned above, the methods described herein can be used to determine whether a subject diagnosed with a mild TBI is more likely than not to have (1) a favorable outcome (optionally, the favorable outcome can be that the subject fully recovers and does not continue to experience one or more symptoms of a mild TBI); or (2) an unfavorable outcome (optionally, the unfavorable outcome can be that the subject does not fully recover and does continue to experience one or more symptoms of a mild TBI).

Alternatively and optionally, a favorable outcome can mean that the subject is more likely than not to suffer no more than one post-concussion syndrome symptom as a result of the mild TBI such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g., personality changes, irritability, depression, apathy, etc.); or (d) sleep difficulties (e.g., insomnia, etc.). Alternatively and option, subject who have an unfavorable outcome are more likely to suffer from more than one post-concussion syndrome symptom such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g, personality changes, irritability, depression, apathy, etc.); (d) sleep difficulties (e.g., insomnia, etc.); or (e) any combinations of (a)-(d)). Alternatively and optionally, an unfavorable outcome can also mean that a subject exhibits one or more symptoms of mild TBI. Alternatively and optionally, an unfavorable outcome can also mean that the subject's conditions worsens from mild TBI to moderate, moderate to severe or severe. Additionally, subjects having a favorable outcome are likely to have a GOSE score of 5 or greater whereas subjects having an unfavorable outcome are likely to have a GOSE score of less than 5.

At the time of the present disclosure it was known in the art that cTnI levels are elevated in subjects following severe traumatic injury. In fact, elevated levels in cTnI in subjects with severe traumatic injury are often associated with poor outcomes (See, Cai et al., Prognostic Value of Cardiac Troponin I Following Severe Traumatic Brain Injury; *Academic Surgical Congress Abstracts* 2015, herein incorporated by reference). Given this, the discovery in the present disclosure that detecting and/or measuring cTnI levels in a subject who has sustained or may have sustained an injury to the head can be used to predict the outcome and severity of injury of a human subject with a mild TBI is surprising.

Specifically, such a method can comprise the steps of determining the level of cardiac troponin I in a sample taken from the subject within 28 hours, such as within 24 hours, after an injury to the head, and predicting the subject as having an unfavorable outcome, for example at 1 month or 6 months, or having a more severe traumatic brain injury if the levels of cTnI are higher than a reference level of the cTnI or predicting the subject as having a favorable outcome, for example at 1 month or 6 months, or having a less severe traumatic brain injury if the levels of cTnI are lower than a reference level of the cTnI. The sample can be a biological sample.

In some embodiments, the sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, within about 25 hours, within about 26 hours, within about 27 hours, or within about 28 hours of an injury to the head.

In some embodiments, the subject may have received a Glasgow Coma Scale score before or after the level of cardiac troponin is determined at one or more time points. In certain embodiments, the subject may be suspected of having a mild traumatic brain injury based on the Glasgow Coma Scale score. In certain embodiments, the subject may be suspected of having a mild traumatic brain injury based on an abnormal head CT. In some embodiments, the subject has received a CT scan before or after the assay is performed. In some embodiments, the subject has a normal head CT.

In some embodiments, the subject has received a GOSE score after the assay is performed. In some embodiments, the subject is suspected as having an unfavorable outcome based on the GOSE score. In some embodiments, the subject has a GOSE score of less than 5 at 1 month, 2 months, 3 months, 4 months, 5 months, or 6 months after the suspected injury. In some embodiments, the reference level of cTnI is correlated with subjects having an unfavorable outcome. In some embodiments, the reference level of cTnI is correlated with a GOSE score of 1-5. In some embodiments, the subject is suspected as having a favorable outcome based on the GOSE score. In some embodiments, the reference level of cTnI is correlated with subjects having a favorable outcome. In some embodiments, the reference level of cTnI is correlated with a GOSE score of 6-8.

In some embodiments, the reference level of cTnI is correlated with subjects having a more severe traumatic brain injury, such as moderate to severe traumatic brain injury. In some embodiments, the reference level of cTnI is correlated with a Glasgow Coma Scale score of 3-12. In some embodiments, the subject is suspected as having mild traumatic brain injury based on the Glasgow Coma Scale score. In some embodiments, the reference level of cTnI is correlated with subjects having a less severe traumatic brain injury, such as mild traumatic brain injury. In some embodiments, the reference level of cTnI is correlated with a Glasgow Coma Scale score of 13-15.

Generally, a reference level of cTnI can also be employed as a benchmark against which to assess results obtained upon assaying a test sample for cTnI. Generally, in making such a comparison, the reference level of cTnI is obtained by running a particular assay a sufficient number of times and under appropriate conditions such that a linkage or association of analyte presence, amount or concentration with a particular stage or endpoint of TBI or with particular indicia can be made. Typically, the reference level of cTnI is obtained with assays of reference subjects (or populations of subjects). The cTnI measured can include fragments thereof, degradation products thereof, and/or enzymatic cleavage products thereof.

In certain embodiments, the reference level may be correlated with control subjects that have not sustained a head injury.

In some embodiments, the method can include obtaining samples from the subject and contacting the samples with an antibody for cardiac troponin I to allow formation of a complex of the antibody and cardiac troponin I. The method also includes detecting the resulting antibody-cardiac troponin I complex.

In some embodiments, the reference level of cTnI is determined by an assay having a sensitivity of between at least about 65% to about 100% and a specificity of between at least about 30% to about 100%. In some embodiments, the sensitivity is between at least about 65% to about 100%, between at least about 65% to at least about 99%, between at least about 65% to at least about 95%, between at least about 65% to at least about 90%, between at least about 65% to at least about 85%, between at least about 65% to at least about 80%, between at least about 65% to at least about 75%, between at least about 65% to at least about 70%, between at least about 75% to about 100%, between at least about 75% to at least about 99%, between at least about 75% to at least about 95%, between at least about 75% to at least about 90%, between at least about 75% to at least about 85%, between at least about 75% to at least about 80%, between at least about 80% to about 100%, between at least about 80% to at least about 99%, between at least about 80% to at least about 95%, between at least about 80% to at least about 90%, between at least about 85% to about 100%, between at least about 85% to at least about 99%, between at least about 85% to at least about 95%, between at least about 85% to at least about 90%, between at least about 95% to about 100%, or between at least about 95% to at least about 99%. In some embodiments, the sensitivity is at least about 65.0%, at least about 70.0%, at least about 75.0%, at least about 80.0%, at least about 83.0%, at least about 83.3%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 45% to about 100%, between at least about 45% to about 99%, between at least about 45% to about 95%, between at least about 45% to about 90%, between at least about 45% to about 85%, between at least about 45% to about 80%, between at least about 45% to about 75%, between at least about 45% to about 70%, between at least about 45% to about 60%, between at least about 45% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 49.2%, at least about 50.0%, at least about 54.9%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is at least about 100% and the specificity is at least about 100%.

In some embodiments, the reference level of cardiac troponin I in the sample is from about 1.0 pg/mL to about 50.0 pg/mL, about 1.5 pg/mL to about 50.0 pg/mL, about 2.0 pg/mL to about 50.0 pg/mL, about 2.5 pg/mL to about 50.0 pg/mL, about 3.0 pg/mL to about 50.0 pg/mL, about 3.5 pg/mL to about 50.0 pg/mL, about 4.0 pg/mL to about 50.0 pg/mL, about 4.5 pg/mL to about 50.0 pg/mL, about 5.0 pg/mL to about 50.0 pg/mL, about 5.5 pg/mL to about 50.0 pg/mL, about 6.0 pg/mL to about 50.0 pg/mL, about 6.5 pg/mL to about 50.0 pg/mL, about 7.0 pg/mL to about 50.0 pg/mL, about 7.5 pg/mL to about 50.0 pg/mL, about 8.0 pg/mL to about 50.0 pg/mL, about 8.5 pg/mL to about 50.0 pg/mL, about 9.0 pg/mL to about 50.0 pg/mL, about 9.5 pg/mL to about 50.0 pg/mL, about 10.0 pg/mL to about 50.0 pg/mL, about 1.0 pg/mL to about 40.0 pg/mL, about 1.5 pg/mL to about 40.0 pg/mL, about 2.0 pg/mL to about 40.0 pg/mL, about 2.5 pg/mL to about 40.0 pg/mL, about 3.0 pg/mL to about 40.0 pg/mL, about 3.5 pg/mL to about 40.0 pg/mL, about 4.0 pg/mL to about 40.0 pg/mL, about 4.5 pg/mL to about 40.0 pg/mL, about 5.0 pg/mL to about 40.0 pg/mL, about 5.5 pg/mL to about 40.0 pg/mL, about 6.0 pg/mL to about 40.0 pg/mL, about 6.5 pg/mL to about 40.0 pg/mL, about 7.0 pg/mL to about 40.0 pg/mL, about 7.5 pg/mL to about 40.0 pg/mL, about 8.0 pg/mL to about 40.0 pg/mL, about 8.5 pg/mL to about 40.0 pg/mL, about 9.0 pg/mL to about 40.0 pg/mL, about 9.5 pg/mL to about 40.0 pg/mL, about 10.0 pg/mL to about 40.0 pg/mL, about 1.0 pg/mL to about 35.0 pg/mL, about 1.5 pg/mL to about 35.0 pg/mL, about 2.0 pg/mL to about 35.0 pg/mL, about 2.5 pg/mL to about 35.0 pg/mL, about 3.0 pg/mL to about 35.0 pg/mL, about 3.5 pg/mL to about 35.0 pg/mL, about 4.0 pg/mL to about 35.0 pg/mL, about 4.5 pg/mL to about 35.0 pg/mL, about 5.0 pg/mL to about 35.0 pg/mL, about 5.5 pg/mL to about 35.0 pg/mL, about 6.0 pg/mL to about 35.0 pg/mL, about 6.5 pg/mL to about 35.0 pg/mL, about 7.0 pg/mL to about 35.0 pg/mL, about 7.5 pg/mL to about 35.0 pg/mL, about 8.0 pg/mL to about 35.0 pg/mL, about 8.5 pg/mL to about 35.0 pg/mL, about 9.0 pg/mL to about 35.0 pg/mL, about 9.5 pg/mL to about 35.0 pg/mL, about 10.0 pg/mL to about 35.0 pg/mL, about 1.0 pg/mL to about 30.0 pg/mL, about 1.5 pg/mL to about 30.0 pg/mL, about 2.0 pg/mL to about 30.0 pg/mL, about 2.5 pg/mL to about 30.0 pg/mL, about 3.0 pg/mL to about 30.0 pg/mL, about 3.5 pg/mL to about 30.0 pg/mL, about 4.0 pg/mL to about 30.0 pg/mL, about 4.5 pg/mL to about 30.0 pg/mL, about 5.0 pg/mL to about 30.0 pg/mL, about 5.5 pg/mL to about 30.0 pg/mL, about 6.0 pg/mL to about 30.0 pg/mL, about 6.5 pg/mL to about 30.0 pg/mL, about 7.0 pg/mL to about 30.0 pg/mL, about 7.5 pg/mL to about 30.0 pg/mL, about 8.0 pg/mL to about 30.0 pg/mL, about 8.5 pg/mL to about 30.0 pg/mL, about 9.0 pg/mL to about 30.0 pg/mL, about 9.5 pg/mL to about 30.0 pg/mL, about 10.0 pg/mL to about 30.0 pg/mL, about 1.0 pg/mL to about 25.0 pg/mL, about 1.5 pg/mL to about 25.0 pg/mL, about 2.0 pg/mL to about 25.0 pg/mL, about 2.5 pg/mL to about 25.0 pg/mL, about 3.0 pg/mL to about 25.0 pg/mL, about 3.5 pg/mL to about 25.0 pg/mL, about 4.0 pg/mL to about 25.0 pg/mL, about 4.5 pg/mL to about 25.0 pg/mL, about 5.0 pg/mL to about 25.0 pg/mL, about 5.5 pg/mL to about 25.0 pg/mL, about 6.0 pg/mL to about 25.0 pg/mL, about 6.5 pg/mL to about 25.0 pg/mL, about 7.0 pg/mL to about 25.0 pg/mL, about 7.5 pg/mL to about 25.0 pg/mL, about 8.0 pg/mL to about 25.0 pg/mL, about 8.5 pg/mL to about 25.0 pg/mL, about 9.0 pg/mL to about 25.0 pg/mL, about 9.5 pg/mL to about 25.0 pg/mL, about 10.0 pg/mL to about 25.0 pg/mL, about 1.0 pg/mL to about 24.0 pg/mL, about 1.5 pg/mL to about 24.0 pg/mL, about 2.0 pg/mL to about 24.0 pg/mL, about 2.5 pg/mL to about 24.0 pg/mL, about 3.0 pg/mL to about 24.0 pg/mL, about 3.5 pg/mL to about 24.0 pg/mL, about 4.0 pg/mL to about 24.0 pg/mL, about 4.5 pg/mL to about 24.0 pg/mL, about 5.0 pg/mL to about 24.0 pg/mL, about 5.5 pg/mL to about 24.0 pg/mL, about 6.0 pg/mL to about 24.0 pg/mL, about 6.5 pg/mL to about 24.0 pg/mL, about 7.0 pg/mL to about 24.0 pg/mL, about 7.5 pg/mL to about 24.0 pg/mL, about 8.0 pg/mL to about 24.0 pg/mL, about 8.5 pg/mL to about 24.0 pg/mL, about 9.0 pg/mL to about 24.0 pg/mL, about 9.5 pg/mL to about 24.0 pg/mL, about 10.0 pg/mL to about 24.0 pg/mL, about 1.0 pg/mL to about 23.0 pg/mL, about 1.5 pg/mL to about 23.0 pg/mL, about 2.0 pg/mL to about 23.0 pg/mL, about 2.5 pg/mL to about 23.0 pg/mL, about 3.0 pg/mL to about 23.0 pg/mL, about 3.5 pg/mL to about 23.0 pg/mL, about 4.0 pg/mL to about 23.0 pg/mL, about 4.5 pg/mL to about 23.0 pg/mL, about 5.0 pg/mL to about 23.0 pg/mL, about 5.5 pg/mL to about 23.0 pg/mL, about 6.0 pg/mL to about 23.0 pg/mL, about 6.5 pg/mL to about 23.0 pg/mL, about 7.0 pg/mL to about 23.0 pg/mL, about 7.5 pg/mL to about 23.0 pg/mL, about 8.0 pg/mL to about 23.0 pg/mL, about 8.5 pg/mL to about 23.0 pg/mL, about 9.0 pg/mL to about 23.0 pg/mL, about 9.5 pg/mL to about 23.0 pg/mL, about 10.0 pg/mL to about 23.0 pg/mL, about 1.0 pg/mL to about 22.0 pg/mL, about 1.5 pg/mL to about 22.0 pg/mL, about 2.0 pg/mL to about 22.0 pg/mL, about 2.5 pg/mL to about 22.0 pg/mL, about 3.0 pg/mL to about 22.0 pg/mL, about 3.5 pg/mL to about 22.0 pg/mL, about 4.0 pg/mL to about 22.0 pg/mL, about 4.5 pg/mL to about 22.0 pg/mL, about 5.0 pg/mL to about 22.0 pg/mL, about 5.5 pg/mL to about 22.0 pg/mL, about 6.0 pg/mL to about 22.0 pg/mL, about 6.5 pg/mL to about 22.0 pg/mL, about 7.0 pg/mL to about 22.0 pg/mL, about 7.5 pg/mL to about 22.0 pg/mL, about 8.0 pg/mL to about 22.0 pg/mL, about 8.5 pg/mL to about 22.0 pg/mL, about 9.0 pg/mL to about 22.0 pg/mL, about 9.5 pg/mL to about 22.0 pg/mL, about 10.0 pg/mL to about 22.0 pg/mL, about 1.0 pg/mL to about 21.0 pg/mL, about 1.5 pg/mL to about 21.0 pg/mL, about 2.0 pg/mL to about 21.0 pg/mL, about 2.5 pg/mL to about 21.0 pg/mL, about 3.0 pg/mL to about 21.0 pg/mL, about 3.5 pg/mL to about 21.0 pg/mL, about 4.0 pg/mL to about 21.0 pg/mL, about 4.5 pg/mL to about 21.0 pg/mL, about 5.0 pg/mL to about 21.0 pg/mL, about 5.5 pg/mL to about 21.0 pg/mL, about 6.0 pg/mL to about 21.0 pg/mL, about 6.5 pg/mL to about 21.0 pg/mL, about 7.0 pg/mL to about 21.0 pg/mL, about 7.5 pg/mL to about 21.0 pg/mL, about 8.0 pg/mL to about 21.0 pg/mL, about 8.5 pg/mL to about 21.0 pg/mL, about 9.0 pg/mL to about 21.0 pg/mL, about 9.5 pg/mL to about 21.0 pg/mL, about 10.0 pg/mL to about 21.0 pg/mL, about 1.0 pg/mL to about 20.0 pg/mL, about 1.5 pg/mL to about 20.0 pg/mL, about 2.0 pg/mL to about 20.0 pg/mL, about 2.5 pg/mL to about 20.0 pg/mL, about 3.0 pg/mL to about 20.0 pg/mL, about 3.5 pg/mL to about 20.0 pg/mL, about 4.0 pg/mL to about 20.0 pg/mL, about 4.5 pg/mL to about 20.0 pg/mL, about 5.0 pg/mL to about 20.0 pg/mL, about 5.5 pg/mL to about 20.0 pg/mL, about 6.0 pg/mL to about 20.0 pg/mL, about 6.5 pg/mL to about 20.0 pg/mL, about 7.0 pg/mL to about 20.0 pg/mL, about 7.5 pg/mL to about 20.0 pg/mL, about 8.0 pg/mL to about 20.0 pg/mL, about 8.5 pg/mL to about 20.0 pg/mL, about 9.0 pg/mL to about 20.0 pg/mL, about 9.5 pg/mL to about 20.0 pg/mL, about 10.0 pg/mL to about 20.0 pg/mL, about 1.0 pg/mL to about 19.0 pg/mL, about 1.5 pg/mL to about 19.0 pg/mL, about 2.0 pg/mL to about 19.0 pg/mL, about 2.5 pg/mL to about 19.0 pg/mL, about 3.0 pg/mL to about 19.0 pg/mL, about 3.5 pg/mL to about 19.0 pg/mL, about 4.0 pg/mL to about 19.0 pg/mL, about 4.5 pg/mL to about 19.0 pg/mL, about 5.0 pg/mL to about 19.0 pg/mL, about 5.5 pg/mL to about 19.0 pg/mL, about 6.0 pg/mL to about 19.0 pg/mL, about 6.5 pg/mL to about 19.0 pg/mL, about 7.0 pg/mL to about 19.0 pg/mL, about 7.5 pg/mL to about 19.0 pg/mL, about 8.0 pg/mL to about 19.0 pg/mL, about 8.5 pg/mL to about 19.0 pg/mL, about 9.0 pg/mL to about 19.0 pg/mL, about 9.5 pg/mL to about 19.0 pg/mL, about 10.0 pg/mL to about 19.0 pg/mL, about 1.0 pg/mL to about 18.0 pg/mL, about 1.5 pg/mL to about 18.0 pg/mL, about 2.0 pg/mL to about 18.0 pg/mL, about 2.5 pg/mL to about 18.0 pg/mL, about 3.0 pg/mL to about 18.0 pg/mL, about 3.5 pg/mL to about 18.0 pg/mL, about 4.0 pg/mL to about 18.0 pg/mL, about 4.5 pg/mL to about 18.0 pg/mL, about 5.0 pg/mL to about 18.0 pg/mL, about 5.5 pg/mL to about 18.0 pg/mL, about 6.0 pg/mL to about 18.0 pg/mL, about 6.5 pg/mL to about 18.0 pg/mL, about 7.0 pg/mL to about 18.0 pg/mL, about 7.5 pg/mL to about 18.0 pg/mL, about 8.0 pg/mL to about 18.0 pg/mL, about 8.5 pg/mL to about 18.0 pg/mL, about 9.0 pg/mL to about 18.0 pg/mL, about 9.5 pg/mL to about 18.0 pg/mL, about 10.0 pg/mL to about 18.0 pg/mL, about 1.0 pg/mL to about 17.0 pg/mL, about 1.5 pg/mL to about 17.0 pg/mL, about 2.0 pg/mL to about 17.0 pg/mL, about 2.5 pg/mL to about 17.0 pg/mL, about 3.0 pg/mL to about 17.0 pg/mL, about 3.5 pg/mL to about 17.0 pg/mL, about 4.0 pg/mL to about 17.0 pg/mL, about 4.5 pg/mL to about 17.0 pg/mL, about 5.0 pg/mL to about 17.0 pg/mL, about 5.5 pg/mL to about 17.0 pg/mL, about 6.0 pg/mL to about 17.0 pg/mL, about 6.5 pg/mL to about 17.0 pg/mL, about 7.0 pg/mL to about 17.0 pg/mL, about 7.5 pg/mL to about 17.0 pg/mL, about 8.0 pg/mL to about 17.0 pg/mL, about 8.5 pg/mL to about 17.0 pg/mL, about 9.0 pg/mL to about 17.0 pg/mL, about 9.5 pg/mL to about 17.0 pg/mL, about 10.0 pg/mL to about 17.0 pg/mL, about 1.0 pg/mL to about 16.0 pg/mL, about 1.5 pg/mL to about 16.0 pg/mL, about 2.0 pg/mL to about 16.0 pg/mL, about 2.5 pg/mL to about 16.0 pg/mL, about 3.0 pg/mL to about 16.0 pg/mL, about 3.5 pg/mL to about 16.0 pg/mL, about 4.0 pg/mL to about 16.0 pg/mL, about 4.5 pg/mL to about 16.0 pg/mL, about 5.0 pg/mL to about 16.0 pg/mL, about 5.5 pg/mL to about 16.0 pg/mL, about 6.0 pg/mL to about 16.0 pg/mL, about 6.5 pg/mL to about 16.0 pg/mL, about 7.0 pg/mL to about 16.0 pg/mL, about 7.5 pg/mL to about 16.0 pg/mL, about 8.0 pg/mL to about 16.0 pg/mL, about 8.5 pg/mL to about 16.0 pg/mL, about 9.0 pg/mL to about 16.0 pg/mL, about 9.5 pg/mL to about 16.0 pg/mL, about 10.0 pg/mL to about 16.0 pg/mL, about 1.0 pg/mL to about 15.0 pg/mL, about 1.5 pg/mL to about 15.0 pg/mL, about 2.0 pg/mL to about 15.0 pg/mL, about 2.5 pg/mL to about 15.0 pg/mL, about 3.0 pg/mL to about 15.0 pg/mL, about 3.5 pg/mL to about 15.0 pg/mL, about 4.0 pg/mL to about 15.0 pg/mL, about 4.5 pg/mL to about 15.0 pg/mL, about 5.0 pg/mL to about 15.0 pg/mL, about 5.5 pg/mL to about 15.0 pg/mL, about 6.0 pg/mL to about 15.0 pg/mL, about 6.5 pg/mL to about 15.0 pg/mL, about 7.0 pg/mL to about 15.0 pg/mL, about 7.5 pg/mL to about 15.0 pg/mL, about 8.0 pg/mL to about 15.0 pg/mL, about 8.5 pg/mL to about 15.0 pg/mL, about 9.0 pg/mL to about 15.0 pg/mL, about 9.5 pg/mL to about 15.0 pg/mL or about 10.0 pg/mL to about 15.0 pg/mL. In some embodiments, the amount of cardiac troponin I in the sample is about 1.0 pg/mL, about 1.5 pg/mL, about 2.0 pg/mL, about 2.5 pg/mL, about 3.0 pg/mL, about 3.5 pg/mL, about 4.0 pg/mL, about 4.5 pg/mL, about 5.0 pg/mL, about 5.5 pg/mL, about 5.6 pg/mL, about 5.7 pg/mL, about 5.8 pg/mL, about 5.9 pg/mL, about 6.0 pg/mL, about 6.5 pg/mL, about 7.0 pg/mL, about 7.5 pg/mL, about 8.0 pg/mL, about 8.5 pg/mL, about 9.0 pg/mL, about 9.5 pg/mL, or about 10.0 pg/mL.

In some embodiments, the method further includes treating the human subject predicted as having an unfavorable outcome with a traumatic brain injury treatment, as described below. In some embodiments, the method further includes monitoring the human subject predicted as having an unfavorable outcome, as described below. In some embodiments, the method further includes ordering additional tests to obtain further clinical information about the mild TBI in the human subject predicted as having an unfavorable outcome. In some embodiments, the method includes treating the human subject predicted to have an unfavorable outcome with a cardioprotective treatment to protect the heart as described below.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Such assays are described in further detail herein in Sections 11-13. Also, the assay can be employed in clinical chemistry format such as would be known by one skilled in the art. For example, a clinical chemistry format can include an assay that involves one antibody or no antibody. Examples of analyzers that can be used for the clinical chemistry format are described in U.S. Patent publication Nos. 2016/0320422 and 2015/0112630.

7. Methods of Aiding in Predicting or Predicting the Outcome of a Human Subject Having Mild Traumatic Brain Injury Based on Changes in Cardiac Troponin I (cTnI) Levels The present disclosure relates, among other methods, to a method of aiding in predicting (or predicting) the outcome of a human subject having mild traumatic brain injury (TBI), e.g., determining whether the subject will have an unfavorable or negative outcome or favorable outcome. As used herein, the phrase "determining whether the subject has a favorable outcome" refers to the fact that the aforementioned method can be used, e.g., with other information (e.g., clinical assessment data), to determine that the subject is more likely than not to have a positive outcome from the mild TBI. Additionally, as used herein, the phrase "determining whether the subject has an unfavorable outcome" refers to the fact that the aforementioned method can be used, e.g., with other information (e.g., clinical assessment data), to determine that the subject is more likely than not to have an unfavorable or negative outcome from the mild TBI As mentioned above, the methods described herein can be used to determine whether a subject diagnosed with a mild TBI is more likely than not to have (1) a favorable outcome (optionally, the favorable outcome can be that the subject fully recovers and does not continue to experience one or more symptoms of a mild TBI); or (2) an unfavorable outcome (optionally, the unfavorable outcome can be that the subject does not fully recover and does continue to experience one or more symptoms of a mild TBI).

Alternatively and optionally, a favorable outcome can mean that the subject is more likely than not to suffer no more than one post-concussion syndrome symptom as a result of the mild TBI such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g., personality changes, irritability, depression, apathy, etc.); or (d) sleep difficulties (e.g., insomnia, etc.). Alternatively and option, subject who have an unfavorable outcome are more likely to suffer from more than one post-concussion syndrome symptom such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g, personality changes, irritability, depression, apathy, etc.); (d) sleep difficulties (e.g., insomnia, etc.); or (e) any combinations of (a)-(d). Alternatively and optionally, an unfavorable outcome can also mean that a subject exhibits one or more symptoms of mild TBI. Alternatively and optionally, an unfavorable outcome can also mean that the subject's conditions worsens from mild TBI to moderate, moderate to severe or severe. Additionally, subjects having a favorable outcome are likely to have a GOSE score of 5 or greater whereas subjects having an unfavorable outcome are likely to have a GOSE score of less than 5.

The methods disclosed herein can include performing at least two or more assays on one or more samples obtained from the human subject within after an injury to the head at two or more different time points and determining the level of cardiac troponin I at each of these time points. If the amount or level of cardiac troponin I in the sample has increased from the first (or previous) sample to the subsequent (e.g., second) sample, then a determination is made that the subject is predicted to have an unfavorable outcome, for example at 6 months, or a more severe traumatic brain injury. However, if the amount or level of cardiac troponin I in the sample has remained the same or decreased from the first (or previous) sample to the second (or subsequent) sample, then a determination is made that the subject is predicted to have a favorable outcome at 6 months or a less severe traumatic brain injury.

Specifically, such a method can comprise the steps of: (a) performing an assay on samples from the human subject to measure or detect a level of cardiac troponin I in a first sample and a second sample, wherein the first sample is taken from the human subject at a first time point within 24 hours after an injury to the head and the second sample is taken from the human subject about 0 hours to 6 hours after the first sample, wherein the samples are biological samples; (b) determining whether the amount of cardiac troponin I has increased or decreased from the first sample to the second sample; and (c) predicting an unfavorable or negative outcome in the human subject if the level of cardiac troponin I detected has increased from the first sample to the second sample. In some embodiments, a human subject is predicted as having an unfavorable or negative outcome if there is an increase by at least an absolute amount from the first sample to the second sample. In some embodiments, a human subject is predicted as having an unfavorable or negative outcome if the level of cardiac troponin I detected has increased by at least about 20% from the first sample to the second sample, and a human subject is predicted as having a favorable outcome in the human subject if the level of cardiac troponin I detected has remained unchanged, decreased, or increased, such as increased less than about 20% from the first sample to the second sample.

The first (or previous) sample may be obtained or taken from the subject 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of an injury to the head. In some embodiments, the (or previous) sample is taken within about 0 to about 1 hours, within about 0 to about 2 hours, within about 0 to about 3 hours, within about 0 to about 4 hours, within about 0 to about 5 hours, within about 0 to about 6 hours, within about 0 to about 7 hours, within about 0 to about 8 hours, within about 0 to about 9 hours, within about 0 to about 10 hours, within about 0 to about 11 hours, within about 0 to about 12 hours, within about 0 to about 18 hours, within about 6 to about 12 hours, within about 12 to about 18 hours, within about 18 to about 24 hours, or greater than 24 hours after the suspected injury. The second (or subsequent) sample can be obtained after about 0 hour to 6 hours after the first (or last) sample was obtained. In some embodiments, the second (or subsequent) sample is taken from the subject within at least about 30 minutes, within at least about 1 hour, within at least about 2 hours, within at least about 3 hours, within at least about 4 hours, within at least about 5 hours, or within at least about 6 hours after the first sample is taken from the subject.

In some embodiments, the subject is predicted as having an unfavorable outcome if the level of cardiac troponin I detected has increased from the first sample to the second sample. For example, the subject can be predicted as having an unfavorable outcome if the level of cardiac troponin I detected has increased from the first sample to the second sample by at least about 15%, at least about 20%, at least about 25%, at least about 30%, at least about 40%, at least about 50%, at least about 60%, at least about 70%, at least about 80%, at least about 90%, at least about 100%, at least about 250%, at least about 500%, or at least about 1000%. In some embodiments, the subject can be predicted as having an unfavorable outcome if the level of cardiac troponin I detected has increased from the first sample to the second sample by at least about 20%.

In some embodiments, the subject may have received a Glasgow Coma Scale score before or after the level of cardiac troponin is determined at one or more time points. In certain embodiments, the subject may be suspected of having a mild traumatic brain injury based on the Glasgow Coma Scale score. In certain embodiments, the subject may be suspected of having a mild traumatic brain injury based on an abnormal head CT. In some embodiments, the subject has received a CT scan before or after the assay is performed. In some embodiments, the subject has a normal head CT.

In some embodiments, the subject has received a GOSE score after the assay is performed. In some embodiments, the subject is suspected as having an unfavorable outcome based on the GOSE score. In some embodiments, the subject has a GOSE score of less than 5 at 1 month, 2 months, 3 months, 4 months, 5 months, or 6 months after the suspected injury. In some embodiments, an increased level of cTnI is correlated with subjects having an unfavorable outcome. In some embodiments, the increased level of cTnI is correlated with a GOSE score of 1-5. In some embodiments, the subject is suspected as having a favorable outcome based on the GOSE score. In some embodiments, a decreased or unchanged level of cTnI is correlated with subjects having a favorable outcome. In some embodiments, the decreased or unchanged level of cTnI is correlated with a GOSE score of 6-8.

In some embodiments, an increased level of cTnI is correlated with subjects having a more severe traumatic brain injury, such as moderate to severe traumatic brain injury. In some embodiments, the increased level of cTnI is correlated with a Glasgow Coma Scale score of 3-12. In some embodiments, the subject is suspected as having mild traumatic brain injury based on the Glasgow Coma Scale score. In some embodiments, a decreased or unchanged level of cTnI is correlated with subjects having a less severe traumatic brain injury, such as mild traumatic brain injury. In some embodiments, the decreased or unchanged level of cTnI is correlated with a Glasgow Coma Scale score of 13-15.

In some embodiments, the method can include obtaining samples from the subject and contacting the samples with an antibody for cardiac troponin I to allow formation of a complex of the antibody and cardiac troponin I. The method also includes detecting the resulting antibody-cardiac troponin I complex.

In some embodiments, the amount of cardiac troponin I in the first or previous sample is from about 1.0 pg/mL to about 50.0 pg/mL, about 1.5 pg/mL to about 50.0 pg/mL, about 2.0 pg/mL to about 50.0 pg/mL, about 2.5 pg/mL to about 50.0 pg/mL, about 3.0 pg/mL to about 50.0 pg/mL, about 3.5 pg/mL to about 50.0 pg/mL, about 4.0 pg/mL to about 50.0 pg/mL, about 4.5 pg/mL to about 50.0 pg/mL, about 5.0 pg/mL to about 50.0 pg/mL, about 5.5 pg/mL to about 50.0 pg/mL, about 6.0 pg/mL to about 50.0 pg/mL, about 6.5 pg/mL to about 50.0 pg/mL, about 7.0 pg/mL to about 50.0 pg/mL, about 7.5 pg/mL to about 50.0 pg/mL, about 8.0 pg/mL to about 50.0 pg/mL, about 8.5 pg/mL to about 50.0 pg/mL, about 9.0 pg/mL to about 50.0 pg/mL, about 9.5 pg/mL to about 50.0 pg/mL, about 10.0 pg/mL to about 50.0 pg/mL, about 1.0 pg/mL to about 40.0 pg/mL, about 1.5 pg/mL to about 40.0 pg/mL, about 2.0 pg/mL to about 40.0 pg/mL, about 2.5 pg/mL to about 40.0 pg/mL, about 3.0 pg/mL to about 40.0 pg/mL, about 3.5 pg/mL to about 40.0 pg/mL, about 4.0 pg/mL to about 40.0 pg/mL, about 4.5 pg/mL to about 40.0 pg/mL, about 5.0 pg/mL to about 40.0 pg/mL, about 5.5 pg/mL to about 40.0 pg/mL, about 6.0 pg/mL to about 40.0 pg/mL, about 6.5 pg/mL to about 40.0 pg/mL, about 7.0 pg/mL to about 40.0 pg/mL, about 7.5 pg/mL to about 40.0 pg/mL, about 8.0 pg/mL to about 40.0 pg/mL, about 8.5 pg/mL to about 40.0 pg/mL, about 9.0 pg/mL to about 40.0 pg/mL, about 9.5 pg/mL to about 40.0 pg/mL, about 10.0 pg/mL to about 40.0 pg/mL, about 1.0 pg/mL to about 35.0 pg/mL, about 1.5 pg/mL to about 35.0 pg/mL, about 2.0 pg/mL to about 35.0 pg/mL, about 2.5 pg/mL to about 35.0 pg/mL, about 3.0 pg/mL to about 35.0 pg/mL, about 3.5 pg/mL to about 35.0 pg/mL, about 4.0 pg/mL to about 35.0 pg/mL, about 4.5 pg/mL to about 35.0 pg/mL, about 5.0 pg/mL to about 35.0 pg/mL, about 5.5 pg/mL to about 35.0 pg/mL, about 6.0 pg/mL to about 35.0 pg/mL, about 6.5 pg/mL to about 35.0 pg/mL, about 7.0 pg/mL to about 35.0 pg/mL, about 7.5 pg/mL to about 35.0 pg/mL, about 8.0 pg/mL to about 35.0 pg/mL, about 8.5 pg/mL to about 35.0 pg/mL, about 9.0 pg/mL to about 35.0 pg/mL, about 9.5 pg/mL to about 35.0 pg/mL, about 10.0 pg/mL to about 35.0 pg/mL, about 1.0 pg/mL to about 30.0 pg/mL, about 1.5 pg/mL to about 30.0 pg/mL, about 2.0 pg/mL to about 30.0 pg/mL, about 2.5 pg/mL to about 30.0 pg/mL, about 3.0 pg/mL to about 30.0 pg/mL, about 3.5 pg/mL to about 30.0 pg/mL, about 4.0 pg/mL to about 30.0 pg/mL, about 4.5 pg/mL to about 30.0 pg/mL, about 5.0 pg/mL to about 30.0 pg/mL, about 5.5 pg/mL to about 30.0 pg/mL, about 6.0 pg/mL to about 30.0 pg/mL, about 6.5 pg/mL to about 30.0 pg/mL, about 7.0 pg/mL to about 30.0 pg/mL, about 7.5 pg/mL to about 30.0 pg/mL, about 8.0 pg/mL to about 30.0 pg/mL, about 8.5 pg/mL to about 30.0 pg/mL, about 9.0 pg/mL to about 30.0 pg/mL, about 9.5 pg/mL to about 30.0 pg/mL, about 10.0 pg/mL to about 30.0 pg/mL, about 1.0 pg/mL to about 25.0 pg/mL, about 1.5 pg/mL to about 25.0 pg/mL, about 2.0 pg/mL to about 25.0 pg/mL, about 2.5 pg/mL to about 25.0 pg/mL, about 3.0 pg/mL to about 25.0 pg/mL, about 3.5 pg/mL to about 25.0 pg/mL, about 4.0 pg/mL to about 25.0 pg/mL, about 4.5 pg/mL to about 25.0 pg/mL, about 5.0 pg/mL to about 25.0 pg/mL, about 5.5 pg/mL to about 25.0 pg/mL, about 6.0 pg/mL to about 25.0 pg/mL, about 6.5 pg/mL to about 25.0 pg/mL, about 7.0 pg/mL to about 25.0 pg/mL, about 7.5 pg/mL to about 25.0 pg/mL, about 8.0 pg/mL to about 25.0 pg/mL, about 8.5 pg/mL to about 25.0 pg/mL, about 9.0 pg/mL to about 25.0 pg/mL, about 9.5 pg/mL to about 25.0 pg/mL, about 10.0 pg/mL to about 25.0 pg/mL, about 1.0 pg/mL to about 24.0 pg/mL, about 1.5 pg/mL to about 24.0 pg/mL, about 2.0 pg/mL to about 24.0 pg/mL, about 2.5 pg/mL to about 24.0 pg/mL, about 3.0 pg/mL to about 24.0 pg/mL, about 3.5 pg/mL to about 24.0 pg/mL, 4.0 pg/mL to about 24.0 pg/mL, about 4.5 pg/mL to about 24.0 pg/mL, about 5.0 pg/mL to about 24.0 pg/mL, about 5.5 pg/mL to about 24.0 pg/mL, about 6.0 pg/mL to about 24.0 pg/mL, about 6.5 pg/mL to about 24.0 pg/mL, about 7.0 pg/mL to about 24.0 pg/mL, about 7.5 pg/mL to about 24.0 pg/mL, about 8.0 pg/mL to about 24.0 pg/mL, about 8.5 pg/mL to about 24.0 pg/mL, about 9.0 pg/mL to about 24.0 pg/mL, about 9.5 pg/mL to about 24.0 pg/mL, about 10.0 pg/mL to about 24.0 pg/mL, about 1.0 pg/mL to about 23.0 pg/mL, about 1.5 pg/mL to about 23.0 pg/mL, about 2.0 pg/mL to about 23.0 pg/mL, about 2.5 pg/mL to about 23.0 pg/mL, about 3.0 pg/mL to about 23.0 pg/mL, about 3.5 pg/mL to about 23.0 pg/mL, about 4.0 pg/mL to about 23.0 pg/mL, about 4.5 pg/mL to about 23.0 pg/mL, about 5.0 pg/mL to about 23.0 pg/mL, about 5.5 pg/mL to about 23.0 pg/mL, about 6.0 pg/mL to about 23.0 pg/mL, about 6.5 pg/mL to about 23.0 pg/mL, about 7.0 pg/mL to about 23.0 pg/mL, about 7.5 pg/mL to about 23.0 pg/mL, about 8.0 pg/mL to about 23.0 pg/mL, about 8.5 pg/mL to about 23.0 pg/mL, about 9.0 pg/mL to about 23.0 pg/mL, about 9.5 pg/mL to about 23.0 pg/mL, about 10.0 pg/mL to about 23.0 pg/mL, about 1.0 pg/mL to about 22.0 pg/mL, about 1.5 pg/mL to about 22.0 pg/mL, about 2.0 pg/mL to about 22.0 pg/mL, about 2.5 pg/mL to about 22.0 pg/mL, about 3.0 pg/mL to about 22.0 pg/mL, about 3.5 pg/mL to about 22.0 pg/mL, about 4.0 pg/mL to about 22.0 pg/mL, about 4.5 pg/mL to about 22.0 pg/mL, about 5.0 pg/mL to about 22.0 pg/mL, about 5.5 pg/mL to about 22.0 pg/mL, about 6.0 pg/mL to about 22.0 pg/mL, about 6.5 pg/mL to about 22.0 pg/mL, about 7.0 pg/mL to about 22.0 pg/mL, about 7.5 pg/mL to about 22.0 pg/mL, about 8.0 pg/mL to about 22.0 pg/mL, about 8.5 pg/mL to about 22.0 pg/mL, about 9.0 pg/mL to about 22.0 pg/mL, about 9.5 pg/mL to about 22.0 pg/mL, about 10.0 pg/mL to about 22.0 pg/mL, about 1.0 pg/mL to about 21.0 pg/mL, about 1.5 pg/mL to about 21.0 pg/mL, about 2.0 pg/mL to about 21.0 pg/mL, about 2.5 pg/mL to about 21.0 pg/mL, about 3.0 pg/mL to about 21.0 pg/mL, about 3.5 pg/mL to about 21.0 pg/mL, about 4.0 pg/mL to about 21.0 pg/mL, about 4.5 pg/mL to about 21.0 pg/mL, about 5.0 pg/mL to about 21.0 pg/mL, about 5.5 pg/mL to about 21.0 pg/mL, about 6.0 pg/mL to about 21.0 pg/mL, about 6.5 pg/mL to about 21.0 pg/mL, about 7.0 pg/mL to about 21.0 pg/mL, about 7.5 pg/mL to about 21.0 pg/mL, about 8.0 pg/mL to about 21.0 pg/mL, about 8.5 pg/mL to about 21.0 pg/mL, about 9.0 pg/mL to about 21.0 pg/mL, about 9.5 pg/mL to about 21.0 pg/mL, about 10.0 pg/mL to about 21.0 pg/mL, about 1.0 pg/mL to about 20.0 pg/mL, about 1.5 pg/mL to about 20.0 pg/mL, about 2.0 pg/mL to about 20.0 pg/mL, about 2.5 pg/mL to about 20.0 pg/mL, about 3.0 pg/mL to about 20.0 pg/mL, about 3.5 pg/mL to about 20.0 pg/mL, about 4.0 pg/mL to about 20.0 pg/mL, about 4.5 pg/mL to about 20.0 pg/mL, about 5.0 pg/mL to about 20.0 pg/mL, about 5.5 pg/mL to about 20.0 pg/mL, about 6.0 pg/mL to about 20.0 pg/mL, about 6.5 pg/mL to about 20.0 pg/mL, about 7.0 pg/mL to about 20.0 pg/mL, about 7.5 pg/mL to about 20.0 pg/mL, about 8.0 pg/mL to about 20.0 pg/mL, about 8.5 pg/mL to about 20.0 pg/mL, about 9.0 pg/mL to about 20.0 pg/mL, about 9.5 pg/mL to about 20.0 pg/mL, about 10.0 pg/mL to about 20.0 pg/mL, about 1.0 pg/mL to about 19.0 pg/mL, about 1.5 pg/mL to about 19.0 pg/mL, about 2.0 pg/mL to about 19.0 pg/mL, about 2.5 pg/mL to about 19.0 pg/mL, about 3.0 pg/mL to about 19.0 pg/mL, about 3.5 pg/mL to about 19.0 pg/mL, about 4.0 pg/mL to about 19.0 pg/mL, about 4.5 pg/mL to about 19.0 pg/mL, about 5.0 pg/mL to about 19.0 pg/mL, about 5.5 pg/mL to about 19.0 pg/mL, about 6.0 pg/mL to about 19.0 pg/mL, about 6.5 pg/mL to about 19.0 pg/mL, about 7.0 pg/mL to about 19.0 pg/mL, about 7.5 pg/mL to about 19.0 pg/mL, about 8.0 pg/mL to about 19.0 pg/mL, about 8.5 pg/mL to about 19.0 pg/mL, about 9.0 pg/mL to about 19.0 pg/mL, about 9.5 pg/mL to about 19.0 pg/mL, about 10.0 pg/mL to about 19.0 pg/mL, about 1.0 pg/mL to about 18.0 pg/mL, about 1.5 pg/mL to about 18.0 pg/mL, about 2.0 pg/mL to about 18.0 pg/mL, about 2.5 pg/mL to about 18.0 pg/mL, about 3.0 pg/mL to about 18.0 pg/mL, about 3.5 pg/mL to about 18.0 pg/mL, about 4.0 pg/mL to about 18.0 pg/mL, about 4.5 pg/mL to about 18.0 pg/mL, about 5.0 pg/mL to about 18.0 pg/mL, about 5.5 pg/mL to about 18.0 pg/mL, about 6.0 pg/mL to about 18.0 pg/mL, about 6.5 pg/mL to about 18.0 pg/mL, about 7.0 pg/mL to about 18.0 pg/mL, about 7.5 pg/mL to about 18.0 pg/mL, about 8.0 pg/mL to about 18.0 pg/mL, about 8.5 pg/mL to about 18.0 pg/mL, about 9.0 pg/mL to about 18.0 pg/mL, about 9.5 pg/mL to about 18.0 pg/mL, about 10.0 pg/mL to about 18.0 pg/mL, about 1.0 pg/mL to about 17.0 pg/mL, about 1.5 pg/mL to about 17.0 pg/mL, about 2.0 pg/mL to about 17.0 pg/mL, about 2.5 pg/mL to about 17.0 pg/mL, about 3.0 pg/mL to about 17.0 pg/mL, about 3.5 pg/mL to about 17.0 pg/mL, about 4.0 pg/mL to about 17.0 pg/mL, about 4.5 pg/mL to about 17.0 pg/mL, about 5.0 pg/mL to about 17.0 pg/mL, about 5.5 pg/mL to about 17.0 pg/mL, about 6.0 pg/mL to about 17.0 pg/mL, about 6.5 pg/mL to about 17.0 pg/mL, about 7.0 pg/mL to about 17.0 pg/mL, about 7.5 pg/mL to about 17.0 pg/mL, about 8.0 pg/mL to about 17.0 pg/mL, about 8.5 pg/mL to about 17.0 pg/mL, about 9.0 pg/mL to about 17.0 pg/mL, about 9.5 pg/mL to about 17.0 pg/mL, about 10.0 pg/mL to about 17.0 pg/mL, about 1.0 pg/mL to about 16.0 pg/mL, about 1.5 pg/mL to about 16.0 pg/mL, about 2.0 pg/mL to about 16.0 pg/mL, about 2.5 pg/mL to about 16.0 pg/mL, about 3.0 pg/mL to about 16.0 pg/mL, about 3.5 pg/mL to about 16.0 pg/mL, about 4.0 pg/mL to about 16.0 pg/mL, about 4.5 pg/mL to about 16.0 pg/mL, about 5.0 pg/mL to about 16.0 pg/mL, about 5.5 pg/mL to about 16.0 pg/mL, about 6.0 pg/mL to about 16.0 pg/mL, about 6.5 pg/mL to about 16.0 pg/mL, about 7.0 pg/mL to about 16.0 pg/mL, about 7.5 pg/mL to about 16.0 pg/mL, about 8.0 pg/mL to about 16.0 pg/mL, about 8.5 pg/mL to about 16.0 pg/mL, about 9.0 pg/mL to about 16.0 pg/mL, about 9.5 pg/mL to about 16.0 pg/mL, about 10.0 pg/mL to about 16.0 pg/mL, about 1.0 pg/mL to about 15.0 pg/mL, about 1.5 pg/mL to about 15.0 pg/mL, about 2.0 pg/mL to about 15.0 pg/mL, about 2.5 pg/mL to about 15.0 pg/mL, about 3.0 pg/mL to about 15.0 pg/mL, about 3.5 pg/mL to about 15.0 pg/mL, about 4.0 pg/mL to about 15.0 pg/mL, about 4.5 pg/mL to about 15.0 pg/mL, about 5.0 pg/mL to about 15.0 pg/mL, about 5.5 pg/mL to about 15.0 pg/mL, about 6.0 pg/mL to about 15.0 pg/mL, about 6.5 pg/mL to about 15.0 pg/mL, about 7.0 pg/mL to about 15.0 pg/mL, about 7.5 pg/mL to about 15.0 pg/mL, about 8.0 pg/mL to about 15.0 pg/mL, about 8.5 pg/mL to about 15.0 pg/mL, about 9.0 pg/mL to about 15.0 pg/mL, about 9.5 pg/mL to about 15.0 pg/mL or about 10.0 pg/mL to about 15.0 pg/mL.

In some embodiments, the amount of cardiac troponin I in the second or subsequent sample is from about 1.0 pg/mL to about 50.0 pg/mL, about 1.5 pg/mL to about 50.0 pg/mL, about 2.0 pg/mL to about 50.0 pg/mL, about 2.5 pg/mL to about 50.0 pg/mL, about 3.0 pg/mL to about 50.0 pg/mL, about 3.5 pg/mL to about 50.0 pg/mL, about 4.0 pg/mL to about 50.0 pg/mL, about 4.5 pg/mL to about 50.0 pg/mL, about 5.0 pg/mL to about 50.0 pg/mL, about 5.5 pg/mL to about 50.0 pg/mL, about 6.0 pg/mL to about 50.0 pg/mL, about 6.5 pg/mL to about 50.0 pg/mL, about 7.0 pg/mL to about 50.0 pg/mL, about 7.5 pg/mL to about 50.0 pg/mL, about 8.0 pg/mL to about 50.0 pg/mL, about 8.5 pg/mL to about 50.0 pg/mL, about 9.0 pg/mL to about 50.0 pg/mL, about 9.5 pg/mL to about 50.0 pg/mL, about 10.0 pg/mL to about 50.0 pg/mL, about 1.0 pg/mL to about 40.0 pg/mL, about 1.5 pg/mL to about 40.0 pg/mL, about 2.0 pg/mL to about 40.0 pg/mL, about 2.5 pg/mL to about 40.0 pg/mL, about 3.0 pg/mL to about 40.0 pg/mL, about 3.5 pg/mL to about 40.0 pg/mL, about 4.0 pg/mL to about 40.0 pg/mL, about 4.5 pg/mL to about 40.0 pg/mL, about 5.0 pg/mL to about 40.0 pg/mL, about 5.5 pg/mL to about 40.0 pg/mL, about 6.0 pg/mL to about 40.0 pg/mL, about 6.5 pg/mL to about 40.0 pg/mL, about 7.0 pg/mL to about 40.0 pg/mL, about 7.5 pg/mL to about 40.0 pg/mL, about 8.0 pg/mL to about 40.0 pg/mL, about 8.5 pg/mL to about 40.0 pg/mL, about 9.0 pg/mL to about 40.0 pg/mL, about 9.5 pg/mL to about 40.0 pg/mL, about 10.0 pg/mL to about 40.0 pg/mL, about 1.0 pg/mL to about 35.0 pg/mL, about 1.5 pg/mL to about 35.0 pg/mL, about 2.0 pg/mL to about 35.0 pg/mL, about 2.5 pg/mL to about 35.0 pg/mL, about 3.0 pg/mL to about 35.0 pg/mL, about 3.5 pg/mL to about 35.0 pg/mL, about 4.0 pg/mL to about 35.0 pg/mL, about 4.5 pg/mL to about 35.0 pg/mL, about 5.0 pg/mL to about 35.0 pg/mL, about 5.5 pg/mL to about 35.0 pg/mL, about 6.0 pg/mL to about 35.0 pg/mL, about 6.5 pg/mL to about 35.0 pg/mL, about 7.0 pg/mL to about 35.0 pg/mL, about 7.5 pg/mL to about 35.0 pg/mL, about 8.0 pg/mL to about 35.0 pg/mL, about 8.5 pg/mL to about 35.0 pg/mL, about 9.0 pg/mL to about 35.0 pg/mL, about 9.5 pg/mL to about 35.0 pg/mL, about 10.0 pg/mL to about 35.0 pg/mL, about 1.0 pg/mL to about 30.0 pg/mL, about 1.5 pg/mL to about 30.0 pg/mL, about 2.0 pg/mL to about 30.0 pg/mL, about 2.5 pg/mL to about 30.0 pg/mL, about 3.0 pg/mL to about 30.0 pg/mL, about 3.5 pg/mL to about 30.0 pg/mL, about 4.0 pg/mL to about 30.0 pg/mL, about 4.5 pg/mL to about 30.0 pg/mL, about 5.0 pg/mL to about 30.0 pg/mL, about 5.5 pg/mL to about 30.0 pg/mL, about 6.0 pg/mL to about 30.0 pg/mL, about 6.5 pg/mL to about 30.0 pg/mL, about 7.0 pg/mL to about 30.0 pg/mL, about 7.5 pg/mL to about 30.0 pg/mL, about 8.0 pg/mL to about 30.0 pg/mL, about 8.5 pg/mL to about 30.0 pg/mL, about 9.0 pg/mL to about 30.0 pg/mL, about 9.5 pg/mL to about 30.0 pg/mL, about 10.0 pg/mL to about 30.0 pg/mL, about 1.0 pg/mL to about 29.0 pg/mL, about 1.5 pg/mL to about 29.0 pg/mL, about 2.0 pg/mL to about 29.0 pg/mL, about 2.5 pg/mL to about 29.0 pg/mL, about 3.0 pg/mL to about 29.0 pg/mL, about 3.5 pg/mL to about 29.0 pg/mL, about 4.0 pg/mL to about 29.0 pg/mL, about 4.5 pg/mL to about 29.0 pg/mL, about 5.0 pg/mL to about 29.0 pg/mL, about 5.5 pg/mL to about 29.0 pg/mL, about 6.0 pg/mL to about 29.0 pg/mL, about 6.5 pg/mL to about 29.0 pg/mL, about 7.0 pg/mL to about 29.0 pg/mL, about 7.5 pg/mL to about 29.0 pg/mL, about 8.0 pg/mL to about 29.0 pg/mL, about 8.5 pg/mL to about 29.0 pg/mL, about 9.0 pg/mL to about 29.0 pg/mL, about 9.5 pg/mL to about 29.0 pg/mL, about 10.0 pg/mL to about 29.0 pg/mL, about 1.0 pg/mL to about 28.0 pg/mL, about 1.5 pg/mL to about 28.0 pg/mL, about 2.0 pg/mL to about 28.0 pg/mL, about 2.5 pg/mL to about 28.0 pg/mL, about 3.0 pg/mL to about 28.0 pg/mL, about 3.5 pg/mL to about 28.0 pg/mL, about 4.0 pg/mL to about 28.0 pg/mL, about 4.5 pg/mL to about 28.0 pg/mL, about 5.0 pg/mL to about 28.0 pg/mL, about 5.5 pg/mL to about 28.0 pg/mL, about 6.0 pg/mL to about 28.0 pg/mL, about 6.5 pg/mL to about 28.0 pg/mL, about 7.0 pg/mL to about 28.0 pg/mL, about 7.5 pg/mL to about 28.0 pg/mL, about 8.0 pg/mL to about 28.0 pg/mL, about 8.5 pg/mL to about 28.0 pg/mL, about 9.0 pg/mL to about 28.0 pg/mL, about 9.5 pg/mL to about 28.0 pg/mL, about 10.0 pg/mL to about 28.0 pg/mL, about 1.0 pg/mL to about 27.0 pg/mL, about 1.5 pg/mL to about 27.0 pg/mL, about 2.0 pg/mL to about 27.0 pg/mL, about 2.5 pg/mL to about 27.0 pg/mL, about 3.0 pg/mL to about 27.0 pg/mL, about 3.5 pg/mL to about 27.0 pg/mL, about 4.0 pg/mL to about 27.0 pg/mL, about 4.5 pg/mL to about 27.0 pg/mL, about 5.0 pg/mL to about 27.0 pg/mL, about 5.5 pg/mL to about 27.0 pg/mL, about 6.0 pg/mL to about 27.0 pg/mL, about 6.5 pg/mL to about 27.0 pg/mL, about 7.0 pg/mL to about 27.0 pg/mL, about 7.5 pg/mL to about 27.0 pg/mL, about 8.0 pg/mL to about 27.0 pg/mL, about 8.5 pg/mL to about 27.0 pg/mL, about 9.0 pg/mL to about 27.0 pg/mL, about 9.5 pg/mL to about 27.0 pg/mL, about 10.0 pg/mL to about 27.0 pg/mL, about 1.0 pg/mL to about 26.0 pg/mL, about 1.5 pg/mL to about 26.0 pg/mL, about 2.0 pg/mL to about 26.0 pg/mL, about 2.5 pg/mL to about 26.0 pg/mL, about 3.0 pg/mL to about 26.0 pg/mL, about 3.5 pg/mL to about 26.0 pg/mL, about 4.0 pg/mL to about 26.0 pg/mL, about 4.5 pg/mL to about 26.0 pg/mL, about 5.0 pg/mL to about 26.0 pg/mL, about 5.5 pg/mL to about 26.0 pg/mL, about 6.0 pg/mL to about 26.0 pg/mL, about 6.5 pg/mL to about 26.0 pg/mL, about 7.0 pg/mL to about 26.0 pg/mL, about 7.5 pg/mL to about 26.0 pg/mL, about 8.0 pg/mL to about 26.0 pg/mL, about 8.5 pg/mL to about 26.0 pg/mL, about 9.0 pg/mL to about 26.0 pg/mL, about 9.5 pg/mL to about 26.0 pg/mL, about 10.0 pg/mL to about 26.0 pg/mL, about 1.0 pg/mL to about 25.0 pg/mL, about 1.5 pg/mL to about 25.0 pg/mL, about 2.0 pg/mL to about 25.0 pg/mL, about 2.5 pg/mL to about 25.0 pg/mL, about 3.0 pg/mL to about 25.0 pg/mL, about 3.5 pg/mL to about 25.0 pg/mL, about 4.0 pg/mL to about 25.0 pg/mL, about 4.5 pg/mL to about 25.0 pg/mL, about 5.0 pg/mL to about 25.0 pg/mL, about 5.5 pg/mL to about 25.0 pg/mL, about 6.0 pg/mL to about 25.0 pg/mL, about 6.5 pg/mL to about 25.0 pg/mL, about 7.0 pg/mL to about 25.0 pg/mL, about 7.5 pg/mL to about 25.0 pg/mL, about 8.0 pg/mL to about 25.0 pg/mL, about 8.5 pg/mL to about 25.0 pg/mL, about 9.0 pg/mL to about 25.0 pg/mL, about 9.5 pg/mL to about 25.0 pg/mL, about 10.0 pg/mL to about 25.0 pg/mL, about 1.0 pg/mL to about 24.0 pg/mL, about 1.5 pg/mL to about 24.0 pg/mL, about 2.0 pg/mL to about 24.0 pg/mL, about 2.5 pg/mL to about 24.0 pg/mL, about 3.0 pg/mL to about 24.0 pg/mL, about 3.5 pg/mL to about 24.0 pg/mL, about 4.0 pg/mL to about 24.0 pg/mL, about 4.5 pg/mL to about 24.0 pg/mL, about 5.0 pg/mL to about 24.0 pg/mL, about 5.5 pg/mL to about 24.0 pg/mL, about 6.0 pg/mL to about 24.0 pg/mL, about 6.5 pg/mL to about 24.0 pg/mL, about 7.0 pg/mL to about 24.0 pg/mL, about 7.5 pg/mL to about 24.0 pg/mL, about 8.0 pg/mL to about 24.0 pg/mL, about 8.5 pg/mL to about 24.0 pg/mL, about 9.0 pg/mL to about 24.0 pg/mL, about 9.5 pg/mL to about 24.0 pg/mL, about 10.0 pg/mL to about 24.0 pg/mL, about 1.0 pg/mL to about 23.0 pg/mL, about 1.5 pg/mL to about 23.0 pg/mL, about 2.0 pg/mL to about 23.0 pg/mL, about 2.5 pg/mL to about 23.0 pg/mL, about 3.0 pg/mL to about 23.0 pg/mL, about 3.5 pg/mL to about 23.0 pg/mL, about 4.0 pg/mL to about 23.0 pg/mL, about 4.5 pg/mL to about 23.0 pg/mL, about 5.0 pg/mL to about 23.0 pg/mL, about 5.5 pg/mL to about 23.0 pg/mL, about 6.0 pg/mL to about 23.0 pg/mL, about 6.5 pg/mL to about 23.0 pg/mL, about 7.0 pg/mL to about 23.0 pg/mL, about 7.5 pg/mL to about 23.0 pg/mL, about 8.0 pg/mL to about 23.0 pg/mL, about 8.5 pg/mL to about 23.0 pg/mL, about 9.0 pg/mL to about 23.0 pg/mL, about 9.5 pg/mL to about 23.0 pg/mL, about 10.0 pg/mL to about 23.0 pg/mL, about 1.0 pg/mL to about 22.0 pg/mL, about 1.5 pg/mL to about 22.0 pg/mL, about 2.0 pg/mL to about 22.0 pg/mL, about 2.5 pg/mL to about 22.0 pg/mL, about 3.0 pg/mL to about 22.0 pg/mL, about 3.5 pg/mL to about 22.0 pg/mL, about 4.0 pg/mL to about 22.0 pg/mL, about 4.5 pg/mL to about 22.0 pg/mL, about 5.0 pg/mL to about 22.0 pg/mL, about 5.5 pg/mL to about 22.0 pg/mL, about 6.0 pg/mL to about 22.0 pg/mL, about 6.5 pg/mL to about 22.0 pg/mL, about 7.0 pg/mL to about 22.0 pg/mL, about 7.5 pg/mL to about 22.0 pg/mL, about 8.0 pg/mL to about 22.0 pg/mL, about 8.5 pg/mL to about 22.0 pg/mL, about 9.0 pg/mL to about 22.0 pg/mL, about 9.5 pg/mL to about 22.0 pg/mL, about 10.0 pg/mL to about 22.0 pg/mL, about 1.0 pg/mL to about 21.0 pg/mL, about 1.5 pg/mL to about 21.0 pg/mL, about 2.0 pg/mL to about 21.0 pg/mL, about 2.5 pg/mL to about 21.0 pg/mL, about 3.0 pg/mL to about 21.0 pg/mL, about 3.5 pg/mL to about 21.0 pg/mL, about 4.0 pg/mL to about 21.0 pg/mL, about 4.5 pg/mL to about 21.0 pg/mL, about 5.0 pg/mL to about 21.0 pg/mL, about 5.5 pg/mL to about 21.0 pg/mL, about 6.0 pg/mL to about 21.0 pg/mL, about 6.5 pg/mL to about 21.0 pg/mL, about 7.0 pg/mL to about 21.0 pg/mL, about 7.5 pg/mL to about 21.0 pg/mL, about 8.0 pg/mL to about 21.0 pg/mL, about 8.5 pg/mL to about 21.0 pg/mL, about 9.0 pg/mL to about 21.0 pg/mL, about 9.5 pg/mL to about 21.0 pg/mL, about 10.0 pg/mL to about 21.0 pg/mL, about 1.0 pg/mL to about 20.0 pg/mL, about 1.5 pg/mL to about 20.0 pg/mL, about 2.0 pg/mL to about 20.0 pg/mL, about 2.5 pg/mL to about 20.0 pg/mL, about 3.0 pg/mL to about 20.0 pg/mL, about 3.5 pg/mL to about 20.0 pg/mL, about 4.0 pg/mL to about 20.0 pg/mL, about 4.5 pg/mL to about 20.0 pg/mL, about 5.0 pg/mL to about 20.0 pg/mL, about 5.5 pg/mL to about 20.0 pg/mL, about 6.0 pg/mL to about 20.0 pg/mL, about 6.5 pg/mL to about 20.0 pg/mL, about 7.0 pg/mL to about 20.0 pg/mL, about 7.5 pg/mL to about 20.0 pg/mL, about 8.0 pg/mL to about 20.0 pg/mL, about 8.5 pg/mL to about 20.0 pg/mL, about 9.0 pg/mL to about 20.0 pg/mL, about 9.5 pg/mL to about 20.0 pg/mL, about 10.0 pg/mL to about 20.0 pg/mL, about 1.0 pg/mL to about 19.0 pg/mL, about 1.5 pg/mL to about 19.0 pg/mL, about 2.0 pg/mL to about 19.0 pg/mL, about 2.5 pg/mL to about 19.0 pg/mL, about 3.0 pg/mL to about 19.0 pg/mL, about 3.5 pg/mL to about 19.0 pg/mL, about 4.0 pg/mL to about 19.0 pg/mL, about 4.5 pg/mL to about 19.0 pg/mL, about 5.0 pg/mL to about 19.0 pg/mL, about 5.5 pg/mL to about 19.0 pg/mL, about 6.0 pg/mL to about 19.0 pg/mL, about 6.5 pg/mL to about 19.0 pg/mL, about 7.0 pg/mL to about 19.0 pg/mL, about 7.5 pg/mL to about 19.0 pg/mL, about 8.0 pg/mL to about 19.0 pg/mL, about 8.5 pg/mL to about 19.0 pg/mL, about 9.0 pg/mL to about 19.0 pg/mL, about 9.5 pg/mL to about 19.0 pg/mL, about 10.0 pg/mL to about 19.0 pg/mL, about 1.0 pg/mL to about 18.0 pg/mL, about 1.5 pg/mL to about 18.0 pg/mL, about 2.0 pg/mL to about 18.0 pg/mL, about 2.5 pg/mL to about 18.0 pg/mL, about 3.0 pg/mL to about 18.0 pg/mL, about 3.5 pg/mL to about 18.0 pg/mL, about 4.0 pg/mL to about 18.0 pg/mL, about 4.5 pg/mL to about 18.0 pg/mL, about 5.0 pg/mL to about 18.0 pg/mL, about 5.5 pg/mL to about 18.0 pg/mL, about 6.0 pg/mL to about 18.0 pg/mL, about 6.5 pg/mL to about 18.0 pg/mL, about 7.0 pg/mL to about 18.0 pg/mL, about 7.5 pg/mL to about 18.0 pg/mL, about 8.0 pg/mL to about 18.0 pg/mL, about 8.5 pg/mL to about 18.0 pg/mL, about 9.0 pg/mL to about 18.0 pg/mL, about 9.5 pg/mL to about 18.0 pg/mL, about 10.0 pg/mL to about 18.0 pg/mL, about 1.0 pg/mL to about 17.0 pg/mL, about 1.5 pg/mL to about 17.0 pg/mL, about 2.0 pg/mL to about 17.0 pg/mL, about 2.5 pg/mL to about 17.0 pg/mL, about 3.0 pg/mL to about 17.0 pg/mL, about 3.5 pg/mL to about 17.0 pg/mL, about 4.0 pg/mL to about 17.0 pg/mL, about 4.5 pg/mL to about 17.0 pg/mL, about 5.0 pg/mL to about 17.0 pg/mL, about 5.5 pg/mL to about 17.0 pg/mL, about 6.0 pg/mL to about 17.0 pg/mL, about 6.5 pg/mL to about 17.0 pg/mL, about 7.0 pg/mL to about 17.0 pg/mL, about 7.5 pg/mL to about 17.0 pg/mL, about 8.0 pg/mL to about 17.0 pg/mL, about 8.5 pg/mL to about 17.0 pg/mL, about 9.0 pg/mL to about 17.0 pg/mL, about 9.5 pg/mL to about 17.0 pg/mL, about 10.0 pg/mL to about 17.0 pg/mL, about 1.0 pg/mL to about 16.0 pg/mL, about 1.5 pg/mL to about 16.0 pg/mL, about 2.0 pg/mL to about 16.0 pg/mL, about 2.5 pg/mL to about 16.0 pg/mL, about 3.0 pg/mL to about 16.0 pg/mL, about 3.5 pg/mL to about 16.0 pg/mL, about 4.0 pg/mL to about 16.0 pg/mL, about 4.5 pg/mL to about 16.0 pg/mL, about 5.0 pg/mL to about 16.0 pg/mL, about 5.5 pg/mL to about 16.0 pg/mL, about 6.0 pg/mL to about 16.0 pg/mL, about 6.5 pg/mL to about 16.0 pg/mL, about 7.0 pg/mL to about 16.0 pg/mL, about 7.5 pg/mL to about 16.0 pg/mL, about 8.0 pg/mL to about 16.0 pg/mL, about 8.5 pg/mL to about 16.0 pg/mL, about 9.0 pg/mL to about 16.0 pg/mL, about 9.5 pg/mL to about 16.0 pg/mL, about 10.0 pg/mL to about 16.0 pg/mL, about 1.0 pg/mL to about 15.0 pg/mL, about 1.5 pg/mL to about 15.0 pg/mL, about 2.0 pg/mL to about 15.0 pg/mL, about 2.5 pg/mL to about 15.0 pg/mL, about 3.0 pg/mL to about 15.0 pg/mL, about 3.5 pg/mL to about 15.0 pg/mL, about 4.0 pg/mL to about 15.0 pg/mL, about 4.5 pg/mL to about 15.0 pg/mL, about 5.0 pg/mL to about 15.0 pg/mL, about 5.5 pg/mL to about 15.0 pg/mL, about 6.0 pg/mL to about 15.0 pg/mL, about 6.5 pg/mL to about 15.0 pg/mL, about 7.0 pg/mL to about 15.0 pg/mL, about 7.5 pg/mL to about 15.0 pg/mL, about 8.0 pg/mL to about 15.0 pg/mL, about 8.5 pg/mL to about 15.0 pg/mL, about 9.0 pg/mL to about 15.0 pg/mL, about 9.5 pg/mL to about 15.0 pg/mL, or about 10.0 pg/mL to about 15.0 pg/mL.

In some embodiments, the absolute amount of cTnI is determined by an assay having a sensitivity of between at least about 65% to about 100% and a specificity of between at least about 30% to about 100%. In some embodiments, the sensitivity is between at least about 65% to about 100%, between at least about 65% to at least about 99%, between at least about 65% to at least about 95%, between at least about 65% to at least about 90%, between at least about 65% to at least about 85%, between at least about 65% to at least about 80%, between at least about 65% to at least about 75%, between at least about 65% to at least about 70%, between at least about 75% to about 100%, between at least about 75% to at least about 99%, between at least about 75% to at least about 95%, between at least about 75% to at least about 90%, between at least about 75% to at least about 85%, between at least about 75% to at least about 80%, between at least about 85% to about 100%, between at least about 85% to at least about 99%, between at least about 85% to at least about 95%, between at least about 85% to at least about 90%, between at least about 95% to about 100%, or between at least about 95% to at least about 99%. In some embodiments, the sensitivity is at least about 65.0%, at least about 70.0%, at least about 75.0%, at least about 80.0%, at least about 82.4%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 40% to about 50%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 69.5%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 82.4% and the specificity is at least about 69.5%, the sensitivity is at least about 99% and the specificity is at least about 75%, the sensitivity is at least about 99% and the specificity is at least about 99%, or the sensitivity is at least about 100% and the specificity is at least about 100%.

In some embodiments, the absolute amount can be between at least about 1 pg/mL to about 25 pg/mL. In some embodiments, the absolute amount can be between at least about 1 pg/mL to about 25 pg/mL, between at least about 1 pg/mL to about 20 pg/mL, between at least about 1 pg/mL to about 15 pg/mL, between at least about 1 pg/mL to about 10 pg/mL, between at least about 1 pg/mL to about 9 pg/mL, between at least about 1 pg/mL to about 8 pg/mL, between at least about 1 pg/mL to about 7 pg/mL, between at least about 1 pg/mL to about 6 pg/mL, between at least about 1 pg/mL to about 5 pg/mL, between at least about 1 pg/mL to about 4 pg/mL, between at least about 1 pg/mL to about 3 pg/mL, between at least about 1 pg/mL to about 2 pg/mL, between at least about 1 pg/mL to about 1.5 pg/mL, between at least about 1.5 pg/mL to about 25 pg/mL, between at least about 1.5 pg/mL to about 20 pg/mL, between at least about 1.5 pg/mL to about 15 pg/mL, between at least about 1.5 pg/mL to about 10 pg/mL, between at least about 1.5 pg/mL to about 9 pg/mL, between at least about 1.5 pg/mL to about 8 pg/mL, between at least about 1.5 pg/mL to about 7 pg/mL, between at least about 1.5 pg/mL to about 6 pg/mL, between at least about 1.5 pg/mL to about 5 pg/mL, between at least about 1.5 pg/mL to about 4 pg/mL, between at least about 1.5 pg/mL to about 3 pg/mL, between at least about 1.5 pg/mL to about 2 pg/mL, between at least about 2 pg/mL to about 25 pg/mL, between at least about 2 pg/mL to about 20 pg/mL, between at least about 2 pg/mL to about 15 pg/mL, between at least about 2 pg/mL to about 10 pg/mL, between at least about 2 pg/mL to about 9 pg/mL, between at least about 2 pg/mL to about 8 pg/mL, between at least about 2 pg/mL to about 7 pg/mL, between at least about 2 pg/mL to about 6 pg/mL, between at least about 2 pg/mL to about 5 pg/mL, between at least about 2 pg/mL to about 4 pg/mL, between at least about 2 pg/mL to about 3 pg/mL, between at least about 3 pg/mL to about 25 pg/mL, between at least about 3 pg/mL to about 20 pg/mL, between at least about 3 pg/mL to about 15 pg/mL, between at least about 3 pg/mL to about 10 pg/mL, between at least about 3 pg/mL to about 9 pg/mL, between at least about 3 pg/mL to about 8 pg/mL, between at least about 3 pg/mL to about 7 pg/mL, between at least about 3 pg/mL to about 6 pg/mL, between at least about 3 pg/mL to about 5 pg/mL, between at least about 3 pg/mL to about 4 pg/mL, between at least about 4 pg/mL to about 25 pg/mL, between at least about 4 pg/mL to about 20 pg/mL, between at least about 4 pg/mL to about 15 pg/mL, between at least about 4 pg/mL to about 10 pg/mL, between at least about 4 pg/mL to about 9 pg/mL, between at least about 4 pg/mL to about 8 pg/mL, between at least about 4 pg/mL to about 7 pg/mL, between at least about 4 pg/mL to about 6 pg/mL, between at least about 4 pg/mL to about 5 pg/mL, between at least about 5 pg/mL to about 25 pg/mL, between at least about 5 pg/mL to about 20 pg/mL, between at least about 5 pg/mL to about 15 pg/mL, between at least about 5 pg/mL to about 10 pg/mL, between at least about 5 pg/mL to about 9 pg/mL, between at least about 5 pg/mL to about 8 pg/mL, between at least about 5 pg/mL to about 7 pg/mL, between at least about 5 pg/mL to about 6 pg/mL, between at least about 6 pg/mL to about 25 pg/mL, between at least about 6 pg/mL to about 20 pg/mL, between at least about 6 pg/mL to about 15 pg/mL, between at least about 6 pg/mL to about 10 pg/mL, between at least about 6 pg/mL to about 9 pg/mL, between at least about 6 pg/mL to about 8 pg/mL, between at least about 6 pg/mL to about 7 pg/mL, between at least about 7 pg/mL to about 25 pg/mL, between at least about 7 pg/mL to about 20 pg/mL, between at least about 7 pg/mL to about 15 pg/mL, between at least about 7 pg/mL to about 10 pg/mL, between at least about 7 pg/mL to about 9 pg/mL, between at least about 7 pg/mL to about 8 pg/mL, between at least about 8 pg/mL to about 25 pg/mL, between at least about 8 pg/mL to about 20 pg/mL, between at least about 8 pg/mL to about 15 pg/mL, between at least about 8 pg/mL to about 10 pg/mL, between at least about 8 pg/mL to about 9 pg/mL, between at least about 9 pg/mL to about 25 pg/mL, between at least about 9 pg/mL to about 20 pg/mL, between at least about 9 pg/mL to about 15 pg/mL, between at least about 9 pg/mL to about 10 pg/mL, between at least about 10 pg/mL to about 25 pg/mL, between at least about 10 pg/mL to about 20 pg/mL, between at least about 10 pg/mL to about 15 pg/mL, between at least about 15 pg/mL to about 25 pg/mL, between at least about 15 pg/mL to about 20 pg/mL, or between at least about 20 pg/mL to about 25 pg/mL. In some embodiments, the absolute amount can be at least about 0.5 pg/mL, at least about 1 pg/mL, at least about 1.5 pg/mL, at least about 2 pg/mL, at least about 3 pg/mL, at least about 4 pg/mL, at least about 5 pg/mL, at least about 6 pg/mL, at least about 7 pg/mL, at least about 8 pg/mL, at least about 9 pg/mL, at least about 10 pg/mL, at least about 11 pg/mL, at least about 12 pg/mL, at least about 13 pg/mL, at least about 14 pg/mL, at least about 15 pg/mL, at least about 20 pg/mL, or at least about 25 pg/mL.

In some embodiments, the absolute amount is between about 1 pg/mL to about 50 pg/mL, between about 1 pg/mL to about 40 pg/mL, between about 1 pg/mL to about 30 pg/mL, between about 1 pg/mL to about 20 pg/mL, between about 1 pg/mL to about 10 pg/mL, between about 1 pg/mL to about 5 pg/mL, between about 2.5 pg/mL to about 50 pg/mL, between about 2.5 pg/mL to about 40 pg/mL, between about 2.5 pg/mL to about 30 pg/mL, between about 2.5 pg/mL to about 20 pg/mL, between about 2.5 pg/mL to about 10 pg/mL, between about 2.5 pg/mL to about 5 pg/mL, between about 5 pg/mL to about 50 pg/mL, between about 5 pg/mL to about 40 pg/mL, between about 5 pg/mL to about 30 pg/mL, between about 5 pg/mL to about 20 pg/mL, or between about 5 pg/mL to about 10 pg/mL. In some embodiments, the absolute amount is at least about 1 pg/mL, at least about 2 pg/mL, at least about 3 pg/mL, at least about 4 pg/mL, at least about 5 pg/mL, at least about 5.5 pg/mL, at least about 5.6 pg/mL, at least about 5.7 pg/mL at least about 5.8 pg/mL at least about 5.9 pg/mL, at least about 6 pg/mL, at least about 7 pg/mL, at least about 8 pg/mL, at least about 9 pg/mL, at least about 10 pg/mL, at least about 20 pg/mL, at least about 30 pg/mL, at least about 40 pg/mL, or at least about 10 pg/mL.

In some embodiments, the method further includes treating the human subject predicted as having an unfavorable outcome with a traumatic brain injury treatment, as described below. In some embodiments, the method further includes monitoring the human subject predicted as having an unfavorable outcome, as described below. In some embodiments, the method further includes ordering additional tests to obtain further clinical information about the mild TBI in the human subject predicted as having an unfavorable outcome. In some embodiments, the method includes treating the human subject predicted to have an unfavorable outcome with a cardioprotective treatment to protect the heart as described below.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Such assays are described in further detail herein in Sections 11-13. Also, the assay can be employed in clinical chemistry format such as would be known by one skilled in the art. For example, a clinical chemistry format can include an assay that involves one antibody or no antibody. Examples of analyzers that can be used for the clinical chemistry format are described in U.S. Patent publication Nos. 2016/0320422 and 2015/0112630.

8. Methods of Aiding in Predicting or Predicting the Outcome of a Human Subject Having Mild Traumatic Brain Injury Using Cardiac Troponin I (cTnI) and Age The present disclosure relates, among other methods, to a method of aiding in predicting (or predicting) the outcome of a human subject having mild traumatic brain injury (TBI), e.g., determining whether the subject will have an unfavorable or negative outcome or favorable outcome. As used herein, the phrase "determining whether the subject has a favorable outcome" refers to the fact that the aforementioned method can be used, e.g., with other information (e.g., clinical assessment data), to determine that the subject is more likely than not to have a positive outcome from the mild TBI. Additionally, as used herein, the phrase "determining whether the subject has an unfavorable outcome" refers to the fact that the aforementioned method can be used, e.g., with other information (e.g., clinical assessment data), to determine that the subject is more likely than not to have an unfavorable or negative outcome from the mild TBI.

As mentioned above, the methods described herein can be used to determine whether a subject diagnosed with a mild TBI is more likely than not to have (1) a favorable outcome (optionally, the favorable outcome can be that the subject fully recovers and does not continue to experience one or more symptoms of a mild TBI); or (2) an unfavorable outcome (optionally, the unfavorable outcome can be that the subject does not fully recover and does continue to experience one or more symptoms of a mild TBI).

Alternatively and optionally, a favorable outcome can mean that the subject is more likely than not to suffer no more than one post-concussion syndrome symptom as a result of the mild TBI such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g., personality changes, irritability, depression, apathy, etc.); or (d) sleep difficulties (e.g., insomnia, etc.). Alternatively and option, subject who have an unfavorable outcome are more likely to suffer from more than one post-concussion syndrome symptom such as: (a) physical difficulties (e.g., headaches, dizziness, fatigue, sensitivity to light noise and light, etc.); (b) cognitive difficulties (e.g., trouble concentration, memory problems, restlessness, etc.); (c) emotional difficulties (e.g, personality changes, irritability, depression, apathy, etc.); (d) sleep difficulties (e.g., insomnia, etc.); or (e) any combinations of (a)-(d)). Alternatively and optionally, an unfavorable outcome can also mean that a subject exhibits one or more symptoms of mild TBI. Alternatively and optionally, an unfavorable outcome can also mean that the subject's conditions worsens from mild TBI to moderate, moderate to severe or severe. Additionally, subjects having a favorable outcome are likely to have a GOSE score of 5 or greater whereas subjects having an unfavorable outcome are likely to have a GOSE score of less than 5.

The methods disclosed herein can include performing an assay on a first sample and second sample obtained from the human subject after an injury to the head and determining the age of the subject. The first sample is taken from the subject within about 24 hours after injury and the second sample is taken from the subject within 0 to about 4 hours after the first sample is taken at two or more different time points. The assay is used to determine the level of cardiac troponin I in each of these samples. If the amount or level of cardiac troponin I in the first sample and/or second sample is higher than a reference level of cardiac troponin I and the age of the subject is lower than a reference age, such as, for example, between 40 and 50 years of age, then a determination is made that the subject is predicted to have an unfavorable outcome, for example at 6 months, or a more severe traumatic brain injury. However, if the amount or level of cardiac troponin I in the first sample and the second sample is lower than the reference level of cardiac troponin I and the age of the subject is less than a reference age, then a determination is made that the subject is predicted to have a favorable outcome at 6 months or a less severe traumatic brain injury.

In some embodiments of the above method, the age of the subject is 18 to 30 years. In other embodiments of the above method, the age of the subject is 31 to 50 years. In yet other embodiments of the above method, the age of the subject is 51 to 70 years. In yet other embodiments of the above method, the age of the subject is 70 to 100 years. In yet other embodiments of the above method, the age is 18 years or less. In yet other embodiments of the above method, the age is 19-50 years. In still further embodiments, the age is 51-70 years. In yet other embodiments of the above method, the age is greater than 70 years. In yet other embodiments of the above method, the age of the subject is 20 to 30 years. In yet other embodiments of the above method, the age of the subject is 31 to 40 years. In yet other embodiments of the above method, the age of the subject is 41 to 50 years. In yet other embodiments of the above method, the age of the subject is 51 to 60 years. In yet other embodiments of the above method, the age of the subject is 61 to 70 years. In yet other embodiments of the above method, the age of the subject is 71 to 80 years. In yet other embodiments of the above method, the age of the subject is 81 to 90 years. In yet other embodiments of the above method, the age of the subject is 91 to 100 years.

In some embodiments, the cTnI levels in samples taken at a first time point and at a second time point are combined with the age of the subject in the following formula:

$$Pr(Y=1) = \frac{\exp(\beta_0 + \beta_1 \ln(\text{initial troponin}) + \beta_2 \ln(4 \text{ hour troponin}) + \beta_3 \text{ age})}{1 + \exp(\beta_0 + \beta_1 \ln(\text{initial troponin}) + \beta_2 \ln(4 \text{ hour troponin}) + \beta_3 \text{ age})}$$

In some embodiments, age is a continuous variable. For examples, if weights are assigned based on the co-efficients, the weight of age can be 1.06, the weight of initial troponin can be 0.25, and the weight of 4 hour troponin can be 4.22. The first (or previous) sample may be obtained or taken from the subject 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of an injury to the head. In some embodiments, the (or previous) sample is taken within about 0 to about 1 hours, within about 0 to about 2 hours, within about 0 to about 3 hours, within about 0 to about 4 hours, within about 0 to about 5 hours, within about 0 to about 6 hours, within about 0 to about 7 hours, within about 0 to about 8 hours, within about 0 to about 9 hours, within about 0 to about 10 hours, within about 0 to about 11 hours, within about 0 to about 12 hours, within about 0 to about 18 hours, within about 6 to about 12 hours, within about 12 to about 18 hours, within about 18 to about 24 hours, or greater than 24 hours after the injury. The second (or subsequent) sample can be obtained after about 0 hour to 6 hours after the first (or last) sample was obtained. In some embodiments, the second (or subsequent) sample is taken from the subject within at least about 30 minutes, within at least about 1 hour, within at least about 2 hours, within at least about 3 hours, within at least about 4 hours, within at least about 5 hours, or within at least about 6 hours after the first sample is taken from the subject.

In some embodiments, the subject may have received a Glasgow Coma Scale score before or after the level of cardiac troponin is determined at one or more time points. In certain embodiments, the subject may be suspected of having a mild traumatic brain injury based on the Glasgow Coma Scale score. In certain embodiments, the subject may be suspected of having a mild traumatic brain injury based on an abnormal head CT. In some embodiments, the subject has received a CT scan before or after the assay is performed. In some embodiments, the subject has a normal head CT.

In some embodiments, the subject has received a GOSE score after the assay is performed. In some embodiments, the subject is suspected as having an unfavorable outcome based on the GOSE score. In some embodiments, the subject has a GOSE score of less than 5 at 1 month, 2 months, 3 months, 4 months, 5 months, or 6 months after the injury. In some embodiments, the reference level of cTnI is correlated with subjects having an unfavorable outcome. In some embodiments, the reference level of cTnI is correlated with a GOSE score of 1-5. In some embodiments, the subject is suspected as having a favorable outcome based on the GOSE score. In some embodiments, the reference level of cTnI is correlated with subjects having a favorable outcome. In some embodiments, the reference level of cTnI is correlated with a GOSE score of 6-8.

In some embodiments, the reference level of cTnI is correlated with subjects having a more severe traumatic brain injury, such as moderate to severe traumatic brain injury. In some embodiments, the reference level of cTnI is correlated with a Glasgow Coma Scale score of 3-12. In some embodiments, the subject is suspected as having mild traumatic brain injury based on the Glasgow Coma Scale score. In some embodiments, the reference level of cTnI is correlated with subjects having a less severe traumatic brain injury, such as mild traumatic brain injury. In some embodiments, the reference level of cTnI is correlated with a Glasgow Coma Scale score of 13-15.

Generally, a reference level of cTnI can also be employed as a benchmark against which to assess results obtained upon assaying a test sample for cTnI. Generally, in making such a comparison, the reference level of cTnI is obtained by running a particular assay a sufficient number of times and under appropriate conditions such that a linkage or association of analyte presence, amount or concentration with a particular stage or endpoint of TBI or with particular indicia can be made. Typically, the reference level of cTnI is obtained with assays of reference subjects (or populations of subjects). The cTnI measured can include fragments thereof, degradation products thereof, and/or enzymatic cleavage products thereof.

In certain embodiments, the reference level may be correlated with control subjects that have not sustained a head injury.

In some embodiments, the method can include obtaining samples from the subject and contacting the samples with an antibody for cardiac troponin I to allow formation of a complex of the antibody and cardiac troponin I. The method also includes detecting the resulting antibody-cardiac troponin I complex.

In some embodiments, the reference level of cTnI is determined by an assay having a sensitivity of between at least about 65% to about 100% and a specificity of between at least about 30% to about 100%. In some embodiments, the sensitivity is between at least about 65% to about 100%, between at least about 65% to at least about 99%, between at least about 65% to at least about 95%, between at least about 65% to at least about 90%, between at least about 65% to at least about 85%, between at least about 65% to at least about 80%, between at least about 65% to at least about 75%, between at least about 65% to at least about 70%, between at least about 75% to about 100%, between at least about 75% to at least about 99%, between at least about 75% to at least about 95%, between at least about 75% to at least about 90%, between at least about 75% to at least about 85%, between at least about 75% to at least about 80%, between at least about 85% to about 100%, between at least about 85% to at least about 99%, between at least about 85% to at least about 95%, between at least about 85% to at least about 90%, between at least about 95% to about 100%, or between at least about 95% to at least about 99%. In some embodiments, the sensitivity is at least about 65.0%, at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%.

In some embodiments, the specificity is between at least about 30% to about 100%, between at least about 30% to about 99%, between at least about 30% to about 95%, between at least about 30% to about 90%, between at least about 30% to about 85%, between at least about 30% to about 80%, between at least about 30% to about 75%, between at least about 30% to about 70%, between at least about 30% to about 60%, between at least about 30% to about 50%, between at least about 40% to about 100%, between at least about 40% to about 99%, between at least about 40% to about 95%, between at least about 40% to about 90%, between at least about 40% to about 85%, between at least about 40% to about 80%, between at least about 40% to about 75%, between at least about 40% to about 70%, between at least about 40% to about 60%, between at least about 50% to about 100%, between at least about 50% to about 99%, between at least about 50% to about 95%, between at least about 50% to about 90%, between at least about 50% to about 85%, between at least about 50% to about 80%, between at least about 50% to about 75%, between at least about 50% to about 70%, between at least about 50% to about 60%, between at least about 60% to about 100%, between at least about 60% to about 99%, between at least about 60% to about 95%, between at least about 60% to about 90%, between at least about 60% to about 85%, between at least about 60% to about 80%, between at least about 60% to about 75%, between at least about 60% to about 70%, between at least about 70% to about 100%, between at least about 70% to about 99%, between at least about 70% to about 95%, between at least about 70% to about 90%, between at least about 70% to about 85%, between at least about 70% to about 80%, between at least about 70% to about 75%, between at least about 80% to about 100%, between at least about 80% to about 99%, between at least about 80% to about 95%, between at least about 80% to about 90%, between at least about 80% to about 85%, between at least about 90% to about 100%, between at least about 90% to about 99%, between at least about 90% to about 95%, between at least about 95% to about 99%, or between at least about 95% to about 100. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is at least about 100% and the specificity is at least about 100%.

In some embodiments, the reference level of cardiac troponin I is from about 0.0100 pg/mL to about 50.0 pg/mL, about 0.0200 pg/mL to about 50.0 pg/mL, about 0.0300 pg/mL to about 50.0 pg/mL, about 0.036 pg/mL to about 50.0 pg/mL, about 0.0400 pg/mL to about 50.0 pg/mL, about 0.0500 pg/mL to about 50.0 pg/mL, about 0.1 pg/mL to about 50.0 pg/mL, about 0.5 pg/mL to about 50.0 pg/mL, about 1.0 pg/mL to about 50.0 pg/mL, about 1.5 pg/mL to about 50.0 pg/mL, about 2.0 pg/mL to about 50.0 pg/mL, about 2.5 pg/mL to about 50.0 pg/mL, about 3.0 pg/mL to about 50.0 pg/mL, about 3.5 pg/mL to about 50.0 pg/mL, about 4.0 pg/mL to about 50.0 pg/mL, about 4.5 pg/mL to about 50.0 pg/mL, about 5.0 pg/mL to about 50.0 pg/mL, about 5.5 pg/mL to about 50.0 pg/mL, about 6.0 pg/mL to about 50.0 pg/mL, about 6.5 pg/mL to about 50.0 pg/mL, about 7.0 pg/mL to about 50.0 pg/mL, about 7.5 pg/mL to about 50.0 pg/mL, about 8.0 pg/mL to about 50.0 pg/mL, about 8.5 pg/mL to about 50.0 pg/mL, about 9.0 pg/mL to about 50.0 pg/mL, about 9.5 pg/mL to about 50.0 pg/mL, about 10.0 pg/mL to about 50.0 pg/mL, about 0.0100 pg/mL to about 40.0 pg/mL, about 0.0200 pg/mL to about 40.0 pg/mL, about 0.0300 pg/mL to about 40.0 pg/mL, about 0.036 pg/mL to about 40.0 pg/mL, about 0.0400 pg/mL to about 40.0 pg/mL, about 0.0500 pg/mL to about 40.0 pg/mL, about 0.1 pg/mL to about 40.0 pg/mL, about 0.5 pg/mL to about 40.0 pg/mL, about 1.0 pg/mL to about 40.0 pg/mL, about 1.5 pg/mL to about 40.0 pg/mL, about 2.0 pg/mL to about 40.0 pg/mL, about 2.5 pg/mL to about 40.0 pg/mL, about 3.0 pg/mL to about 40.0 pg/mL, about 3.5 pg/mL to about 40.0 pg/mL, about 4.0 pg/mL to about 40.0 pg/mL, about 4.5 pg/mL to about 40.0 pg/mL, about 5.0 pg/mL to about 40.0 pg/mL, about 5.5 pg/mL to about 40.0 pg/mL, about 6.0 pg/mL to about 40.0 pg/mL, about 6.5 pg/mL to about 40.0 pg/mL, about 7.0 pg/mL to about 40.0 pg/mL, about 7.5 pg/mL to about 40.0 pg/mL, about 8.0 pg/mL to about 40.0 pg/mL, about 8.5 pg/mL to about 40.0 pg/mL, about 9.0 pg/mL to about 40.0 pg/mL, about 9.5 pg/mL to about 40.0 pg/mL, about 10.0 pg/mL to about 40.0 pg/mL, about 0.0100 pg/mL to about 35.0 pg/mL, about 0.0200 pg/mL to about 35.0 pg/mL, about 0.0300 pg/mL to about 35.0 pg/mL, about 0.036 pg/mL to about 35.0 pg/mL, about 0.0400 pg/mL to about 35.0 pg/mL, about 0.0500 pg/mL to about 35.0 pg/mL, about 0.1 pg/mL to about 35.0 pg/mL, about 0.5 pg/mL to about 35.0 pg/mL, about 1.0 pg/mL to about 35.0 pg/mL, about 1.5 pg/mL to about 35.0 pg/mL, about 2.0 pg/mL to about 35.0 pg/mL, about 2.5 pg/mL to about 35.0 pg/mL, about 3.0 pg/mL to about 35.0 pg/mL, about 3.5 pg/mL to about 35.0 pg/mL, about 4.0 pg/mL to about 35.0 pg/mL, about 4.5 pg/mL to about 35.0 pg/mL, about 5.0 pg/mL to about 35.0 pg/mL, about 5.5 pg/mL to about 35.0 pg/mL, about 6.0 pg/mL to about 35.0 pg/mL, about 6.5 pg/mL to about 35.0 pg/mL, about 7.0 pg/mL to about 35.0 pg/mL, about 7.5 pg/mL to about 35.0 pg/mL, about 8.0 pg/mL to about 35.0 pg/mL, about 8.5 pg/mL to about 35.0 pg/mL, about 9.0 pg/mL to about 35.0 pg/mL, about 9.5 pg/mL to about 35.0 pg/mL, about 10.0 pg/mL to about 35.0 pg/mL, about 0.0100 pg/mL to about 30.0 pg/mL, about 0.0200 pg/mL to about 30.0 pg/mL, about 0.0300 pg/mL to about 30.0 pg/mL, about 0.036 pg/mL to about 30.0 pg/mL, about 0.0400 pg/mL to about 30.0 pg/mL, about 0.0500 pg/mL to about 30.0 pg/mL, about 0.1 pg/mL to about 30.0 pg/mL, about 0.5 pg/mL to about 30.0 pg/mL, about 1.0 pg/mL to about 30.0 pg/mL, about 1.5 pg/mL to about 30.0 pg/mL, about 2.0 pg/mL to about 30.0 pg/mL, about 2.5 pg/mL to about 30.0 pg/mL, about 3.0 pg/mL to about 30.0 pg/mL, about 3.5 pg/mL to about 30.0 pg/mL, about 4.0 pg/mL to about 30.0 pg/mL, about 4.5 pg/mL to about 30.0 pg/mL, about 5.0 pg/mL to about 30.0 pg/mL, about 5.5 pg/mL to about 30.0 pg/mL, about 6.0 pg/mL to about 30.0 pg/mL, about 6.5 pg/mL to about 30.0 pg/mL, about 7.0 pg/mL to about 30.0 pg/mL, about 7.5 pg/mL to about 30.0 pg/mL, about 8.0 pg/mL to about 30.0 pg/mL, about 8.5 pg/mL to about 30.0 pg/mL, about 9.0 pg/mL to about 30.0 pg/mL, about 9.5 pg/mL to about 30.0 pg/mL, about 10.0 pg/mL to about 30.0 pg/mL, about 0.0100 pg/mL to about 25.0 pg/mL, about 0.0200 pg/mL to about 25.0 pg/mL, about 0.0300 pg/mL to about 25.0 pg/mL, about 0.036 pg/mL to about 25.0 pg/mL, about 0.0400 pg/mL to about 25.0 pg/mL, about 0.0500 pg/mL to about 25.0 pg/mL, about 0.1 pg/mL to about 25.0 pg/mL, about 0.5 pg/mL to about 25.0 pg/mL, about 1.0 pg/mL to about 25.0 pg/mL, about 1.5 pg/mL to about 25.0 pg/mL, about 2.0 pg/mL to about 25.0 pg/mL, about 2.5 pg/mL to about 25.0 pg/mL, about 3.0 pg/mL to about 25.0 pg/mL, about 3.5 pg/mL to about 25.0 pg/mL, about 4.0 pg/mL to about 25.0 pg/mL, about 4.5 pg/mL to about 25.0 pg/mL, about 5.0 pg/mL to about 25.0 pg/mL, about 5.5 pg/mL to about 25.0 pg/mL, about 6.0 pg/mL to about 25.0 pg/mL, about 6.5 pg/mL to about 25.0 pg/mL, about 7.0 pg/mL to about 25.0 pg/mL, about 7.5 pg/mL to about 25.0 pg/mL, about 8.0 pg/mL to about 25.0 pg/mL, about 8.5 pg/mL to about 25.0 pg/mL, about 9.0 pg/mL to about 25.0 pg/mL, about 9.5 pg/mL to about 25.0 pg/mL, about 10.0 pg/mL to about 25.0 pg/mL, about 0.0100 pg/mL to about 24.0 pg/mL, about 0.0200 pg/mL to about 24.0 pg/mL, about 0.0300 pg/mL to about 24.0 pg/mL, about 0.036 pg/mL to about 24.0 pg/mL, about 0.0400 pg/mL to about 24.0 pg/mL, about 0.0500 pg/mL to about 24.0 pg/mL, about 0.1 pg/mL to about 24.0 pg/mL, about 0.5 pg/mL to about 24.0 pg/mL, about 1.0 pg/mL to about 24.0 pg/mL, about 1.5 pg/mL to about 24.0 pg/mL, about 2.0 pg/mL to about 24.0 pg/mL, about 2.5 pg/mL to about 24.0 pg/mL, about 3.0 pg/mL to about 24.0 pg/mL, about 3.5 pg/mL to about 24.0 pg/mL, about 4.0 pg/mL to about 24.0 pg/mL, about 4.5 pg/mL to about 24.0 pg/mL, about 5.0 pg/mL to about 24.0 pg/mL, about 5.5 pg/mL to about 24.0 pg/mL, about 6.0 pg/mL to about 24.0 pg/mL, about 6.5 pg/mL to about 24.0 pg/mL, about 7.0 pg/mL to about 24.0 pg/mL, about 7.5 pg/mL to about 24.0 pg/mL, about 8.0 pg/mL to about 24.0 pg/mL, about 8.5 pg/mL to about 24.0 pg/mL, about 9.0 pg/mL to about 24.0 pg/mL, about 9.5 pg/mL to about 24.0 pg/mL, about 10.0 pg/mL to about 24.0 pg/mL, about 0.0100 pg/mL to about 23.0 pg/mL, about 0.0200 pg/mL to about 23.0 pg/mL, about 0.0300 pg/mL to about 23.0 pg/mL, about 0.036 pg/mL to about 23.0 pg/mL, about 0.0400 pg/mL to about 23.0 pg/mL, about 0.0500 pg/mL to about 23.0 pg/mL, about 0.1 pg/mL to about 23.0 pg/mL, about 0.5 pg/mL to about 23.0 pg/mL, about 1.0 pg/mL to about 23.0 pg/mL, about 1.5 pg/mL to about 23.0 pg/mL, about 2.0 pg/mL to about 23.0 pg/mL, about 2.5 pg/mL to about 23.0 pg/mL, about 3.0 pg/mL to about 23.0 pg/mL, about 3.5 pg/mL to about 23.0 pg/mL, about 4.0 pg/mL to about 23.0 pg/mL, about 4.5 pg/mL to about 23.0 pg/mL, about 5.0 pg/mL to about 23.0 pg/mL, about 5.5 pg/mL to about 23.0 pg/mL, about 6.0 pg/mL to about 23.0 pg/mL, about 6.5 pg/mL to about 23.0 pg/mL, about 7.0 pg/mL to about 23.0 pg/mL, about 7.5 pg/mL to about 23.0 pg/mL, about 8.0 pg/mL to about 23.0 pg/mL, about 8.5 pg/mL to about 23.0 pg/mL, about 9.0 pg/mL to about 23.0 pg/mL, about 9.5 pg/mL to about 23.0 pg/mL, about 10.0 pg/mL to about 23.0 pg/mL, about 0.0100 pg/mL to about 22.0 pg/mL, about 0.0200 pg/mL to about 22.0 pg/mL, about 0.0300 pg/mL to about 22.0 pg/mL, about 0.036 pg/mL to about 22.0 pg/mL, about 0.0400 pg/mL to about 22.0 pg/mL, about 0.0500 pg/mL to about 22.0 pg/mL, about 0.1 pg/mL to about 22.0 pg/mL, about 0.5 pg/mL to about 22.0 pg/mL, about 1.0 pg/mL to about 22.0 pg/mL, about 1.5 pg/mL to about 22.0 pg/mL, about 2.0 pg/mL to about 22.0 pg/mL, about 2.5 pg/mL to about 22.0 pg/mL, about 3.0 pg/mL to about 22.0 pg/mL, about 3.5 pg/mL to about 22.0 pg/mL, about 4.0 pg/mL to about 22.0 pg/mL, about 4.5 pg/mL to about 22.0 pg/mL, about 5.0 pg/mL to about 22.0 pg/mL, about 5.5 pg/mL to about 22.0 pg/mL, about 6.0 pg/mL to about 22.0 pg/mL, about 6.5 pg/mL to about 22.0 pg/mL, about 7.0 pg/mL to about 22.0 pg/mL, about 7.5 pg/mL to about 22.0 pg/mL, about 8.0 pg/mL to about 22.0 pg/mL, about 8.5 pg/mL to about 22.0 pg/mL, about 9.0 pg/mL to about 22.0 pg/mL, about 9.5 pg/mL to about 22.0 pg/mL, about 10.0 pg/mL to about 22.0 pg/mL, about 0.0100 pg/mL to about 21.0 pg/mL, about 0.0200 pg/mL to about 21.0 pg/mL, about 0.0300 pg/mL to about 21.0 pg/mL, about 0.036 pg/mL to about 21.0 pg/mL, about 0.0400 pg/mL to about 21.0 pg/mL, about 0.0500 pg/mL to about 21.0 pg/mL, about 0.1 pg/mL to about 21.0 pg/mL, about 0.5 pg/mL to about 21.0 pg/mL, about 1.0 pg/mL to about 21.0 pg/mL, about 1.5 pg/mL to about 21.0 pg/mL, about 2.0 pg/mL to about 21.0 pg/mL, about 2.5 pg/mL to about 21.0 pg/mL, about 3.0 pg/mL to about 21.0 pg/mL, about 3.5 pg/mL to about 21.0 pg/mL, about 4.0 pg/mL to about 21.0 pg/mL, about 4.5 pg/mL to about 21.0 pg/mL, about 5.0 pg/mL to about 21.0 pg/mL, about 5.5 pg/mL to about 21.0 pg/mL, about 6.0 pg/mL to about 21.0 pg/mL, about 6.5 pg/mL to about 21.0 pg/mL, about 7.0 pg/mL to about 21.0 pg/mL, about 7.5 pg/mL to about 21.0 pg/mL, about 8.0 pg/mL to about 21.0 pg/mL, about 8.5 pg/mL to about 21.0 pg/mL, about 9.0 pg/mL to about 21.0 pg/mL, about 9.5 pg/mL to about 21.0 pg/mL, about 10.0 pg/mL to about 21.0 pg/mL, about 0.0100 pg/mL to about 20.0 pg/mL, about 0.0200 pg/mL to about 20.0 pg/mL, about 0.0300 pg/mL to about 20.0 pg/mL, about 0.036 pg/mL to about 20.0 pg/mL, about 0.0400 pg/mL to about 20.0 pg/mL, about 0.0500 pg/mL to about 20.0 pg/mL, about 0.1 pg/mL to about 20.0 pg/mL, about 0.5 pg/mL to about 20.0 pg/mL, about 1.0 pg/mL to about 20.0 pg/mL, about 1.5 pg/mL to about 20.0 pg/mL, about 2.0 pg/mL to about 20.0 pg/mL, about 2.5 pg/mL to about 20.0 pg/mL, about 3.0 pg/mL to about 20.0 pg/mL, about 3.5 pg/mL to about 20.0 pg/mL, about 4.0 pg/mL to about 20.0 pg/mL, about 4.5 pg/mL to about 20.0 pg/mL, about 5.0 pg/mL to about 20.0 pg/mL, about 5.5 pg/mL to about 20.0 pg/mL, about 6.0 pg/mL to about 20.0 pg/mL, about 6.5 pg/mL to about 20.0 pg/mL, about 7.0 pg/mL to about 20.0 pg/mL, about 7.5 pg/mL to about 20.0 pg/mL, about 8.0 pg/mL to about 20.0 pg/mL, about 8.5 pg/mL to about 20.0 pg/mL, about 9.0 pg/mL to about 20.0 pg/mL, about 9.5 pg/mL to about 20.0 pg/mL, about 10.0 pg/mL to about 20.0 pg/mL, about 0.0100 pg/mL to about 19.0 pg/mL, about 0.0200 pg/mL to about 19.0 pg/mL, about 0.0300 pg/mL to about 19.0 pg/mL, about 0.036 pg/mL to about 19.0 pg/mL, about 0.0400 pg/mL to about 19.0 pg/mL, about 0.0500 pg/mL to about 19.0 pg/mL, about 0.1 pg/mL to about 19.0 pg/mL, about 0.5 pg/mL to about 19.0 pg/mL, about 1.0 pg/mL to about 19.0 pg/mL, about 1.5 pg/mL to about 19.0 pg/mL, about 2.0 pg/mL to about 19.0 pg/mL, about 2.5 pg/mL to about 19.0 pg/mL, about 3.0 pg/mL to about 19.0 pg/mL, about 3.5 pg/mL to about 19.0 pg/mL, about 4.0 pg/mL to about 19.0 pg/mL, about 4.5 pg/mL to about 19.0 pg/mL, about 5.0 pg/mL to about 19.0 pg/mL, about 5.5 pg/mL to about 19.0 pg/mL, about 6.0 pg/mL to about 19.0 pg/mL, about 6.5 pg/mL to about 19.0 pg/mL, about 7.0 pg/mL to about 19.0 pg/mL, about 7.5 pg/mL to about 19.0 pg/mL, about 8.0 pg/mL to about 19.0 pg/mL, about 8.5 pg/mL to about 19.0 pg/mL, about 9.0 pg/mL to about 19.0 pg/mL, about 9.5 pg/mL to about 19.0 pg/mL, about 10.0 pg/mL to about 19.0 pg/mL, about 0.0100 pg/mL to about 18.0 pg/mL, about 0.0200 pg/mL to about 18.0 pg/mL, about 0.0300 pg/mL to about 18.0 pg/mL, about 0.036 pg/mL to about 18.0 pg/mL, about 0.0400 pg/mL to about 18.0 pg/mL, about 0.0500 pg/mL to about 18.0 pg/mL, about 0.1 pg/mL to about 18.0 pg/mL, about 0.5 pg/mL to about 18.0 pg/mL, about 1.0 pg/mL to about 18.0 pg/mL, about 1.5 pg/mL to about 18.0 pg/mL, about 2.0 pg/mL to about 18.0 pg/mL, about 2.5 pg/mL to about 18.0 pg/mL, about 3.0 pg/mL to about 18.0 pg/mL, about 3.5 pg/mL to about 18.0 pg/mL, about 4.0 pg/mL to about 18.0 pg/mL, about 4.5 pg/mL to about 18.0 pg/mL, about 5.0 pg/mL to about 18.0 pg/mL, about 5.5 pg/mL to about 18.0 pg/mL, about 6.0 pg/mL to about 18.0 pg/mL, about 6.5 pg/mL to about 18.0 pg/mL, about 7.0 pg/mL to about 18.0 pg/mL, about 7.5 pg/mL to about 18.0 pg/mL, about 8.0 pg/mL to about 18.0 pg/mL, about 8.5 pg/mL to about 18.0 pg/mL, about 9.0 pg/mL to about 18.0 pg/mL, about 9.5 pg/mL to about 18.0 pg/mL, about 10.0 pg/mL to about 18.0 pg/mL, about 0.0100 pg/mL to about 17.0 pg/mL, about 0.0200 pg/mL to about 17.0 pg/mL, about 0.0300 pg/mL to about 17.0 pg/mL, about 0.036 pg/mL to about 17.0 pg/mL, about 0.0400 pg/mL to about 17.0 pg/mL, about 0.0500 pg/mL to about 17.0 pg/mL, about 0.1 pg/mL to about 17.0 pg/mL, about 0.5 pg/mL to about 17.0 pg/mL, about 1.0 pg/mL to about 17.0 pg/mL, about 1.5 pg/mL to about 17.0 pg/mL, about 2.0 pg/mL to about 17.0 pg/mL, about 2.5 pg/mL to about 17.0 pg/mL, about 3.0 pg/mL to about 17.0 pg/mL, about 3.5 pg/mL to about 17.0 pg/mL, about 4.0 pg/mL to about 17.0 pg/mL, about 4.5 pg/mL to about 17.0 pg/mL, about 5.0 pg/mL to about 17.0 pg/mL, about 5.5 pg/mL to about 17.0 pg/mL, about 6.0 pg/mL to about 17.0 pg/mL, about 6.5 pg/mL to about 17.0 pg/mL, about 7.0 pg/mL to about 17.0 pg/mL, about 7.5 pg/mL to about 17.0 pg/mL, about 8.0 pg/mL to about 17.0 pg/mL, about 8.5 pg/mL to about 17.0 pg/mL, about 9.0 pg/mL to about 17.0 pg/mL, about 9.5 pg/mL to about 17.0 pg/mL, about 10.0 pg/mL to about 17.0 pg/mL, about 0.0100 pg/mL to about 16.0 pg/mL, about 0.0200 pg/mL to about 16.0 pg/mL, about 0.0300 pg/mL to about 16.0 pg/mL, about 0.036 pg/mL to about 16.0 pg/mL, about 0.0400 pg/mL to about 16.0 pg/mL, about 0.0500 pg/mL to about 16.0 pg/mL, about 0.1 pg/mL to about 16.0 pg/mL, about 0.5 pg/mL to about 16.0 pg/mL, about 1.0 pg/mL to about 16.0 pg/mL, about 1.5 pg/mL to about 16.0 pg/mL, about 2.0 pg/mL to about 16.0 pg/mL, about 2.5 pg/mL to about 16.0 pg/mL, about 3.0 pg/mL to about 16.0 pg/mL, about 3.5 pg/mL to about 16.0 pg/mL, about 4.0 pg/mL to about 16.0 pg/mL, about 4.5 pg/mL to about 16.0 pg/mL, about 5.0 pg/mL to about 16.0 pg/mL, about 5.5 pg/mL to about 16.0 pg/mL, about 6.0 pg/mL to about 16.0 pg/mL, about 6.5 pg/mL to about 16.0 pg/mL, about 7.0 pg/mL to about 16.0 pg/mL, about 7.5 pg/mL to about 16.0 pg/mL, about 8.0 pg/mL to about 16.0 pg/mL, about 8.5 pg/mL to about 16.0 pg/mL, about 9.0 pg/mL to about 16.0 pg/mL, about 9.5 pg/mL to about 16.0 pg/mL, about 10.0 pg/mL to about 16.0 pg/mL, about 0.0100 pg/mL to about 15.0 pg/mL, about 0.0200 pg/mL to about 15.0 pg/mL, about 0.0300 pg/mL to about 15.0 pg/mL, about 0.036 pg/mL to about 15.0 pg/mL, about 0.0400 pg/mL to about 15.0 pg/mL, about 0.0500 pg/mL to about 15.0 pg/mL, about 0.1 pg/mL to about 15.0 pg/mL, about 0.5 pg/mL to about 15.0 pg/mL, about 1.0 pg/mL to about 15.0 pg/mL, about 1.5 pg/mL to about 15.0 pg/mL, about 2.0 pg/mL to about 15.0 pg/mL, about 2.5 pg/mL to about 15.0 pg/mL, about 3.0 pg/mL to about 15.0 pg/mL, about 3.5 pg/mL to about 15.0 pg/mL, about 4.0 pg/mL to about 15.0 pg/mL, about 4.5 pg/mL to about 15.0 pg/mL, about 5.0 pg/mL to about 15.0 pg/mL, about 5.5 pg/mL to about 15.0 pg/mL, about 6.0 pg/mL to about 15.0 pg/mL, about 6.5 pg/mL to about 15.0 pg/mL, about 7.0 pg/mL to about 15.0 pg/mL, about 7.5 pg/mL to about 15.0 pg/mL, about 8.0 pg/mL to about 15.0 pg/mL, about 8.5 pg/mL to about 15.0 pg/mL, about 9.0 pg/mL to about 15.0 pg/mL, about 9.5 pg/mL to about 15.0 pg/mL or about 10.0 pg/mL to about 15.0 pg/mL. In some embodiments, the reference level of cardiac troponin I is about 1.0 pg/mL, about 1.5 pg/mL, about 2.0 pg/mL, about 2.5 pg/mL, about 3.0 pg/mL, about 3.5 pg/mL, about 4.0 pg/mL, about 4.5 pg/mL, about 5.0 pg/mL, about 5.5 pg/mL, about 5.6 pg/mL, about 5.7 pg/mL, about 5.8 pg/mL, about 5.9 pg/mL, about 6.0 pg/mL, about 6.5 pg/mL, about 7.0 pg/mL, about 7.5 pg/mL, about 8.0 pg/mL, about 8.5 pg/mL, about 9.0 pg/mL, about 9.5 pg/mL, or about 10.0 pg/mL.

In some embodiments, the reference age is less than 70 years of age, such as between at least about 35 to about 70 years of age. In some embodiments, the reference age is at least 35 years of age, at least 40 years of age, at least 41 years of age, at least 42 years of age, at least 43 years of age, at least 44 years of age, at least 45 years of age, at least 46 years of age, at least 47 years of age, at least 48 years of age, at least 49 years of age, at least 50 years of age, at least 55 years of age, at least 60 years of age, at least 65 years of age, or at least 70 years of age.

In some embodiments, the method further includes treating the human subject predicted as having an unfavorable outcome with a traumatic brain injury treatment, as described below. In some embodiments, the method further includes monitoring the human subject predicted as having an unfavorable outcome, as described below. In some embodiments, the method further includes ordering additional tests to obtain further clinical information about the mild TBI in the human subject predicted as having an unfavorable outcome. In some embodiments, the method includes treating the human subject predicted to have an unfavorable outcome with a cardioprotective treatment to protect the heart as described below.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Such assays are described in further detail herein in Sections 11-13. Also, the assay can be employed in clinical chemistry format such as would be known by one skilled in the art. For example, a clinical chemistry format can include an assay that involves one antibody or no antibody. Examples of analyzers that can be used for the clinical chemistry format are described in U.S. Patent publication Nos. 2016/0320422 and 2015/0112630.

9. Methods of Treating a Human Subject Having Traumatic Brain Injury with Cardioprotective Therapy The present disclosure relates, among other methods, to a method for treating a human subject having or suspected as having a traumatic brain injury. The occurrence of myocardial injury during the acute phase of traumatic brain injury (TBI) may be a contributor to poor TBI outcome. As such, administering one or more cardioprotective therapies or therapeutics (e.g., therapies that improve the heart) may improve TBI outcome and can be employed in the methods described herein. These cardioprotective therapies can be administered alone without any other therapeutics. Alternatively, these cardioprotective therapies can be administered in combination with other therapeutics administered to treat the TBI, such as those disclosed in Section 10, below.

Specifically, the methods of the disclosure involving one or more cardioprotective therapies or therapeutics includes: a) performing an assay on a sample taken from the human subject within about 24 hours after an actual or suspected injury to the head to measure or detect a level of cardiac troponin I, wherein the sample is a biological sample; and b) providing a cardioprotective therapy or therapeutic to the subject if the level of cardiac troponin I in the sample is higher than a reference level of cardiac troponin I. In some embodiments, the cardioprotective therapy optionally can include administering one or more beta-blockers, diuretics, Angiotensin-Converting Enzyme (ACE) inhibitors, calcium channel blockers, lipid lowering therapies, statins (also known as 3-hydroxy-3-methylglutaryl coenzyme A (HMG-CoA) reductase inhibitors), nitrates, antiplatelets, anticlotting agents, anticoagulation agents, and the like, such as is known in the art. The nature, amounts and timing for the administration of such cardioprotective therapies and therapeutics are well known in the art.

In some embodiments, the sample may be obtained or taken from the subject within about 0 minutes, within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 20 minutes, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours of a suspect injury to the head.

Generally, a reference level of cTnI can also be employed as a benchmark against which to assess results obtained upon assaying a test sample for cTnI. Generally, in making such a comparison, the reference level of cTnI is obtained by running a particular assay a sufficient number of times and under appropriate conditions such that a linkage or association of analyte presence, amount or concentration with a particular stage or endpoint of TBI or with particular indicia can be made. Typically, the reference level of cTnI is obtained with assays of reference subjects (or populations of subjects). The cTnI measured can include fragments thereof, degradation products thereof, and/or enzymatic cleavage products thereof.

In some embodiments, the method can include obtaining samples from the subject and contacting the samples with an antibody for cardiac troponin I to allow formation of a complex of the antibody and cardiac troponin I. The method also includes detecting the resulting antibody-cardiac troponin I complex.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC) or liquid chromatography-mass spectrometry (LC/MS). Such assays are described in further detail herein in Sections 11-13. Also, the assay can be employed in clinical chemistry format such as would be known by one skilled in the art. For example, a clinical chemistry format can include an assay that involves one antibody or no antibody. Examples of analyzers that can be used for the clinical chemistry format are described in U.S. Patent publication Nos. 2016/0320422 and 2015/0112630.

10. Treatment and Monitoring of Subjects Suffering from Traumatic Brain Injury The subject identified or assessed in the methods described above as having traumatic brain injury, such as mild traumatic brain injury or a moderate, severe, or moderate to severe traumatic brain injury, may be treated or monitored. In some embodiments, the method further includes treating the human subject assessed as having traumatic brain injury with a traumatic brain injury treatment, such as any treatments known in the art. For example, treatment of traumatic brain injury can take a variety of forms depending on the severity of the injury to the head. For example, for subjects suffering from mild TBI, the treatment may include one or more of rest, abstaining from physical activities, such as sports, avoiding light or wearing sunglasses when out in the light, administration of one or more therapeutics (e.g., such as a medication for relief of a headache or migraine, anti-nausea medication, etc). Treatment for patients suffering from a moderate, severe, or moderate to severe TBI might include administration of one or more appropriate therapeutics (such as, for example, diuretics, anti-convulsant medications, medications to sedate and put an individual in a drug-induced coma, or other pharmaceutical or biopharmaceutical medications (either known or developed in the future for treatment of TBI), one or more surgical procedures (such as, for example, removal of a hematoma, repairing a skull fracture, decompressive craniectomy, etc.) protecting the airway, and one or more therapies (such as, for example one or more rehabilitation, physical therapy, occupational therapy, cognitive behavioral therapy, anger management, counseling psychology, etc.). In some embodiments, the method further includes monitoring the human subject assessed as having traumatic brain injury (e.g., mild or moderate, severe, or moderate to severe traumatic). In some embodiments, a subject identified as having traumatic brain injury, such as mild traumatic brain injury or severe traumatic brain injury, may be monitored with CT scan or MRI. The treatments employed for mild or moderate, severe, or moderate to severe TBI described herein can be administered in connection with one or more cardioprotective therapies or therapeutics described in Section 9.

11. Methods for Measuring the Level of cTnI

In the methods described above, cTnI levels can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one skilled in the art.

In some embodiments, measuring the level of cTnI includes contacting the sample with a first specific binding member and second specific binding member. In some embodiments the first specific binding member is a capture antibody and the second specific binding member is a detection antibody. In some embodiments, measuring the level of cTnI includes contacting the sample, either simultaneously or sequentially, in any order: (1) a capture antibody (e.g., cTnI-capture antibody), which binds to an epitope on cTnI or cTnI fragment to form a capture antibody-cTnI antigen complex (e.g., cTnI-capture antibody-cTnI antigen complex), and (2) a detection antibody (e.g., cTnI-detection antibody), which includes a detectable label and binds to an epitope on cTnI that is not bound by the capture antibody, to form a cTnI antigen-detection antibody complex (e.g., cTnI antigen-cTnI-detection antibody complex), such that a capture antibody-cTnI antigen-detection antibody complex (e.g., cTnI-capture antibody-cTnI antigen-cTnI-detection antibody complex) is formed, and measuring the amount or concentration of cTnI in the sample based on the signal generated by the detectable label in the capture antibody-cTnI antigen-detection antibody complex.

In some embodiments, the first specific binding member is immobilized on a solid support. In some embodiments, the second specific binding member is immobilized on a solid support. In some embodiments, the first specific binding member is a cTnI antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instrument ARCHITECT®, and other core laboratory instruments) other than a point-of-care device may be capable of measuring levels of cTnI in a sample at about 0.032 pg/L at 10% CV or lower.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety 12. Cardiac Troponin I Antibodies The methods described herein may use an isolated antibody that specifically binds to cardiac troponin I, such as, for example, human cardiac troponin I (or fragments thereof), referred to as "cardiac troponin I antibody." Cardiac troponin I antibodies can be used to assess the cardiac troponin I status as a measure of traumatic brain injury, detect the presence of cardiac troponin I in a biological sample, quantify the amount of cardiac troponin I present in a biological sample, or detect the presence of and quantify the amount of cardiac troponin I in a biological sample.

a. Human Cardiac Troponin I (cTnI)

Human cardiac troponin I (cTnI) along with troponin T (TnT) and troponin C (TnC), are the 3 subunits that form the troponin complex of the thin filaments of striated muscle. Cardiac troponin I is the inhibitory subunit; blocking actin-myosin interactions and thereby mediating striated muscle relaxation. The cTnI subfamily contains three genes: cTnIskeletal-fast-twitch, cTnI-skeletal-slow-twitch, and cTnI-cardiac. This gene encodes the cTnI-cardiac protein and is exclusively expressed in cardiac muscle tissues.

Human cardiac troponin I may have the following amino acid sequence:

```
                                       (SEQ ID NO: 1)
MADGSSDAAR EPRPAPAPIR RRSSNYRAYA TEPHAKKKSK

ISASRKLQLK TLLLQIAKQE LEREAEERRG EKGRALSTRC

QPLELAGLGF AELQDLCRQL HARVDKVDEE RYDIEAKVTK

NITEIADLTQ KIFDLRGKFK RPTLRRVRIS ADAMMQALLG

ARAKESLDLR AHLKQVKKED TEKENREVGD WRKNIDALSG

MEGRKKKFES
```

The human cardiac troponin I may be a fragment or variant of SEQ ID NO: 1. The fragment of cardiac troponin I may be between 5 and 210 amino acids, between 10 and 210 amino acids, between 50 and 210 amino acids, between 60 and 210 amino acids, between 65 and 210 amino acids, between 100 and 210 amino acids, between 150 and 210 amino acids, between 100 and 210 amino acids, or between 175 and 210 amino acids in length. The fragment may comprise a contiguous number of amino acids from SEQ ID NO: 1.

b. Cardiac Troponin I-Recognizing Antibody

The antibody is an antibody that binds to cardiac troponin I, a fragment thereof, an epitope of cardiac troponin I, or a variant thereof. The antibody may be a fragment of the anti-cardiac troponin I antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise $F(ab')_2$, Fv or scFv fragments. The antibody derivatives can be produced by peptidomimetics. Further, techniques described for the production of single chain antibodies can be adapted to produce single chain antibodies.

The anti-cardiac troponin I antibodies may be a chimeric anti-cardiac troponin I or humanized anti-cardiac troponin I antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-cardiac troponin I antibodies. For example, libraries of naïve human single chain variable fragments (scFv) may be used to select human anti-cardiac troponin I antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to human cardiac troponin I (SEQ ID NO: 1), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human troponin I) and the other heavy and light chain are specific for an antigen other than human cardiac troponin I by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with cardiac troponin I or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad Sci. USA*, 94:4937-4942; Hanes et al. (1998) *Proc. Natl. Acad Sci. USA*, 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad Sci. USA* 93:7843-7848); gel microdroplet and flow cytometry (Powell et al. (1990) *Biotechnol.* 8:333-337; One Cell Systems, (Cambridge, Mass).; Gray et al. (1995) *J. Imm. Meth.* 182:155-163; Kenny et al. (1995) *Bio/Technol.* 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology*, 10: 779-783 (1992) describes affinity maturation by VH and VL domain shuffling. Random mutagenesis of CDR and/or framework residues is described by Barbas et al., *Proc. Nat. Acad Sci. USA*, 91: 3809-3813 (1994); Schier et al., *Gene,* 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992).

Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) *Protein Eng.* 8(10):1057-1062. Briefly, these antibodies comprise a pair of tandem Fd segments (VH—CH1-VH—CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

(1) Anti-Cardiac Troponin I Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods of generating monoclonal antibodies as well as antibodies produced by the method may comprise culturing a hybridoma cell secreting an antibody of the disclosure wherein, preferably, the hybridoma is generated by fusing splenocytes isolated from an animal, e.g., a rat or a mouse, immunized with cardiac troponin I with myeloma cells and then screening the hybridomas resulting from the fusion for hybridoma clones that secrete an antibody able to bind a polypeptide of the disclosure. Briefly, rats can be immunized with a cardiac troponin I antigen. In a preferred embodiment, the cardiac troponin I antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a cardiac troponin I antigen, antibodies and/or antibody-producing cells may be obtained from the animal. An anti-cardiac troponin I antibody-containing serum is obtained from the animal by bleeding or sacrificing the animal. The serum may be used as it is obtained from the animal, an immunoglobulin fraction may be obtained from the serum, or the anti-cardiac troponin I antibodies may be purified from the serum. Serum or immunoglobulins obtained in this manner are polyclonal, thus having a heterogeneous array of properties.

Once an immune response is detected, e.g., antibodies specific for the antigen cardiac troponin I are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding troponin I. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using troponin I, or a portion thereof, or a cell expressing troponin I. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-cardiac troponin I antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-cardiac troponin I antibody.

Antibody fragments that recognize specific epitopes may be generated by known techniques. For example, Fab and F(ab')$_2$ fragments of the disclosure may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of crosslinking antigen molecules like the parent IgG molecule.

(2) Anti-Cardiac Troponin I Monoclonal Antibodies Using SLAM

In another aspect of the disclosure, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA*, 93: 7843-7848 (1996). In this method, single cells secreting antibodies of interest, e.g., lymphocytes derived from any one of the immunized animals are screened using an antigen-specific hemolytic plaque assay, wherein the antigen cardiac troponin I, a subunit of cardiac troponin I, or a fragment thereof, is coupled to sheep red blood cells using a linker, such as biotin, and used to identify single cells that secrete antibodies with specificity for cardiac troponin I. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to cardiac troponin I. The amplified immunoglobulin sequences further can be manipulated in vitro, such as by in vitro affinity maturation method. See, for example, PCT Publication No. WO 97/29131 and PCT Publication No. WO 00/56772.

(3) Anti-Cardiac Troponin I Monoclonal Antibodies Using Transgenic Animals

In another embodiment of the disclosure, antibodies are produced by immunizing a non-human animal comprising some, or all, of the human immunoglobulin locus with a cardiac troponin I antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics*, 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741;

WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics*, 15: 146-156 (1997), Green and Jakobovits, *J. Exp. Med.*, 188: 483-495 (1998), the disclosures of which are hereby incorporated by reference.

(4) Anti-Cardiac Troponin I Monoclonal Antibodies Using Recombinant Antibody Libraries In vitro methods also can be used to make the antibodies of the disclosure, wherein an antibody library is screened to identify an antibody having the desired cardiac troponin I-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., *Bio/Technology*, 9: 1369-1372 (1991); Hay et al., *Hum. Antibod. Hybridomas*, 3: 81-85 (1992); Huse et al., *Science*, 246: 1275-1281 (1989); McCafferty et al., *Nature*, 348: 552-554 (1990); Griffiths et al., *EMBO J.*, 12: 725-734 (1993); Hawkins et al., *J. Mol. Biol.*, 226: 889-896 (1992); Clackson et al., *Nature*, 352: 624-628 (1991); Gram et al., *Proc. Natl. Acad. Sci. USA*, 89: 3576-3580 (1992); Garrard et al., *Bio Technology*, 9: 1373-1377 (1991); Hoogenboom et al., *Nucl. Acids Res.*, 19: 4133-4137 (1991); Barbas et al., *Proc. Natl. Acad. Sci. USA*, 88: 7978-7982 (1991); U.S. Patent Application Publication No. 2003/0186374; and PCT Publication No. WO 97/29131, the contents of each of which are incorporated herein by reference.

The recombinant antibody library may be from a subject immunized with cardiac troponin I, or a portion of cardiac troponin I. Alternatively, the recombinant antibody library may be from a naive subject, i.e., one who has not been immunized with cardiac troponin I, such as a human antibody library from a human subject who has not been immunized with human cardiac troponin I. Antibodies of the disclosure are selected by screening the recombinant antibody library with the peptide comprising human cardiac troponin I to thereby select those antibodies that recognize troponin I. Methods for conducting such screening and selection are well known in the art, such as described in the references in the preceding paragraph. To select antibodies of the disclosure having particular binding affinities for cardiac troponin I, such as those that dissociate from human cardiac troponin I with a particular $K_{off}$ rate constant, the art-known method of surface plasmon resonance can be used to select antibodies having the desired $K_{off}$ rate constant. To select antibodies of the disclosure having a particular neutralizing activity for cardiac troponin I, such as those with a particular $IC_{50}$, standard methods known in the art for assessing the inhibition of cardiac troponin I activity may be used.

In one aspect, the disclosure pertains to an isolated antibody, or an antigen-binding portion thereof, that binds human cardiac troponin I. Preferably, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., *J Immunol. Methods*, 182: 41-50 (1995); Ames et al., *J. Immunol. Methods*, 184:177-186 (1995); Kettleborough et al., *Eur. J. Immunol.*, 24: 952-958 (1994); Persic et al., *Gene*, 187: 9-18 (1997); Burton et al., *Advances in Immunology*, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques*, 12(6): 864-869 (1992); Sawai et al., *Am. J. Reprod. Immunol.*, 34: 26-34 (1995); and Better et al., *Science*, 240: 1041-1043 (1988). Examples of techniques which can be used to produce single-chain Fvs and antibodies include those described in U.S. Pat. Nos. 4,946,778 and 5,258,498; Huston et al., *Methods in Enzymology*, 203: 46-88 (1991); Shu et al., *Proc. Natl. Acad. Sci.* USA, 90: 7995-7999 (1993); and Skerra et al., *Science*, 240: 1038-1041 (1988).

Alternative to screening of recombinant antibody libraries by phage display, other methodologies known in the art for screening large combinatorial libraries can be applied to the identification of antibodies of the disclosure. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA*, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach, the antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.) incorporated herein by reference.

d. Production of Recombinant Cardiac Troponin I Antibodies

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the disclosure in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the disclosure include Chinese Hamster Ovary (CHO cells) (including dhfr-CHO cells, described in Urlaub and Chasin, *Proc. Natl. Acad. Sci. USA,* 77: 4216-4220 (1980), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody of this disclosure. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure (i.e., binds human cardiac troponin I) and the other heavy and light chain are specific for an antigen other than human cardiac troponin I by crosslinking an antibody of the disclosure to a second antibody by standard chemical crosslinking methods.

In a preferred system for recombinant expression of an antibody, or antigen-binding portion thereof, of the disclosure, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the disclosure provides a method of synthesizing a recombinant antibody of the disclosure by culturing a host cell of the disclosure in a suitable culture medium until a recombinant antibody of the disclosure is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present disclosure can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for cardiac troponin I and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for cardiac troponin I, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g., mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

e. Anti-Cardiac Troponin I Antibodies

Anti-cardiac troponin I antibodies may be generated using the techniques described above as well as using routine techniques known in the art. In some embodiments, the anti-cardiac troponin I antibody may be an unconjugated cardiac troponin I antibody, such as cardiac troponin I antibodies available from Abcam (such as Anti-Cardiac troponin I antibody (ab47003)), Thermofisher (such as cardiac troponin I monoclonal antibody (12F10), cardiac troponin I polyclonal antibody, cardiac troponin I antibody (1HCLC), ABFINITY™ rabbit oligoclonal, cardiac troponin I antibody (1H11L19), ABFINITY™ rabbit monoclonal), Santa Cruz (such as cardiac troponin I antibody (C-4) (Catalog number sc-133117), cardiac troponin I antibody (4) (Catalog number sc-130351), cardiac troponin I antibody (12) (Catalog number sc-130350), cardiac troponin I antibody (H-170) (Catalog number sc-15368), cardiac troponin I antibody (C-19) (Catalog number sc-8118), cardiac troponin I-C antibody (G-11) (Catalog number sc-376662), cardiac troponin I-C antibody (M46) (Catalog number sc-52277), cardiac troponin I-C antibody (10B11) (Catalog number sc-52266) and hytest (Monoclonal mouse anti-cardiac troponin I (catalog number 4T21).

13. Variations on Methods

The disclosed methods of determining the presence or amount of analyte of interest (e.g., cTnI) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc.

a. Immunoassay

The analyte of interest, and/or peptides of fragments thereof (e.g., cTnI and/or peptides or fragments thereof, i.e., cTnI fragments), may be analyzed using cTnI antibodies in an immunoassay. The presence or amount of analyte (e.g., cTnI) can be determined using antibodies and detecting specific binding to the analyte (e.g., cTnI). For example, the antibody, or antibody fragment thereof, may specifically bind to the analyte (e.g., cTnI). If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of analyte (e.g., cTnI) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, MN)). An example of a point-of-care device that can be used is i-STAT® (Abbott, Laboratories, Abbott Park, IL). Other methods that can be used include a chemiluminescent microparticle immunoassay, in particular one employing the ARCHITECT® automated analyzer (Abbott Laboratories, Abbott Park, IL), as an example. Other methods include, for example, mass spectrometry, and immunohistochemistry (e.g., with sections from tissue biopsies), using anti-analyte (e.g., anti-cTnI) antibodies (monoclonal, polyclonal, chimeric, humanized, human, etc.) or antibody fragments thereof against analyte (e.g., cTnI). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte (e.g., cTnI) can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., cTnI) and a specific binding partner. The order in which the test sample and the specific binding partner are added to form the mixture is not critical. The test sample is simultaneously contacted with the specific binding partner. In some embodiments, the specific binding partner and any cTnI contained in the test sample may form a specific binding partner-analyte (e.g., cTnI)-antigen complex. The specific binding partner may be an anti-analyte antibody (e.g., anti-cTnI antibody that binds to an epitope having an amino acid sequence comprising at least three contiguous (3) amino acids of SEQ ID NO: 1. Moreover, the specific binding partner may be labeled with or contains a detectable label as described above.

A heterogeneous format may be used. For example, after the test sample is obtained from a subject, a first mixture is prepared. The mixture contains the test sample being assessed for analyte (e.g., cTnI) and a first specific binding partner, wherein the first specific binding partner and any cTnI contained in the test sample form a first specific binding partner-analyte (e.g., cTnI)-antigen complex. The first specific binding partner may be an anti-analyte antibody (e.g., anti-cTnI antibody that binds to an epitope having an amino acid sequence comprising at least three contiguous (3) amino acids of SEQ ID NO: 1). The order in which the test sample and the first specific binding partner are added to form the mixture is not critical.

The first specific binding partner may be immobilized on a solid phase. The solid phase used in the immunoassay (for the specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., cTnI) antigen complex is formed, any unbound analyte (e.g., cTnI) is removed from the complex using any technique known in the art. For example, the unbound analyte (e.g., cTnI) can be removed by washing. Desirably, however, the first specific binding partner is present in excess of any analyte (e.g., cTnI) present in the test sample, such that all analyte (e.g., cTnI) that is present in the test sample is bound by the first specific binding partner.

After any unbound analyte (e.g., cTnI) is removed, a second specific binding partner is added to the mixture to form a first specific binding partner-analyte of interest (e.g., cTnI)-second specific binding partner complex. The second specific binding partner may be an anti-analyte antibody (e.g., cTnI antibody that binds to an epitope having an amino acid sequence comprising at least three contiguous (3) amino acids of SEQ ID NO: 1). Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

(1) Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as cTnI). Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., cTnI) in a test sample. More specifically, the at least two antibodies bind to certain epitopes of analyte (e.g., cTnI) forming an immune complex which is referred to as a "sandwich". One or more antibodies can be used to capture the analyte (e.g., cTnI) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte (e.g., cTnI) do not bind to all or part of an epitope recognized by the second or subsequent antibodies, thereby interfering with the ability of the one or more second detection antibodies to bind to the analyte (e.g., cTnI).

The antibodies may be used as a first antibody in said immunoassay. The antibody immunospecifically binds to epitopes on analyte (e.g., cTnI). In addition to the antibodies of the present disclosure, said immunoassay may comprise a second antibody that immunospecifically binds to epitopes that are not recognized or bound by the first antibody.

A test sample suspected of containing analyte (e.g., cTnI) can be contacted with at least one first capture antibody (or antibodies) and at least one second detection antibodies either simultaneously or sequentially. In the sandwich assay format, a test sample suspected of containing analyte (e.g., cTnI) is first brought into contact with the at least one first capture antibody that specifically binds to a particular epitope under conditions which allow the formation of a first antibody-analyte (e.g., cTnI) antigen complex. If more than one capture antibody is used, a first multiple capture antibody-cTnI antigen complex is formed. In a sandwich assay, the antibodies, preferably, the at least one capture antibody, are used in molar excess amounts of the maximum amount of analyte (e.g., cTnI) expected in the test sample. For example, from about 5 µg/mL to about 1 mg/mL of antibody per ml of microparticle coating buffer may be used.

i. Anti-cTnI Capture Antibody

Optionally, prior to contacting the test sample with the at least one first capture antibody, the at least one first capture antibody can be bound to a solid support which facilitates the separation the first antibody-analyte (e.g., cTnI) complex from the test sample. Any solid support known in the art can be used, including but not limited to, solid supports made out of polymeric materials in the forms of wells, tubes, or beads (such as a microparticle). The antibody (or antibodies) can be bound to the solid support by adsorption, by covalent bonding using a chemical coupling agent or by other means known in the art, provided that such binding does not interfere with the ability of the antibody to bind analyte (e.g., cTnI). Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing analyte (e.g., cTnI) is incubated in order to allow for the formation of a first capture antibody (or multiple antibody)-analyte (e.g., cTnI) complex. The incubation can be carried out at a pH of from about 4.5 to about 10.0, at a temperature of from about 2° C. to about 45° C., and for a period from at least about one (1) minute to about eighteen (18) hours, from about 2-6 minutes, from about 7-12 minutes, from about 5-15 minutes, or from about 3-4 minutes.

ii. Detection Antibody

After formation of the first/multiple capture antibody-analyte (e.g., cTnI) complex, the complex is then contacted with at least one second detection antibody (under conditions that allow for the formation of a first/multiple antibody-analyte (e.g., cTnI) antigen-second antibody complex). In some embodiments, the test sample is contacted with the detection antibody simultaneously with the capture antibody. If the first antibody-analyte (e.g., cTnI) complex is contacted with more than one detection antibody, then a first/multiple capture antibody-analyte (e.g., cTnI)-multiple antibody detection complex is formed. As with first antibody, when the at least second (and subsequent) antibody is brought into contact with the first antibody-analyte (e.g., cTnI) complex, a period of incubation under conditions similar to those described above is required for the formation of the first/multiple antibody-analyte (e.g., cTnI)-second/multiple antibody complex. Preferably, at least one second antibody contains a detectable label. The detectable label can be bound to the at least one second antibody prior to, simultaneously with or after the formation of the first/multiple antibody-analyte (e.g., cTnI)-second/multiple antibody complex. Any detectable label known in the art can be used.

Chemiluminescent assays can be performed in accordance with the methods described in Adamczyk et al., *Anal.*

Chim. Acta 579(1): 61-67 (2006). While any suitable assay format can be used, a microplate chemiluminometer (Mithras LB-940, Berthold Technologies U.S.A., LLC, Oak Ridge, TN) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-antigen (e.g., cTnI) complexes form. Alternatively, if a second specific binding partner is used and the second specific binding partner is detectably labeled with an acridinium compound, detectably labeled first specific binding partner-analyte (e.g., cTnI)-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of analyte (e.g., cTnI) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. Other labels other than chemiluminescent labels can be employed. For instance, enzymatic labels (including but not limited to alkaline phosphatase) can be employed.

The chemiluminescent signal, or other signal, that is generated can be detected using routine techniques known to those skilled in the art. Based on the intensity of the signal generated, the amount of analyte of interest (e.g., cTnI) in the sample can be quantified. Specifically, the amount of analyte (e.g., cTnI) in the sample is proportional to the intensity of the signal generated. The amount of analyte (e.g., cTnI) present can be quantified by comparing the amount of light generated to a standard curve for analyte (e.g., cTnI) or by comparison to a reference standard. The standard curve can be generated using serial dilutions or solutions of known concentrations of analyte (e.g., cTnI) by mass spectroscopy, gravimetric methods, and other techniques known in the art.

(2) Forward Competitive Inhibition Assay

In a forward competitive format, an aliquot of labeled analyte of interest (e.g., cTnI) having a fluorescent label, a tag attached with a cleavable linker, etc.) of a known concentration is used to compete with analyte of interest (e.g., cTnI) in a test sample for binding to analyte of interest antibody (e.g., a cTnI antibody).

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

(3) Reverse Competitive Inhibition Assay

In a reverse competition assay, an immobilized analyte of interest (e.g., cTnI) can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

(4) One-Step Immunoassay or "Capture on the Fly" Assay

In a capture on the fly immunoassay, a solid substrate is pre-coated with an immobilization agent. The capture agent, the analyte (e.g., cTnI) and the detection agent are added to the solid substrate together, followed by a wash step prior to detection. The capture agent can bind the analyte (e.g., cTnI) and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest (e.g., cTnI). The second specific binding member comprises a detectable label and binds to an analyte of interest (e.g., cTnI). The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected, or their amounts, levels or concentrations, measured, determined or assessed.

The use of a capture on the fly assay can be done in a variety of formats as described herein, and known in the art. For example the format can be a sandwich assay such as described above, but alternately can be a competition assay, can employ a single specific binding member, or use other variations such as are known.

14. Other Factors

The methods of diagnosing, prognosticating, and/or assessing, as described above, can further include using other factors for the diagnosis, prognostication, and assessment. In some embodiments, traumatic brain injury may be diagnosed using the Glasgow Coma Scale or the Extended Glasgow Outcome Scale (GOSE). Other tests, scales or indices can also be used either alone or in combination with the Glasgow Coma Scale. An example is the Ranchos Los Amigos Scale. The Ranchos Los Amigos Scale measures the levels of awareness, cognition, behavior and interaction with the environment. The Ranchos Los Amigos Scale includes: Level I: No Response; Level II: Generalized Response; Level III: Localized Response; Level IV: Confused-agitated; Level V: Confused-inappropriate; Level VI: Confused-appropriate; Level VII: Automatic-appropriate; and Level VIII: Purposeful-appropriate.

15. Samples

In some embodiments, the sample is obtained after the human subject sustained an injury to the head caused by physical shaking, blunt impact by an external mechanical or other force that results in a closed or open head trauma, one or more falls, explosions or blasts or other types of blunt force trauma. In some embodiments, the sample is obtained after the human subject has ingested or been exposed to a chemical, toxin or combination of a chemical and toxin. Examples of such chemicals and/or toxins include, fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. In some embodiments, the sample is obtained from a human subject that suffers from an autoimmune disease, a metabolic disorder, a brain tumor, hypoxia, one or more viruses, meningitis, hydrocephalus or combinations thereof.

In yet another embodiment, the methods described herein use samples that also can be used to determine whether or not a subject has or is at risk of developing mild traumatic brain injury by determining the levels of cTnI in a subject using the anti-cTnI antibodies described below, or antibody fragments thereof. Thus, in particular embodiments, the disclosure also provides a method for determining whether a subject having, or at risk for, traumatic brain injuries, discussed herein and known in the art, is a candidate for therapy or treatment. Generally, the subject is at least one who: (i) has experienced an injury to the head; (ii) ingested and/or been exposed to one or more chemicals and/or toxins; (iii) suffers from an autoimmune disease, a metabolic disorder, a brain tumor, hypoxia, one or more viruses, meningitis, hydrocephalus or suffers from any combinations thereof, or (iv) any combinations of (i)-(iii); or, who has actually been diagnosed as having, or being at risk for TBI (such as, for example, subjects suffering from an autoimmune disease, a metabolic disorder, a brain tumor, hypoxia, one or more viruses, meningitis, hydrocephalus or combinations thereof), and/or who demonstrates an unfavorable (i.e., clinically undesirable) concentration or amount of cTnI or cTnI fragment, as described herein.

a. Test or Biological Sample

As used herein, "sample", "test sample", "biological sample" refer to fluid sample containing or suspected of containing cTnI. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing cTnI may be assayed directly. In a particular example, the source containing cTnI is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source containing cTnI is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing cTnI is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

b. Controls

It may be desirable to include a control sample. The control sample may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of the cTnI in normal healthy tissue, as well as for "at-risk" levels of the cTnI in tissue taken from donors, who may have one or more of the characteristics set forth above.

Thus, in view of the above, a method for determining the presence, amount, or concentration of cTnI in a test sample is provided. The method comprises assaying the test sample for cTnI by an immunoassay, for example, employing at least one capture antibody that binds to an epitope on cTnI and at least one detection antibody that binds to an epitope on cTnI which is different from the epitope for the capture antibody and optionally includes a detectable label, and comprising comparing a signal generated by the detectable label as a direct or indirect indication of the presence, amount or concentration of cTnI in the test sample to a signal generated as a direct or indirect indication of the presence, amount or concentration of cTnI in a calibrator. The calibrator is optionally, and is preferably, part of a series of calibrators in which each of the calibrators differs from the other calibrators in the series by the concentration of cTnI.

16. Kit

Provided herein is a kit, which may be used for assaying or assessing a test sample for cTnI and/or cTnI fragment. The kit comprises at least one component for assaying the test sample for cTnI and instructions for assaying the test sample for cTnI. For example, the kit can comprise instructions for assaying the test sample for cTnI by immunoassay, e.g., chemiluminescent microparticle immunoassay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to cTnI. The antibody may be a cTnI detection antibody and/or capture antibody.

Alternatively or additionally, the kit can comprise a calibrator or control, e.g., purified, and optionally lyophilized, cTnI and/or at least one container (e.g., tube, microtiter plates or strips, which can be already coated with an anti-cTnI antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying cTnI. The reference standards may be employed to establish standard curves for interpolation and/or extrapolation of cTnI concentrations. In some embodiments, the reference standards for cTnI can correspond to the 99th percentile derived from a healthy reference population. Such reference standards can be determined using routine techniques known in the art.

Any antibodies, which are provided in the kit, such as recombinant antibodies specific for cTnI, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes (e.g., cTnI) or reagents for detecting the analyte (e.g., cTnI). The antibodies, calibrators, and/or controls can be provided in separate containers or pre-dispensed into an appropriate assay format, for example, into microtiter plates, Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, whole blood, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of traumatic brain injury or disorder.

a. Adaptation of Kit and Method

The kit (or components thereof), as well as the method for assessing or determining the concentration of cTnI in a test sample by an immunoassay as described herein, can be adapted for use in a variety of automated and semi-automated systems (including those wherein the solid phase comprises a microparticle), as described, e.g., U.S. Pat. No. 5,063,081, U.S. Patent Application Publication Nos. 2003/0170881, 2004/0018577, 2005/0054078, and 2006/0160164 and as commercially marketed e.g., by Abbott Laboratories (Abbott Park, IL) as Abbott Point of Care (i-STAT® or i-STAT Alinity, Abbott Laboratories) as well as those described in U.S. Pat. Nos. 5,089,424 and 5,006,309, and as commercially marketed, e.g., by Abbott Laboratories (Abbott Park, IL) as ARCHITECT® or the series of Abbott Alinity devices.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits, and kit components can be employed in other formats, for example, on electrochemical or other hand-held or point-of-care assay systems. As mentioned previously, the present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent App. Publication Nos. 2003/0170881, 2004/0018577, 2005/0054078, and 2006/0160164, which are incorporated in their entireties by reference for their teachings regarding same.

In particular, with regard to the adaptation of an assay to the i-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an i-STAT® cartridge with a fluidics format suitable for immunoassay. On a portion of the silicon chip, there is a specific binding partner for cTnI, such as one or more cTnI antibodies one or more monoclonal/polyclonal antibody or a fragment thereof, a variant thereof, or a fragment of a variant thereof that can bind cTnI) or one or more anti-cTnI DVD-Igs (or a fragment thereof, a variant thereof, or a fragment of a variant thereof that can bind cTnI), any of which can be detectably labeled. Within the fluid pouch of the cartridge is an aqueous reagent that includes p-aminophenol phosphate.

In operation, a sample from a subject suspected of suffering from TBI is added to the holding chamber of the test cartridge, and the cartridge is inserted into the i-STAT® reader. A pump element within the cartridge pushes the sample into a conduit containing the chip. The sample is brought into contact with the sensors allowing the enzyme conjugate to dissolve into the sample. The sample is oscillated across the sensors to promote formation of the sandwich of approximately 2-12 minutes. In the penultimate step of the assay, the sample is pushed into a waste chamber and wash fluid, containing a substrate for the alkaline phosphatase enzyme, is used to wash excess enzyme conjugate and sample off the sensor chip. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of cTnI in the sample by means of an embedded algorithm and factory-determined calibration curve.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, IL) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, IL), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an i-STAT® cartridge format, using a nucleic acid sequence linked to the signal antibody as a signal amplifier.

While certain embodiments herein are advantageous when employed to assess disease, such as traumatic brain injury, the assays and kits also optionally can be employed to assess cTnI in other diseases, disorders, and conditions as appropriate.

The method of assay also can be used to identify a compound that ameliorates diseases, such as traumatic brain injury. For example, a cell that expresses cTnI can be contacted with a candidate compound. The level of expression of cTnI in the cell contacted with the compound can be compared to that in a control cell using the method of assay described herein.

The present disclosure has multiple aspects, illustrated by the following non-limiting examples.

17. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Study 1—TBI Population

Study 1 was a large and complex project. Its institutional and public-private partnership is comprised of over 11 clinical sites, 7 Cores, for a total of nearly 50 collaborating institutions, corporations, and philanthropy. An earlier Pilot study, based on clinical data from three clinical sites, helped refine TBI Common Data Elements and created a prototype of the TBI Information Commons for Study 1.

Subject Groups: A total of 2,700 to 3000 TBI patients were enrolled evenly across 3 clinical groups, differentiated by clinical care path: 1. Patients evaluated in the Emergency Department and discharged (ED); 2. Patients admitted to the hospital, but not to ICU (ADM); and 3. Patients admitted to the ICU (ICU). An additional 100 patients per clinical group (n=300) with extracranial trauma but no TBI were enrolled as controls for a total enrollment of 3000 patients. This stratification plan facilitated comparative effectiveness research (CER) analysis and was not constrained by traditional differentiation into "Mild/Moderate/Severe" TBI. Data collection was dependent on the clinical care path (ED, ADM, ICU) and requirements of each aim. Patients in each group were stratified into 3 cohorts that define the extent of data to be collected.

The controls were adult orthopedic trauma patients who met the following criteria: 1. An Abbreviated Injury Score of ≤4 (not life threatening) for their extremity and/or pelvis injury and/or rib fracture; 2. Met the same inclusion and exclusion criteria as the TBI subjects except that the criterion of having undergone a CT or MRI in the ED for suspected head injury did not apply. TBI was ruled out for the current injury by interviewing potential controls about loss of consciousness (LOC), disturbance of consciousness, and posttraumatic amnesia (PTA)/RA; 3. Each site was provided a plan for the number of controls to target according to age and gender distributions derived from the TBI Cohort; and 4. Controls were enrolled into the CA-MRI cohort for follow-up and drop to comprehensive assessment (CA) at 2-weeks if unable to complete the MRI visit.

Subject Eligibility: Adult patients were enrolled of all ages presenting to the Emergency Department (ED) with a history of acute TBI as per American Congress of Rehabilitation Medicine (ACRM) Criteria, in which the patient had sustained a traumatically induced physiological disruption of brain function, as manifested by ≥one of the following: any period of loss of consciousness (LOC); any loss of memory for events (e.g., amnesia) immediately before or after the accident; any alteration of mental state at the time of the accident (feeling dazed, disoriented, and/or confused); and/or focal neurologic deficits that may or may not be permanent. Traumatically induced included the head being struck, the head striking an object, or the brain undergoing an acceleration/deceleration movement (e.g., whiplash) without direct external trauma to the head.

The Inclusion/Exclusion Criteria used is shown in Table 2.

TABLE 2

| Criterion | Data Source | Comments |
| --- | --- | --- |
| Inclusion Criteria | | |
| 1. Age 0-100 | Chart | |
| 2. Documented/verified TBI (ACRM Criteria) | Chart, Interview | |
| 3. Injury occurred < 24 hours ago | Chart, Interview | |
| 4. Acute brain CT for clinical care | Chart | Subject must have brain CT scan |
| 5. Visual acuity/hearing adequate for testing | Chart, Interview | |
| 6. Fluency in English or Spanish | Chart, Interview | Test battery or personnel availability |
| 7. Ability to provide informed consent | Interview | |
| Exclusion Criteria | | |
| 1. Significant polytrauma that would interfere with follow-up and outcome assessment | Chart | Significant body trauma may confound TBI outcomes testing. |
| 2. Prisoners or patients in custody | Chart, Interview | |
| 3. Pregnancy in female subjects | Chart, Interview | |
| 4. Patients on psychiatric hold (e.g., 5150, 5250) | Chart | |
| 5. Major debilitating baseline mental health disorders (e.g., schizophrenia or bipolar disorder) that would interfere with follow-up and the validity of outcome assessment | Chart, Interview | Debilitating psychiatric disorders can significantly impact the reliability of follow up and/or pose difficulties in attributing to index TBI. |
| 6. Major debilitating neurological disease (e.g., stroke, CVA, dementia, tumor) impairing baseline awareness cognition or validity of follow-up and outcome assessment | Chart, Interview | Documented debilitating baseline cognitive impairment will confound outcome assessment in addition to not being fully consentable. |
| 7. Significant history of pre-existing conditions that would interfere with follow-up and outcome assessment (e.g., substance abuse, alcoholism, HIV/AIDS, major transmittable diseases that may interfere with consent, end-stage cancers, learning disabilities, developmental disorders) | Chart, Interview | |
| 8. Contraindications to MRI (for CA + MRI cohort) | MRI Screening | |
| 9. Low likelihood of follow-up (e.g., participant or family indicating low interest, residence in another state or country, homelessness or lack of reliable contacts) | Interview | |
| 10. Current participant in an interventional trial (e.g., drug, device, behavioral) | Chart, Interview | Exception to co-enrollment exclusion is made for sites participating in Resuscitation Outcomes Consortium Prehospital Tranexamic Acid for TBI Study. |
| 11. Penetrating TBI | Chart | |
| 12. Spinal cord injury with ASIA score of C or worse | Chart | |

For each of the 3 clinical groups (i.e., ED, ADM, and ICU), the subjects were further placed into one of three different assessment cohorts: Brief Assessment (BA Cohort), Compressive Assessment (CA) Cohort, or Comprehensive Assessment+MRI (CA+MRI) Cohort. See Table 3 for Milestone plan with 80% follow up rate.

TABLE 3

| (Add) Group | Year 1 | | | Year 2 | | | Year 3 | | | Year 4 | Total |
|---|---|---|---|---|---|---|---|---|---|---|---|
| | CA+ MRI | CA | N | CA+ MRI | CA | N | CA | BA | N | BA | N |
| ED | 150 | 87 | 237 | 50 | 58 | 108 | 155 | 100 | 255 | 300 | 900 |
| ADM | 150 | 87 | 237 | 50 | 58 | 108 | 155 | 100 | 255 | 300 | 900 |
| ICU | 150 | 87 | 237 | 50 | 58 | 108 | 155 | 100 | 255 | 300 | 900 |
| Controls | 0 | 99 | 99 | 0 | 66 | 66 | 135 | 0 | 135 | 0 | 300 |
| Total | 450 | 360 | 810 | 150 | 240 | 390 | 600 | 300 | 900 | 900 | 3000 |

The Brief Assessment (BA) Cohort included 1200 total subjects, with 400 subjects each for ED, ADM, and ICU Groups. The following data was gathered for the BA Cohort: demographic and full clinical course data; blood draw for serum, plasma, DNA and RNA on Day 1 (<24 hours of injury); repeat blood draw for serum within 3-6 hours of the Day 1 baseline collection (optional for sites to include this component); clinical brain CT scan from Day 1 acquired as part of hospital course; and outcome data collected via structured telephone interview at 2 weeks, 3, 6, and 12 months using NIH TBI-CDEs v.2.0 Core outcome measures as published on the NINDS CDE website.

The Compressive Assessment (CA) Cohort included 1200 total subjects, with 300 subjects+100 controls each for ED, ADM, and ICU Groups. The following data was gathered for the CA Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma and RNA of Day 3 (48-72 hours) and 5 (96-120 hours) for ADM and ICU; collection of cerebrospinal fluid on days 1 through 5 (optional for sites to include this component); all clinical brain CT scans acquired as part of hospital course; blood draw for serum, plasma and RNA at 2 weeks and 6 months; and outcome data collected via structured in-person interview at 2 weeks, 6, and 12 months and at 3 months via structured telephone interview using NIH TBI-CDEs v.2.0 Core, Basic and Supplemental outcome measures.

The Comprehensive Assessment+MRI (CA+MRI) Cohort included 600 total subjects, with 200 each for ED, ADM, and ICU Groups. The following data was gathered for the CA+MRI Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma, and RNA on Day 3 (48-72 hours) and 5 (96-120 hours) for ADM and ICU; collection of cerebrospinal fluid on days 1 through 5 (optional for sites to include this component); all clinical head CT scans acquired as part of hospital course; blood draw for serum, plasma and RNA at 2 weeks and 6 months; 3T research MRI acquired at 2 weeks and 6 months; and outcome data collected via structured in-person interview at 2 weeks, 6, and 12 months and at 3 month via structured telephone interview using NIH TBI-CDEs v.2.0 Core, Basic, and Supplemental outcome measures.

Upon enrollment, data collection began in the hospital. For CA+MRI patients, the 2-week MRI was completed at 14 days 14 days from the date of injury. Corresponding 2-week outcomes were completed ±3 days of the 2-week MRI. For CA and BA patients, 2-week outcomes were completed ±4 days of 14 days from the date of injury. Outcomes at 3 months were completed ±7 days of 90 days from the date of injury. For CA+MRI patients, MRIs at 6 months were completed ±14 days of 180 days from the date of injury, with corresponding 6-month outcomes ±14 days of the 6-month MRI. For CA and BA patients, 6-month outcomes were completed ±14 days of 180 days from the date of injury. BTACT should be completed with ±7 days of Outcomes (but not on the same day and no greater than 201 days from injury). Outcomes at 12 months were completed+30 days of 360 days from the date of injury.

hsTnI was measured in a small sample size of 59 patients from Study 1 using the Abbott Architect STAT hsTnI assay (Table 4).

TABLE 4

Subject Characteristics by CT Scan and MRI Result

| Subject Characteristics | Total (n = 59) | CT or MRI Positive* (n = 46, 77.97%) | CT and MRI Negative* (n = 13, 22.03%) | P value |
|---|---|---|---|---|
| Age | 46.0 [24.0 to 60.0] | 45.5 [23.0 to 60.0] | 50.0 [39.0 to 57.0] | 0.7419 |
| Sex | | | | |
| Male | 50/59 (85%) | 39/46 (85%) | 11/13 (85%) | 1.0000 |
| Female | 9/59 (15%) | 7/46 (15%) | 2/13 (15%) | |
| Race/Ethnicity | | | | |
| African-American or African | 6/58 (10%) | 4/45 (9%) | 2/13 (15%) | 0.2398 |
| Caucasian | 48/58 (83%) | 39/45 (87%) | 9/13 (69%) | |
| Hispanic | 4/58 (7%) | 2/45 (4%) | 2/13 (15%) | |
| TBI History | | | | |
| Yes, with No LOC | 9/56 (16%) | 3/43 (7%) | 6/13 (46%) | 0.0037 |
| Yes, with LOC | 8/86 (14%) | 6/43 (14%) | 2/13 (15%) | |
| No Prior TBI | 39/56 (70%) | 34/43 (79%) | 5/13 (38%) | |

TABLE 4-continued

Subject Characteristics by CT Scan and MRI Result

| Subject Characteristics | Total (n = 59) | CT or MRI Positive* (n = 46, 77.97%) | CT and MRI Negative* (n = 13, 22.03%) | P value |
|---|---|---|---|---|
| ED Presentation Loss of Consciousness | | | | |
| No | 6/58 (10%) | 2/45 (4%) | 4/13 (31%) | 0.0227 |
| Yes | 47/58 (81%) | 38/45 (84%) | 9/13 (69%) | |
| Unknown | 5/58 (9%) | 5/45 (11%) | | |
| Glasgow Coma Scale | 15.0 [3.0 to 15.0] | 14.0 (3.0 to 15.0] | 15.0 [15.0 to 15.0] | 0.0162 |
| Glasgow Coma Scale Classification | | | | |
| Severe (3-8) | 16/59 (27%) | 16/46 (35%) | | 0.0177 |
| Moderate (9-12) | 3/59 (5%) | 3/46 (7%) | | |
| Mild (13-15) | 40/59 (68%) | 27/46 (59%) | 13/13 (100%) | |
| Mechanism of Injury | | | | |
| Motor vehicle (driver/passenger) | 10/59 (17%) | 9/46 (20%) | 1/13 (8%) | 0.2975 |
| Motorcycle/ATV/golf cart (driver/passenger) | 5/59 (8%) | 3/46 (7%) | 2/13 (15%) | |
| Individual struck by any type of vehicle | 3/59 (8%) | 2/46 (4%) | 1/13 (8%) | |
| Fall from a moving object (bike/skateboard/horse/etc.) | 3/59 (8%) | 3/46 (7%) | | |
| Fall from stationary object (roof/ladder/etc.) | 27/59 (46%) | 20/46 (43%) | 7/13 (54%) | |
| Assault | 10/59 (17%) | 9/46(20%) | 1/13 (8%) | |
| Struck on head by object, not assault (tree/etc.) | 1/59 (2%) | | 1/13 (8%) | |
| Alcohol Level (g/dL) | 0.1 [0.0 to 0.2] | 0.1 0.0 to 0.2] | 0.0 [0.0 to 0.0] | 0.1586 |
| Drug Screen | | | | |
| Negative | 51/59 (86%) | 41/46 (89%) | 10/13 (77%) | 0.3567 |
| Positive | 8/59 (11%) | 5/46 (11%) | 3/13 (23%) | |
| Biomarker Results | | | | |
| Collection Time Since Injury (Minutes) | 771.0 (+/−339.8) | 779.4 (+/−296.8) | 743.0 (+/−468.7) | 0.7383 |
| Prognostic Scores | | | | |
| Glasgow Outcome Scale (3 months) | 6.0 [5.0 to 7.0] | 5.5 [4.0 to 7.0] | 7.0 [7.0 to 7.0] | 0.0130 |
| Glasgow Outcome Scale (6 months) | 6.0 [5.0 to 7.0] | 6.0 [4.0 to 7.0] | 7.0 [7.0 to 7.5] | 0.1941 |
| Glasgow Outcome Scale (12 months) | 7.0 [5.0 to 8.0] | 6.5 [5.0 to 8.0] | 7.0 [6.0 to 8.0] | 0.4412 |
| Rivermead Questionnaire First 3 Items (6 months) | 0.0 [0.0 to 2.0] | 0.0 [0.0 to 2.5] | 0.0 [0.0 to 2.0] | 0.8378 |
| Rivermead Questionnaire Last 13 Items(6 months) | 9.0 [4.0 to 15.0] | 8.5 [4.0 to 15.0] | 13.0 [0.0 to 27.0] | 0.5449 |
| WAIS-III Processing Speed Index (6 months) | 30.0 [5.0 to 55.0] | 30.0 [5.0 to 50.0] | 43.0 [18.0 to 77.0] | 0.3235 |
| Satisfaction with Life Scale (6 months) | 21.5 (+/−6.2) | 21.7 (+/−6.7) | 20.4 (+/−8.6) | 0.6205 |
| Functional Independence Measure (6 months) | 126.0 [125.0 to 126.0] | 126.0 [124.0 to 126.0] | 126.0 [126.0 to 126.0] | 0.2958 |

*24 subjects received an MRI.
Continuous variables are presented as median [25-75% Inter Quartile Range] and compared using Wilcoxon rank sum test or Mean (+/−SD) and compared using a t-test based on the distribution of the data.
Categorical variables are presented as number/total (percent) and compared using Chi-Square or Fisher's exact test.

In addition to a blood draw within 24 hours of brain injury, each patient had an extensive medical evaluation including head CT, neuropsychiatric testing, Glasgow Coma Score (GCS), and many patients also had a follow up MRI within 2 weeks of injury. Following a meticulous standardized blood draw protocol and processing, plasma samples were aliquoted for storage at −80° C., later thawed and tested. Each sample was run in duplicate with the listed results being an average of the two runs. Table 4 shows that ethanol (ETOH) levels did not correlate with biomarker levels (Pearson Correlation=0.023, p-value=0.89) as ETOH consumption is frequently related to TBI, in particular sever TBI.

Table 5 shows the analysis of data in a small sample size of 191 patients from Study 1, specifically, the analysis of the change between Time Point 2 and Time Point 1 in hsTnI levels. The Time Point 1 sample is taken within 24 hours from injury and Time Point 2 sample is taken about 3-6 hours after the Time Point 1 sample is taken. HsTnI appears to have a significant change from Time Point 1 to Time Point 2 (n=89, median delta (i.e., change from Time Point 1 to Time Point 2)=0.091537 pg/ML, Wilcoxon Signed-Rank Test p-value<0.6085). See also FIG. 1. FIG. 1 shows a box and whisker plot indicating the hsTnI levels determined in all of the patients of the study at Time Point 1 and Time Point 2. These data were simply analyses comparing the time points, and are not based on CT, MRI or GCS +/−.

TABLE 5

| Assay | Sample Size (n) | Median Delta | Minimum Delta | Maximum Delta | Wilcoxon Signed-Rank Statistic | P value |
|---|---|---|---|---|---|---|
| hsTnI | 89 | 0.091537 | −226.4837 | 29419.421 | 122 | 0.6085 |

The data from the 191 samples from Study 1 was further analyzed based on when the Time Point 1 sample was taken, e.g., 0 to about 6 hours after injury ("0-6 hour group"), about 6 to about 12 hours after injury ("6-12 hour group") and correlated with head CT scan results and/or GCS scores. The hsTnI levels in the Time Point 1 and Time Point 2 samples were compared to the positive or negative head CT scan results and/or GCS scores indicating mild or moderate/severe TBI. As this analysis was based on the time of when the Time Point 1 sample was taken, the number of subjects per group was small. See Table 6.

TABLE 6

| | | Time Range (hours)* | | | | Total # of Subjects |
|---|---|---|---|---|---|---|
| | | 0-6 | 6-12 | 12-18 | 18-24 | >24 | |
| CT Scan | Positive | 6 | 21 | 33 | 31 | 4 | 95 |
| | Negative | 8 | 17 | 25 | 25 | 0 | 75 |
| GCS Score | Mild | 12 | 27 | 45 | 41 | 1 | 126 |
| | Moderate/Severe | 2 | 10 | 15 | 15 | 2 | 44 |

*time of first sample taken from time of injury

Figure 2:
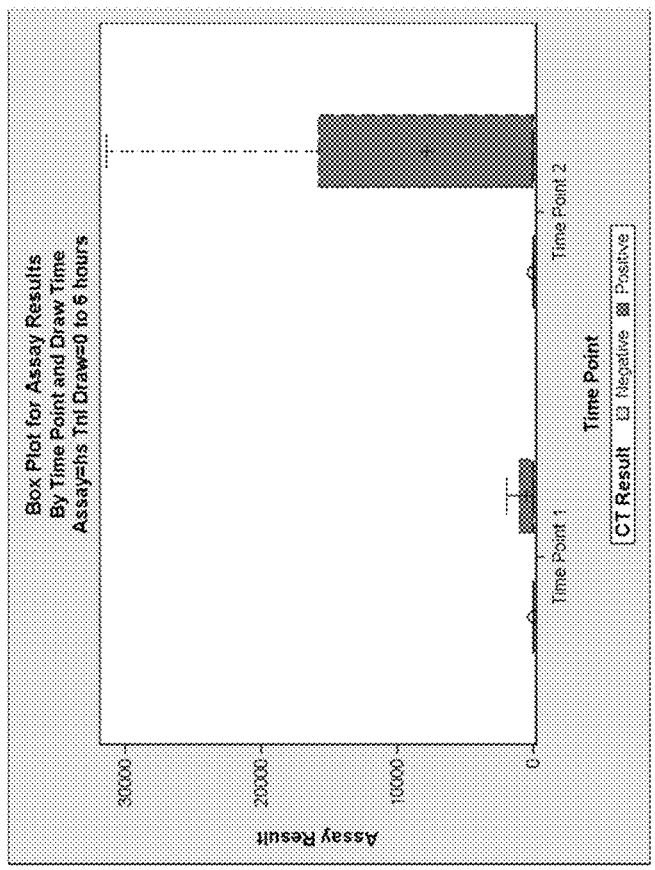
FIG. 2 shows box plot of hsTnI assay results at Time Point 1 (taken within 0 to 6 hours after head injury) and Time Point 2 (taken 3 to 6 hours after the sample of Time Point 1) correlated with positive vs. negative CT scan results.

CT Scan. FIG. 2 shows the hsTnI results in the subjects from the 0-6 hour group that had positive or negative head CT scans. FIG. 2 shows the distribution of the hsTnI levels at Time Point 1 and Time Point 2 in the subjects that had a positive or negative CT scan. The hsTnI levels in the CT positive subjects were higher than the CT negative subjects at both Time Point 1 and Time Point 2 for the 0-6 hour group. The hsTnI levels in the subjects from the 0-6 hour group having a positive CT scan had a striking increase from Time Point 1 to Time Point 2.

Figure 3:
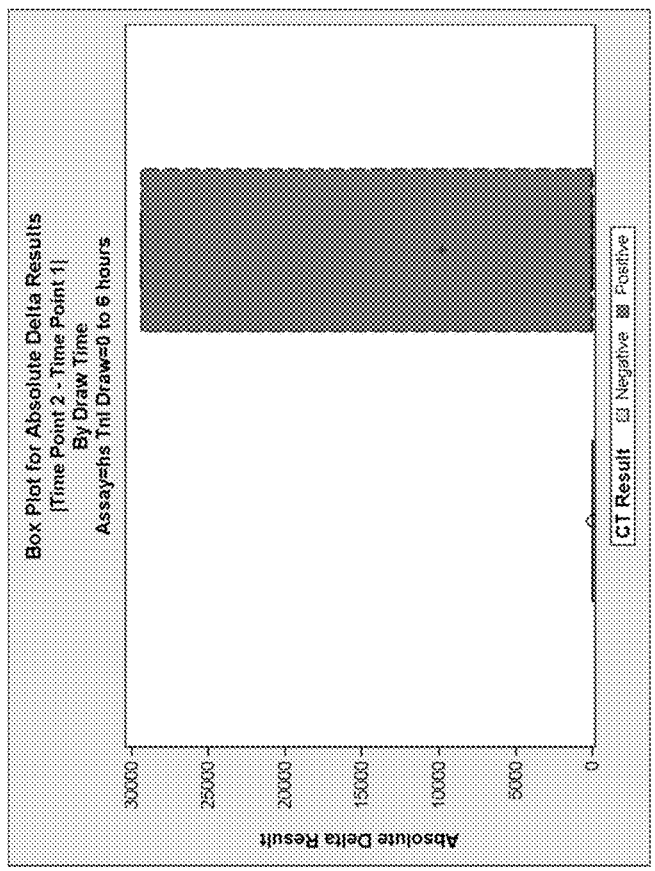
FIG. 3 shows box plots of absolute amount ("absolute delta") of hsTnI results (i.e., the absolute difference between Time Point 2 (taken 3 to 6 hours after the sample of Time Point 1) and Time Point 1 (taken within 0 to 6 hours after head injury)) correlated with positive vs. negative CT scan results.

FIG. 3 shows the absolute amount ("absolute delta") in hsTnI levels in subjects from the 0-6 hour group. Subjects having a positive head CT scan had a greater change in hsTnI levels from Time Point 1 to Time Point 2 compared to subjects having a negative head CT scan.

Figure 4:
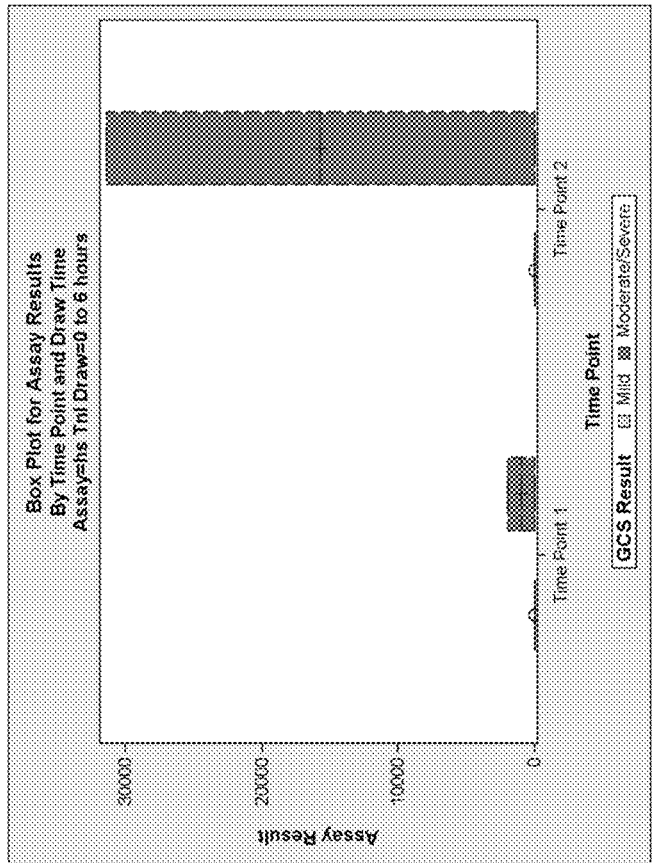
FIG. 4 shows box plot of hsTnI assay results at Time Point 1 (taken within 0 to 6 hours after head injury) and Time Point 2 (taken 3 to 6 hours after the sample of Time Point 1) correlated with mild vs. moderate/severe TBI GCS scores.

GCS Scores. FIG. 4 shows the hsTnI results in the subjects from the 0-6 hour group that were identified as having mild or moderate to severe ("moderate/severe") TBI based on their GCS score. FIG. 4 shows the distribution of the hsTnI levels at Time Point 1 and Time Point 2 in the subjects determined to have mild or moderate/severe. The hsTnI levels in the moderate/severe subjects were significantly higher than the mild subjects at both Time Point 1 and Time Point 2 for the 0-6 hour group. The hsTnI levels in the 0-6 hour group had a striking increase from Time Point 1 to Time Point 2.

Figure 5:
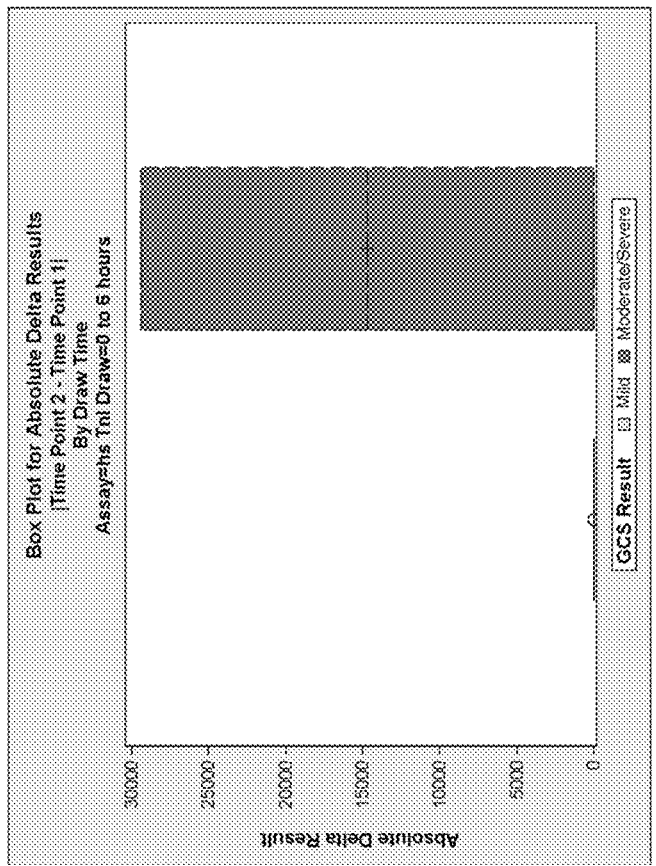
FIG. 5 shows box plot of absolute amount ("absolute delta") hsTnI assay results (i.e., the absolute difference between Time Point 1 (taken within 0 to 6 hours after head injury) and Time Point 2 (taken 3 to 6 hours after the sample of Time Point 1)) correlated with mild vs. moderate/severe TBI GCS scores.

FIG. 5 shows the absolute amount (or change between Time Point 1 and Time Point 2; "absolute delta") in hsTnI levels of 0-6 hour group. Subjects determined to have moderate/severe TBI based on the GCS score had a larger change in hsTnI levels from Time Point 1 to Time Point 2 compared to subjects determined to have mild TBI based on the GCS score.

Example 2

Study 2—Development of a Multi-Modality Classification Scheme for Traumatic Brain Injury The goal of this study was to develop a classification scheme for brain injury that indicates the nature (type) and severity of injury. For example, serum biomarkers revealed cell type. Trauma patients were divided into three groups for analysis: only brain injured, only non-brain injured, and combined injury. Brain injured and non-brain injured trauma groups were compared to each other and to the combination of brain/nonbrain trauma. These trauma groups were compared to non-trauma controls. CSF from trauma patients was compared to CSF from non-trauma patients. A secondary goal was to determine whether any of the measures, alone or in combination, had utility as a predictor of clinical outcome after TBI.

An objective multi-modality classification scheme and outcome measure for traumatic brain injury was developed based on several measures: 1) blood-based biomarkers; 2) physiologic measures and evaluation; and 3) radiographic measures (CT and 3T MRI). Blood-based biomarkers can indicate which cell types are damaged (e.g., glial vs. neuronal) and radiography can detect structural changes.

Study Site: Trauma patient were recruited at Hennepin County Medical Center (HCMC) in the state of Minnesota. Participants included trauma patients of all ages presenting to the HCMC Emergency Department (ED), trauma bay, or as direct transfer to neurosurgery. Trauma patients were excluded if they had a major psychiatric or neurologic disorder, were developmentally abnormal, or were prisoners. Subjects were identified by searching medical records for all trauma admissions and cross-checking with the American College of Surgeons trauma registry utilized in the hospital.

All trauma patients were recruited for screening at the time of presentation and underwent: 1) a standardized (templated) history and physical examination; 2) analysis of serum biomarkers if blood is drawn for other indications; 3) radiographic study as clinically indicated; 4) follow-up as clinically indicated with 1)-3); 5) pathologic specimen analysis in patients going to the operating room only; 6) CSF analysis in patients receiving ventriculostomy catheters only; 7) brain tissue oxygenation analysis in patients receiving Licox only; and 8) outcome assessment in the TBI center as clinically indicated. At the time of admission, the potential participants underwent a 24 hour screening process (Table 7) before providing informed consent.

TABLE 7

| Screening Assessments | | |
|---|---|---|
| | Adult | Pediatric |
| All | Surgery-Trauma History and Physical | |
| | Selections from Neurosurgery-Trauma History and Physical | |
| Awake | SCAT3: SAC, SSS-C | Child SCAT3: SAC-C, SSS-C |
| OR | Pathogenic Specimen | |
| VC | CSF Analysis | |
| Licox | Brain Tissue Oxygenation | |

OR: Patients going to the operating room;
VC: Patients receiving ventriculostomy catheters;
Licox: Patients receiving Licox In addition, patients who consented and controls (age and gender matched) undergone the above plus the following additional studies: 1 genomic, serum, and CSF; and 2) 3T MRI in select circumstances (serum markers in the test group; normal markers in the control group). Trauma patients included the full spectrum ranging from non-brain injured, CT-negative to structurally brain injured, requiring surgery. A patients and controls were recruited over approximately 15 months. Surviving trauma subjects were followed until they were discharged from HCMC services. Subjects evaluated in the ER and released were invited for research follow-up.

The screening process included a standardized and templated medical history and physical examination. The template was the current "Surgery-Trauma History and Physical" template in EPIC with one additional question that asks if the patient suffered a head trauma. If the patient did, three sections automatically dropped down for additional information. The first was information from the Neurosurgery trauma history and physical template, including subarachnoid grade, hemorrhage grade, intracerebral hemorrhage, and social history (level of education, employment, living arrangements, and ethnicity). The final two were standardized brain injury assessment tools: the Standardized Assessment of Concussion (SAC) and the Symptom Severity Score (SSS). Pediatric versions of these assessments were available and used when indicated. Additionally, the loss of consciousness question already included in the "Surgery Trauma History and Physical" template was copied into this drop down section with a subset of questions that provided a more clear understanding of the loss of consciousness event and the patient's current orientation. The most clinically accurate assessment taken during the first 24 hours of admission was used for future data analysis.

Non-TBI subjects were also included based on the following criteria: be between 15 and 50 years of age at the time of enrollment; have similar characteristics as the TBI population in terms of gender, age, handedness, educational level, and scanner criteria; and be capable of sufficiently clear communication and language fluency to allow the subject to provide written informed consent, or assent with parental or guardian consent for minors, and to complete study assessments for participation in all parts of the study. Non-TBI subjects were excluded if they have: been diagnosed of mild TBI within the past 6 months; a prior moderate to severe TBI (GCS<13) within past 10 years; epilepsy with recurring seizures in the past 10 years; drug abuse (except marijuana) in the past 10 years based on DAST-10 screening; alcohol abuse based on AUDIT-C screening; current primary Axis I or II psychiatric disorders, except for disorders classified as minor and not expected to impact study conduct or integrity; a history of brain mass, neurosurgery, stroke, white matter disease, and/or dementia; a known cognitive dysfunction or structural brain disease/malformation; a structural brain injury on prior neuroimaging findings; been prescribed antipsychotic/antiepileptic medications; been unable (such as due to urgent medical care needs) or unwilling to complete study procedures accurately or have any conflict of interest that could affect study results, in the opinion of the investigator; or contraindications to MRI scanning, including: a. current or suspected pregnancy per site practice; b. other conditions that may constitute a hazard to the subject during study participation, per investigator; and c. inability to comply with any part of the site's MR safety policy.

Specimen Collection and Handling. Up to 40 mL (approximately 3 tablespoons) of blood were obtained at each specimen collection. 2 tubes of serum and 2 tubes of plasma were drawn at Encounters 1, 2 4, and 5. At Encounter 3, 2 tubes of serum, 1 tube of plasma and 1 or 2 tubes of whole blood were drawn. These study specimens were processed, aliquoted, frozen, and shipped to Abbott Laboratories for biomarker testing and storage. Sample aliquots were sent to testing sites for additional TBI biomarker testing. A specimen was considered unevaluable for the study if: it contained insufficient volume to perform necessary measurements, it was grossly hemolyzed, lipemic, or icteric; it was not collected in the proper type of collection tube; it was not properly labeled; or it was not properly stored by the collection site or at Abbott Laboratories.

Serum specimens were obtained via blood draw. If a blood draw was obtained at the time of admission for clinical purposes, additional specimen was obtained and retained for research purposes. If blood was not drawn for clinical purposes, trained research personnel drawn the blood required for research. The blood was drawn through venipuncture unless a central venous access was required by the standard of care, in which case the blood was withdrawn via that access. The first blood draw was taken upon admission, the second 3-6 hours after the first, and the third was taken at 24 hours after the trauma. Discovery efforts were also ongoing to find genetic markers of susceptibility to TBI or predictive markers of TBI. At each time point, 40 mL (less than 3 tablespoons) of blood was collected: 20 mL of serum (2 tubes) and 20 mL of plasma (2 tubes). During Encounter 1, only 2 tubes of serum and 1 tube of plasma were collected for blood biomarker analysis. This whole blood collection was 6.0 mL in a whole blood tube. If a patient was enrolled at Encounter 2 instead of Encounter 1, they had 2 tubes of serum and 1 tube of plasma collected for blood biomarker analysis. This whole blood collection was 6.0 mL in a whole blood tube.

The amount of blood drawn was limited according to the NINOS standardized table (Table 8). The number of attempts to draw blood was limited for children under the age of seven to two attempts. In the case that the NINOS standardized table did not allow enough blood to be drawn for the study or there were two failed attempts to draw blood in a child patient, access to leftover blood samples drawn under the clinical standard of care was requested for complete biomarker analysis in this study. This blood draw allowed for the analysis of up to 390 blood-based biomarkers related to traumatic brain injuries.

TABLE 8

Maximum Allowable Total Blood Draw Volumes

| Body Wt (Kg) | Body Wt (lbs) | Total blood volume (mL) | Maximum allowable volume (mL) in one blood draw (=2.5% of total blood volume) | Maximum volume (clinical + research) (mL) in a 30 day period | Minimum Hgb required at time of blood draw | Minimum Hgb required at time of blood draw if subject has respiratory/CV compromise |
|---|---|---|---|---|---|---|
| 1 | 2.2 | 100 | 2.5 | 5 | 7.0 | 9.0-10.0 |
| 2 | 4.4 | 200 | 5 | 10 | 7.0 | 9.0-10.0 |
| 3 | 6.3 | 240 | 6 | 12 | 7.0 | 9.0-10.0 |
| 4 | 8.8 | 320 | 8 | 16 | 7.0 | 9.0-10.0 |

TABLE 8-continued

Maximum Allowable Total Blood Draw Volumes

| Body Wt (Kg) | Body Wt (lbs) | Total blood volume (mL) | Maximum allowable volume (mL) in one blood draw (=2.5% of total blood volume) | Maximum volume (clinical + research) (mL) in a 30 day period | Minimum Hgb required at time of blood draw | Minimum Hgb required at time of blood draw if subject has respiratory/ CV compromise |
|---|---|---|---|---|---|---|
| 5 | 11 | 400 | 10 | 20 | 7.0 | 9.0-10.0 |
| 6 | 13.2 | 480 | 12 | 24 | 7.0 | 9.0-10.0 |
| 7 | 15.4 | 560 | 14 | 28 | 7.0 | 9.0-10.0 |
| 8 | 17.6 | 640 | 16 | 32 | 7.0 | 9.0-10.0 |
| 9 | 19.8 | 720 | 18 | 36 | 7.0 | 9.0-10.0 |
| 10 | 22 | 800 | 20 | 40 | 7.0 | 9.0-10.0 |
| 11-15 | 24-33 | 880-1200 | 22-30 | 44-60 | 7.0 | 9.0-10.0 |
| 16-20 | 35-44 | 1280-1600 | 32-40 | 64-80 | 7.0 | 9.0-10.0 |
| 21-25 | 46-55 | 1680-2000 | 42-50 | 64-100 | 7.0 | 9.0-10.0 |
| 26-30 | 57-58 | 2080-2400 | 52-60 | 104-120 | 7.0 | 9.0-10.0 |
| 31-35 | 68-77 | 2480-2800 | 62-70 | 124-140 | 7.0 | 9.0-10.0 |
| 36-40 | 79-88 | 2880-3200 | 72-80 | 144-160 | 7.0 | 9.0-10.0 |
| 41-45 | 90-99 | 3280-3600 | 82-90 | 164-180 | 7.0 | 9.0-10.0 |
| 46-50 | 101-110 | 3680-4000 | 92-100 | 184-200 | 7.0 | 9.0-10.0 |
| 51-55 | 112-121 | 4080-4400 | 102-110 | 204-220 | 7.0 | 9.0-10.0 |
| 56-60 | 123-132 | 4480-4800 | 112-120 | 224-240 | 7.0 | 9.0-10.0 |
| 61-65 | 134-143 | 4880-5200 | 122-130 | 244-260 | 7.0 | 9.0-10.0 |
| 66-70 | 145-154 | 5280-5600 | 132-140 | 264-280 | 7.0 | 9.0-10.0 |
| 71-75 | 156-185 | 5680-6000 | 142-150 | 284-300 | 7.0 | 9.0-10.0 |
| 76-80 | 167-176 | 6080-6400 | 152-160 | 304-350 | 7.0 | 9.0-10.0 |
| 81-85 | 178-187 | 6480-6800 | 162-170 | 324-340 | 7.0 | 9.0-10.0 |
| 86-90 | 189-198 | 6880-7200 | 172-180 | 344-360 | 7.0 | 9.0-10.0 |
| 91-95 | 200-209 | 7280-7600 | 182-190 | 364-380 | 7.0 | 9.0-10.0 |
| 96-100 | 211-220 | 7680-8000 | 192-200 | 384-400 | 7.0 | 9.0-10.0 |

In addition to the initial physical exam, those patients that were sent to the operating room undergone pathologic specimen analysis, those patients that received Licox had brain tissue oxygenation information recorded, and those patients that received ventriculostomy catheters had CSF collected for analysis. In order to analyze the CSF, 5.0 mL was collected at the same intervals that blood was drawn. Radiographic studies were performed in accordance with the standard of care. None of the assessments performed during the screening processes were analyzed with the rest of the data until informed consent was obtained. If the patient did not ultimately consent to research, the specimens, and initial assessments were discarded.

After the participants were discharged, the patients' medical records were accessed for information about the clinical course, including time spent in the ED, any surgeries or other neuromonitoring methods used, and the acute care outcome evaluation. If the patient spent time in the ICU, information was extracted from that time period as well, including data from Moberg monitors and daily therapeutic intensity level.

Trauma patients were divided into three groups for analysis: only brain injured, only non-brain injured, and combined injury. Two age- and gender-matched control groups were included in this study and recruited from the ED: non-trauma and CSF controls. Non-trauma controls were those who did not experience any trauma, and this group composed largely of family and friends of the patients admitted for brain injury. Both control groups were consented to undergo a single intensive assessment that included a blood draw and cognitive, neurological, and quality of life assessments (SAC, NOS-TBI, QoLABI). Patients receiving elective ventriculostomy or lumbar drain catheters were (pre-operatively) consented to be a part of the CSF control group. 5 mL of CSF was collected from the ventriculostomy catheter of patients in this control group for comparison with the CSF collected from the portion of the study group that received a ventriculostomy catheter as a part of their standard of care. The CSF control group was also offered the chance to participate in the same intensive assessment as the other two controls groups that included a blood draw and a 3T MRI scan.

Follow-Up: All patients that consented to participate in the follow-up portion of the study were asked to return to the hospital. Patients who returned were seen in the TBI Outpatient Clinic at 2 weeks, 4 weeks, months, 6 months, and 1 year. If they did not have a scheduled appointment at the TBI Outpatient Clinic, they were scheduled a time to come into the Brain Injury Research Lab (PL.610) at those time points. Table 9 provides a timeline for each of the assessments. Blood draws for biomarker analysis were done at each of the five follow-up time points in the same method, as described above. The outcome assessment battery listed in Tables 10 and 11 were completed at 3 months, 6 months, and one year. Radiographic scans that were a part of the standard of care were accessed through the participant's medical records, but select consented participants and controls also underwent 3T MRI scans at 2 weeks and 6 months after their brain injury. Each MRI examination took approximately one hour and included the following pulse sequences: (1) Sagittal short TR localizer, (2) Axial Fse, (3) Axial FLAIR, (4) Axial SWI, (5) Axial T2* imaging. In the case that patients were not able to come into the hospital for follow-up, they were contacted via phone at three months and one year after their injury to complete the BT ACT, which was a 15-20 minute cognitive assessment designed to be administered over the phone.

TABLE 9

Outcome Timeline

|  | Blood Draw | 3T MRI | CSF Collection | CT Scan | Assessments | Total Time (minutes) |
|---|---|---|---|---|---|---|
| ADM | X |  | X (if indicated) |  |  | 10 |
| 2 weeks | X | X |  |  |  | 70 |
| 4 weeks | X |  |  |  |  | 10 |
| 3 months | X |  |  |  | X | 70 |
| 6 months | X | X |  |  |  | 70 |
| 1 year | X | X |  | X* | X | 160 (130 without CT) |

TABLE 10

Outcome Assessments-Not Finalized

|  |  | Adult | Pediatric |
|---|---|---|---|
| Outcome | All Awake | GOS and GOSE SCAT3: SSS and SAC GOAT Duration of Amnesia NOS-TBI Quality of Life: MPAI-4 | Pediatric GOSE Child SCAT3: Child & Parent Report; SAC-C COAT Duration of Amnesia NOS-TBI Quality of Life: Neuropsychiatric Rating Schedule Pediatric Quality of Life Inventory (For Child and for Proxy) |
|  | Not Awake |  | CRS-R (Just Brain Stem Reflex Grid?) |

TABLE 11

Possible Infant Assessments

| Name | Age | Time | Description |
|---|---|---|---|
| Bayley III, BSID* | 0-3.5 | 30-90 | Cognitive, language (receptive and expressive) and motor development Most commonly used in test for this age range |
| BITSEA* | 1-3 | 7-12 | Parent perception of Social and Emotional behavior 17 items of 42 are for autism, so may be able to be made shorter |
| CBCL | 1.5-5 | 25-30 | Parent perception of performance on Activities, Social, and School performance |
| MSEL* | 1 3 5 | 15 25-35 40-60 | Cognitive and Motor Ability (Gross Motor, Visual Reception, Fine Motor, Language Mostly for readiness for school |
| Shape School* | 3-6 | 45-75 | Inhibition and Switching Processes: Emerging Executive Functions |
| Trails-Preschool* | 2-6 | 5-10 | Neuropsychological Function: Psychomotor speed, Complex Attention, Executive Function Advanced Trail Making Test |

*Requested Access

Statistical Analysis Plan. Biomarker data was analyzed by examining maximum concentration draw for each biomarker per patient, or by time from incident buckets, or both. To address the primary objective of determining associations between biomarker concentrations in blood and clinical neurological and magnetic resonance imaging data, multiple analyses was employed. Principal components analysis was used to examine which biomarkers may be explaining the same variance, or if a biomarker was contributing very little variance. The biomarkers were used in a logistic regression analysis, and some biomarkers were excluded based on the results from the principal components analysis, and clinical input. A significance level of 0.05 was used for the logistic regression analysis. ROC analysis was also used to examine the predictive ability of each biomarker in determining MRI status or neurological testing outcomes, for this set of data.

Example 3

Study 2—Analysis

Figure 6:
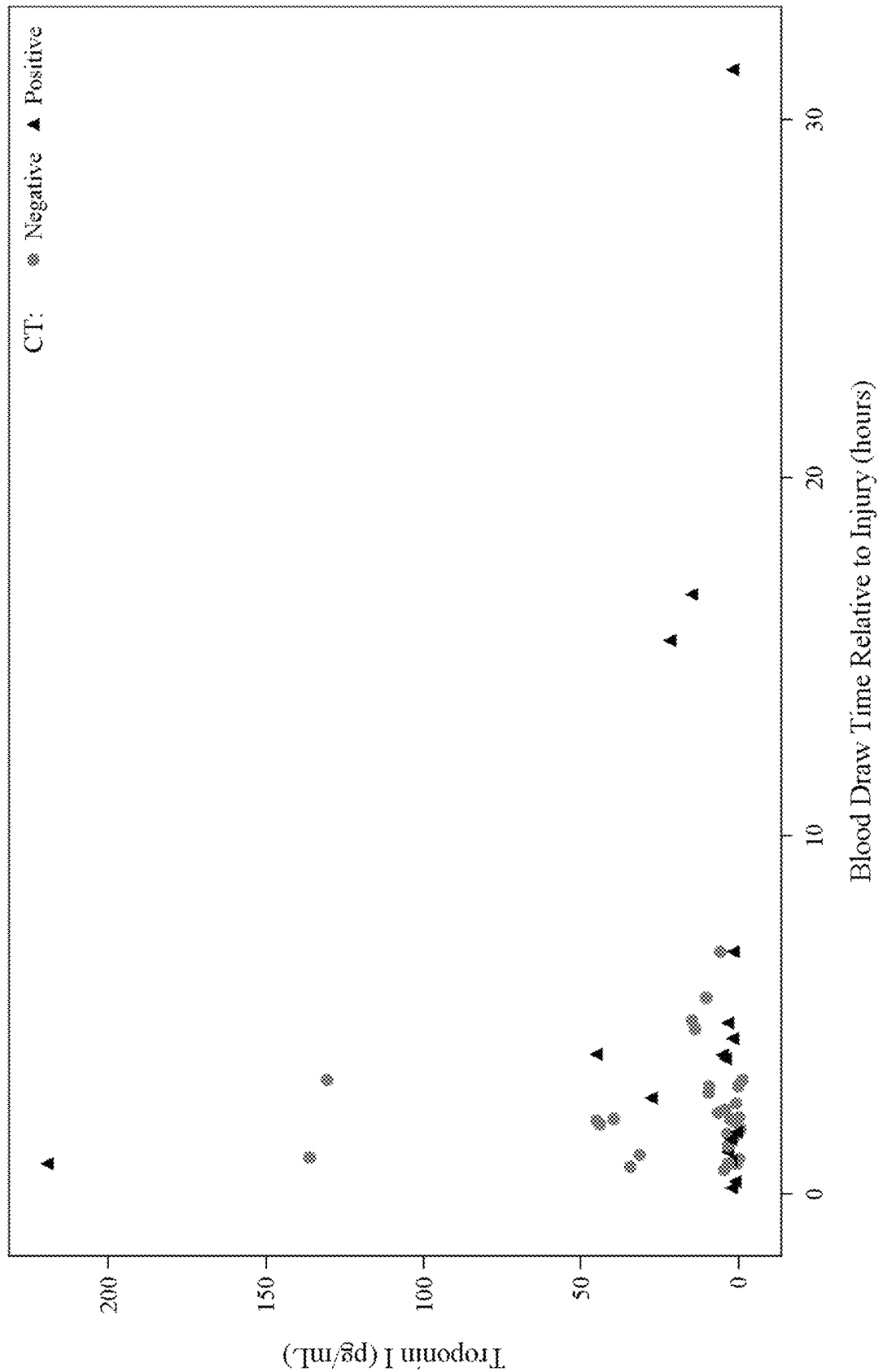
FIG. 6 shows biomarker hsTnI result vs. time from injury based on CT scan results.
Figure 7:
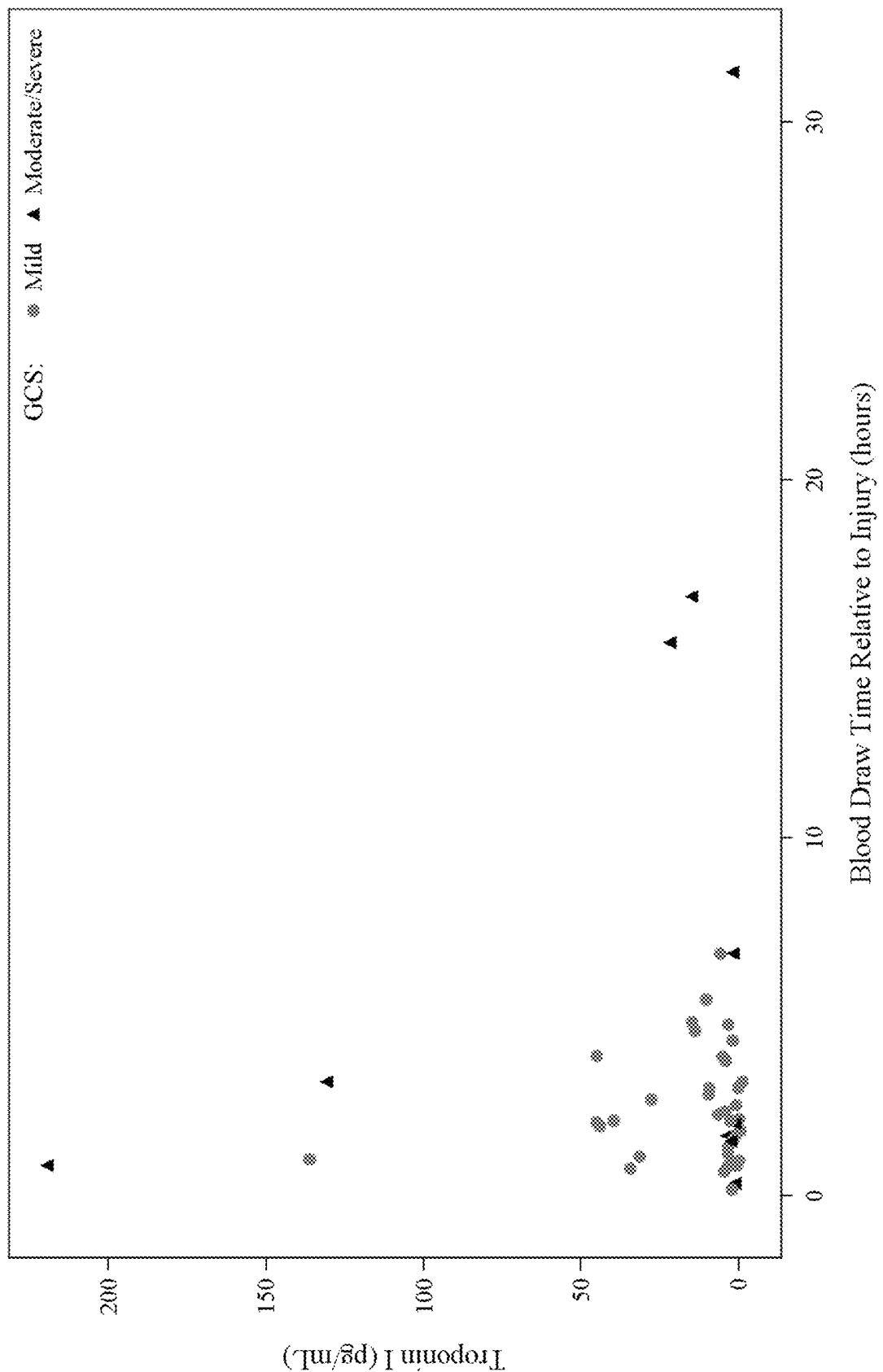
FIG. 7 shows biomarker hsTnI result vs. time from injury based on Glasgow Coma Scale (GCS) scores.

High sensitivity troponin I (hsTnI) was measured using the Abbott Architect STAT hsTnI assay in samples taken from subjects, as described in Example 5. FIGS. 6 and 7 show that hsTnI levels correlated with injury throughout the first 24 hours after injury (range approximately 2-23 hours) based on CT scan results (FIG. 6) and GCS score (FIG. 7).

Figure 8:
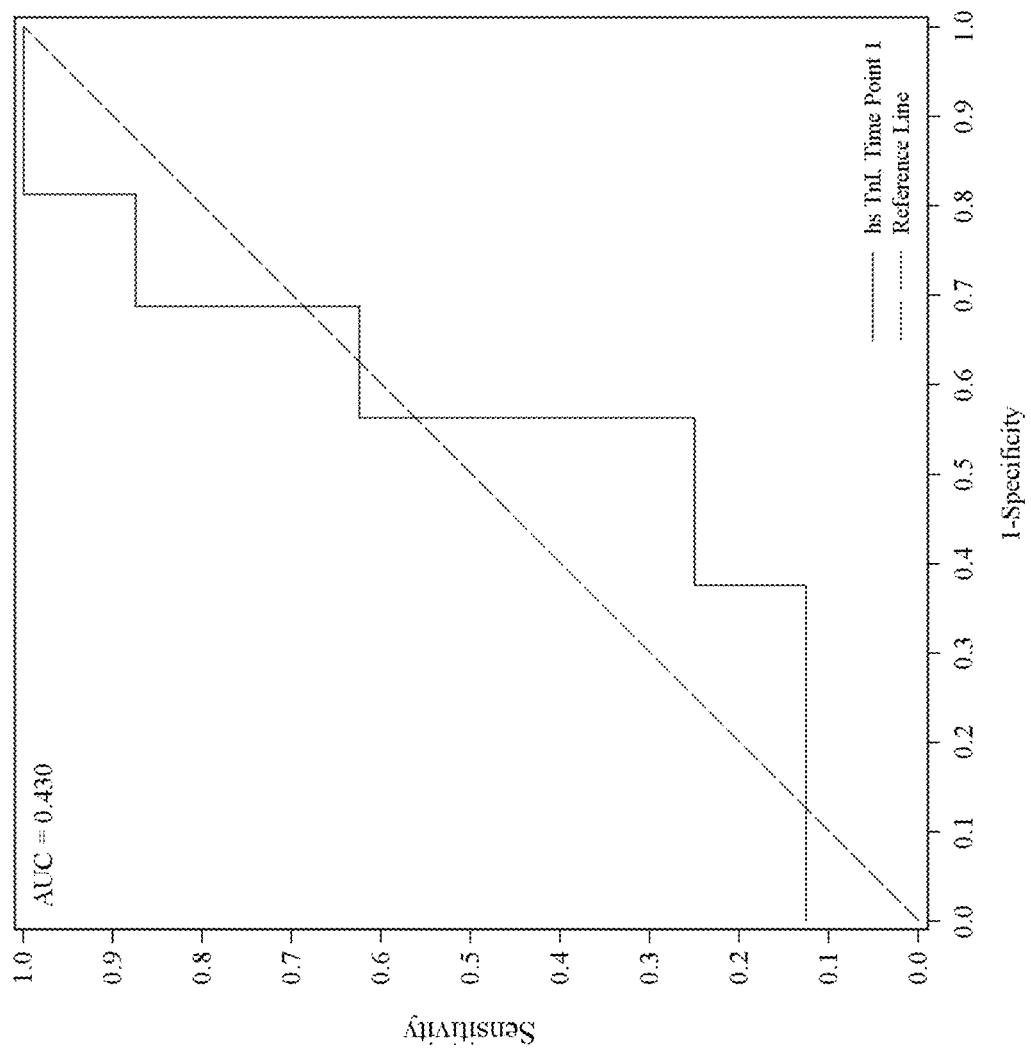
FIG. 8 shows a receiver operating characteristic (ROC) analysis of hsTnI levels correlated with CT status (positive vs. negative CT scan result) in samples taken within about 2 hours of suspected injury. The sample at Time Point 1 is taken within 2 hours of head injury while the sample at Time Point 2 is taken about 3 to about 6 hours after the Time Point 1 sample is taken.

Samples Taken from Subjects within 2 hours of Injury: hsTnI levels in samples taken from human subjects within about 2 hours of suspected injury were measured. FIG. 8 shows ROC analysis of hsTnI levels correlated with CT status (positive vs. negative CT scan result; AUC=0.430). Table 12 shows the sensitivities and specificities of using hsTnI cut-off levels to predict a positive CT scan result.

TABLE 12

CT Scan-hsTnI Reference Levels Analysis

| Biomarker | Levels (pg/mL) | Sensitivity (%) | Specificity (%) |
|---|---|---|---|
| hsTnI | 1.15 | 87.5 | 31.25 |
|  | 1.29 | 75.0 | 31.25 |

Figure 9:
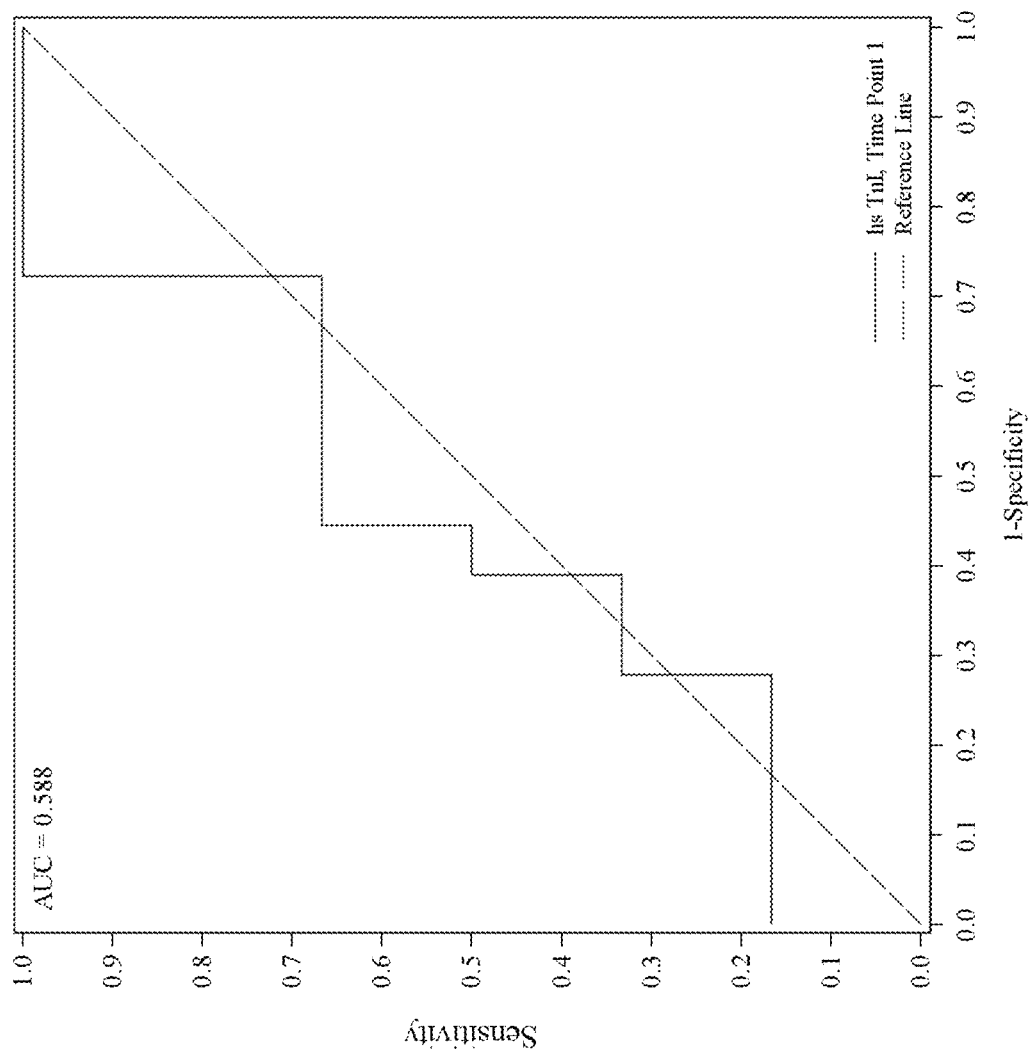
FIG. 9 shows a receiver operating characteristic (ROC) analysis of hsTnI levels correlated with mild vs. moderate/severe TBI GCS scores in samples taken within about 2 hours of suspected injury. The sample at Time Point 1 is taken within 2 hours of head injury while the sample at Time Point 2 is taken about 3 to about 6 hours after the Time Point 1 sample is taken.

FIG. 9 shows ROC analysis of hsTnI correlated with GCS Score results (mild vs. moderate/severe TBI; AUC=0.588). Table 13 shows the sensitivities and specificities of using hsTnI cut-off levels to predict moderate/severe TBI based on GCS scores.

TABLE 13

GCS Score-hsTnI Reference Levels Analysis

| Biomarker | Levels (pg/mL) | Sensitivity (%) | Specificity (%) |
|---|---|---|---|
| hsTnI | 5.80 | 85.71 | 33.33 |
|  | 4.71 | 85.71 | 40.0 |

Figure 10:
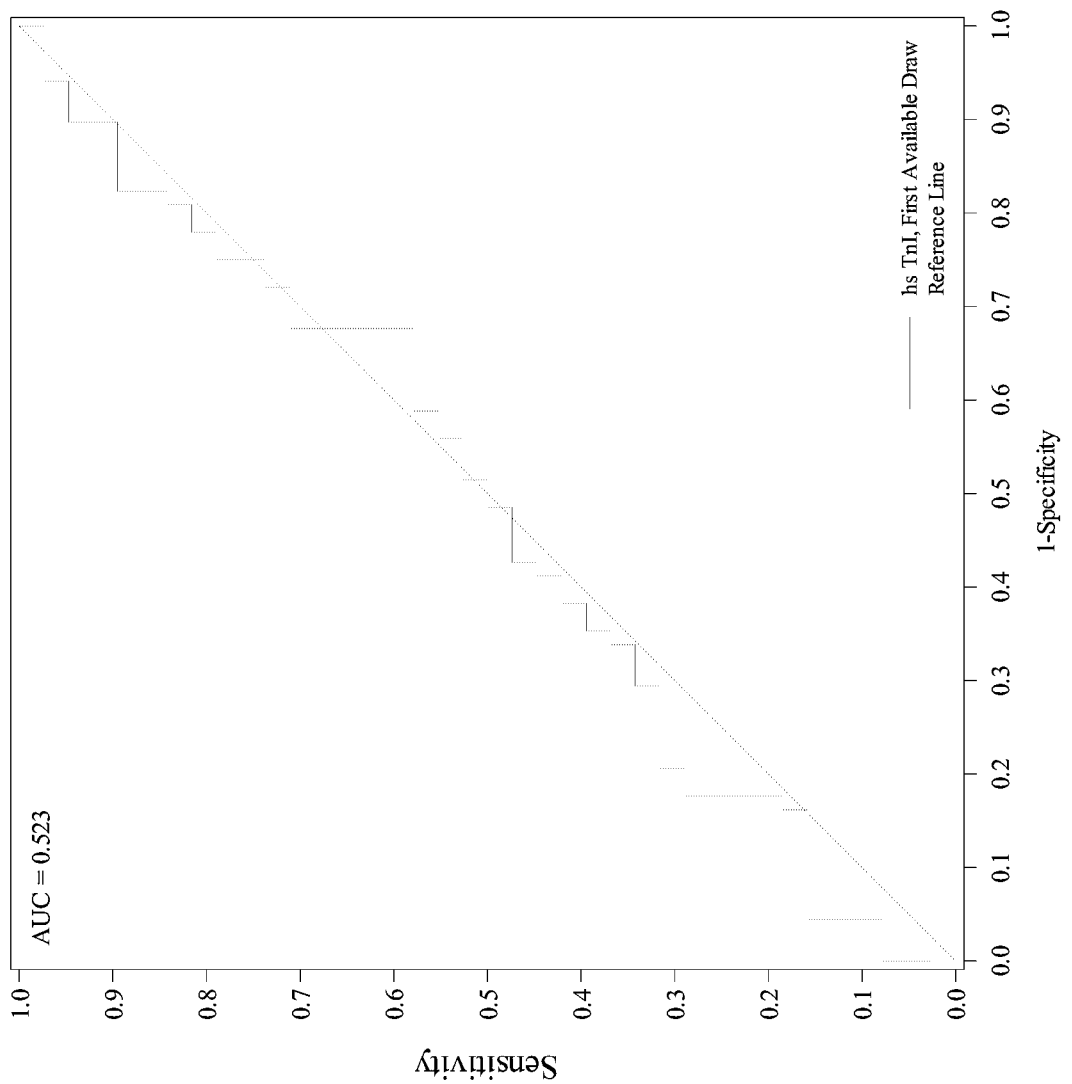
FIG. 10 shows ROC curve of hsTnI assay results for all of the subjects at Time Point 1 correlated with positive vs. negative CT scan results.

Samples Taken from All Subjects: FIG. 10 shows the ROC curve correlating the hsTnI levels for all of the subjects at Time Point 1 with CT scan result. The sensitivity and specificity of reference levels for all of the subjects based on the ROC curve is shown in Table 14.

TABLE 14

| Reference Level (pg/mL) | Sensitivity (%) | Specificity (%) |
| --- | --- | --- |
| 1.65 | 81.58 | 20.59 |
| 2.16 | 71.05 | 30.88 |
| 14.75 | 31.58 | 79.41 |
| 30.43 | 21.05 | 82.35 |

Figure 11:
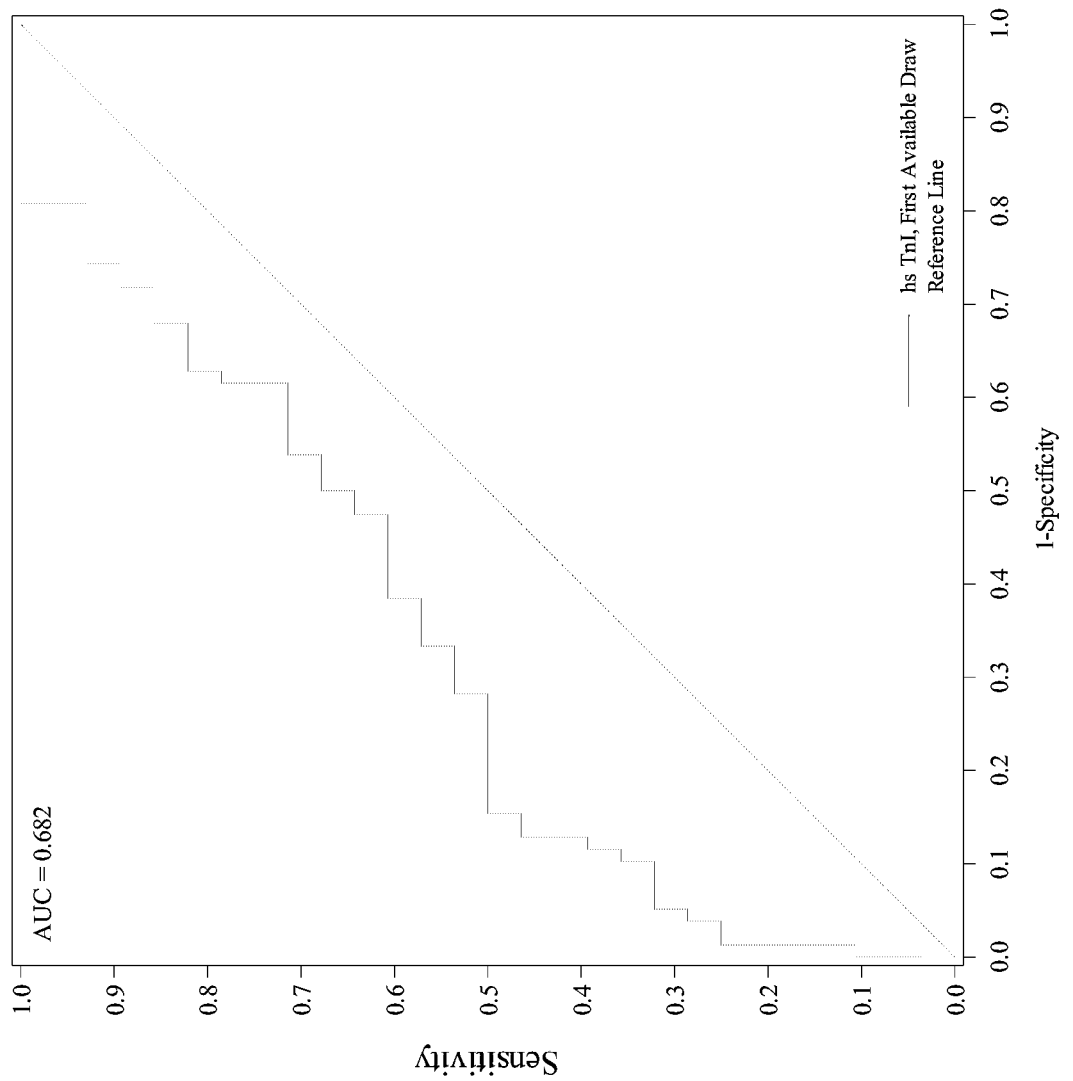
FIG. 11 shows ROC curve of hsTnI assay results for all of the subjects at Time Point 1 correlated with mild vs. moderate/severe TBI GCS scores.

FIG. 11 shows the ROC curve correlating the hsTnI levels for all of the subjects at Time Point 1 with GCS scores. The sensitivity and specificity of reference levels for 0-6 hour group based on the ROC curve is shown in Table 15.

TABLE 15

| Reference Level (pg/mL) | Sensitivity (%) | Specificity (%) |
| --- | --- | --- |
| 43.79 | 32.14 | 94.87 |
| 21.23 | 46.43 | 85.90 |
| 1.94 | 85.71 | 30.77 |
| 2.54 | 75 | 38.46 |

Example 4

Study 2—Absolute Amount Analysis

Figure 12:
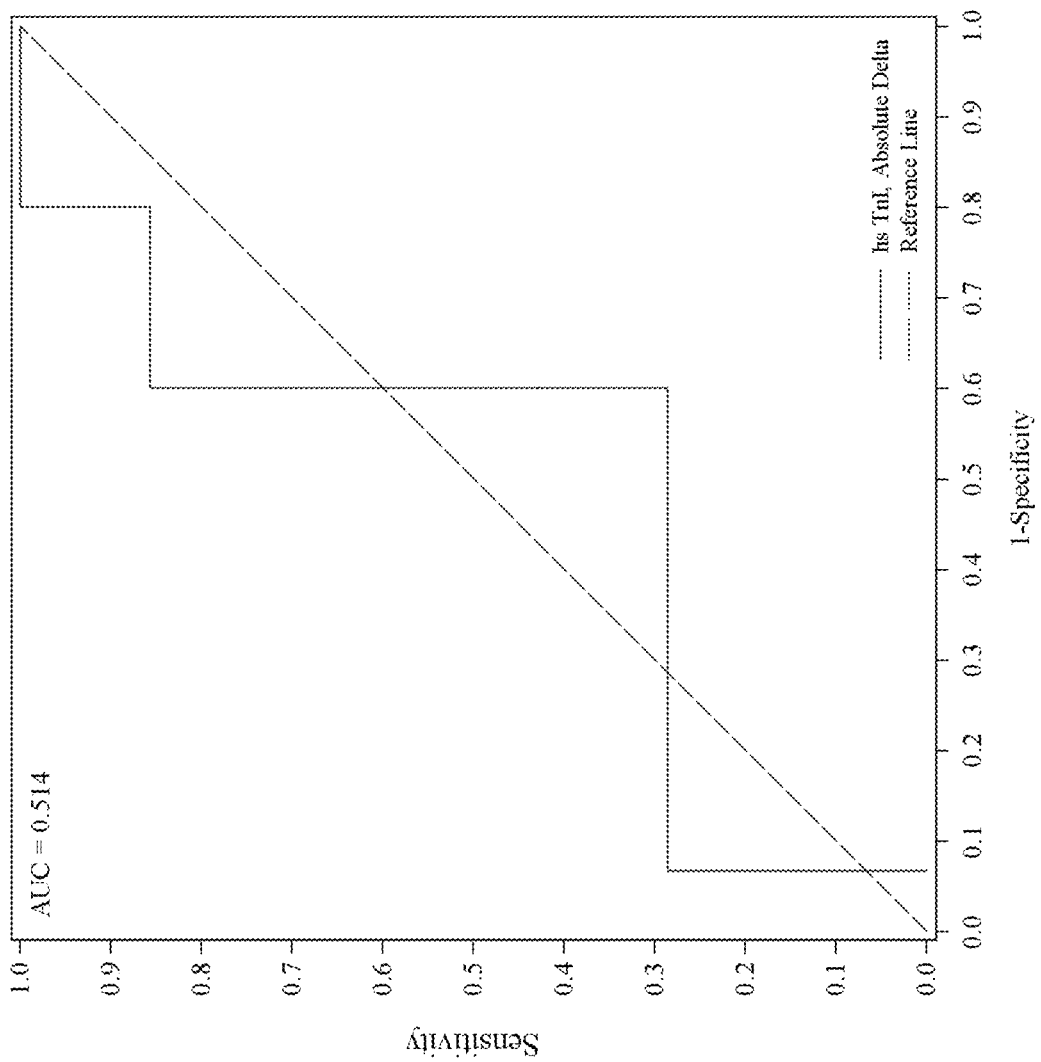
FIG. 12 shows ROC analysis of absolute amount ("absolute delta") of hsTnI results (i.e., the absolute difference between hsTnI levels at Time Point 2 and hsTnI levels at Time Point 1) correlated with CT status (positive vs. negative CT scan result). The sample at Time Point 1 is taken within 2 hours of head injury while the sample at Time Point 2 is taken about 3 to about 6 hours after the Time Point 1 sample is taken.

Samples Taken from Subjects within 2 hours of Injury: hsTnI levels were measured in samples taken from human subjects at a first time point within about 2 hours of suspected injury and samples taken from the human subjects at a second time point 3-6 hours after the first time point. FIG. 12 shows ROC analysis of absolute amount ("absolute delta") of hsTnI results (i.e., the absolute difference between hsTnI levels at Time Point 2 and hsTnI levels at Time Point 1) correlated with CT status (positive vs. negative CT scan result; AUC=0.514). Table 16 shows the sensitivities and specificities of using hsTnI cut-off levels to predict a positive CT scan result, wherein a value less than the cutoff is predicted to have a positive CT scan result.

TABLE 16

CT Scan-hsTnI Absolute Delta Analysis

| Biomarker | Absolute Amount (pg/mL) | Sensitivity (%) | Specificity (%) |
| --- | --- | --- | --- |
| hsTnI | 2.54 | 66.67 | 55.56 |
|  | 1.16 | 83.33 | 27.78 |

Figure 13:
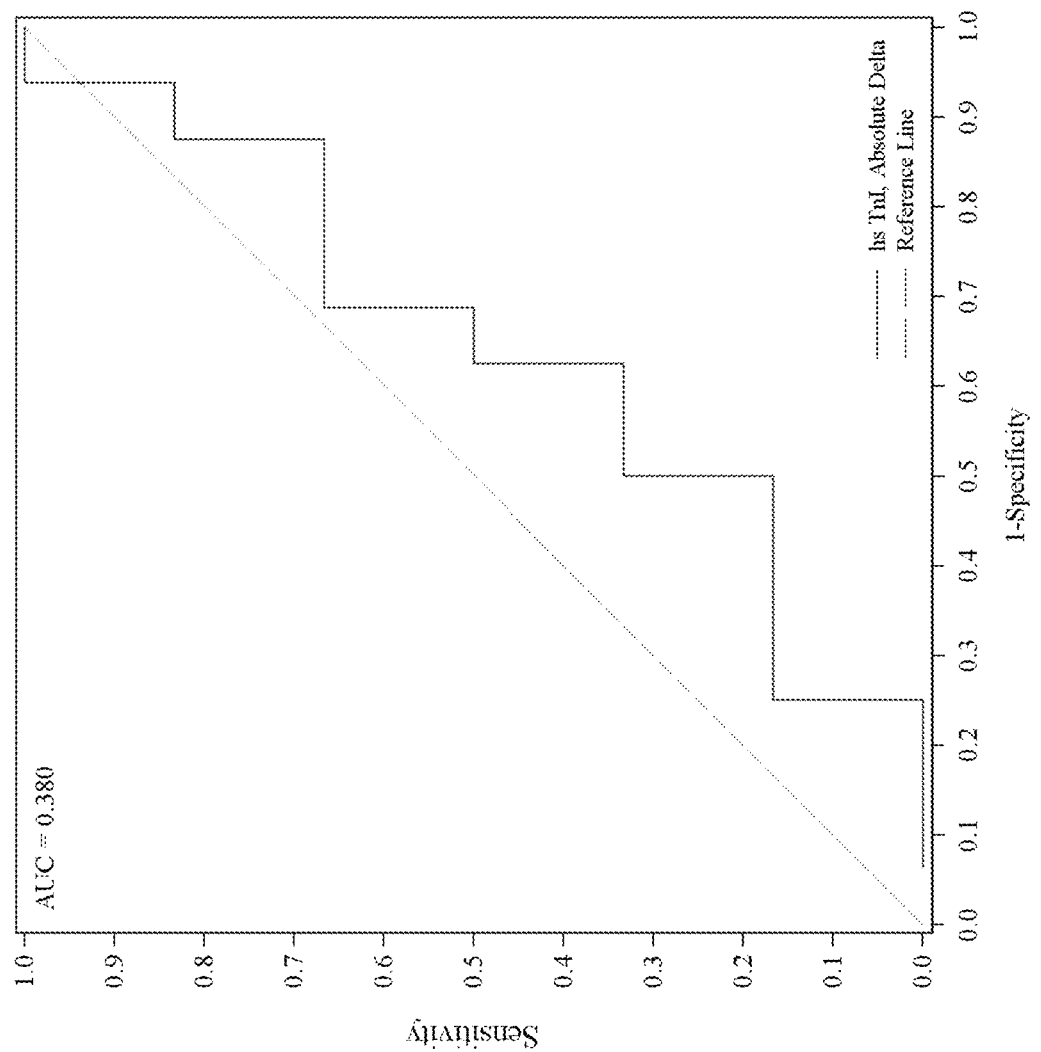
FIG. 13 shows ROC analysis of absolute amount ("absolute delta") of hsTnI results (i.e., the absolute difference between hsTnI levels at Time Point 2 and hsTnI levels at Time Point 1) correlated with mild vs. moderate/severe TBI GCS scores. The sample at Time Point 1 is taken within 2 hours of head injury while the sample at Time Point 2 is taken about 3 to about 6 hours after the Time Point 1 sample is taken.

FIG. 13 shows ROC analysis of absolute amount ("absolute delta") of hsTnI results (i.e., the absolute difference between hsTnI levels at Time Point 2 and hsTnI levels at Time Point 1) correlated with GCS Score result (mild vs. moderate/severe; AUC=0.380). Table 17 shows the sensitivities and specificities of using hsTnI cut-off levels to predict moderate/severe TBI based on GCS scores, wherein a value less than the cutoff is predicted to have moderate/severe TBI.

TABLE 17

GCS Score-hsTnI Absolute Delta Analysis

| Biomarker | Absolute Amount (pg/mL) | Sensitivity (%) | Specificity (%) |
| --- | --- | --- | --- |
| hsTnI | 4.73 | 66.67 | 31.25 |
|  | 20.62 | 83.33 | 12.5 |

Figure 14:
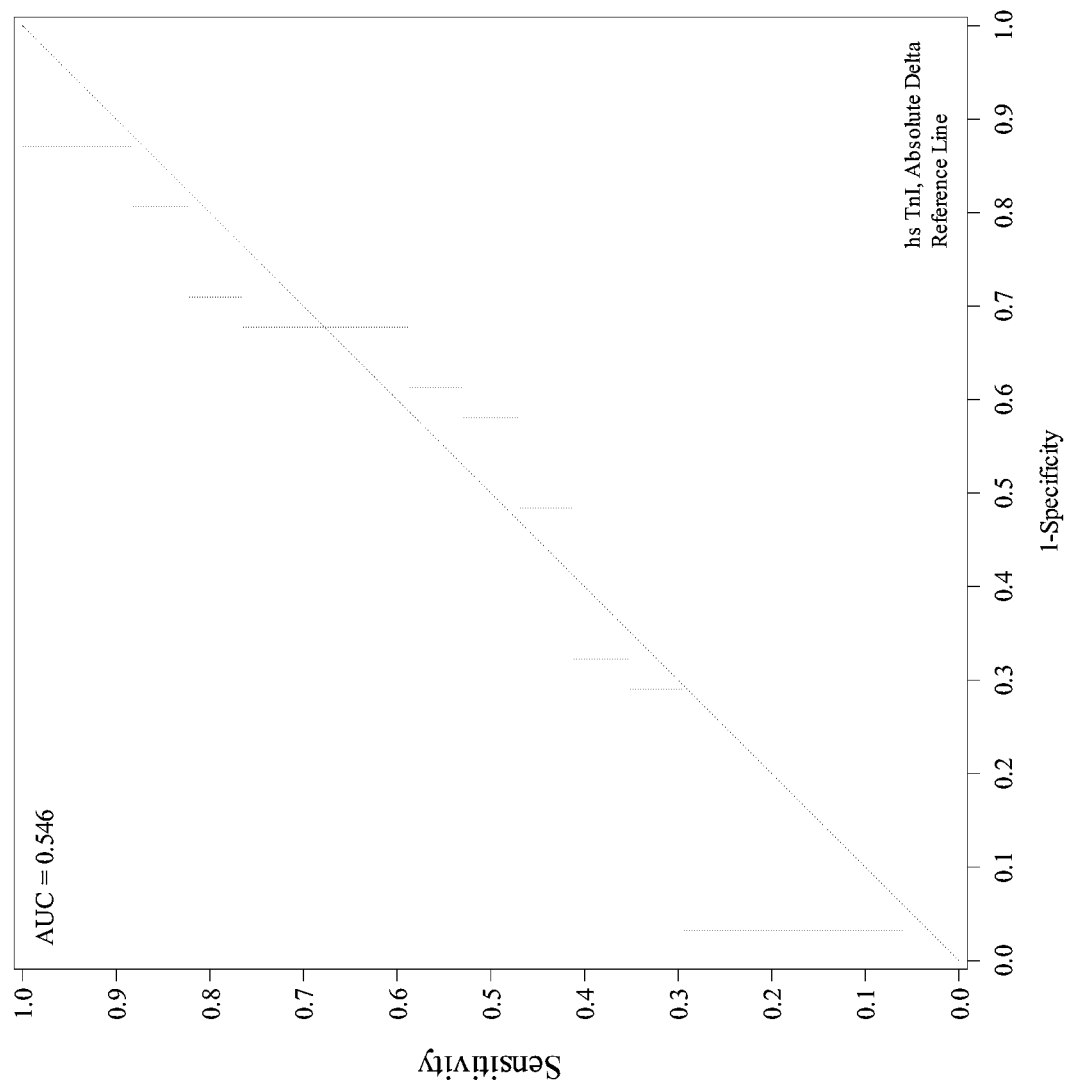
FIG. 14 shows ROC curve of absolute amount ("absolute delta") hsTnI assay results for all of the subjects correlated with positive vs. negative CT scan results.

Samples Taken from All Subjects: FIG. 14 shows the ROC curve correlating the hsTnI levels for all of the subjects at Time Point 1 with CT scan result. The sensitivity and specificity of absolute amounts (or change between Time Point 1 and Time Point 2) in hsTnI levels for all of the subjects based on the ROC curve are shown in Table 18.

TABLE 18

| Absolute amount (pg/mL) | Sensitivity (%) | Specificity (%) |
| --- | --- | --- |
| 16.050 | 88.24 | 19.36 |
| 10.755 | 82.35 | 19.36 |
| 0.720 | 35.29 | 70.97 |
| 0.389 | 29.41 | 90.32 |

Figure 15:
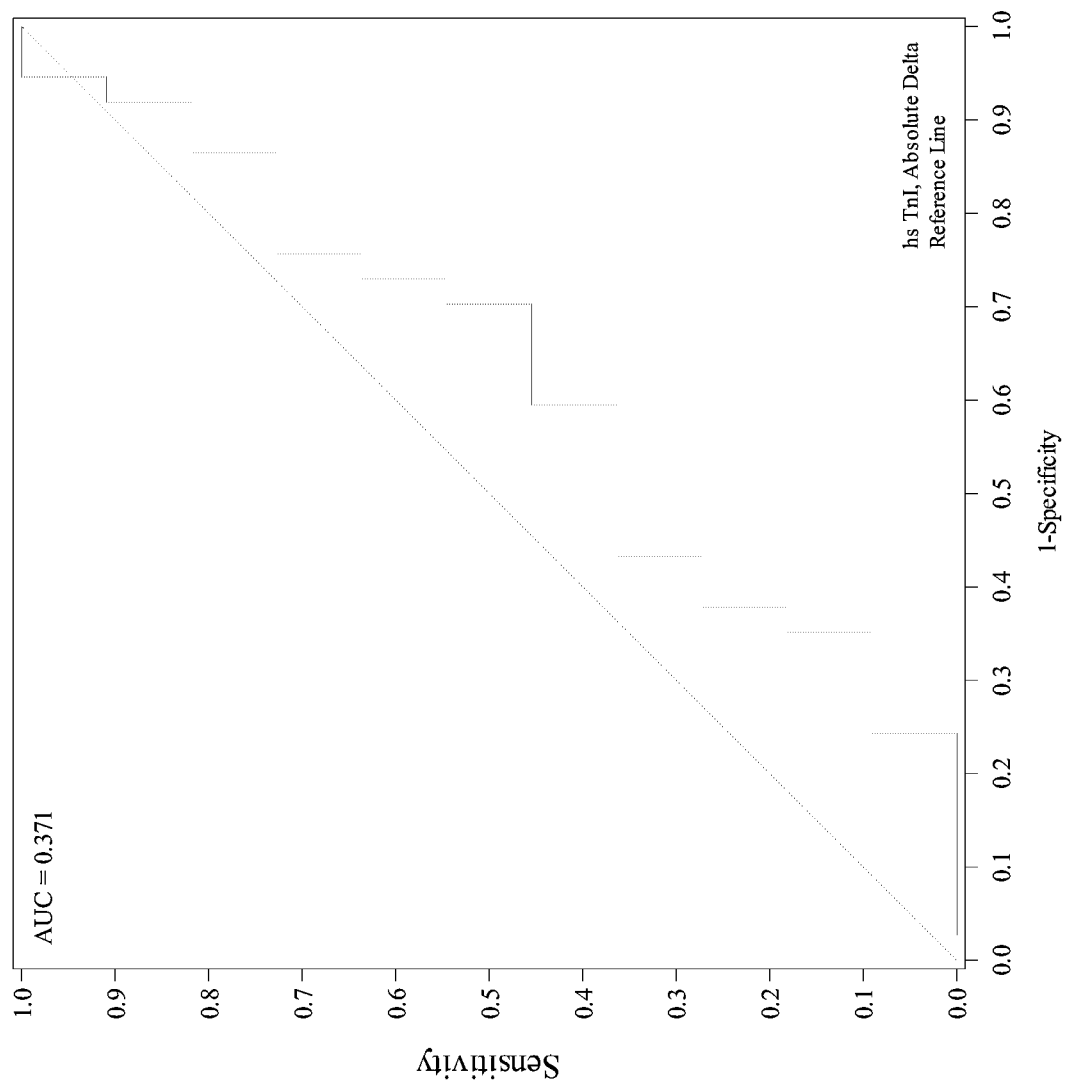
FIG. 15 shows ROC curve of absolute amount ("absolute delta") hsTnI assay results for all of the subjects correlated with mild vs. moderate/severe TBI GCS scores.

FIG. 15 shows a ROC curve correlating the absolute amount of change in hsTnI levels for all of the subjects at Time Point 1 and Time Point 2 with GCS scores (mild vs. moderate/severe). The sensitivity and specificity of the absolute amounts (or change between Time Point 1 and Time Point 2) in hsTnI levels for all of the subjects based on the ROC curve is shown in Table 19.

TABLE 19

| Absolute amount (pg/mL) | Sensitivity (%) | Specificity (%) |
| --- | --- | --- |
| 3.33 | 45.46 | 32.43 |
| 5.80 | 72.73 | 21.62 |
| 17.17 | 81.82 | 13.51 |

Example 5

TBI Population

Recent introduction of high sensitivity troponin assays (hsTn) provide a new window of opportunity for improved characterization of cardiac injury. hsTn assays measure up to ten-fold lower concentrations of cardiac troponin than conventional troponin assays with improved precision. They allow improved detection of cardiac injury in non-cardiac conditions and therefore afford an unprecedented opportunity for improved characterization of cardiac injury across the spectrum of TBI severities. The objectives of this study were: to estimate the incidence cardiac injury across the spectrum of TBI with precision; to identify the risk factors associated with cardiac injury; to determine whether cardiac injury is associated with functional and symptomatic outcomes post-TBI; and to characterize longitudinal changes in troponin values in TBI.

High sensitivity troponin I (hsTnI) was measured in samples from subjects using the Abbott Architect STAT hsTnI assay. HsTnI was measured on blood samples obtained at 0, 4, 24, and 1 month after presentation.

Study population. A 6-month prospective cohort study of patients evaluated for TBI in the emergency department and age and gender matched traumatically injured non-TBI control subjects. Participants were recruited from two academic EDs. Eligible TBI participants were 18 years or older and 1) presented to the ED within 24 hours of blunt head injury, 2) met the ACEP criteria for evaluation with a head CT scan, and 3) consented to research blood draws. Excluded from the study were subjects with: brain tumor; severe dementia; prior history of intracranial hemorrhage or intracranial surgery; seizure induced head injury; pregnancy; no working telephone number; inability to communicate in English; or blood transfusion before initial research blood draw was obtained. Age and gender matched trauma control participants were 18 years or older, presented to the ED within 24 hours of traumatic injury but had no evidence of head injury, and consented to research blood draws. Exclusion criteria for trauma control participants were the same as that for TBI participants.

Clinical data. Demographic and clinical data were collected by trained research coordinators using structured data collection tools recommended by the National Institute of Neurological Disorders and Stroke (NINdS) Common Data Elements. Data were collected and managed using REDCap electronic data capture tools hosted at the Johns Hopkins School of Public Health.

Outcome data. Mild TBI (mTBI) was defined as per the American Congress of Rehabilitation Medicine (ACRM) which defines mTBI as a traumatically induced physiological disruption of brain function as a consequence of the head being struck, striking an object, or undergoing an acceleration/deceleration movement without direct external head trauma and resulting in at least one of the following: any period of loss of consciousness of 30 minutes or less; any loss of memory for events immediately before or after the accident (post-traumatic amnesia) lasting no more than 24 hours; any alteration in mental status at the time of the accident (e.g., confusion, disorientation); focal neurological deficit(s); or a Glasgow Coma Scale (GCS) score of 13-15 at presentation.

Head CT images were read by one board certified neuroradiologist. The presence/absence of traumatic lesions, including the size and location of these lesions were classified according to the NINDS common data elements for radiologic imaging of TBI (Duhaime et al., Arch Phys Med Rehabil. (2010) 91:1661-1666). Outcome data were collected at 1, 3, and 6 months after enrollment either via telephone interview (61.8% of the TBI population) or in-person assessment (38.2% of the population). Functional outcome was ascertained using the Extended Glasgow Outcome Scale (GOSE) which categorizes on a scale of 1 (Dead) to 8 (upper good recovery). Delayed functional recovery at 1 month was defined as GOSE<8. As per the International Statistical Classification of Diseases and Related Health Problems 10th Revision (ICD-10) criteria, subjects were deemed to have mild post-concussion syndrome (PCS) if they reported a mild/moderate/severe problem in 2 of the following ICD-10 symptoms categories as measured by the Rivermead Post-Concussion Questionnaire (RPQ): (1) headaches, dizziness, general malaise, excessive fatigue, or noise intolerance; (2) irritability, emotional lability, depression, or anxiety; (3) subjective complaints of concentration or memory difficulty; (4) insomnia; (5) reduced tolerance to alcohol; (6) preoccupation with these symptoms and fear of permanent brain damage. Similarly subjects were deemed to have at least moderate PCS if they reported mild/moderate/severe problems in at least 3 of the ICD-10 symptom categories listed above. Moderate/severe depressive symptoms were defined as a total score of 10 or more on the Patient Health Questionnaire 9 (PHQ9).

Statistical analysis. hsTnI values between TBI and trauma control subjects were compared. Additionally, hsTnI values were compared among TBI subjects with traumatic intracranial abnormalities (positive head CT) on head CT scan, TBI with a negative head CT who meet the ACRM criteria for TBI, and TBI subjects with a negative CT who don't meet the ACRM criteria. Group comparisons of median hsTnI values were made using the Kruskall-Wallis test. Whether the location and size of intracranial lesions were associated with hsTnI was also determined. A multiple linear regression model with generalized estimating equations (GEE) and robust variance estimation to account for correlations within repeated measurements of hsTnI was used to examine longitudinal changes in hsTnI measured at 0, 4, 24, 72 hours, 1 week, and 1 month after presentation. Logistic regression models were constructed to determine whether hsTnI measured at presentation was associated with functional disability (measured by the Glasgow Outcome Scale Extended), post-concussive symptoms (measured by the Rivermead Post-concussion symptom inventory) and depression (measured by the Patient Health Questionnaire 9) at 1, 3, and 6 months post-injury.

Sample size. The number of samples for each criterion is shown in Table 20.

TABLE 20

| Time | Number |
| --- | --- |
| TBI-0 hour | 500 |
| TBI-4 hour | 338 |
| TBI-24 hour | 134 |
| TBI-1 month | 73 |
| Trauma control-0 hour | 94 |

Example 6 hsTnI Analysis

Figure 16:
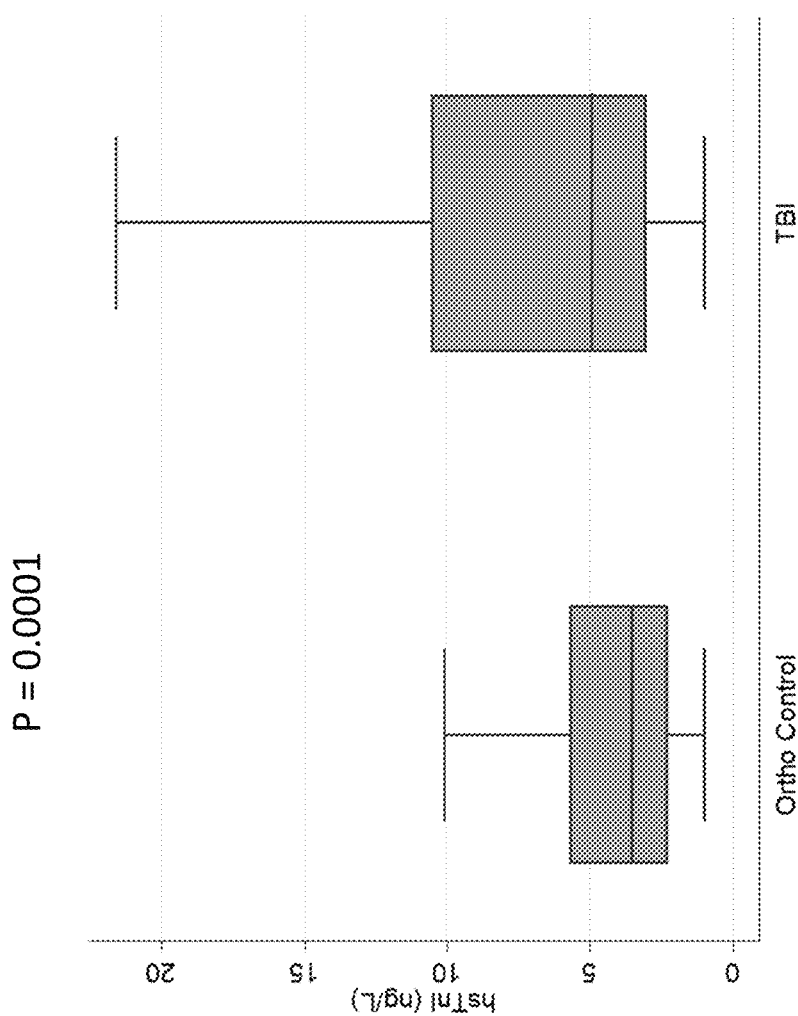
FIG. 16 shows the distribution of hsTnI levels in TBI patients and Trauma control patients (p=0.0001).
Figure 17:
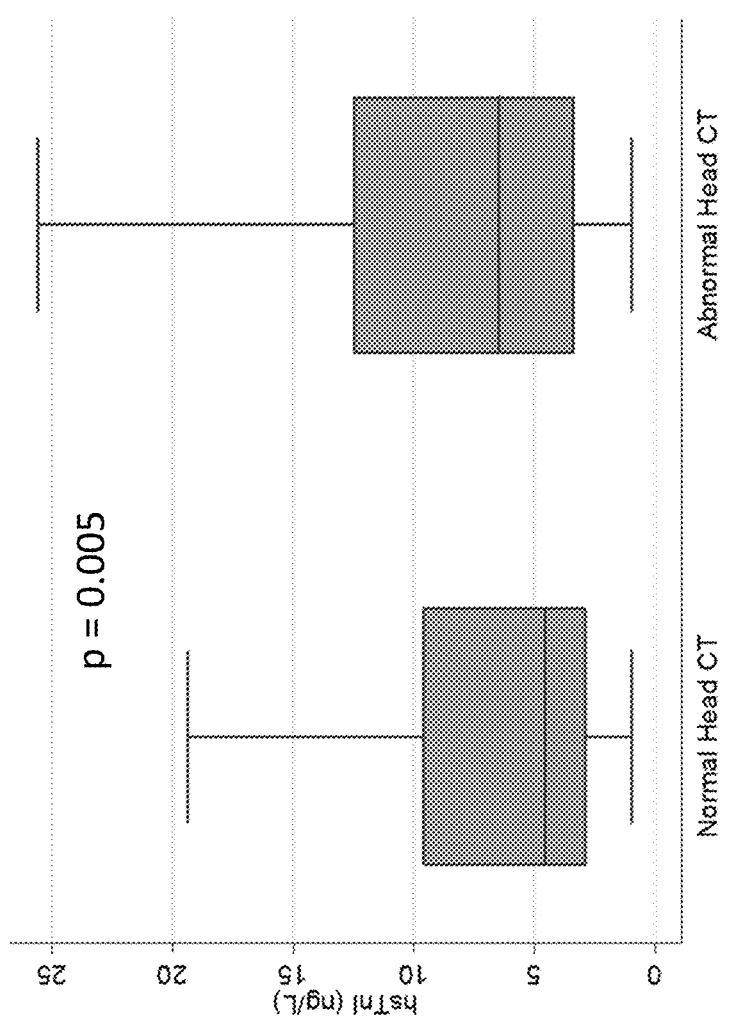
FIG. 17 shows the distribution of hsTnI levels in TBI patients having abnormal head CT and normal head CT scan (p=0.005).
Figure 18:
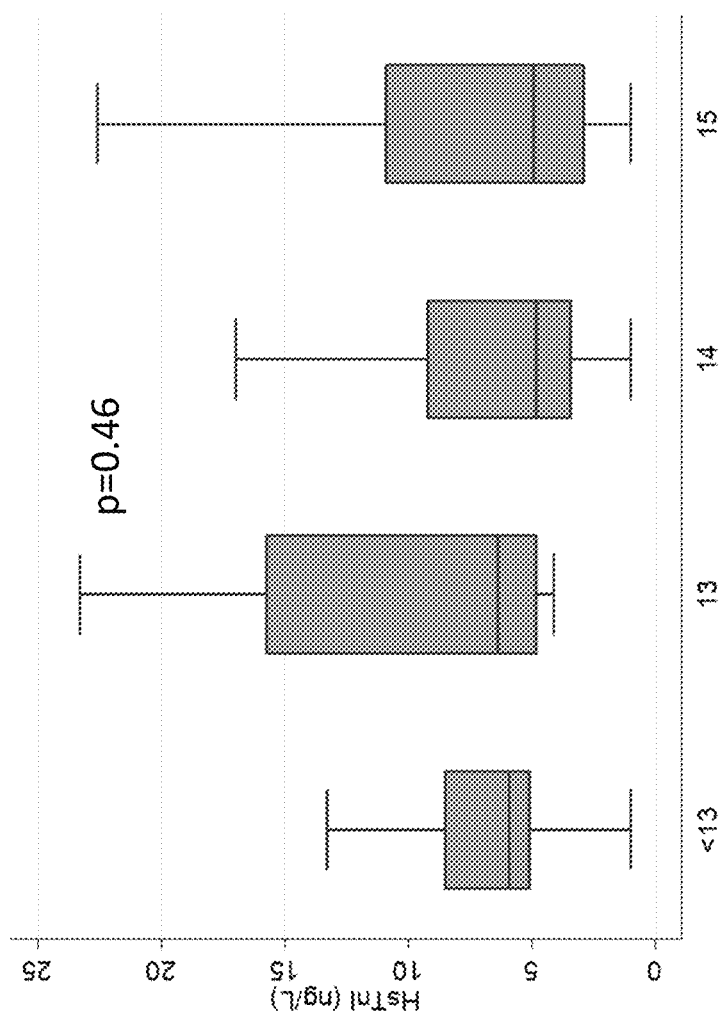
FIG. 18 shows the distribution of hsTnI levels in TBI patients with GCS scores of <13, 13, 14, or 15 (p=0.46).

FIG. 16 shows box plots of hsTnI levels in TBI patients (n=500) and Trauma control patients (n=94) (p=0.0001). Initial hsTnI values on the day of injury are higher in TBI patients than in controls FIG. 17 shows box plots of hsTnI levels in TBI patients with abnormal head CT (n=98) versus normal head CT scan (n=402) (p=0.005). Initial HsTnI values on the day of injury were higher in participants with abnormal head CTs than in those with normal head CT FIG. 18 shows box plots of hsTnI levels in TBI patients with GCS scores of <13 (n=9), 13 (n=8), 14 (n=54), or 15 (n=429) (p=0.46). There was no statistically significant difference in initial hsTnI values on the day of injury, according to GCS level.

Figure 19:
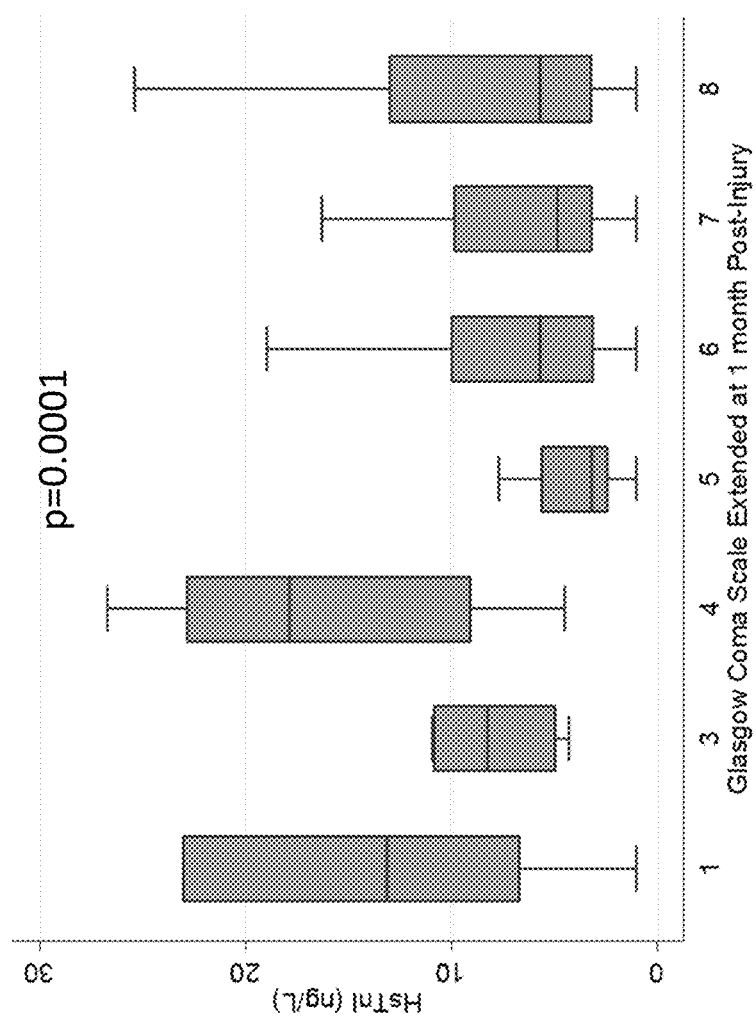
FIG. 19 shows the distribution of hsTnI levels in TBI patients having GOSE scores of 1, 3, 4, 5, 6, 7, or 8 at 1 month post-injury (p=0.0001).

FIG. 19 shows box plots of hsTnI levels in TBI patients having GOSE scores at 1 month post-injury of 1 (n=6), 3 (n=4), 4 (n=8), 5 (n=46), 6 (n=67), 7 (n=100), or 8 (n=149) (p=0.001). Patients with severe disability or worse at 1 month i.e. GOSE of less than 5, had higher initial hsTnI on the day of injury, than those with better functional outcome (i.e. GOSE of 5 or greater)

Figure 20:
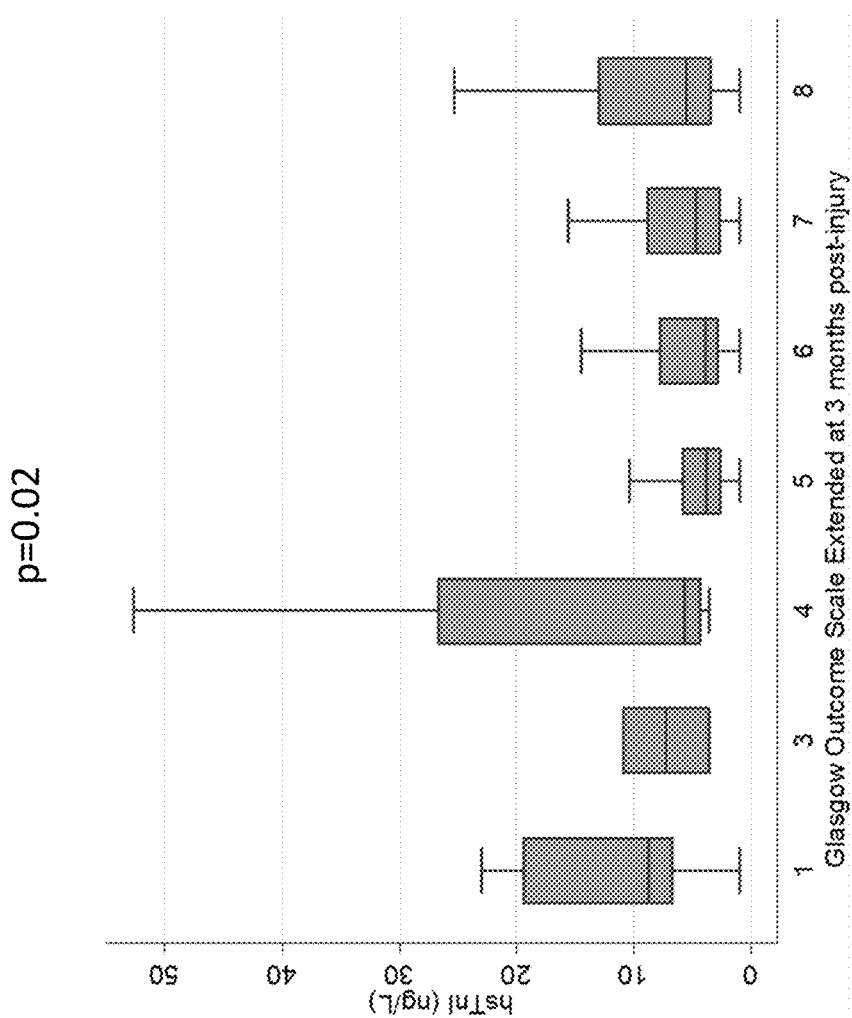
FIG. 20 shows the distribution of hsTnI levels in TBI patients having GOSE scores of 1, 2, 3, 4, 5, 6, 7, or 8 at 3 months post-injury (p=0.02).

FIG. 20 shows box plot of hsTnI levels in TBI patients having GOSE scores at 3 months post-injury of 1 (n=9), 3 (n=2), 4 (n=7), 5 (n=22), 6 (n=45), 7 (n=109), or 8 (n=154) (p=0.02). Initial hsTnI values on the day of injury were higher among subjects with severe disability or worse at 3 months i.e. GOSE of less than 5, had a higher initial hsTnI on the day of injury, than those with better functional outcome (i.e. GOSE of 5 or greater)

Figure 21:
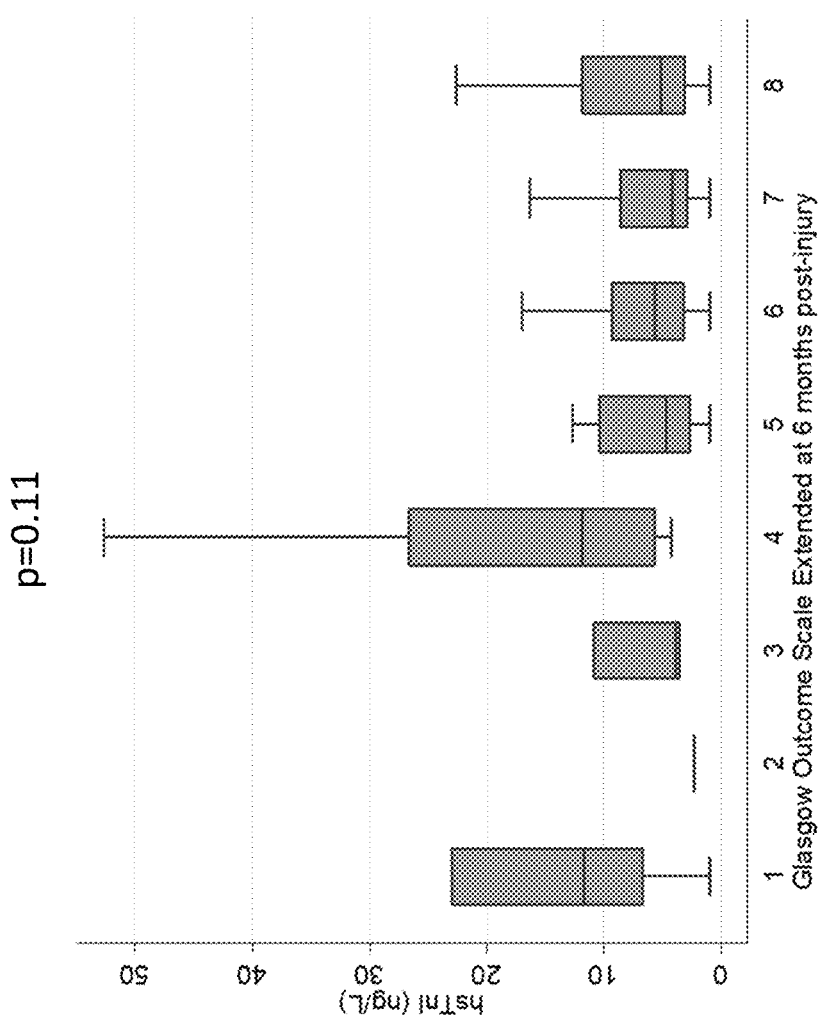
FIG. 21 shows the distribution of hsTnI levels in TBI patients having GOSE scores of 1, 3, 4, 5, 6, 7, or 8 at 6 months post-injury (p=0.11).

FIG. 21 shows box plot of hsTnI levels in TBI patients having GOSE scores at 6 months post-injury of 1 (n=10), 2 (n=1), 3 (n=3), 4 (n=5), 5 (n=17), 6 (n=41), 7 (n=102), or 8 (n=158) (p=0.11). There was a trend towards higher initial hsTnI on the day of injury in subjects with severe disability or worse at 3 months i.e. GOSE of less than 5, than those with better functional outcome (i.e. GOSE of 5 or greater).

Due to the smaller sample size at this time point, the difference approximated by did not reach statistical significance.

Figure 22:
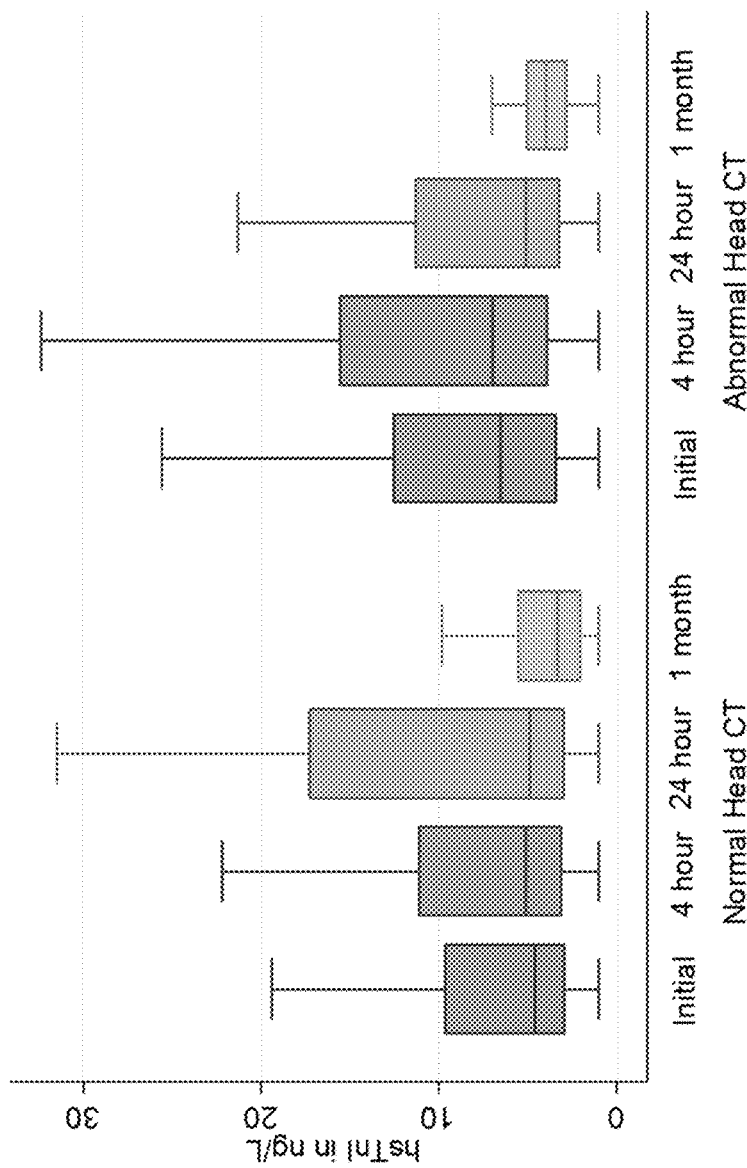
FIG. 22 shows the distribution of hsTnI levels in samples taken at 0 hours, 4 hours, 24 hours, and 1 month after injury from TBI patients having abnormal head CT scan and normal head CT scan.

FIG. 22 shows box plot of hsTnI levels in samples taken at 0 hours (n=98 for abnormal; n=402 for normal), 4 hours (n=88 for abnormal; n=250 for normal), 24 hours (n=51 for abnormal; n=83 for normal), or 1 month (n=14 for abnormal; n=59 for normal) after injury from TBI patients having abnormal head CT scan and normal head CT scan. In both groups (those with abnormal head CT cans and those with normal head CT scans), troponin values were elevated during the first 24 hours after injury and returned to lower values at 1 month post-injury.

Figure 23:
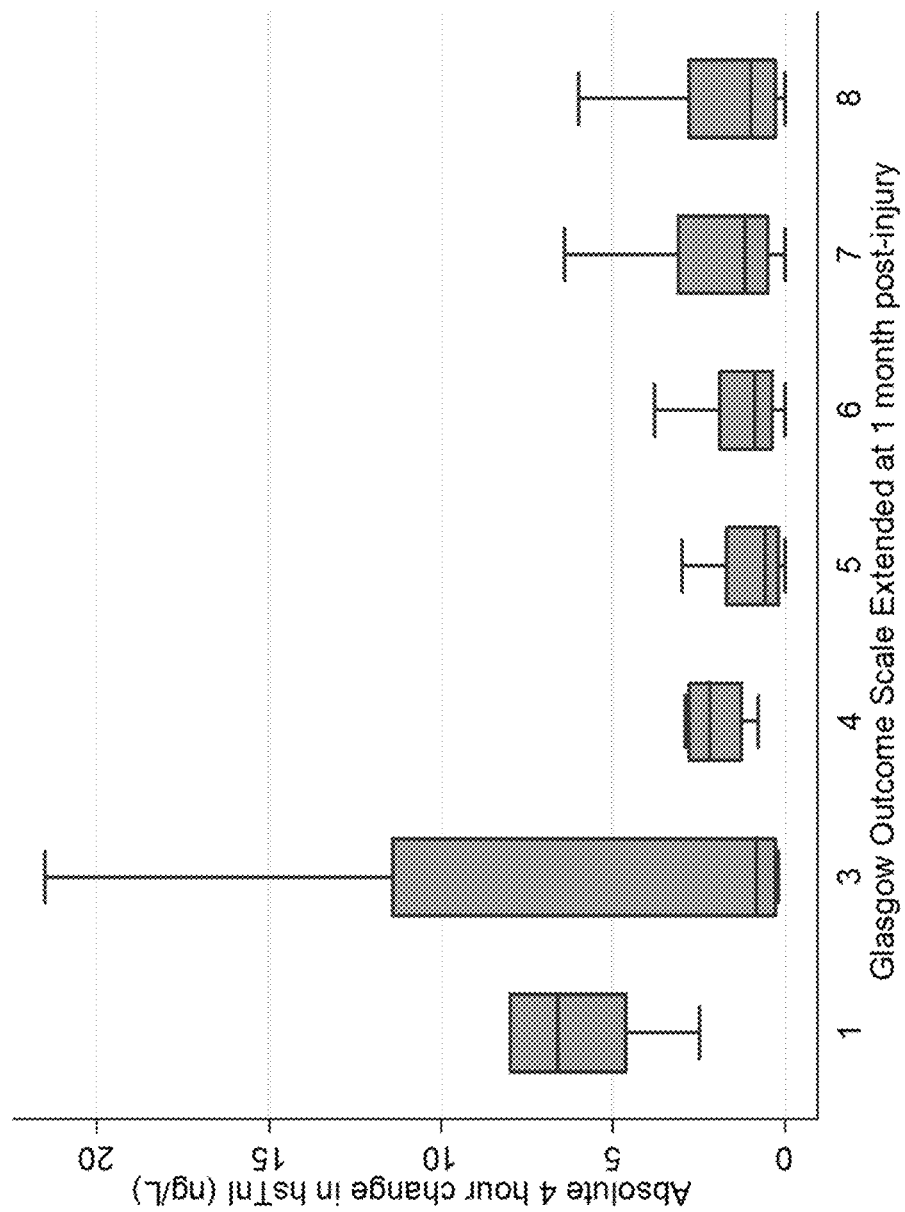
FIG. 23 shows the distribution of the 4 hour absolute change in hsTnI levels in TBI patients having GOSE scores at 1 month post-injury of 1, 3, 4, 5, 6, 7, or 8.

FIG. 23 shows box plot of the 4 hour absolute change in hsTnI levels in TBI patients having GOSE scores at 1 month post-injury of 1 (n=5), 3 (n=4), 4 (n=8), 5 (n=31), 6 (n=45), 7 (n=71), or 8 (n=99) (p=0.004). Subjects with severe disability or worse at 1 month post-injury (i.e. GOSE less than 5) had higher 4 hour absolute changes in hsTnI levels than those with better functional outcome (i.e. GOSE of 5 or greater).

Figure 24:
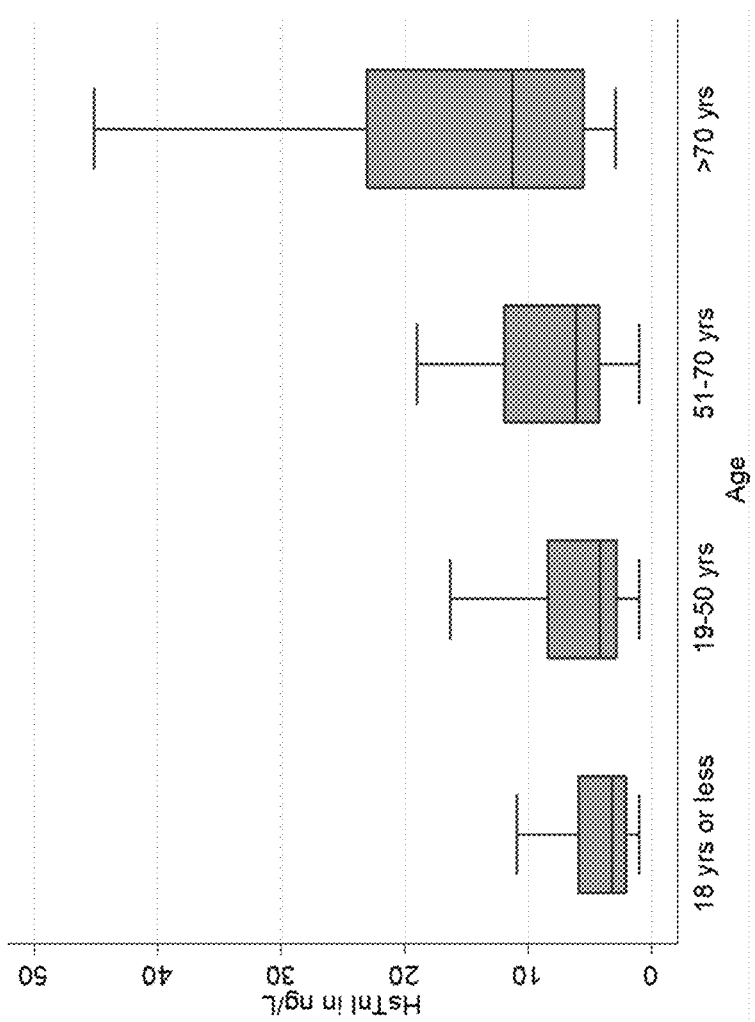
FIG. 24 shows the distribution of hsTnI levels in TBI patients based on age: 18 years or less, 19 to 50 years, 51 to 70 years, and greater than 70 years.

FIG. 24 shows box plot of hsTnI levels in TBI patients based on age: 18 to 30 years, 30 to 50 years, 50 to 70 years, and >70 years (p=0.0001). Older subjects had higher hsTnI values than younger subjects.

Example 7

Association of Myocardial Injury in TBI Patients and Poor Outcome

The objective of this study was to determine the association between TBI and serum high sensitivity troponin I (hsTnI) levels; identify independent risk factors for elevated hsTnI levels in TBI patients; and determine the association between hsTnI levels and functional outcome post-TBI.

Analysis of the enrolled subjects, as described in Example 5, was performed. Emergency department (ED) patients who were 18 years or older and were evaluated for either TBI or extra-cranial traumatic injury (Trauma Controls) were prospectively enrolled. Participants were eligible for the TBI arm if they had blunt traumatic head injury, received a head CT scan as part of their ED evaluation, and met the American College of Emergency Physicians' (ACEP) criteria for evaluation of TBI with a head CT scan. Participants in the trauma control arm were deemed eligible if they were evaluated for a traumatic injury but did not sustain head injury per self-report. Participants were excluded from both the TBI and trauma control arms if they met any of the following criteria: could not communicate in English, had no working telephone number, were pregnant, or had a past medical history of intracranial surgery, intracranial hemorrhage, brain tumor or severe dementia. Patients transferred from other hospitals were eligible for enrollment if they met study inclusion criteria and were enrolled within 24 hours of injury.

Predictor Variables: Data on patient demographics (age, gender, race, marital and employment status), injury mechanism, and alcohol and recreational drug use within 24 hours of injury were obtained directly from participants by trained research coordinators who used structured data collection tools recommended as part of the National Institute of Neurological Disorders and Stroke (NINDS) Common Data Elements for TBI studies (Wilde et al. *Arch Phys Med Rehabil.* (2010) 91(11):1650-1660). Data were entered directly into REDCap, an online electronic data entry and storage tool. Data on cardiovascular disease risk factors, which included hypertension, high cholesterol, diabetes, coronary revascularization, congestive heart failure, estimated glomerular filtration rate (GFR) on the day of injury, blood pressure, and heart rate at emergency department presentation, were obtained by a structured review of participant electronic medical records. Renal function was based on GFR and was categorized as normal, moderately reduced kidney function, and severely reduced kidney function (>=60, 30-59, and <30 per mL/min/1.73 m, respectively) (Zhang et al. *J Stroke Cerebrovasc Dis.* (2015) 24(10): 2375-2384). Abbreviated Injury Scale (AIS) for the different body regions were coded by Digital Innovation Inc. using their proprietary Tri-Code software. AIS is a consensus derived, injury severity scoring system that classifies injuries by six body regions: (1) (Head/Neck/Cervical Spine; (2) Face (excluding frontal bone or skull); (3) Chest/Thoracic Spine; (4) Abdominal/Lumbar Spine/Pelvic Contents; (5) Extremities/Pelvic Girdle; and (6) Superficial/External including Burns/Corrosions/Frostbite according to their relative severity on a 6 point scale (1=minor and 6=unsurvivable) (Civil et al. *J Trauma.* (1988) 28(1): 87-90). Since relatively few injuries were classified as serious, severe, critical or unsurvivable (AIS 3-6), all injuries with these classifications were reclassified as serious/more severe (AIS≥3). Patients without injury to a given body region were assigned a value of 1. AIS determination was performed similarly for the TBI and trauma control groups.

Troponin measurements. 500 TBI and 94 trauma control participants were studied. HsTnI was measured in serum samples obtained at enrollment (initial blood draw) and at 4 hours after the initial blood draw in the TBI group and only at enrollment in the trauma control group. The initial blood sample was obtained within 24 hours of injury and was aliquoted and stored in a −80 degree Celsius freezer within 2 hours of collection. HsTnI was measured by the clinical chemistry lab at Johns Hopkins Hospital using the Abbott Architect STAT hsTnI assay. The limit of detection (LOD) of the assay was 2 ng/L. The gender-specific upper reference limit (URL) was 16 ng/L for females and 34 ng/L for males. The lowest hsTnI concentration with a co-efficient of variation (CV) of 10% was 6 ng/L. The relative change in hsTnI at 4 hours in the TBI group was categorized as: unchanged (between −20% and +20% difference in hsTnI levels between initial blood draw and 4 hours after initial blood draw), decreasing (<−20% difference in hsTnI levels between initial blood draw and 4 hours after initial blood draw) or increasing (>+20% difference in hsTnI levels between initial blood draw and 4 hours after initial blood draw). Elevated hsTnI was defined as hsTnI greater than the 99th % gender-neutral URL. Subjects with undetectable hsTnI were assigned a value of 1 ng/L, which was the mid-point between 0 and the LOD.

Outcome Variables. Head CT images were re-read by one board certified neuroradiologist. The presence/absence of traumatic lesions, including the size and location of these lesions were classified according to the NINDS common data elements for radiologic imaging of TBI (Duhaime et al. *Arch Phys Med Rehabil.* (2010) 91(11):1661-1666). Functional outcome was ascertained using the Extended Glasgow Outcome Scale (GOSE), which categorizes functional outcome on a scale of 1 (Dead) to 8 (upper good recovery). Severe disability/worse outcome was defined as GOSE<5 at 6 months post-injury.

Statistical Analysis. Linear regression models were used to determine the differences in initial troponin levels between the TBI and trauma control participants and to identify independent predictors of hsTnI. These models were adjusted for age and baseline head injury severity which were both associated with study group and hsTnI. To identify predictors of hsTnI, unadjusted and adjusted models were fit, the latter adjusting for known predictors of hsTnI that had statistically significant univariate associations (p<0.05). These included: age, gender, race, hypertension, high cholesterol, diabetes, coronary revascularization, congestive heart failure, renal function, blood pressure, and heart rate. The models were also adjusted for injury severity as measured by abbreviated injury severity scores (AIS). To improve approximations to normality, hsTnI levels were log-transformed prior to inclusion in the models. Hence all linear regression parameters were interpreted as multiplicative on the exponential scale, and were reported as such. Unadjusted and adjusted logistic regression models were also constructed to evaluate the associations between initial hsTnI and the relative 4 hour change in hsTnI and functional recovery at 6 months. These models were adjusted for age and head/neck/c-spine injury severity, both of which were associated with functional outcome post-TBI.

There was considerable missing data in the follow-up: 338 (68%) TBI participants had troponin measured at both time points and 337 (67%) had functional outcome measured at 6 months. To consider the impact of missing data on the analysis, non-response weights equal to the reciprocal of the predicted probability of response at a given time point were constructed from a logistic regression of response on baseline troponin, age, gender, race, marital status, employment status, and presence of an abnormal CT scan, and weighted generalized estimating equation (GEE) analyses was conducted.

Statistical significance was defined at the $\alpha=0.05$ level. Statistical analyses were conducting using SAS V 9.4 (SAS Institute, Cary, N C, 2015).

Figure 25:
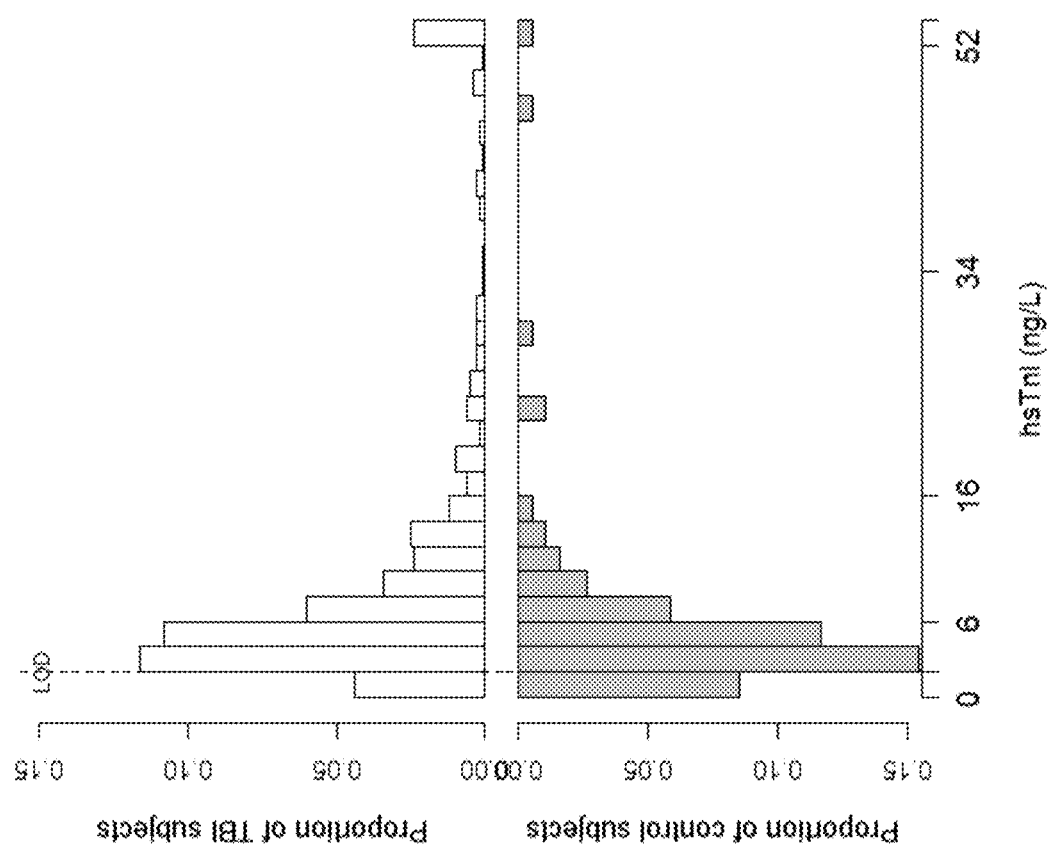
FIG. 25 shows a distribution of hsTnI values in TBI and trauma control participants. TBI participants had higher hsTnI values than trauma control participants.

Results: Serum samples from 500 TBI and 94 trauma control participants were assayed for hsTnI. The distribution of demographic characteristics and cardiovascular risk factors between TBI and trauma control participants were similar with the exception of the TBI group being older (Table 21). TBI participants were more likely to have head and face injuries whereas trauma controls were more likely to have extremity, pelvic girdle and superficial/external injuries. Among TBI participants, 98 (19.6%) had a traumatic intracranial abnormality on head CT scan, and 339 (68%) completed follow-up assessment at 6 months post-injury. However, the 6-month outcome data for two subjects could not be used because one had a stroke between 1 and 3 months and the other had repeat TBI between 3 and 6 months. Among TBI participants with reliable follow-up data, 19 (5.6%) had severe disability or worse.

hsTnI values in study population. The median time between injury and initial blood sampling was 4.4 hours (Interquartile range [IQR] 3.13-7.11) hours. Among TBI participants, 44 (8.8%) had undetectable hsTnI, whereas among trauma controls, 16 (17.0%) had undetectable hsTnI. hsTnI values were higher within the TBI group than in trauma controls (median hsTnI: 5 [Interquartile range (IQR): 3-11] ng/L versus 4 [IQR: 2-6] ng/L respectively), see FIG. 25. A hsTnI level cut-off of 5.7 ng/L at initial blood draw predicted a poor outcome (GOSE<5) at 1 month with a sensitivity of 83.3% and a specificity of 54.9%. A hsTnI level cut-off of 5.6 ng/L at 4 hours blood draw predicted a poor outcome (GOSE<5) at 1 month with a sensitivity of 100% and a specificity of 49.2%. A difference in hsTnI levels between initial blood draw and 4 hours blood draw of 5.6 ng/L predicted a poor outcome (GOSE<5) at 1 month with a sensitivity of 82.4% and a specificity of 69.5%.

Using the gender-specific cutoff for the URL, 52 (10.4%) participants in the TBI group and 3 (3.2%) trauma controls had initial hsTnI values greater than the 99th percentile (p=0.027). Initial hsTnI values remained higher in the TBI group after adjusting for age and head injury severity (regression co-efficient 1.66 [95% Confidence Interval (CI): 1.29-2.12], p<0.001).

Unadjusted predictors of higher initial hsTnI levels within the TBI group included: older age, white race, history of hypertension, coronary revascularization, congestive heart failure, diabetes, high cholesterol, renal dysfunction, elevated mean arterial pressure at ED presentation, serious/more severe head/neck/c-spine injury, and serious/more severe chest/t-spine injury. After adjusting for gender for confounders, independent predictors of higher initial hsTnI levels were: older age, male gender, history of congestive heart failure, history high cholesterol, elevated mean arterial pressure, renal dysfunction, and serious/more severe chest/T-spine injury (Table 22).

Figure 26:
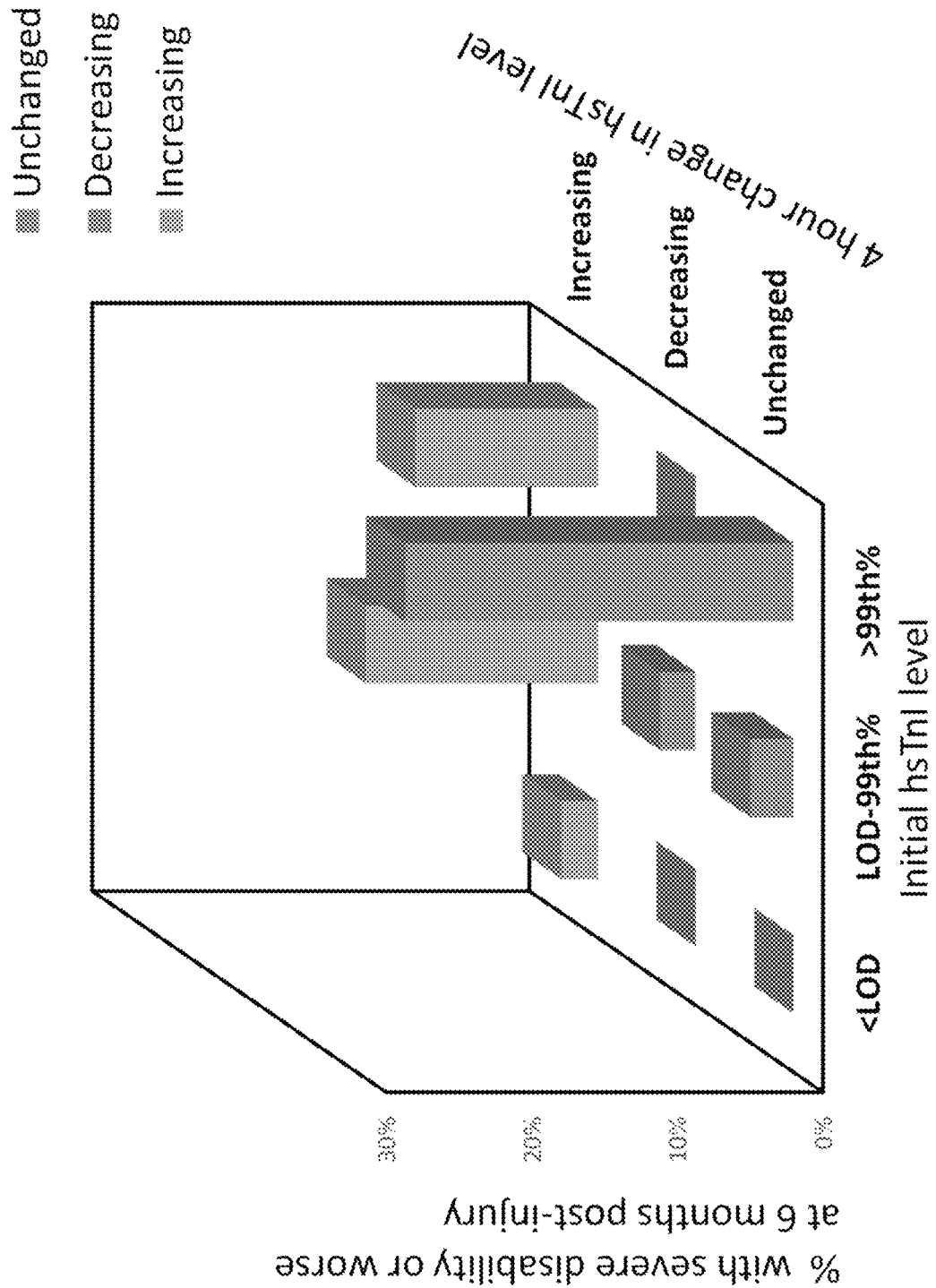
FIG. 26 shows a graphical display of the association between cardiac troponin I values and TBI outcome.

Among those with a 4 hour sample, 193 (57.1%), 62 (18.3%) and 83 (24.6%) had unchanged, decreasing and increasing hsTnI values, respectively. Initial hsTnI was associated with severe disability/worse outcome at 6 months post-injury (odds ratio: 1.44 [95% CI: 1.02-2.02]). This association was no longer significant after adjusting for age and baseline head injury severity (odds ratio: 1.04 (95% CI: 0.65-1.68)). Participants with increasing hsTnI at 4 hours had 4.52 (95% CI: 1.56-13.11) times higher odds of having severe disability or worse at 6 months post-injury than those with either unchanged or decreasing hsTnI, see FIG. 26. This association remained significant after adjusting for age and baseline head injury severity (odds ratio: 5.32 [95% CI: 1.60-17.68]).

Imputation of Missing Data. As a sensitivity analysis and alternative to the non-response weights, multiple imputation (MI) was used to impute the missing data in the hsTnI change variable and GOSE at 6 months-post injury. MI uses a model to impute the missing data multiple times, using Rubin's combining rules (Schafer (1997) Analysis of incomplete multivariate data. Boca Raton: Chapman & Hall) to obtain inference about a parameter of interest (here the regression coefficient associated with hsTnI changed over four hours on severe disability at 6 months). The point estimate was the mean of the imputed values and the variance estimate was a linear combination of the mean variance estimate using the fully imputed data and the between-imputation variance of the point estimate in each fully imputed dataset. To simultaneously impute both variables, a sequential regression procedure (Raghunathan et al., *Survey Methodology* (2001) 27: 85-95; Van Buuren (2007) *Statistical Methods in Medical Research.* 16: 219-242) was employed in which the hsTnI change variable was imputed based on the latest imputation of GOSE at 6 months-post injury, and then the GOSE at 6 months-post injury was imputed based on this imputation of the hsTnI change variable. Both imputations used multinomial logistic regression, and also conditioned on age, gender, cholesterol level, hypertension, diabetes, and presence of stent/CABG, baseline (log)hsTnI, and baseline injury status. This result was broadly consistent with the finding using non-response weights, with participants with increasing hsTnI at 4 hours having 4.31 (95% CI: 1.55-11.93) times higher odds of having severe disability or worse at 6 months post-injury than those with either unchanged or decreasing hsTnI, and 5.00 (95% CI: 1.36-18.42) times higher odds of having severe disability or worse at 6 months post-injury after adjusting for age and baseline head injury severity. The imputation of missing data did not result in a change in the overall conclusions.

TABLE 21

Demographic and clinical characteristics of study population

| | TBI n = 500 | Trauma Control n = 94 | p-value |
|---|---|---|---|
| Median age in years (IQR) | 44 (28-63) | 36 (26-56) | 0.02 |
| Female (%) | 201 (40.2) | 39 (41.5) | 0.82 |
| Race (%) | | | 0.58 |
| White | 266 (53.2) | 52 (55.9) | |
| Black | 198 (39.6) | 37 (39.8) | |
| Other | 36 (7.2) | 4 (4.3) | |
| Alcohol within 24 hours of enrollment | 147 (29.4) | 22 (23.4) | 0.24 |
| Recreational drug within 24 hours | 62 (12.4) | 7 (7.5) | 0.28 |
| Hypertension | 178 (35.6) | 27 (28.7) | 0.20 |
| Coronary revascularization | 38 (7.6) | 2 (2.1) | 0.05 |
| Congestive heart failure | 22 (4.4) | 1 (1.1) | 0.12 |
| Diabetes | 65 (13.0) | 8 (8.5) | 0.22 |
| High cholesterol | 90 (18.0) | 21 (22.3) | 0.32 |
| Mean arterial pressure in mmHg (IQR) | 102 (93-114) | 99 (99-110) | 0.03 |
| Glomerular filtration rate (mL/min/1.73 m$^2$) | | | 0.21 |
| ≥60 | 399 (87.5) | 35 (81.4) | |
| 30-59 | 51 (11.2) | 6 (14.0) | |
| <30 | 6 (1.3) | 2 (4.7) | |
| Mechanism | | | <0.01 |
| Fall | 176 (35.2) | 31 (33.0) | |
| MVC | 122 (24.4) | 0 (0.0) | |
| Pedestrian Struck | 49 (9.8) | 1 (1.1) | |
| Assault | 87 (17.4) | 0 (0.0) | |
| Cycle | 39 (7.8) | 0 (0.0) | |
| Struck by/against | 23 (4.6) | 1 (1.1) | |
| Other | 5 (0.8) | 55 (58.5) | |
| AIS Severity: Head/Neck/C-Spine | | | <0.01 |
| 1 | 393 (78.6) | 94 (100) | |
| 2 | 17 (3.4) | 0 (0.0) | |
| 3 or greater | 90 (18.0) | 0 (.0) | |
| AIS Severity: Face | | | <0.01 |
| 1 | 452 (90.4) | 94 (100.0) | |
| 2 | 48 (9.6) | 0 (0.0) | |
| 3 or greater | 0 (0.0) | 0 (0.0) | |
| AIS Severity: Chest/T-spine | | | 0.19 |
| 1 | 469 (93.8) | 91 (96.8) | |
| 2 | 14 (2.8) | 3 (3.2) | |
| 3 or greater | 17 (3.4) | 0 (0.0) | |
| AIS Severity: Abdomen/Pelvis/L-spine | | | 0.15 |
| 1 | 489 (97.8) | 94 (0.0) | |
| 2 | 11 (2.2) | 0 (0.0) | |
| 3 or greater | 0 (0.0) | 0 (0.0) | |
| AIS Severity: Extremities and Pelvic girdle | | | <0.01 |
| 0 | 467 (93.4) | 44 (46.8) | |
| 1 | | | |
| 2 | 28 (5.6) | 43 (45.7) | |
| 3 or greater | 5 (1.0) | 7 (7.5) | |
| AIS Severity: Superficial and external | | | <0.01 |
| 1 | 467 (93.4) | 44 (46.8) | |
| 2 | 28 (5.6) | 43 (45.7) | |
| 3 or greater | 5 (1.0) | 17 3.4) | |

TABLE 22

Determinants of initial high sensitivity troponin I levels

| | Univariable models | | Multivariable models* | |
|---|---|---|---|---|
| Characteristic | Regression coefficient (95% confidence interval) | P-value | Regression coefficient (95% confidence interval) | P-value |
| Age per decile | 1.27 (1.21-1.33) | <0.001 | 1.12 (1.04-1.20) | 0.002 |
| Female (%) | 0.90 (0.73-1.11) | 0.31 | | |
| Race (%) | | | | |
| White | 1.00 (Reference) | | | |
| Black | 0.73 (0.59-0.91) | <0.001 | 1.07 (0.86-1.32) | 0.55 |
| Other | 0.47 (0.31-0.7) | <0.001 | 0.71 (0.48-1.04) | 0.08 |
| Married (%) | 1.14 (0.91-1.43) | 0.25 | | |
| Employed (%) | 1.40 (1.14-1.71) | <0.001 | | |
| Alcohol within 24 hours | 0.82 (0.65-1.02) | 0.08 | | |
| Recreational drug within 24 hours | 1.00 (0.98-1.01) | 0.79 | | |
| Hypertension | 1.97 (1.61-2.43) | <0.001 | 0.87 (0.71-1.08) | 0.21 |
| Coronary revascularization | 3.26 (2.24-4.73) | <0.001 | 0.99 (0.76-1.29) | 0.94 |
| Congestive heart failure | 3.77 (2.32-6.13) | <0.001 | 1.21 (0.79-1.87) | 0.38 |
| Diabetes | 1.95 (1.45-2.63) | <0.001 | 1.75 (1.05-2.92) | 0.03 |
| High cholesterol | 2.61 (2.02-3.36) | <0.001 | 1.03 (0.75-1.41) | 0.87 |
| Mean arterial pressure per 10 mmHg | 1.16 (1.10-1.24) | <0.001 | 1.57 (1.14-2.16) | <0.001 |
| Heart rate per 10 beats per minute | 1.01 (0.96-1.07) | 0.67 | | |
| Glomerular filtration rate (mL/min/1.73 m$^2$) | | | | |
| ≥60 | 1.00 (Reference) | | | |
| 30-59 | 2.75 (2.03-3.71) | <0.001 | 1.51 (1.07-2.13) | 0.02 |
| <30 | 7.41 (3.45-15.9) | <0.001 | 5.51 (2.31-13.12) | <0.001 |
| Mechanism | | | | |
| Fall | 1.28 (0.87-1.87) | 0.21 | | |
| MVC | 1.91 (1.33-2.75) | <0.001 | | |
| Pedestrian Struck | 1.44 (0.96-2.16) | 0.08 | | |
| Assault | 1.04 (0.59-1.84) | 0.89 | | |
| Cycle | 0.96 (0.59-1.55) | 0.86 | | |
| Struck by/against | 1.38 (0.43-4.46) | 0.59 | | |
| Other | 1.28 (0.87-1.87) | 0.21 | | |
| AIS Severity: Head/Neck/C-Spine | | | | |
| 1 | 1.00 (Reference) | | | |
| 2 | 0.99 (0.56-1.74) | 0.96 | 0.98 (0.58-1.65) | 0.93 |
| 3 or greater | 1.33 (1.02-1.74) | 0.04 | 1.11 (0.87-1.42) | 0.40 |

TABLE 22-continued

Determinants of initial high sensitivity troponin I levels

| Characteristic | Univariable models | | Multivariable models* | |
|---|---|---|---|---|
| | Regression coefficient (95% confidence interval) | P-value | Regression coefficient (95% confidence interval) | P-value |
| AIS Severity: Face | | | | |
| 1 | 1.00 (Reference) | | | |
| 2 | 1.18 (0.83-1.66) | 0.36 | | |
| 3 or greater | NA | NA | | |
| AIS Severity: Chest/T-spine | | | | |
| 1 | 1.00 (Reference) | | | |
| 2 | 1.08 (0.58-2.01) | 0.81 | 1.02 (0.58-1.77) | 0.95 |
| 3 or greater | 1.98 (1.12-3.47) | 0.02 | 1.75 (1.04-2.96) | 0.04 |
| AIS Severity: Abdomen/Pelvis/L-spine | | | | |
| 1 | 1.00 (Reference) | | | |
| 2 | 1.51 (0.75-3.04) | 0.25 | | |
| 3 or greater | NA | NA | | |
| AIS Severity: Extremities and Pelvic girdle | | | | |
| 1 | 1.00 (Reference) | | | |
| 2 | 0.88 (0.56-1.37) | 0.56 | | |
| 3 or greater | 1.08 (0.38-3.03) | 0.88 | | |
| AIS Severity: Superficial and external | | | | |
| 1 | 1.00 (Reference) | | | |
| 2 | 0.75 (0.24-2.38) | 0.63 | | |
| 3 or greater | NA | NA | | |

Figure 27:
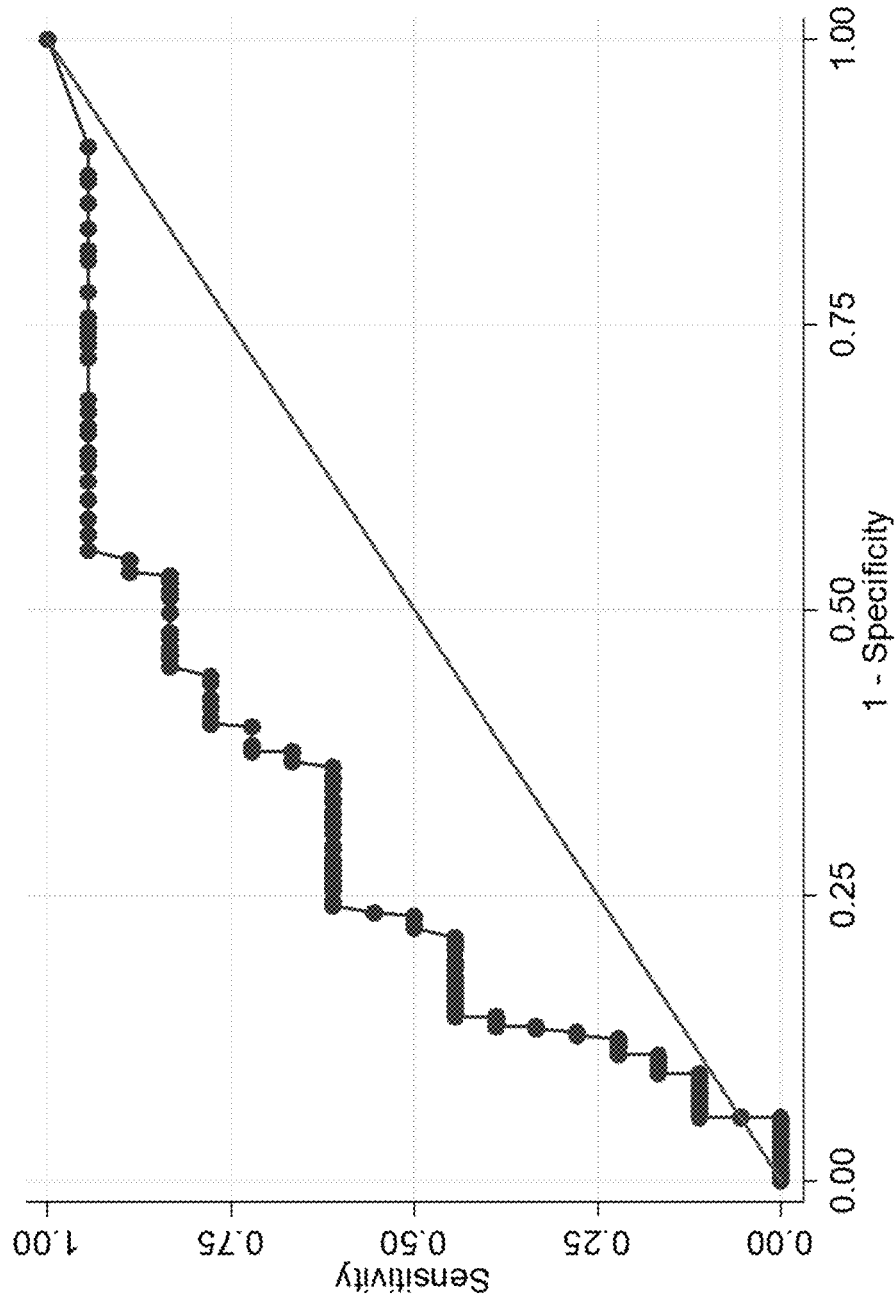
FIG. 27 shows Area Under the Receiver Operator Characteristics (AUROC) analysis for discriminating between subjects with 1 month GOSE<5 versus GOSE>5 using the initial hsTnI levels (AUROC curve=0.7135).
Figure 28:
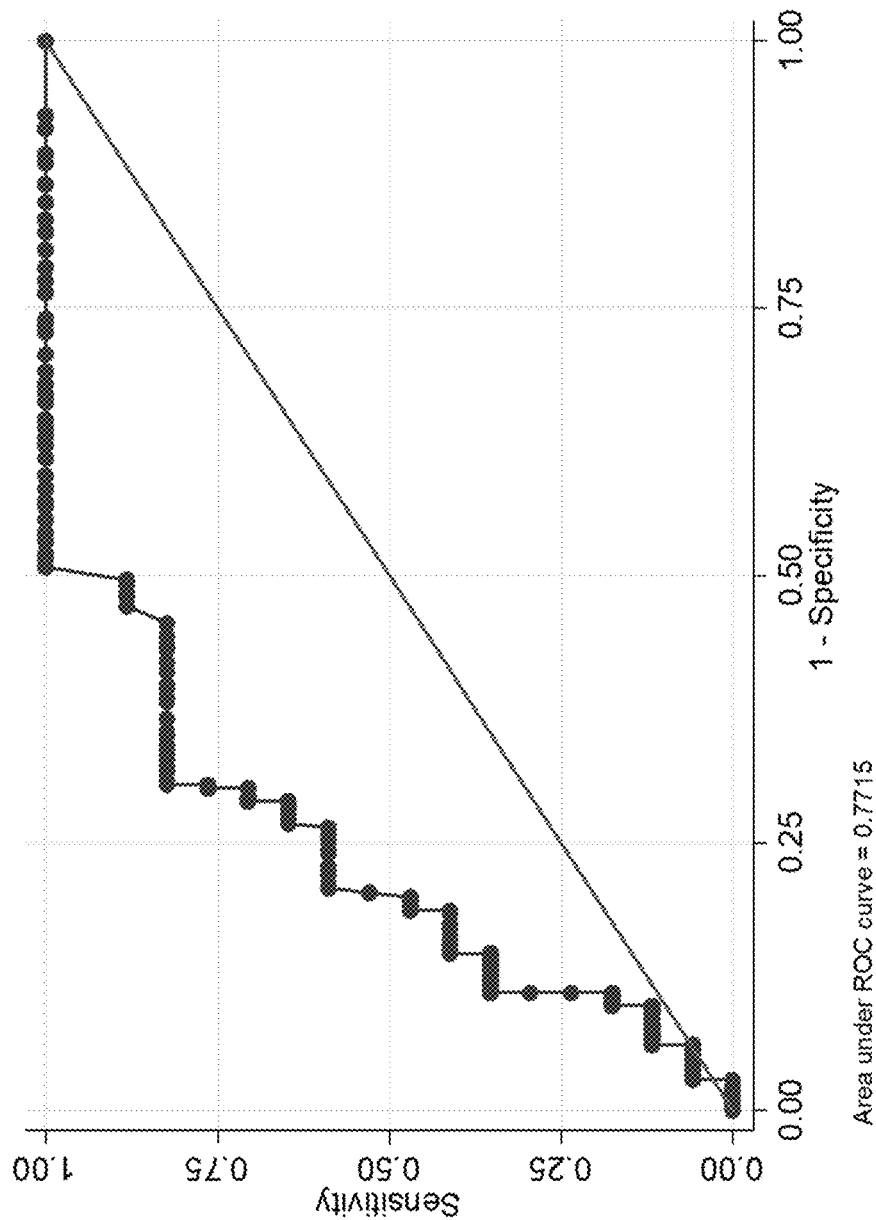
FIG. 28 shows AUROC analysis for discriminating between subjects with 1 month GOSE<5 versus GOSE>5 using the 4 hour hsTnI levels (AUROC curve=0.7715).
Figure 29:
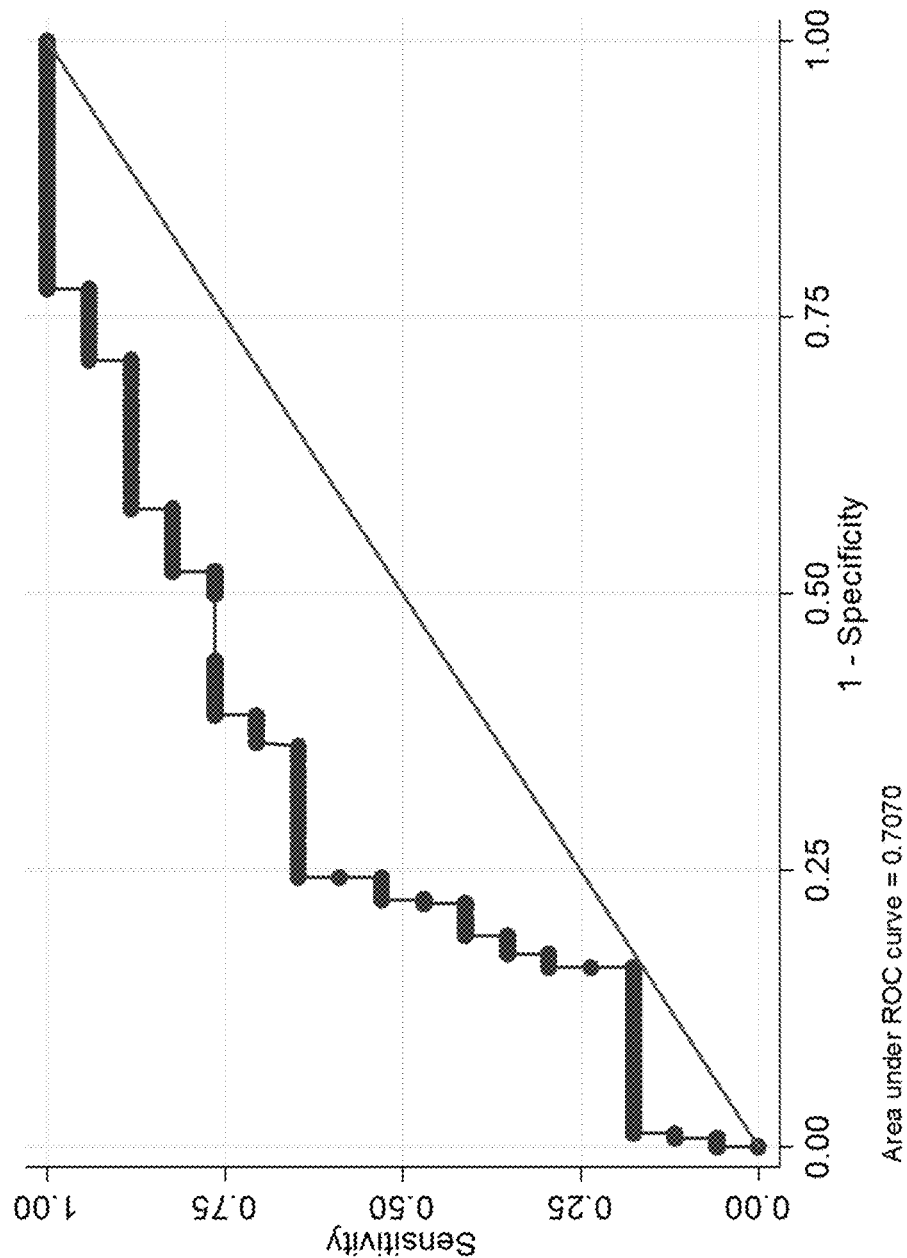
FIG. 29 shows AUROC analysis for discriminating between subjects with 1 month GOSE<5 versus GOSE>5 using the relative change between the initial and 4 hour hsTnI levels (AUROC curve=0.7070).
Figure 30:
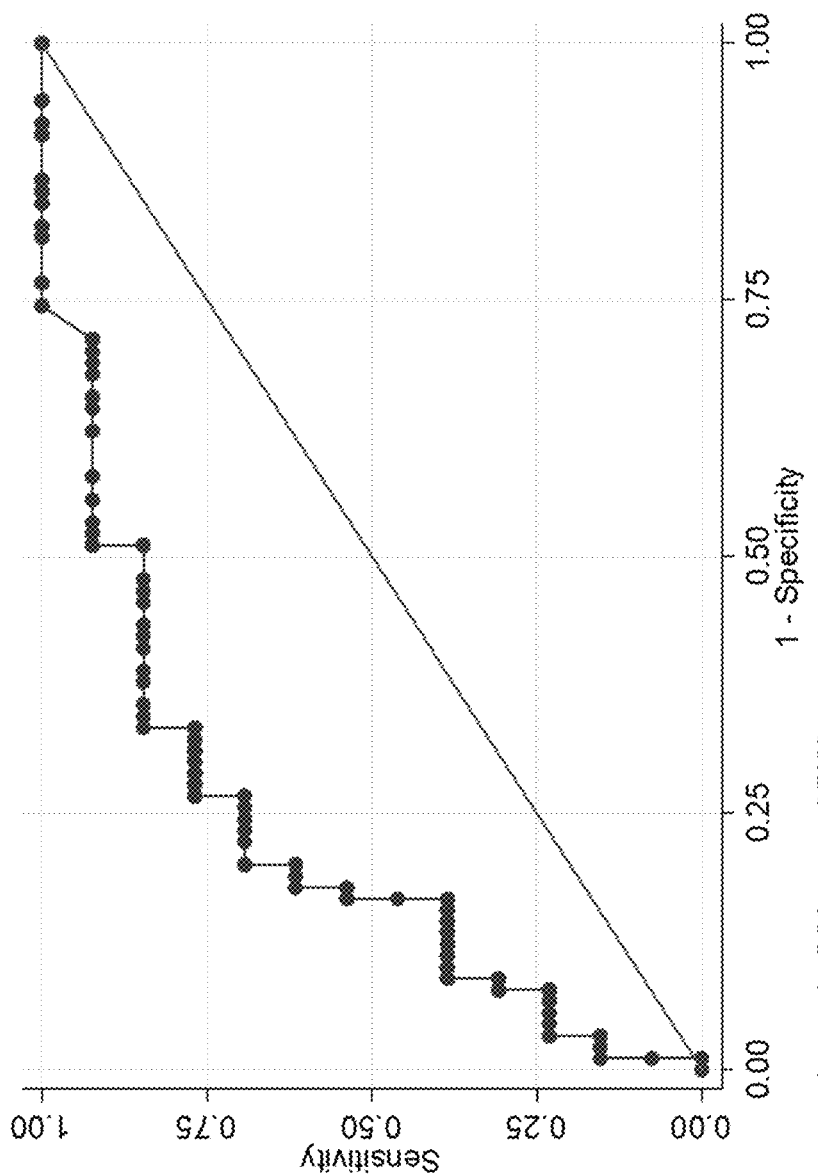
FIG. 30 shows AUROC analysis for discriminating between subjects with 1 month GOSE<5 versus GOSE>5 using the 24 hour hsTnI levels (AUROC curve=0.7868).

FIG. 27 shows AUC (0.7135) for the initial hsTnI. The initial hsTnI discriminates between subjects severe disability or worse at 1 month versus those with better functional outcome (GOSE>5) with an AUC of 0.71. FIG. 28 shows the area under the receiver operator curve for discriminating between subjects with GOSE<5 versus those with GOSE>5 at 1 month using the 4 hour troponin. The AUC=0.77. FIG. 29 shows AUC the area under the receiver operator curve for discriminating between subjects with 1 month GOSE<5 versus GOSE>5 using the relative change between the initial and 4 hour troponin. FIG. 30 shows the area under the receiver operator curve for discriminating between subjects with 1 month GOSE<5 versus GOSE>5 using the 24 hour hsTnI.

A logistic regression model was generated to incorporate age, hsTnI levels at the initial time point, and hsTnI levels at a time point 4 hours after the initial time point, as follows:

$$Pr(Y=1) = \frac{\exp(\beta_0 + \beta_1 \ln(\text{initial troponin}) + \beta_2 \ln(4 \text{ hour troponin}) + \beta_3 \text{ age})}{1 + \exp(\beta_0 + \beta_1 \ln(\text{initial troponin}) + \beta_2 \ln(4 \text{ hour troponin}) + \beta_3 \text{ age})}$$

Figure 31:
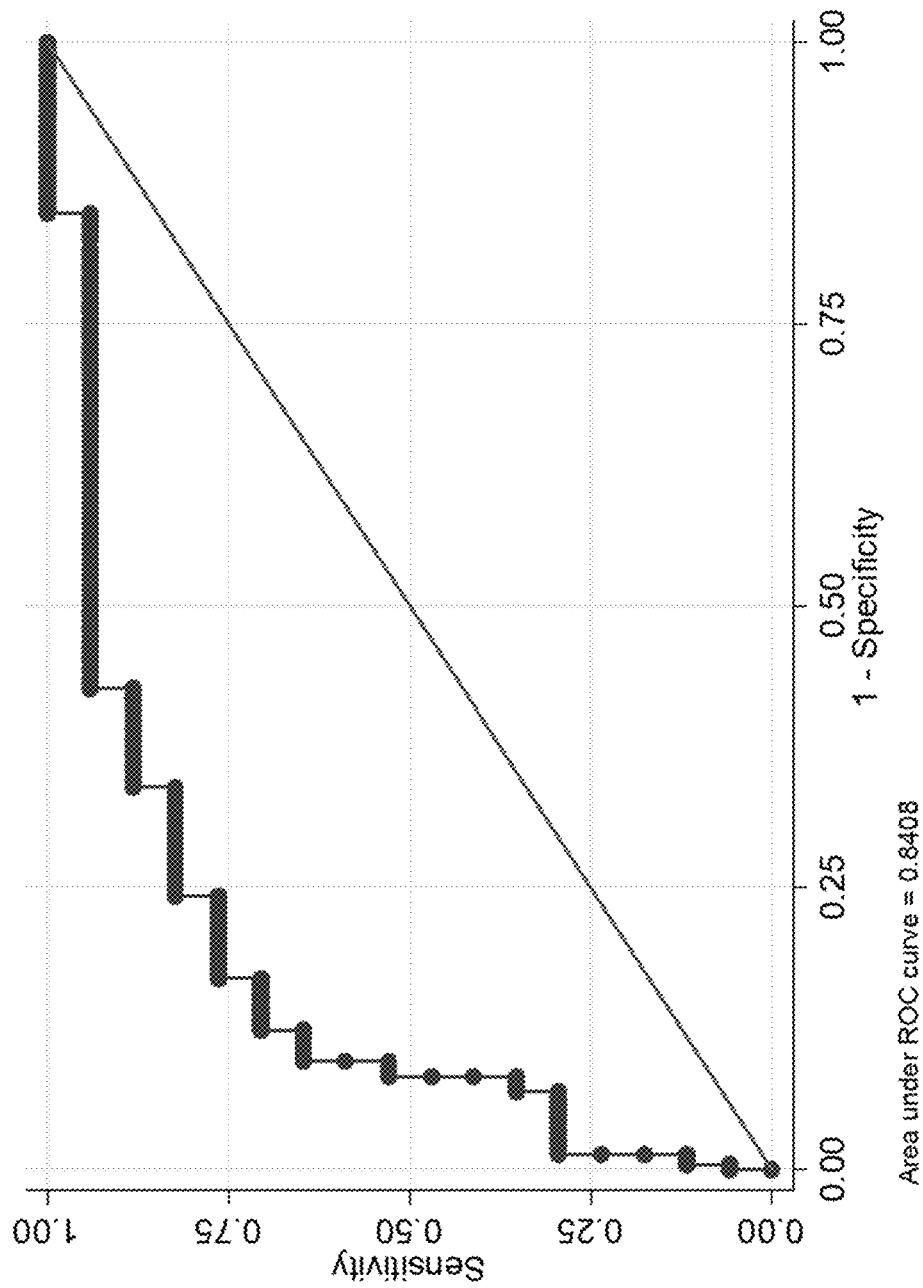
FIG. 31 shows AUROC analysis for predictive model that includes initial hsTnI levels, 4 hour hsTnI levels, and age (AUROC=0.8408).

The AUC of the model was 0.84 (see FIG. 31). Using this model, a cut-off value is a predicted probability of 0.036 and has a sensitivity of 94.1% and a specificity of 57.3% for identifying subjects with poor outcome (i.e., GOSE<5).

Myocardial injury occurred in TBI patients and it was independently associated with poor functional outcome. See FIGS. 19-21 and 27-31. Elevated hsTnI values were found in TBI patients compared to trauma controls. TBI subjects with increasing hsTnI were at risk for severe disability/worse outcome. HsTnI was detectable in the majority (91.2%) of patients evaluated for TBI and was elevated (>99th percentile) in 10.4% of them. Furthermore, hsTnI values were higher in TBI patients compared to those trauma controls. The present study provides additional corroborating evidence to support the occurrence of cardiac injury in TBI patients.

Participants with increasing hsTnI levels 4 hours after the initial sampling (on the day of injury) had a 5 times higher odds of having severe/worse disability at 6 months post-injury. Rising troponin levels upon repeat measurement beyond values consistent with analytical variation, were indicative of acute processes. Patients with acute myocardial injury, as signified by the increasing troponin values, may be at risk for poor functional outcome post-TBI.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

Clause 1. A method for aiding in the diagnosis and evaluation of mild traumatic brain injury in a human subject, the method comprising:
  a) performing an assay on a sample obtained from the subject within about 24 hours after a suspected injury to the head to measure or detect a level of cardiac troponin I (cTnI); and
  b) determining whether the subject has sustained a mild or a moderate to severe traumatic brain injury (TBI), wherein the subject is determined as having (1) a moderate, severe, or a moderate to severe traumatic brain injury when the level of cTnI in the sample is higher than a reference level of cTnI or (2) a mild traumatic brain injury when the level of cTnI in the sample is lower than a reference level of cTnI.

Clause 2. The method of clause 1, wherein the subject has received a Glasgow Coma Scale score before or after the assay is performed.

Clause 3. The method of clause 2, wherein the subject is suspected as having a moderate, severe, or a moderate to severe traumatic brain injury based on the Glasgow Coma Scale score.

Clause 4. The method of clause 3, wherein the reference level is correlated with subjects having a moderate, severe, or a moderate to severe traumatic brain injury.

Clause 5. The method of clause 4, wherein the reference level is correlated with a Glasgow Coma Scale score of 3-12.

Clause 6. The method of clause 2, wherein the subject is suspected as having mild traumatic brain injury based on the Glasgow Coma Scale score.

Clause 7. The method of clause 6, wherein the reference level is correlated with subjects having mild traumatic brain injury.

Clause 8. The method of clause 7, wherein the reference level is correlated with a Glasgow Coma Scale score of 13-15.

Clause 9. The method of any one of clauses 1 to 8, wherein the reference level for cTnI is about 1.94 pg/mL, about 2.54 pg/mL, about 21.23 pg/mL, or about 43.79 pg/mL.

Clause 10. The method of any one of clauses 1 to 9, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 1 pg/mL to about 50 pg/mL.

Clause 11. The method of any one of clauses 1 to 10, wherein the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the suspected injury to the head.

Clause 12. The method of any one of clauses 1 to 11, further comprising treating the subject assessed as having moderate to severe traumatic brain injury with a traumatic brain injury treatment.

Clause 13. The method of any one of clauses 1 to 12, further comprising monitoring the subject assessed as having mild traumatic brain injury.

Clause 14. A method of aiding in the determination of whether to perform a head computerized tomography (CT) scan on a human subject that has sustained or may have sustained an injury to the head, the method comprising:
  a) performing an assay on a sample obtained from the subject within about 24 hours after a suspected injury to the head to measure or detect a level of cTnI in the sample; and
  b) performing a CT scan on the subject when the level of cTnI in the sample is higher than a reference level of cTnI and not performing a CT scan on the subject when the level of cTnI in the sample is lower than a reference level of cTnI.

Clause 15. The method of clause 14, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the suspected injury to the head.

Clause 16. The method of clause 14 or 15, wherein the subject has received a CT scan before or after the assay is performed.

Clause 17. The method of clause 16, wherein the subject is suspected of having a traumatic brain injury based on the CT scan.

Clause 18. The method of any one of clauses 14 to 17, wherein the reference level is correlated with positive head computed tomography.

Clause 19. The method of clause 18, wherein the reference level is correlated with control subjects that have not sustained a head injury.

Clause 20. The method of any one of clauses 14 to 19, wherein the reference level for cTnI is about 1.65 pg/mL, about 2.16 pg/mL, about 14.75 pg/mL, or about 30.43 pg/mL.

Clause 21. The method of any one of clauses 14 to 20, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 1.0 pg/mL to about 50 pg/mL.

Clause 22. A method for aiding in the diagnosis and evaluation of mild traumatic brain injury in a human subject, the method comprising:
  a) performing an assay on samples from the human subject to measure or detect a level of cTnI in a first sample and a second sample, wherein the first sample is taken from the human subject at a first time point within about 24 hours after head injury and the second sample is taken from the human subject about 3 hours to about 6 hours after the first sample, wherein the samples are biological samples;
  b) determining whether the amount of cTnI has increased or decreased from the first sample to the second sample; and
  c) confirming the occurrence of moderate to severe traumatic brain injury if the level of troponin I detected has increased from the first sample to the second sample and confirming the absence of mild traumatic brain injury if the level of cTnI detected has remained unchanged or has decreased from the first sample to the second sample.

Clause 23. The method of clause 22, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of a suspected injury to the head.

Clause 24. The method of clause 22 or 23, wherein the subject has an abnormal head CT.

Clause 25. The method of any one of clauses 22 to 24, wherein the amount of cTnI in the first sample is from about 1.0 to about 50 pg/mL.

Clause 26. The method of any one of clauses 22 to 25, wherein the amount of cTnI in the second sample is from about 1.0 to about 50 pg/mL.

Clause 27. The method of any one of clauses 22 to 26, further comprising treating the subject assessed as having moderate to severe traumatic brain injury with a traumatic brain injury treatment.

Clause 28. The method of any one of clauses 22 to 27, further comprising monitoring the subject assessed as having mild traumatic brain injury.

Clause 29. A method of aiding in the diagnosis and evaluation of a human subject that has sustained or may have sustained an injury to the head, the method comprising:
a) performing an assay on a sample obtained from the subject within about 2 hours after a suspected injury to the head to measure or detect a level of cTnI; and
b) determining whether the subject has sustained a mild or a moderate to severe traumatic brain injury (TBI), wherein the subject is determined as having (1) a moderate, severe, or a moderate to severe traumatic brain injury when the level of cTnI in the sample is higher than a reference level of cTnI or (2) a mild traumatic brain injury when the level of cTnI in the sample is lower than a reference level of cTnI.

Clause 30. The method of clause 29, wherein the subject has received a Glasgow Coma Scale score before or after the assay is performed.

Clause 31. The method of clause 30, wherein the subject is suspected as having a moderate, severe, or a moderate to severe traumatic brain injury based on the Glasgow Coma Scale score.

Clause 32. The method of clause 31, wherein the reference level is correlated with subjects having a moderate, severe, or a moderate to severe traumatic brain injury.

Clause 33. The method of clause 32, wherein the reference level is correlated with a Glasgow Coma Scale score of 3-12.

Clause 34. The method of clause 30, wherein the subject is suspected as having mild traumatic brain injury based on the Glasgow Coma Scale score.

Clause 35. The method of clause 34, wherein the reference level is correlated with subjects having mild traumatic brain injury.

Clause 36. The method of clause 35, wherein the reference level is correlated with a Glasgow Coma Scale score of 13-15.

Clause 37. The method of clause 36, wherein the reference level for cTnI is about 1.15 pg/mL or about 1.29 pg/mL.

Clause 38. The method of any one of clauses 29 to 37, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 0.5 pg/mL to about 30 pg/mL.

Clause 39. The method of any one of clauses 29 to 38, wherein the sample is taken within about 5 minutes, within about 10 minutes, within about 12 minutes, within about 15 minutes, within about 20 minutes, within about 30 minutes, within about 60 minutes, or within about 90 minutes after a suspected injury to the head.

Clause 40. The method of any one of clauses 29 to 39, further comprising treating the subject assessed as having moderate to severe traumatic brain injury with a traumatic brain injury treatment.

Clause 41. The method of any one of clauses 29 to 40, further comprising monitoring the subject assessed as having mild traumatic brain injury.

Clause 42. A method of aiding in the determination of whether to perform a head computerized tomography (CT) scan on a human subject that has sustained or may have sustained an injury to the head, the method comprising:
a) performing an assay on a sample obtained from the subject within about 2 hours after a suspected injury to the head to measure or detect a level of cTnI in the sample; and
b) performing a CT scan on the subject when the level of cTnI in the sample is higher than a reference level of cTnI and not performing a CT scan on the subject when the level of cTnI in the sample is lower than a reference level of cTnI.

Clause 43. The method of clause 42, wherein the subject has received a CT scan before or after the assay is performed.

Clause 44. The method of clause 43, wherein the subject is suspected of having a traumatic brain injury based on the CT scan.

Clause 45. The method of any one of clauses 42 to 44, wherein the reference level is correlated with positive head computed tomography.

Clause 46. The method of clause 45, wherein the reference level is correlated with control subjects that have not sustained a head injury.

Clause 47. The method of any one of clauses 42 to 46, wherein the reference level for cTnI is about 5.8 pg/mL or about 4.7 pg/mL.

Clause 48. The method of any one of clauses 42 to 47, wherein the reference level is
(a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL.

Clause 49. The method of any one of clauses 42 to 48, wherein the sample is taken within about 5 minutes, within about 10 minutes, within about 12 minutes, within about 15 minutes, within about 20 minutes, within about 30 minutes, within about 60 minutes, or within about 90 minutes after a suspected injury to the head.

Clause 50. The method of any one of clauses 1 to 49, wherein measuring the level of cTnI is done by an immunoassay or clinical chemistry assay.

Clause 51. The method of any one of clauses 1 to 50, wherein measuring the level of cTnI comprises:
C. contacting the sample, either simultaneously or sequentially, in any order with:
(1) a cTnI-capture antibody, which binds to an epitope on cTnI or cTnI fragment to form a cTnI-capture antibody-cTnI antigen complex, and
(2) a cTnI-detection antibody which includes a detectable label and binds to an epitope on cTnI that is not bound by the cTnI-capture antibody, to form a cTnI antigen-cTnI-detection antibody complex, such that a cTnI-capture antibody-cTnI antigen-cTnI-detection antibody complex is formed, and
D. measuring the amount or concentration of cTnI in the sample based on the signal generated by the detectable label in the cTnI-capture antibody-cTnI antigen-cTnI-detection antibody complex.

Clause 52. The method of any one of clauses 1 to 51, wherein the sample is selected from the group consisting of a whole blood sample, a serum sample, a cerebrospinal fluid sample, and a plasma sample.

Clause 53. The method of any one of clauses 1 to 52, wherein the sample is obtained after the subject sustained an injury to the head caused by physical shaking, blunt impact by an external mechanical or other force that results in a closed or open head trauma, one or more falls, explosions or blasts or other types of blunt force trauma.

Clause 54. The method of any one of clauses 1 to 53, wherein the sample is obtained after the subject has ingested or been exposed to a chemical, toxin or combination of a chemical and toxin.

Clause 55. The method of clause 54, wherein the chemical or toxin is fire, mold, asbestos, a pesticide, an insecticide, an organic solvent, a paint, a glue, a gas, an organic metal, a drug of abuse or one or more combinations thereof.

Clause 56. The method of any one of clauses 1 to 53, wherein the sample is obtained from a subject that suffers from an autoimmune disease, a metabolic disorder, a brain tumor, hypoxia, a virus, meningitis, hydrocephalus or combinations thereof.

Clause 58. The method of any one of clauses 1 to 56, wherein said method can be carried out on any subject without regard to factors selected from the group consisting of the subject's clinical condition, the subject's laboratory values, the subject's classification as suffering from mild, moderate, severe, or a moderate to severe traumatic brain injury, the subject's exhibition of low or high levels of cTnI, and the timing of any event wherein said subject may have sustained an injury to the head.

Clause 59. The method of any one of clauses 1 to 56, wherein the sample is a whole blood sample.

Clause 60. The method of any one of clauses 1 to 56, wherein the sample is a serum sample.

Clause 61. The method of any one of clauses 1 to 56, wherein the sample is a plasma sample.

Clause 62. The method of any one of clauses 58 to 60, wherein the assay is an immunoassay.

Clause 63. The method of any one of clauses 58 to 60, wherein the assay is a clinical chemistry assay.

Clause 64. The method of any one of clauses 58 to 60, wherein the assay is a single molecule detection assay.

Clause 65. A method for aiding in the diagnosis and evaluation of mild traumatic brain injury in a human subject, the method comprising:
  a) performing an assay on a sample obtained from the subject within about 24 hours after an actual or suspected injury to the head to measure or detect a level of cTnI; and
  b) determining whether the subject has sustained a mild or a moderate, severe, or moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI.

Clause 66. The method of clause 65, wherein the subject has received a Glasgow Coma Scale score before or after the assay is performed.

Clause 67. The method of clause 66, wherein the subject is suspected as having a moderate, severe, or moderate to severe traumatic brain injury based on the Glasgow Coma Scale score.

Clause 68. The method of clause 67, wherein the reference level is correlated with subjects having a moderate, severe, or moderate to severe traumatic brain injury.

Clause 69. The method of clause 68, wherein the reference level is correlated with a Glasgow Coma Scale score of 3-12.

Clause 70. The method of clause 66, wherein the subject is suspected as having mild traumatic brain injury based on the Glasgow Coma Scale score.

Clause 71. The method of clause 70, wherein the reference level is correlated with subjects having mild traumatic brain injury.

Clause 72. The method of clause 71, wherein the reference level is correlated with a Glasgow Coma Scale score of 13-15.

Clause 73. The method of any one of clauses 65 to 72, wherein the reference level for cTnI is about 1.94 pg/mL, about 2.54 pg/mL, about 21.23 pg/mL, or about 43.79 pg/mL.

Clause 74. The method of any one of clauses 65 to 73, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 1 pg/mL to about 50 pg/mL.

Clause 75. The method of any one of clauses 65 to 74, wherein the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 76. The method of any one of clauses 65 to 75, further comprising treating the subject assessed as having a moderate, severe, or moderate to severe traumatic brain injury with a traumatic brain injury treatment.

Clause 77. The method of any one of clauses 65 to 76, further comprising monitoring the subject assessed as having mild traumatic brain injury.

Clause 78. A method of aiding in the determination of whether to perform a head computerized tomography (CT) scan on a human subject that has sustained or may have sustained a suspected injury to the head, the method comprising:
  a) performing an assay on a sample obtained from the subject within about 24 hours after a suspected injury to the head to measure or detect a level of cTnI in the sample; and
  b) performing a CT scan on the subject when the level of cTnI in the sample is higher than a reference level of cTnI and not performing a CT scan on the subject when the level of cTnI in the sample is lower than a reference level of cTnI.

Clause 79. The method of clause 78, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 80. The method of clause 78 or 79, wherein the subject has received a CT scan before or after the assay is performed.

Clause 81. The method of clause 80, wherein the subject is suspected of having a traumatic brain injury based on the CT scan.

Clause 82. The method of any one of clauses 78 to 81, wherein the reference level is correlated with positive head computed tomography.

Clause 83. The method of clause 82, wherein the reference level is correlated with control subjects that have not sustained a head injury.

Clause 84. The method of any one of clauses 78 to 83, wherein the reference level for cTnI is about 1.65 pg/mL, about 2.16 pg/mL, about 14.75 pg/mL, or about 30.43 pg/mL.

Clause 85. The method of any one of clauses 78 to 84, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 1.0 pg/mL to about 50 pg/mL.

Clause 86. A method for aiding in the diagnosis and evaluation of mild traumatic brain injury in a human subject, the method comprising:
a) performing an assay on samples from the human subject to measure or detect a level of cTnI in a first sample and a second sample, wherein the first sample is taken from the human subject at a first time point within about 24 hours after head injury and the second sample is taken from the human subject about 3 hours to about 6 hours after the first sample, wherein the samples are biological samples;
b) determining whether the amount of cTnI has increased or decreased from the first sample to the second sample; and
c) confirming the occurrence of a moderate, severe, or moderate to severe traumatic brain injury if the level of cTnI detected has increased from the first sample to the second sample and confirming the absence of mild traumatic brain injury if the level of cTnI detected has remained unchanged or has decreased from the first sample to the second sample.

Clause 87. The method of clause 86, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of a actual or suspected injury to the head.

Clause 88. The method of clause 86 or 87, wherein the subject has an abnormal head CT.

Clause 89. The method of any one of clauses 86 to 88, wherein the amount of cTnI in the first sample is from about 1.0 to about 50 pg/mL.

Clause 90. The method of any one of clauses 86 to 89, wherein the amount of cTnI in the second sample is from about 1.0 to about 50 pg/mL.

Clause 91. The method of any one of clauses 86 to 90, further comprising treating the subject assessed as having a moderate, severe, or moderate to severe traumatic brain injury with a traumatic brain injury treatment.

Clause 92. The method of any one of clauses 86 to 91, further comprising monitoring the subject assessed as having mild traumatic brain injury.

Clause 93. A method of aiding in the diagnosis and evaluation of a human subject that has sustained or may have sustained an injury to the head, the method comprising:
a) performing an assay on a sample obtained from the subject within about 2 hours after a actual or suspected injury to the head to measure or detect a level of cTnI; and
b) determining whether the subject has sustained a mild or a moderate, severe, or a moderate to severe traumatic brain injury (TBI), wherein the subject is determined as having (1) a moderate, severe, or a moderate to severe traumatic brain injury when the level of cTnI in the sample is higher than a reference level of cTnI or (2) a mild traumatic brain injury when the level of cTnI in the sample is lower than a reference level of cTnI.

Clause 94. The method of clause 93, wherein the subject has received a Glasgow Coma Scale score before or after the assay is performed.

Clause 95. The method of clause 94, wherein the subject is suspected as having a moderate, severe, or a moderate to severe traumatic brain injury based on the Glasgow Coma Scale score.

Clause 96. The method of clause 95, wherein the reference level is correlated with subjects having a moderate, severe, or a moderate to severe traumatic brain injury.

Clause 97. The method of clause 96, wherein the reference level is correlated with a Glasgow Coma Scale score of 3-12.

Clause 98. The method of clause 97, wherein the subject is suspected as having mild traumatic brain injury based on the Glasgow Coma Scale score.

Clause 99. The method of clause 98, wherein the reference level is correlated with subjects having mild traumatic brain injury.

Clause 100. The method of clause 99, wherein the reference level is correlated with a Glasgow Coma Scale score of 13-15.

Clause 101. The method of clause 100, wherein the reference level for cTnI is about 1.15 pg/mL or about 1.29 pg/mL.

Clause 102. The method of any one of clauses 93 to 101, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 0.5 pg/mL to about 30 pg/mL.

Clause 103. The method of any one of clauses 93 to 102, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 104. The method of any one of clauses 93 to 103, further comprising treating the subject assessed as having a moderate, severe, or moderate to severe traumatic brain injury with a traumatic brain injury treatment.

Clause 105. The method of any one of clauses 93 to 104, further comprising monitoring the subject assessed as having mild traumatic brain injury.

Clause 106. A method of aiding in the determination of whether to perform a head computerized tomography (CT) scan on a human subject that has sustained or may have sustained a suspected injury to the head, the method comprising:
 a) performing an assay on a sample obtained from the subject within about 2 hours after a suspected injury to the head to measure or detect a level of cTnI in the sample; and
 b) performing a CT scan on the subject when the level of cTnI in the sample is higher than a reference level of cTnI and not performing a CT scan on the subject when the level of cTnI in the sample is lower than a reference level of cTnI.

Clause 107. The method of clause 106, wherein the subject has received a CT scan before or after the assay is performed.

Clause 108. The method of clause 107, wherein the subject is suspected of having a traumatic brain injury based on the CT scan.

Clause 109. The method of any one of clauses 106 to 108, wherein the reference level is correlated with positive head computed tomography.

Clause 110. The method of clause 108, wherein the reference level is correlated with control subjects that have not sustained a head injury.

Clause 111. The method of any one of clauses 106 to 110, wherein the reference level for cTnI is about 5.8 pg/mL or about 4.7 pg/mL.

Clause 112. The method of any one of clauses 106 to 111, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL.

Clause 113. The method of any one of clauses 106 to 112, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 114. The method of any one of clauses 65 to 113, wherein measuring the level of cTnI is done by an immunoassay or clinical chemistry assay.

Clause 115. The method of any one of clauses 65 to 114, wherein measuring the level of cTnI comprises:
 E. contacting the sample, either simultaneously or sequentially, in any order with:
  (1) a cTnI-capture antibody, which binds to an epitope on cTnI or cTnI fragment to form a cTnI-capture antibody-cTnI antigen complex, and
  (2) a cTnI-detection antibody which includes a detectable label and binds to an epitope on cTnI that is not bound by the cTnI-capture antibody, to form a cTnI antigen-cTnI-detection antibody complex, such that a cTnI-capture antibody-cTnI antigen-cTnI-detection antibody complex is formed, and
 F. measuring the amount or concentration of cTnI in the sample based on the signal generated by the detectable label in the cTnI-capture antibody-cTnI antigen-cTnI-detection antibody complex.

Clause 116. The method of any one of clauses 65 to 115, wherein the sample is selected from the group consisting of a whole blood sample, a serum sample, a cerebrospinal fluid sample, and a plasma sample.

Clause 117. The method of any one of clauses 65 to 116, wherein the sample is obtained after the subject sustained an injury to the head caused by physical shaking, blunt impact by an external mechanical or other force that results in a closed or open head trauma, one or more falls, explosions or blasts or other types of blunt force trauma.

Clause 118. The method of any one of clauses 65 to 117, wherein the sample is obtained after the subject has ingested or been exposed to a chemical, toxin or combination of a chemical and toxin.

Clause 119. The method of clause 118, wherein the chemical or toxin is fire, mold, asbestos, a pesticide, an insecticide, an organic solvent, a paint, a glue, a gas, an organic metal, a drug of abuse or one or more combinations thereof.

Clause 120. The method of any one of clauses 65 to 116, wherein the sample is obtained from a subject that suffers from an autoimmune disease, a metabolic disorder, a brain tumor, hypoxia, a virus, meningitis, hydrocephalus or combinations thereof.

Clause 121. The method of any one of clauses 65 to 120, wherein said method can be carried out on any subject without regard to factors selected from the group consisting of the subject's clinical condition, the subject's laboratory values, the subject's classification as suffering from mild, moderate, severe, or a moderate to severe traumatic brain injury, the subject's exhibition of low or high levels of cTnI, and the timing of any event wherein said subject may have sustained an injury to the head.

Clause 122. The method of any one of clauses 65 to 121, wherein the sample is a whole blood sample.

Clause 123. The method of any one of clauses 65 to 121, wherein the sample is a serum sample.

Clause 124. The method of any one of clauses 65 to 121, wherein the sample is a plasma sample.

Clause 125. The method of any one of clauses 122 to 124, wherein the assay is an immunoassay.

Clause 126. The method of any one of clauses 122 to 124, wherein the assay is a clinical chemistry assay.

Clause 127. The method of any one of clauses 122 to 124, wherein the assay is a single molecule detection assay.

Clause 128. A method for aiding in the diagnosis and evaluation of mild traumatic brain injury in a human subject, the method comprising:
 a) performing an assay on a sample obtained from the subject within about 24 hours after a actual or suspected injury to the head to measure or detect a level of cTnI; and
 b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI.

Clause 129. The method of clause 128, wherein the subject has received a Glasgow Coma Scale score before or after the assay is performed.

Clause 130. The method of clause 129, wherein the subject is suspected as having moderate, severe, or moderate to severe traumatic brain injury based on the Glasgow Coma Scale score.

Clause 131. The method of clause 130, wherein the reference level is correlated with subjects having a moderate, severe, or a moderate to severe traumatic brain injury.

Clause 132. The method of clause 131, wherein the reference level is correlated with a Glasgow Coma Scale score of 3-12.

Clause 133. The method of clause 129, wherein the subject is suspected as having mild traumatic brain injury based on the Glasgow Coma Scale score.

Clause 134. The method of clause 133, wherein the reference level is correlated with subjects having mild traumatic brain injury.

Clause 135. The method of clause 134, wherein the reference level is correlated with a Glasgow Coma Scale score of 13-15.

Clause 136. The method of any one of clauses 128 to 135, wherein the reference level for cTnI is about 1.94 pg/mL, about 2.54 pg/mL, about 21.23 pg/mL, or about 43.79 pg/mL.

Clause 137. The method of any one of clauses 128 to 136, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 1 pg/mL to about 50 pg/mL.

Clause 138. The method of any one of clauses 128 to 137, wherein the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 139. A method of treating a mild or moderate, severe, or moderate to severe traumatic brain injury in a human subject, the method comprising:
  a) performing an assay on a sample obtained from the subject within about 24 hours after an actual or suspected injury to the head to measure or detect a level of cTnI;
  b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI; and
  c) treating the subject assessed as having a mild, moderate, severe, or moderate to severe traumatic brain injury with a traumatic brain injury treatment.

Clause 140. The method of clause 139, further comprising monitoring the subject assessed as having a mild, moderate, severe, or moderate to severe traumatic brain injury.

Clause 141. A method of aiding in the determination of whether to perform a head computerized tomography (CT) scan on a human subject that has an actual or suspected injury to the head, the method comprising:
  a) performing an assay on a sample obtained from the subject within about 24 hours after a actual or suspected injury to the head to measure or detect a level of cTnI in the sample; and
  b) performing a CT scan on the subject when the level of cTnI in the sample is higher than a reference level of cTnI and not performing a CT scan on the subject when the level of cTnI in the sample is lower than a reference level of cTnI.

Clause 142. The method of clause 141, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 143. The method of clause 141 or 142, wherein the subject has received a CT scan before or after the assay is performed.

Clause 144. The method of clause 143, wherein the subject is suspected of having a traumatic brain injury based on the CT scan.

Clause 145. The method of any one of clauses 141 to 144, wherein the reference level is correlated with positive head computed tomography.

Clause 146. The method of clause 141, wherein the reference level is correlated with control subjects that have not sustained a head injury.

Clause 147. The method of any one of clauses 141 to 146, wherein the reference level for cTnI is about 1.65 pg/mL, about 2.16 pg/mL, about 14.75 pg/mL, or about 30.43 pg/mL.

Clause 148. The method of any one of clauses 141 to 147, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 1.0 pg/mL to about 50 pg/mL.

Clause 149. A method for aiding in the diagnosis and evaluation of mild traumatic brain injury in a human subject, the method comprising:
  a) performing an assay on samples from the human subject to measure or detect a level of cTnI in a first sample and a second sample, wherein the first sample is taken from the human subject at a first time point within about 24 hours after head injury and the second sample is taken from the human subject about 3 hours to about 6 hours after the first sample, wherein the samples are biological samples;
  b) determining whether the amount of cTnI has increased or decreased from the first sample to the second sample; and
  c) confirming the occurrence of moderate, severe, or moderate to severe traumatic brain injury if the level of cTnI detected has increased from the first sample to the second sample and confirming the absence of mild traumatic brain injury if the level of cTnI detected has remained unchanged or has decreased from the first sample to the second sample.

Clause 150. A method for aiding in the diagnosis and evaluation of mild traumatic brain injury in a human subject, the method comprising:
  a) performing an assay on samples from the human subject to measure or detect a level of cTnI in a first sample and a second sample, wherein the first sample is taken from the human subject at a first time point and the second sample is taken from the human subject about 1 hours to about 4 hours after the first sample, wherein the samples are biological samples;

b) determining whether the amount of cTnI has increased or decreased from the first sample to the second sample; and c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample.

Clause 151. The method of clause 149 or 150, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of a actual or suspected injury to the head.

Clause 152. The method of any of clauses 149 to 152, wherein the subject has an abnormal head CT.

Clause 153. The method of any one of clauses 149 to 152, wherein the amount of cTnI in the first sample is from about 1.0 to about 50 pg/mL.

Clause 154. The method of any one of clauses 149 to 153, wherein the amount of cTnI in the second sample is from about 1.0 to about 50 pg/mL.

Clause 155. A method of treating a mild or moderate, severe, or moderate to severe traumatic brain injury in a human subject, the method comprising:

a) performing an assay on samples from the human subject to measure or detect a level of cTnI in a first sample and a second sample, wherein the first sample is taken from the human subject at a first time point and the second sample is taken from the human subject about 3 hours to about 6 hours or about 1 hours to about 4 hours after the first sample, wherein the samples are biological samples;

b) determining whether the amount of cTnI has increased or decreased from the first sample to the second sample;

c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample; and d) treating the subject assessed as having a mild, moderate, severe, or moderate to severe traumatic brain injury with a traumatic brain injury treatment.

Clause 156. The method of clause 155, further comprising monitoring the subject assessed as having a mild, moderate, severe, or moderate to severe traumatic brain injury.

Clause 157. A method of aiding in the diagnosis and evaluation of a human subject that has sustained or may have sustained an injury to the head, the method comprising:

a) performing an assay on a sample obtained from the subject within about 2 hours after a actual or suspected injury to the head to measure or detect a level of cTnI; and b) determining whether the subject has sustained a mild or a moderate to severe traumatic brain injury (TBI), wherein the subject is determined as having (1) a moderate, severe, or a moderate, severe or a moderate to severe traumatic brain injury when the level of cTnI in the sample is higher than a reference level of cTnI or (2) a mild traumatic brain injury when the level of cTnI in the sample is lower than a reference level of cTnI.

Clause 158. The method of clause 157, wherein the subject has received a Glasgow Coma Scale score before or after the assay is performed.

Clause 159. The method of clause 158, wherein the subject is suspected as having moderate, severe, or moderate to severe traumatic brain injury based on the Glasgow Coma Scale score.

Clause 160. The method of clause 159, wherein the reference level is correlated with subjects having a moderate, severe, or a moderate to severe traumatic brain injury.

Clause 161. The method of clause 160, wherein the reference level is correlated with a Glasgow Coma Scale score of 3-12.

Clause 162. The method of clause 157, wherein the subject is suspected as having mild traumatic brain injury based on the Glasgow Coma Scale score.

Clause 163. The method of clause 158, wherein the reference level is correlated with subjects having mild traumatic brain injury.

Clause 164. The method of clause 163, wherein the reference level is correlated with a Glasgow Coma Scale score of 13-15.

Clause 165. The method of any one of clauses 157 to 164, wherein the reference level for cTnI is about 1.15 pg/mL or about 1.29 pg/mL.

Clause 166. The method of any one of clauses 157 to 165, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 0.5 pg/mL to about 30 pg/mL.

Clause 167. The method of any one of clauses 157 to 166, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 168. A method of treating a mild, moderate, severe, or moderate to severe TBI, the method comprising:

a) performing an assay on a sample obtained from the subject within about 2 hours after an actual or suspected injury to the head to measure or detect a level of cTnI;

b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI; and c) treating the subject assessed as having a mild, moderate, severe, or moderate to severe traumatic brain injury with a traumatic brain injury treatment.

Clause 169. The method of clause 168, further comprising monitoring the subject assessed as having mild, moderate, severe, or moderate to severe traumatic brain injury.

Clause 170. A method of aiding in the determination of whether to perform a head computerized tomography (CT) scan on a human subject that has an actual or suspected injury to the head, the method comprising:
 a) performing an assay on a sample obtained from the subject within about 2 hours after a actual or suspected injury to the head to measure or detect a level of cTnI in the sample; and
 b) performing a CT scan on the subject when the level of cTnI in the sample is higher than a reference level of cTnI and not performing a CT scan on the subject when the level of cTnI in the sample is lower than a reference level of cTnI.

Clause 171. The method of clause 170, wherein the subject has received a CT scan before or after the assay is performed.

Clause 172. The method of clause 171, wherein the subject is suspected of having a traumatic brain injury based on the CT scan.

Clause 173. The method of any one of clauses 170 to 172, wherein the reference level is correlated with positive head computed tomography.

Clause 174. The method of clause 170, wherein the reference level is correlated with control subjects that have not sustained a head injury.

Clause 175. The method of any one of clauses 170 to 174, wherein the reference level for cTnI is about 5.8 pg/mL or about 4.7 pg/mL.

Clause 176. The method of any one of clauses 170 to 175, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL.

Clause 177. The method of any one of clauses 170 to 176, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 178. A method for predicting the outcome of human subjects having mild traumatic brain injury, the method comprising:
 a) performing an assay on samples from the human subject to measure or detect a level of cTnI in a first sample and a second sample, wherein the first sample is taken from the human subject at a first time point within 24 hours after a injury to the head and the second sample is taken from the human subject about 0 to about 4 hours after the first sample, wherein the samples are biological samples;
 b) determining whether the amount of cTnI has increased or decreased from the first sample to the second sample; and
 c) predicting an unfavorable outcome in the human subject if the level of cTnI detected has increased from the first sample to the second sample by at least about 20% and predicting a favorable outcome in the human subject if the level of cTnI detected has remained unchanged, decreased, or increased less than about 20% from the first sample to the second sample.

Clause 179. The method of clause 178, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the to the head.

Clause 180. The method of clause 178 or 179, wherein the method predicts the outcome at about 1 month, 3 months, or 6 months after the injury to the head.

Clause 181. The method of clause 180, wherein the subject is predicted to have an Extended Glasgow Outcome Scale (GOSE) score of 5 or less.

Clause 182. The method of any one of clauses 178 to 181, wherein the subject has a normal head CT scan.

Clause 183. The method of any one of clauses 178 to 182, wherein the subject has received a Glasgow Coma Scale score before or after the assay is performed.

Clause 184. The method of clause any one of clauses 178 to 183, wherein the subject has received a Glasgow Coma Scale score of 13-15 and is suspected as having mild traumatic brain injury based on the Glasgow Coma Scale score.

Clause 185. The method of any one of clauses 178 to 184, wherein the subject has received an Extended Glasgow Outcome Scale (GOSE) score before or after the assay is performed.

Clause 186. A method for predicting the outcome of human subjects having mild traumatic brain injury, the method comprising:
 a) performing an assay on a sample obtained from the subject within about 28 hours after a injury to the head to measure or detect a level of cTnI, wherein the sample is a biological sample; and
 b) predicting an unfavorable outcome in the human subject if the level of cTnI in the sample is higher than a reference level of cTnI and predicting a favorable outcome in the human subject if the level of cTnI in the sample is lower than a reference level of cTnI.

Clause 187. The method of clause 186, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, within about 25 hours, within about 26 hours, within about 27 hours, or within about 28 hours of the injury to the head.

Clause 188. The method of clause 186 or 187, wherein the method predicts the outcome at about 1 month, 3 months, or 6 months after the injury to the head.

Clause 189. The method of clause 188, wherein the subject is predicted to have an Extended Glasgow Outcome Scale (GOSE) score of 5 or less.

Clause 190. The method of any one of clauses 186 to 190, wherein the reference level is (a) determined by an assay having a sensitivity of between at least about 80% to 100% and a specificity of between at least about 45% to 100%; (b) determined by an assay having a sensitivity of at least about 83.3% and a specificity of at least about 54.9%; (c) determined by an assay having a sensitivity of at least about 100% and a specificity of at least about 49.2%; or (d) between at least about 1 pg/mL to about 50 pg/mL.

Clause 191. The method of any one of clauses 186 to 190, wherein the reference level for cTnI is about 5.6 pg/mL or about 5.7 pg/mL.

Clause 192. A method for predicting the outcome of human subjects having mild traumatic brain injury, the method comprising:
 a) performing an assay on samples from the human subject to measure or detect a level of cTnI in a first sample and a second sample, wherein the first sample is taken from the human subject at a first time point within about 24 hours after head injury and the second sample is taken from the human subject about 4 hours after the first sample, wherein the samples are biological samples;
 b) determining whether the amount of cTnI has increased or decreased from the first sample to the second sample; and
 c) predicting an unfavorable outcome in the human subject if the level of cTnI in the sample has increased from the first sample to the second sample and predicting a favorable outcome in the human subject if the level of cTnI in the sample has remained unchanged or has decreased from the first sample to the second sample.

Clause 193. The method of clause 192, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours.

Clause 194. The method of clause 192 or 193, wherein the method predicts the outcome at about 1 month, 3 months, or 6 months after the injury to the head.

Clause 195. The method of clause 194, wherein the subject is predicted to have an Extended Glasgow Outcome Scale (GOSE) score of 5 or less.

Clause 196. The method of any one of clauses 192 to 195, wherein the amount of cTnI in the first sample is from about 1.0 to about 50 pg/mL.

Clause 197. The method of any one of clauses 192 to 196, wherein the amount of cTnI in the second sample is from about 1.0 to about 50 pg/mL.

Clause 198. The method of any one of clauses 192 to 197, wherein the level of cTnI decreases or increase by at least an absolute amount from the first sample to the second sample.

Clause 199. The method of clause 198, wherein the absolute amount is (a) determined by an assay having a sensitivity of between at least about 80% to 100% and a specificity of between at least about 45% to 100%; (b) determined by an assay having a sensitivity of at least about 82.4% and a specificity of at least about 69.5%; or (c) between at least about 1 pg/mL to about 50 pg/mL.

Clause 200. The method of any one of clauses 199, wherein the absolute amount is about 5.6 pg/mL.

Clause 201. The method of any one of clauses 192 to 200, further comprising treating the subject assessed as having an unfavorable outcome with a traumatic brain injury treatment.

Clause 202. The method of any one of clauses 192 to 201, further comprising monitoring the subject assessed as having an unfavorable outcome with a traumatic brain injury treatment.

Clause 203. A method for predicting the outcome of human subjects having mild traumatic brain injury, the method comprising:
 a) performing an assay on samples from the human subject to measure or detect a level of cTnI in a first sample and a second sample, wherein the first sample is taken from the human subject at a first time point within 24 hours after a actual or suspected injury to the head and the second sample is taken from the human subject about 0 to about 4 hours after the first sample, wherein the samples are biological samples;
 b) determining the age of the subject; and
 c) predicting an unfavorable outcome in the human subject if the level of cTnI in the first sample and/or second sample are higher than a reference level of cTnI and the age of the subject is above a reference age and predicting a favorable outcome in the human subject if the level of cTnI in the first sample and second sample are lower than a reference levels of cTnI and/or the age of the subject is below the reference age.

Clause 204. The method of any one clauses 128 to 203 further comprising of treating the subject with at least one cardioprotective therapy.

Clause 205. The method of clause 204, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

Clause 206. The method of any one of clauses 128 to 205, wherein measuring the level of cTnI is done by an immunoassay or clinical chemistry assay.

Clause 207. The method of any one of clauses 128 to 206, wherein measuring the level of cTnI comprises:
 A. contacting the sample, either simultaneously or sequentially, in any order with:
  (1) a cTnI-capture antibody, which binds to an epitope on cTnI or cTnI fragment to form a cTnI-capture antibody-cTnI antigen complex, and
  (2) a cTnI-detection antibody which includes a detectable label and binds to an epitope on cTnI that is not bound by the cTnI-capture antibody, to form a cTnI antigen-cTnI-detection antibody complex, such that a cTnI-capture antibody-cTnI antigen-cTnI-detection antibody complex is formed, and
 B. measuring the amount or concentration of cTnI in the sample based on the signal generated by the detectable label in the cTnI-capture antibody-cTnI antigen-cTnI-detection antibody complex.

Clause 208. The method of any one of clauses 128 to 207, wherein the sample is selected from the group consisting of a whole blood sample, a serum sample, a cerebrospinal fluid sample, and a plasma sample.

Clause 209. The method of any one of clauses 128 to 208, wherein the sample is obtained after the subject sustained an injury to the head caused by physical shaking, blunt impact by an external mechanical or other force that results in a closed or open head trauma, one or more falls, explosions or blasts or other types of blunt force trauma.

Clause 210. The method of any one of clauses 128 to 208, wherein the sample is obtained after the subject has ingested or been exposed to a chemical, toxin or combination of a chemical and toxin.

Clause 211. The method of clause 210, wherein the chemical or toxin is fire, mold, asbestos, a pesticide, an insecticide, an organic solvent, a paint, a glue, a gas, an organic metal, a drug of abuse or one or more combinations thereof.

Clause 212. The method of any one of clauses 128 to 208, wherein the sample is obtained from a subject that suffers from an autoimmune disease, a metabolic disorder, a brain tumor, hypoxia, a virus, meningitis, hydrocephalus or combinations thereof.

Clause 213. The method of any one of clauses 128 to 212, wherein said method can be carried out on any subject without regard to factors selected from the group consisting of the subject's clinical condition, the subject's laboratory values, the subject's classification as suffering from mild, moderate, severe, or a moderate to severe traumatic brain injury, the subject's exhibition of low or high levels of cTnI, and the timing of any event wherein said subject may have sustained an injury to the head.

Clause 214. The method of any one of clauses 128 to 214, wherein the sample is a whole blood sample.

Clause 215. The method of any one of clauses 128 to 214, wherein the sample is a serum sample.

Clause 216. The method of any one of clauses 128 to 214, wherein the sample is a plasma sample.

Clause 217. The method of any one of clauses 214 to 216, wherein the assay is an immunoassay.

Clause 218. The method of any one of clauses 214 to 216, wherein the assay is a clinical chemistry assay.

Clause 219. The method of any one of clauses 214 to 216, wherein the assay is a single molecule detection assay.

Clause 220. A method for evaluating a human subject for mild traumatic brain injury in a human subject, the method comprising:
  a) performing an assay on a sample obtained from the subject within about 24 hours after a actual or suspected injury to the head to measure or detect a level of cardiac troponin I (cTnI); and
  b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI.

Clause 221. The method of clause 220, wherein the subject has received a Glasgow Coma Scale score before or after the assay is performed.

Clause 222. The method of clause 221, wherein the subject is suspected as having moderate, severe, or moderate to severe traumatic brain injury based on the Glasgow Coma Scale score.

Clause 223. The method of clause 222, wherein the reference level is correlated with subjects having a moderate, severe or a moderate to severe traumatic brain injury.

Clause 224. The method of clause 223, wherein the reference level is correlated with a Glasgow Coma Scale score of 3-12.

Clause 225. The method of clause 221, wherein the subject is suspected as having mild traumatic brain injury based on the Glasgow Coma Scale score.

Clause 226. The method of clause 225, wherein the reference level is correlated with subjects having mild traumatic brain injury.

Clause 227. The method of clause 226, wherein the reference level is correlated with a Glasgow Coma Scale score of 13-15.

Clause 228. The method of any one of clauses 220 to 227, wherein the reference level for cTnI is about 1.94 pg/mL, about 2.54 pg/mL, about 21.23 pg/mL, or about 43.79 pg/mL.

Clause 229. The method of any one of clauses 220 to 228, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 1 pg/mL to about 50 pg/mL.

Clause 230. The method of any one of clauses 220 to 228, wherein the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 231. A method of treating a mild or moderate, severe, or moderate to severe traumatic brain injury in a human subject, the method comprising:
  a) performing an assay on a sample obtained from the subject within about 24 hours after an actual or suspected injury to the head to measure or detect a level of cTnI;
  b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI; and
  c) treating the subject assessed as having a mild, moderate, severe, or moderate to severe traumatic brain injury with a traumatic brain injury treatment.

Clause 232. The method of clause 12, further comprising monitoring the subject assessed as having a mild, moderate, severe, or moderate to severe traumatic brain injury.

Clause 233. A method of determining whether to perform a head computerized tomography (CT) scan on a human subject that has an actual or suspected injury to the head, the method comprising:
  a) performing an assay on a sample obtained from the subject within about 24 hours after a actual or suspected injury to the head to measure or detect a level of cTnI in the sample; and
  b) performing a CT scan on the subject when the level of cTnI in the sample is higher than a reference level of cTnI and not performing a CT scan on the subject when the level of cTnI in the sample is lower than a reference level of cTnI.

Clause 234. The method of clause 233, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head.

Clause 235. The method of clauses 233 or 234, wherein the subject has received a CT scan before or after the assay is performed.

Clause 236. The method of clauses 235, wherein the subject is suspected of having a traumatic brain injury based on the CT scan.

Clause 237. The method of any one of clauses 233 to 236, wherein the reference level is correlated with positive head computed tomography.

Clause 238. The method of clauses 233, wherein the reference level is correlated with control subjects that have not sustained a head injury.

Clause 239. The method of any one of clauses 233 to 238, wherein the reference level for cTnI is about 1.65 pg/mL, about 2.16 pg/mL, about 14.75 pg/mL, or about 30.43 pg/mL.

Clause 240. The method of any one of clauses 233 to 239, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 1.0 pg/mL to about 50 pg/mL.

Clause 241. A method for evaluating a human subject for mild traumatic brain injury in a human subject, the method comprising:
  a) performing an assay on samples from the human subject to measure or detect a level of cTnI in a first sample and a second sample, wherein the first sample is taken from the human subject at a first time point within about 24 hours after head injury and the second sample is taken from the human subject about 3 hours to about 6 hours after the first sample, wherein the samples are biological samples;
  b) determining whether the amount of cTnI has increased or decreased from the first sample to the second sample; and
  c) confirming the occurrence of moderate, severe, or moderate to severe traumatic brain injury if the level of cTnI detected has increased from the first sample to the second sample and confirming the absence of mild traumatic brain injury if the level of cTnI detected has remained unchanged or has decreased from the first sample to the second sample.

Clause 242. A method for evaluating a human subject for mild traumatic brain injury in a human subject, the method comprising:
  a) performing an assay on samples from the human subject to measure or detect a level of cTnI in a first sample and a second sample, wherein the first sample is taken from the human subject at a first time point and the second sample is taken from the human subject about 1 hours to about 4 hours after the first sample, wherein the samples are biological samples;
  b) determining whether the amount of cTnI has increased or decreased from the first sample to the second sample; and
  c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample.

Clause 243. The method of clauses 241 or 242, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of a actual or suspected injury to the head.

Clause 244. The method of any of clauses 241 to 243, wherein the subject has an abnormal head CT.

Clause 245. The method of any one of clauses 241 to 244, wherein the amount of cTnI in the first sample is from about 1.0 to about 50 pg/mL.

Clause 246. The method of any one of clauses 241 to 245, wherein the amount of cTnI in the second sample is from about 1.0 to about 50 pg/mL.

Clause 247. A method of treating a mild or moderate, severe, or moderate to severe traumatic brain injury in a human subject, the method comprising:
  a) performing an assay on samples from the human subject to measure or detect a level of cTnI in a first sample and a second sample, wherein the first sample is taken from the human subject at a first time point and the second sample is taken from the human subject about 3 hours to about 6 hours or about 1 hours to about 4 hours after the first sample, wherein the samples are biological samples;
  b) determining whether the amount of cTnI has increased or decreased from the first sample to the second sample;
  c) confirming the occurrence of moderate to severe traumatic brain injury if the level of cTnI detected has increased from the first sample to the second sample and confirming the absence of mild traumatic brain injury if the level of cTnI detected has remained unchanged or has decreased from the first sample to the second sample; and
  d) treating the subject assessed as having a mild, moderate, severe, or moderate to severe traumatic brain injury with a traumatic brain injury treatment.

Clause 248. The method of clause 247, further comprising monitoring the subject assessed as having a mild, moderate, severe, or moderate to severe traumatic brain injury.

Clause 249. A method of aiding in the diagnosis and evaluation of a human subject that has sustained or may have sustained an injury to the head, the method comprising: a) performing an assay on a sample obtained from the subject within about 2 hours after a actual or suspected injury to the head to measure or detect a level of cTnI; and
  b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI.

Clause 250. The method of clauses 249, wherein the subject has received a Glasgow Coma Scale score before or after the assay is performed.

Clause 251. The method of clause 250, wherein the subject is suspected as having moderate, severe, or moderate to severe traumatic brain injury based on the Glasgow Coma Scale score.

Clause 252. The method of clause 251, wherein the reference level is correlated with subjects having a moderate, severe, or a moderate to severe traumatic brain injury.

Clause 253. The method of clause 252, wherein the reference level is correlated with a Glasgow Coma Scale score of 3-12.

Clause 254. The method of clause 250, wherein the subject is suspected as having mild traumatic brain injury based on the Glasgow Coma Scale score.

Clause 255. The method of clause 254, wherein the reference level is correlated with subjects having mild traumatic brain injury.

Clause 256. The method of clause 255, wherein the reference level is correlated with a Glasgow Coma Scale score of 13-15.

Clause 257. The method of any one of clauses 249 to 256, wherein the reference level for cTnI is about 1.15 pg/mL or about 1.29 pg/mL.

Clause 258. The method of any one of clauses 249 to 257, wherein the reference level is (a) determined by an assay having a sensitivity of between at least about 85% to 100% and a specificity of between at least about 30% to 100%; (b) determined by an assay having a sensitivity of at least about 87.5% and a specificity of at least about 31%; or (c) between at least about 0.5 pg/mL to about 30 pg/mL.

Clause 259. The method of any one of clauses 249 to 258, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 260. A method of treating a mild, moderate, severe, or moderate to severe TBI, the method comprising:
a) performing an assay on a sample obtained from the subject within about 2 hours after an actual or suspected injury to the head to measure or detect a level of cTnI;
b) determining whether the subject has sustained a mild or a moderate to severe traumatic brain injury (TBI), wherein the subject is determined as having (1) a moderate, severe, or moderate to severe traumatic brain injury when the level of cTnI in the sample is higher than a reference level of cTnI or (2) a mild traumatic brain injury when the level of cTnI in the sample is lower than a reference level of cTnI; and
c) treating the subject assessed as having a mild, moderate, severe, or moderate to severe traumatic brain injury with a traumatic brain injury treatment.

Clause 261. The method of clauses 260, further comprising monitoring the subject assessed as having mild, moderate, severe, or moderate to severe traumatic brain injury.

Clause 262. A method of aiding in the determination of whether to perform a head computerized tomography (CT) scan on a human subject that has an actual or suspected injury to the head, the method comprising:
a) performing an assay on a sample obtained from the subject within about 2 hours after an actual or suspected injury to the head to measure or detect a level of cTnI in the sample; and
b) performing a CT scan on the subject when the level of cTnI in the sample is higher than a reference level of cTnI and not performing a CT scan on the subject when the level of cTnI in the sample is lower than a reference level of cTnI.

Clause 263. The method of clause 262, wherein the subject has received a CT scan before or after the assay is performed.

Clause 264. The method of clause 263, wherein the subject is suspected of having a traumatic brain injury based on the CT scan.

Clause 265. The method of any one of clauses 262 to 264, wherein the reference level is correlated with positive head computed tomography.

Clause 266. The method of clause 262, wherein the reference level is correlated with control subjects that have not sustained a head injury.

Clause 267. The method of any one of clauses 262 to 266, wherein the reference level for cTnI is about 5.8 pg/mL or about 4.7 pg/mL.

Clause 268. The method of any one of clauses 262 to 267, wherein the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL.

Clause 269. The method of any one of clauses 262 to 268, wherein the sample is taken within about 5 minutes, within about 10 minutes, within about 12 minutes, within about 15 minutes, within about 20 minutes, within about 30 minutes, within about 60 minutes, or within about 90 minutes after a actual or suspected injury to the head.

Clause 270. A method for predicting the outcome of human subjects having mild traumatic brain injury, the method comprising:
a) performing an assay on samples from the human subject to measure or detect a level of cTnI in a first sample and a second sample, wherein the first sample is taken from the human subject at a first time point within 24 hours after an injury to the head and the second sample is taken from the human subject about 0 to about 4 hours after the first sample, wherein the samples are biological samples;
b) determining whether the amount of cTnI has increased or decreased from the first sample to the second sample; and
c) predicting an unfavorable outcome in the human subject if the level of cTnI detected has increased from the first sample to the second sample by at least about 20% and predicting a favorable outcome in the human subject if the level of cTnI detected has remained unchanged, decreased, or increased less than about 20% from the first sample to the second sample.

Clause 271. The method of clauses 270, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the injury to the head.

Clause 272. The method of clauses 270 or 271, wherein the method predicts the outcome at about 1 month, 3 months, or 6 months after the actual or suspected injury to the head.

Clause 273. The method of clauses 272, wherein the subject is predicted to have an Extended Glasgow Outcome Scale (GOSE) score of 5 or less.

Clause 274. The method of any one of clauses 270 to 273, wherein the subject has a normal head CT scan.

Clause 275. The method of any one of clauses 270 to 274, wherein the subject has received a Glasgow Coma Scale score before or after the assay is performed.

Clause 276. The method of claim any one of clauses 270 to 275, wherein the subject has received a Glasgow Coma Scale score of 13-15 and is suspected as having mild traumatic brain injury based on the Glasgow Coma Scale score.

Clause 277. The method of any one of clauses 270 to 276, wherein the subject has received an Extended Glasgow Outcome Scale (GOSE) score before or after the assay is performed.

Clause 278. A method for predicting the outcome of human subject having mild traumatic brain injury, the method comprising:
a) performing an assay on a sample obtained from the subject within about 28 hours after a injury to measure or detect a level of cTnI, wherein the sample is a biological sample; and
b) predicting an unfavorable outcome in the human subject if the level of cTnI in the sample is higher than a reference level of cTnI and predicting a favorable outcome in the human subject if the level of cTnI in the sample is lower than a reference level of cTnI.

Clause 279. The method of claim 278, wherein the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, within about 25 hours, within about 26 hours, within about 27 hours, or within about 28 hours of the injury to the head.

Clause 280. The method of clauses 278 or 279, wherein the method predicts the outcome at about 1 month, 3 months, or 6 months after the injury to the head.

Clause 281. The method of clause 280, wherein the subject is predicted to have an Extended Glasgow Outcome Scale (GOSE) score of 5 or less.

Clause 282. The method of any one of clauses 278 to 281, wherein the reference level is (a) determined by an assay having a sensitivity of between at least about 80% to 100% and a specificity of between at least about 45% to 100%; (b) determined by an assay having a sensitivity of at least about 83.3% and a specificity of at least about 54.9%; (c) determined by an assay having a sensitivity of at least about 100% and a specificity of at least about 49.2%; or (d) between at least about 1 pg/mL to about 50 pg/mL.

Clause 283. The method of any one of clauses 278 to 282, wherein the reference level for cTnI is about 5.6 pg/mL or about 5.7 pg/mL.

Clause 284. A method for predicting the outcome of human subjects having mild traumatic brain injury, the method comprising:
a) performing an assay on samples from the human subject to measure or detect a level of cTnI in a first sample and a second sample, wherein the first sample is taken from the human subject at a first time point within about 24 hours after head injury and the second sample is taken from the human subject about 4 hours after the first sample, wherein the samples are biological samples;
b) determining whether the amount of cTnI has increased or decreased from the first sample to the second sample; and
c) predicting an unfavorable outcome in the human subject if the level of cTnI in the sample has increased from the first sample to the second sample and predicting a favorable outcome in the human subject if the level of cTnI in the sample has remained unchanged or has decreased from the first sample to the second sample.

Clause 285. The method of clause 284, wherein the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours or within about 24 hours.

Clause 286. The method of clauses 284 or 285, wherein the method predicts the outcome at about 1 month, 3 months, or 6 months after the injury to the head.

Clause 287. The method of clause 286, wherein the subject is predicted to have an Extended Glasgow Outcome Scale (GOSE) score of 5 or less.

Clause 288. The method of any one of clauses 284 to 287, wherein the amount of cTnI in the first sample is from about 1.0 to about 50 pg/mL.

Clause 289. The method of any one of clauses 284 to 288, wherein the amount of cTnI in the second sample is from about 1.0 to about 50 pg/mL.

Clause 290. The method of any one of clauses 284 to 289, wherein the level of cTnI decreases or increase by at least an absolute amount from the first sample to the second sample.

Clause 291. The method of claim 290, wherein the absolute amount is (a) determined by an assay having a sensitivity of between at least about 80% to 100% and a specificity of between at least about 45% to 100%; (b) determined by an assay having a sensitivity of at least about 82.4% and a specificity of at least about 69.5%; or (c) between at least about 1 pg/mL to about 50 pg/mL.

Clause 292. The method of any one of clauses 291, wherein the absolute amount is about 5.6 pg/mL.

Clause 293. The method of any one of clauses 270 to 292, further comprising treating the subject assessed as having an unfavorable outcome with a traumatic brain injury treatment.

Clause 294. The method of any one of clauses 270 to 293, further comprising monitoring the subject assessed as having an unfavorable outcome with a traumatic brain injury treatment.

Clause 295. A method for predicting the outcome of human subjects having mild traumatic brain injury, the method comprising:
- a) performing an assay on samples from the human subject to measure or detect a level of cTnI in a first sample and a second sample, wherein the first sample is taken from the human subject at a first time point within 24 hours after a injury to the head and the second sample is taken from the human subject about 0 to about 4 hours after the first sample, wherein the samples are biological samples;
- b) determining the age of the subject; and
- c) predicting an unfavorable outcome in the human subject if the level of cTnI in the first sample and/or second sample are higher than a reference level of cTnI and the age of the subject is above a reference age and predicting a favorable outcome in the human subject if the level of cTnI in the first sample and second sample are lower than a reference levels of cTnI and/or the age of the subject is below the reference age.

Clause 296. The method of any one clauses 220 to 295 further comprising treating the subject with at least one cardioprotective therapy.

Clause 297. The method of clauses 296, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

Clause 298. The method of any one of clauses 220 to 297, wherein measuring the level of cTnI is done by an immunoassay or clinical chemistry assay.

Clause 299. The method of any one of clauses 220 to 298, wherein measuring the level of cTnI comprises:
- A. contacting the sample, either simultaneously or sequentially, in any order with:
  - (1) a cTnI-capture antibody, which binds to an epitope on cTnI or cTnI fragment to form a cTnI-capture antibody-cTnI antigen complex, and
  - (2) a cTnI-detection antibody which includes a detectable label and binds to an epitope on cTnI that is not bound by the cTnI-capture antibody, to form a cTnI antigen-cTnI-detection antibody complex, such that a cTnI-capture antibody-cTnI antigen-cTnI-detection antibody complex is formed, and
- B. measuring the amount or concentration of cTnI in the sample based on the signal generated by the detectable label in the cTnI-capture antibody-cTnI antigen-cTnI-detection antibody complex.

Clause 300. The method of any one of clauses 220 to 299, wherein the sample is selected from the group consisting of a whole blood sample, a serum sample, a cerebrospinal fluid sample, and a plasma sample.

Clause 301. The method of any one of clauses 220 to 300, wherein the sample is obtained after the subject sustained an injury to the head caused by physical shaking, blunt impact by an external mechanical or other force that results in a closed or open head trauma, one or more falls, explosions or blasts or other types of blunt force trauma.

Clause 302. The method of any one of clauses 220 to 300, wherein the sample is obtained after the subject has ingested or been exposed to a chemical, toxin or combination of a chemical and toxin.

Clause 303. The method of clause 102, wherein the chemical or toxin is fire, mold, asbestos, a pesticide, an insecticide, an organic solvent, a paint, a glue, a gas, an organic metal, a drug of abuse or one or more combinations thereof.

Clause 304. The method of any one of clauses 220 to 303, wherein the sample is obtained from a subject that suffers from an autoimmune disease, a metabolic disorder, a brain tumor, hypoxia, a virus, meningitis, hydrocephalus or combinations thereof.

Clause 305. The method of any one of clauses 220 to 304, wherein said method can be carried out on any subject without regard to factors selected from the group consisting of the subject's clinical condition, the subject's laboratory values, the subject's classification as suffering from mild, moderate, severe, or a moderate to severe traumatic brain injury, the subject's exhibition of low or high levels of cTnI, and the timing of any event wherein said subject may have sustained an injury to the head.

Clause 306. The method of any one of clauses 220 to 305, wherein the sample is a whole blood sample.

Clause 307. The method of any one of clauses 220 to 305, wherein the sample is a serum sample.

Clause 308. The method of any one of clauses 220 to 305, wherein the sample is a plasma sample.

Clause 309. The method of any one of clauses 306 to 308, wherein the assay is an immunoassay.

Clause 310. The method of any one of clauses 306 to 308, wherein the assay is a clinical chemistry assay.

Clause 311. The method of any one of clauses 306 to 308, wherein the assay is a single molecule detection assay.

What is claimed is:

1. A method comprising:
   a) performing at least one assay for cardiac troponin I (cTnI) in at least one sample that is whole blood, serum, plasma, or cerebrospinal fluid obtained from a subject within about 24 hours after an actual or suspected injury to the head; and
   b) treating the subject for (1) a moderate, severe, or moderate to severe traumatic brain injury (TBI) when the level of cTnI in the sample is higher than a reference level of cTnI, or (2) a mild TBI when the level of cTnI in the sample is lower than a reference level of cTnI; and
   wherein the subject levels of cTnI are distinct from levels of cTnI in a control subject that has no TBI.

2. The method of claim 1, wherein:
   (a) the assay is selected from the group consisting of an immunoassay, a clinical chemistry assay, and a point-of-care assay and/or the assay is performed using single molecule detection;
   (b) the subject has received a Glasgow Coma Scale score before or after the assay is performed, and wherein the reference level is correlated with:
      (i) a Glasgow Coma Scale score of 3-12 and the subject is suspected of having mild TBI based on the Glasgow Coma Scale score; or
      (ii) a Glasgow Coma Scale score of 13-15 and the subject is suspected of having a moderate, severe, or moderate to severe TBI based on the Glasgow Coma Scale score;
   (c) the reference level for cTnI is about 1.94 pg/mL, about 2.54 pg/mL, about 21.23 pg/mL, or about 43.79 pg/mL;
   (d) the reference level is (i) determined by an assay having a sensitivity of between at least about 85% to 100% and a specificity of between at least about 30% to 100%; (ii) determined by an assay having a sensitivity of at least about 87.5% and a specificity of at least about 31%; or (iii) between at least about 1 pg/mL to about 50 pg/mL;
   (e) the sample is taken within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head; or
   (f) a subject with (1) a moderate, severe, or moderate to severe TBI is treated (a) with one or more therapeutic agents; (b) with one or more surgical procedures; (c) by protecting the subject's airway; (d) with one or more therapies selected from the group consisting of rehabilitation, physical therapy, occupational therapy, cognitive behavioral therapy, anger management, counseling and any combinations thereof; or (e) with any combination of (a)-(d); or (2) a mild TBI is treated (a') with rest; (b') by abstaining from physical activities; (c') by avoiding light; (d') by wearing protective eyewear when in light; (e') with one or more therapeutic agents; or (f) with any combination of (a')-(e').

3. The method of claim 1, further comprising monitoring the subject assessed as having a mild, moderate, severe, or moderate to severe TBI.

4. The method of claim 1, wherein the assay is performed on the sample obtained from the subject with about 2 hours after an actual or suspected injury to the head to measure or detect a level of cTnI.

5. The method of claim 1, wherein:
   (a) the reference level for cTnI is about 1.15 pg/mL or about 1.29 pg/mL;
   (b) the reference level is (i) determined by an assay having a sensitivity of between at least about 85% to 100% and a specificity of between at least about 30% to 100%; (ii) determined by an assay having a sensitivity of at least about 87.5% and a specificity of at least about 31%; or (iii) between at least about 0.5 pg/mL to about 30 pg/mL; or
   (c) the sample is taken within about 5 minutes, within about 10 minutes, within about 12 minutes, within about 15 minutes, within about 20 minutes, within about 30 minutes, within about 60 minutes, or within about 90 minutes after an actual or suspected injury to the head.

6. The method of claim 2, wherein the one or more therapeutic agents is at least one cardioprotective therapy, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

7. A method comprising:
   a) performing at least one assay for cardiac troponin I (cTnI) in at least one sample that is whole blood, serum, plasma, or cerebrospinal fluid obtained from a subject within about 24 hours after an actual or suspected injury to the head; and
   b) performing a head computed tomography (CT) scan on the subject when the level of cTnI in the sample is higher than a reference level of cTnI; and wherein the subject levels of cTnI are distinct from levels of cTnI in a control subject that has no traumatic brain injury; and
   (c) treating the subject for
      (1) a moderate, severe, or moderate to severe TBI when the level of cTnI in the sample is higher than a reference level of cTnI (a) with one or more therapeutic agents; (b) with one or more surgical procedures; (c) by protecting the subject's airway; (d) with one or more therapies selected from the group consisting of rehabilitation, physical therapy, occupational therapy, cognitive behavioral therapy, anger management, counseling and any combinations thereof; or (e) with any combination of (a)-(d); or
      (2) a mild TBI when the level of cTnI in the sample is lower than a reference level of cTnI (a') with rest; (b') by abstaining from physical activities; (c') by avoiding light; (d') by wearing protective eyewear when in light; (e') with one or more therapeutic agents; or (f) with any combination of (a')-(e').

8. The method of claim 7, wherein:
   (a) the assay is selected from the group consisting of an immunoassay, a clinical chemistry assay, and a point-of-care assay and/or the assay is performed using single molecule detection;
   (b) the sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head;
(c) the reference level for cTnI is about 1.65 pg/mL, about 2.16 pg/mL, about 14.75 pg/mL, or about 30.43 pg/mL;
(d) the reference level is (i) determined by an assay having a sensitivity of between at least about 65% to 100% and a specificity of between at least about 30% to 100%; (ii) determined by an assay having a sensitivity of at least about 85% and a specificity of at least about 33%; or (iii) between at least about 1.0 pg/mL to about 50 pg/mL; or
(e) the assay is performed on the sample obtained from the subject with about 2 hours after an actual or suspected injury to the head to measure or detect a level of cTnI.

9. The method of claim 8, wherein:
(a) the reference level for cTnI is about 5.8 pg/mL or about 4.7 pg/mL;
(b) the reference level is (a) determined by an assay having a sensitivity of between at least about 65% to 100% and a specificity of between at least about 30% to 100%; (b) determined by an assay having a sensitivity of at least about 85% and a specificity of at least about 33%; or (c) between at least about 0.5 pg/mL to about 25 pg/mL; or
(c) sample is taken within about 5 minutes, within about 10 minutes, within about 12 minutes, within about 15 minutes, within about 20 minutes, within about 30 minutes, within about 60 minutes, or within about 90 minutes after an actual or suspected injury to the head.

10. The method of claim 7, wherein the method further comprises:
(a) not performing a head CT scan on the subject and treating the subject for a mild TBI when the level of cTnI in the sample is lower than a reference level of cTnI; or
(b) ruling out the need to perform a head CT scan on the subject when the level of cTnI in the sample is lower than a reference level of cTnI.

11. The method of claim 10, wherein the one or more therapeutic agents is at least one cardioprotective therapy, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

12. A method comprising:
a) performing at least one assay for cardiac troponin I (cTnI) in at least a first sample taken at a first time point and a second sample taken at a second time point and obtained from a human subject after an actual or suspected injury to the head; and
b) treating the subject for mild, a moderate, severe, or moderate to severe traumatic brain injury (TBI) when the level of cTnI in the sample has increased from the first sample to the second sample; and
wherein the sample is whole blood, serum, plasma, or cerebrospinal fluid obtained wherein the first time point is within about 24 hours after the actual or suspected head injury and the second time point is within about 3 to about 6 hours, and
further wherein the subject levels of cTnI are distinct from levels of cTnI in a control subject that has no TBI.

13. The method of 12, wherein:
(a) the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head;
(b) the assay is selected from the group consisting of an immunoassay, a clinical chemistry assay, and a point-of-care assay and/or the assay is performed using single molecule detection; or
(c) a subject with (1) a moderate, severe, or moderate to severe TBI is treated (a) with one or more therapeutic agents; (b) with one or more surgical procedures; (c) by protecting the subject's airway; (d) with one or more therapies selected from the group consisting of rehabilitation, physical therapy, occupational therapy, cognitive behavioral therapy, anger management, counseling and any combinations thereof; or (e) with any combination of (a)-(d); or (2) a mild TBI is treated (a') with rest; (b') by abstaining from physical activities; (c') by avoiding light; (d') by wearing protective eyewear when in light; (e') with one or more therapeutic agents; or (f) with any combination of (a')-(e').

14. The method of claim 13, wherein the one or more therapeutic agents is at least one cardioprotective therapy, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

15. A method comprising:
a) performing at least one assay for cardiac troponin I (cTnI) in at least a first sample taken at a first time point and a second sample taken at a second time point and obtained from a human subject after an actual or suspected injury to the head; and
b) treating the subject for mild, a moderate, severe, or moderate to severe traumatic brain injury (TBI) when the level of cTnI in the sample has increased from the first sample to the second sample; and
wherein the sample is whole blood, serum, plasma, or cerebrospinal fluid obtained wherein the first time point is within about 24 hours after the actual or suspected head injury and the second time point is within about 1 to about 4 hours, and further wherein the subject levels of cTnI are distinct from levels of cTnI in a control subject that has no TBI.

16. The method of 15, wherein:
(a) the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head;
(b) the assay is selected from the group consisting of an immunoassay, a clinical chemistry assay, and a point-of-care assay and/or the assay is performed using single molecule detection;
(c) the amount of cTnI in the first sample or second sample is from about 1.0 to about 50 pg/mL; or
(d) a subject with (1) a moderate, severe, or moderate to severe TBI is treated (a) with one or more therapeutic agents; (b) with one or more surgical procedures; (c) by protecting the subject's airway; (d) with one or more therapies selected from the group consisting of rehabilitation, physical therapy, occupational therapy, cognitive behavioral therapy, anger management, counseling and any combinations thereof; or (e) with any combination of (a)-(d); or (2) a mild TBI is treated (a') with rest; (b') by abstaining from physical activities; (c') by avoiding light; (d') by wearing protective eyewear when in light; (e') with one or more therapeutic agents; or (f) with any combination of (a')-(e').

17. The method of claim 16, wherein the one or more therapeutic agents is at least one cardioprotective therapy, wherein the at least one cardioprotective therapy comprises a beta-blocker, a diuretic, an Angiotensin-Converting Enzyme (ACE) inhibitor, a calcium channel blocker, a lipid lowering therapy, a statin, a nitrate, an antiplatelet, an anticlotting agent, an anticoagulation agent or combinations thereof.

18. A method comprising:
a) performing at least one assay for cardiac troponin I (cTnI) in at least a first sample taken at a first time point and a second sample taken at a second time point and obtained from a human subject after an actual or suspected injury to the head; and
b) treating the subject for mild, a moderate, severe, or moderate to severe traumatic brain injury (TBI) when the level of cTnI in the sample has increased by at least about 20% from the first sample to the second sample; and
wherein the sample is whole blood, serum, plasma, or cerebrospinal fluid wherein the first time point is within about 24 hours after the actual or suspected head injury and the second time point is within about 0 to about 4 hours, and further wherein the subject levels of cTnI are distinct from levels of cTnI in a control subject that has no TBI.

19. The method of 18, wherein:
(a) the first sample is taken from the subject within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of the actual or suspected injury to the head; or
(b) the assay is selected from the group consisting of an immunoassay, a clinical chemistry assay, and a point-of-care assay and/or the assay is performed using single molecule detection.

* * * * *